United States Patent
Pandya et al.

(10) Patent No.: US 12,324,444 B2
(45) Date of Patent: *Jun. 10, 2025

(54) COMPOSITIONS COMPRISING A CASEIN AND METHODS OF PRODUCING THE SAME

(71) Applicant: Perfect Day, Inc., Berkeley, CA (US)

(72) Inventors: Ryan Pandya, South San Francisco, CA (US); Perumal Gandhi, Santa Clara, CA (US); Shaowen Ji, Ann Arbor, MI (US); Derek Beauchamp, Dexter, MI (US); Louis Hom, San Carlos, CA (US)

(73) Assignee: PERFECT DAY, INC., Berkeley, CA (US)

( * ) Notice: Subject to any disclaimer, the term of this patent is extended or adjusted under 35 U.S.C. 154(b) by 1242 days.

This patent is subject to a terminal disclaimer.

(21) Appl. No.: 17/081,167

(22) Filed: Oct. 27, 2020

(65) Prior Publication Data

US 2021/0037849 A1    Feb. 11, 2021

Related U.S. Application Data

(63) Continuation of application No. 15/505,557, filed as application No. PCT/US2015/046428 on Aug. 21, 2015, now Pat. No. 11,076,615.

(60) Provisional application No. 62/040,393, filed on Aug. 21, 2014.

(51) Int. Cl.
| | |
|---|---|
| A23G 9/40 | (2006.01) |
| A23C 9/123 | (2006.01) |
| A23C 9/13 | (2006.01) |
| A23C 9/15 | (2006.01) |
| A23C 9/152 | (2006.01) |
| A23C 11/04 | (2025.01) |
| A23C 11/08 | (2006.01) |
| A23C 15/12 | (2006.01) |
| A23C 19/05 | (2006.01) |
| A23C 19/055 | (2006.01) |
| A23J 3/10 | (2006.01) |
| A23L 9/20 | (2016.01) |
| C07K 14/00 | (2006.01) |
| C07K 14/47 | (2006.01) |
| C07K 14/76 | (2006.01) |

(52) U.S. Cl.
CPC ............... *A23G 9/40* (2013.01); *A23C 9/123* (2013.01); *A23C 9/1307* (2013.01); *A23C 9/1315* (2013.01); *A23C 9/1512* (2013.01); *A23C 11/04* (2013.01); *A23C 11/08* (2013.01); *A23C 15/12* (2013.01); *A23C 19/053* (2013.01); *A23C 19/055* (2013.01); *A23J 3/10* (2013.01); *A23L 9/22* (2016.08); *C07K 14/00* (2013.01); *C07K 14/4717* (2013.01); *C07K 14/4732* (2013.01); *C07K 14/76* (2013.01); *A23V 2002/00* (2013.01)

(58) Field of Classification Search
CPC ... A23C 19/053; A23C 11/06; C07K 14/4717; C07K 14/4732
See application file for complete search history.

(56) References Cited

U.S. PATENT DOCUMENTS

| | | | |
|---|---|---|---|
| 4,614,653 | A | 9/1986 | Kakade |
| 4,834,994 | A | 5/1989 | Kueata |
| 5,061,504 | A | 10/1991 | Kong-Chan et al. |
| 5,882,704 | A | 3/1999 | Yamaguchi et al. |
| 5,882,705 | A | 3/1999 | Sato et al. |
| 5,942,274 | A | 8/1999 | Slattery et al. |
| 6,181,421 | B1 | 1/2001 | Aspnes et al. |
| 6,232,094 | B1 | 5/2001 | Hansson |
| 6,270,827 | B1 | 8/2001 | Gaull et al. |
| 6,290,974 | B1 | 9/2001 | Swaisgood et al. |
| 8,809,259 | B2 | 8/2014 | Berry et al. |
| 9,591,872 | B2 | 3/2017 | Rosado Loria et al. |
| 2003/0078392 | A1 | 4/2003 | Leaver |
| 2005/0170062 | A1 | 8/2005 | Burling |
| 2007/0116830 | A1 | 5/2007 | Prakash |
| 2010/0119691 | A1 | 5/2010 | Huang et al. |
| 2010/0223682 | A1 | 9/2010 | Katz |
| 2013/0189398 | A1 | 7/2013 | Rosado Loria et al. |
| 2014/0065264 | A1 | 3/2014 | Do et al. |
| 2014/0013294 | A1 | 5/2014 | Merril |
| 2014/0134294 | A1 | 5/2014 | Merill et al. |
| 2014/0099444 | A1 | 10/2014 | Catchmark et al. |
| 2017/0273328 | A1 | 9/2017 | Pandya et al. |
| 2018/0271111 | A1 | 9/2018 | Pandya et al. |
| 2021/0037848 | A1 | 2/2021 | Pandaya et al. |
| 2023/0371547 | A1 | 11/2023 | Pandaya et al. |

FOREIGN PATENT DOCUMENTS

| | | |
|---|---|---|
| EP | 2649884 | 10/2013 |
| JP | 3475221 | 12/2009 |
| WO | WO 1991/08675 | 6/1991 |
| WO | WO 1995/02692 | 1/1995 |
| WO | WO 2004/091306 | 10/2004 |
| WO | WO 2013/09182 | 1/2013 |

(Continued)

OTHER PUBLICATIONS

AU Opposition, "Amended Statement of Grounds and Particulars," in Australian Appln. No. 2015305271, Dec. 24, 2020, 2 pages.
AU Opposition, "Opposition Statement of Grounds and Particulars," in Australian Appln. No. 2015305271, Jan. 5, 2021, 15 pages.
AU Opposition, "Applicant-Initiated Interview Summary," Exhibit G in Australian Appln. No. 2015305271, dated Sep. 22, 2020, 4 pages.
AU Opposition, "Correspondence," in Australian Appl. No. 2015305271, dated Feb. 2021, 2 pages.

(Continued)

*Primary Examiner* — Jeffrey P Mornhinweg
(74) *Attorney, Agent, or Firm* — David R. Conklin; Kirton McConkie

(57) ABSTRACT

Disclosed herein are methods and compositions including casein, and methods for making these compositions.

50 Claims, 9 Drawing Sheets

Specification includes a Sequence Listing.

(56) References Cited

FOREIGN PATENT DOCUMENTS

| WO | WO 2013/148221 | 10/2013 |
|---|---|---|
| WO | WO 2013/148328 | 10/2013 |
| WO | WO 2013/148330 | 10/2013 |
| WO | WO 2013/148331 | 10/2013 |
| WO | WO 2013/148332 | 10/2013 |
| WO | WO 2016/029193 | 2/2016 |

OTHER PUBLICATIONS

AU Opposition, "Declaration by Dr. Jeremy Paul Hill," Exhibit JH-1 in Australian Appln. No. 2015305271,dated Dec. 18, 2020, 14 pages.
AU Opposition, "Declaration of Tiffany Reiter, Ph.D.,J.D.," Exhibit A in Australian Appln. No. 2015305271, dated, Sep. 20, 2020, 4 pages.
AU Opposition, "Declaration of Tiffany Reiter, Ph.D.,J.D.," in Australian Appln. No. 2015305271, dated, Sep. 20, 2020, 4 pages.
AU Opposition, "First Declaration of Donald McMahon, Ph.D.," Exhibit A in Australian Appln. No. 2015305271, dated Oct. 12, 2020, 29 pages.
AU Opposition, "First Declaration of Donald McMahon, Ph.D.," Exhibit B in Australian Appln. No. 2015305271, dated Oct. 12, 2020, 14 pages.
AU Opposition, "First Declaration of Donald McMahon, Ph.D.," Exhibit C in Australian Appln. No. 2015305271, dated Oct. 12, 2020, 4 pages.
AU Opposition, "First Declaration of Donald McMahon, Ph.D.," Exhibit D in Australian Appln. No. 2015305271, dated Oct. 12, 2020, 4 pages.
AU Opposition, "First Declaration of Donald McMahon, Ph.D.," in Australian Appln. No. 2015305271, dated Oct. 12, 2020, 30 pages.
AU Opposition, "First Declaration of Tonya Schoenfuss, Ph.D, Huppertz et al.,"Effect of NaCl on some physico-chemical properties of concentrated bovine milk,"International Diary J., 2005, 16(2006):1142-1148" Exhibit I in Australian Appl No. 2015305271, dated Sep. 2020, 8 pages.
AU Opposition, "First Declaration of Tonya Schoenfuss, Ph.D," "Loch et al.,"Two modes of fatty acid binding to bovine β-lactoglobulin-crystallographic and spectroscopic studies, J. of Molecular Recognition, 2011, 24:341-349, Exhibit D in Australian Appln. No. 2015305271, dated Sep. 22, 2020, 10 pages.
AU Opposition, "First Declaration of Tonya Schoenfuss, Ph.D.," "Expert Evidence of practice note(GPN-EXPT)" Federal Court of Australia, Exhibit B in Australian Appln. No. 201530271, dated Sep. 22, 2020, 14 pages.
AU Opposition, "First Declaration of Tonya Schoenfuss, Ph.D.," Chrysina et al., "Crystal structures of apo- and holo-bovine x-lacralbumin at 2.2-a resolution reveal an effect of calcium on inter-lobe interactions," J. of Biology Chemistry, 2000, 37021-37029, Exhibit E in Australian Appl. No. 2015305271, dated Sep. 22, 2020, 10 pages.
AU Opposition, "First Declaration of Tonya Schoenfuss, Ph.D.," Curriculum Vitae, Exhibit A in Australian Appl. No. 2015305271, dated Sep. 22, 2020, 6 pages.
AU Opposition, "First Declaration of Tonya Schoenfuss, Ph.D.," dated Sep. 22, 2020, 32 pages.
AU Opposition, "First Declaration of Tonya Schoenfuss, Ph.D.," Exhibit F in Australian Appln. No. 2015305271, dated Sep. 22, 2020, 12 pages.
AU Opposition, "First Declaration of Tonya Schoenfuss, Ph.D.," Exhibit H in Australian Appln. No. 2015305271, dated Sep. 22, 2020, 4 pages.
AU Opposition, "First Declaration of Tonya Schoenfuss, Ph.D.," Exhibit J in Australian Appln. No. 2015305271, dated Sep. 22, 2020, 36 pages.
AU Opposition, "First Declaration of Tonya Schoenfuss, Ph.D.,"Farrell et al., "Nomenclature of the proteins of cows' milk—sixth revision," J. Diary Sci., , 2004, 1641-1674, Exhibit C in Australian Appl. No. 2015305271, dated Sep. 22, 2020, 35 pages.
AU Opposition, "Reply declaration by Dr. Jeremy Paul Hill," in Australian Appln. No. 2015305271, dated Dec. 18, 2020, 10 pages.
AU Opposition, Reply Declaration by Dr. Stephen Richard Davis, dated Dec. 21, 2020, 8 pages.
AU Opposition, "Reply declaration of Dr. Colin Robert South," Exhibit CS-11 in Australian Appln. No. 2015305271, dated Dec. 21, 2020, 7 pages.
AU Opposition, "Reply declaration of Dr.Stephen Richard Davis," Exhibit SRD-10 in Australian Appln. No. 2015305271, dated Dec. 21, 2020, 7 pages.
AU Opposition, "Reply Declaration of Professor Matt Duncan Golding," in Australian Appln. No. 2015305271,dated Dec. 23, 2020, 14 pages.
AU Opposition, "Reply declaration of Professor Matt Duncan Golding,"Exhibit MDG-1 in Australian Appln. No. 2015305271, 20 pages.
AU Opposition, "Reply Declaration" by Dr. Colin South, dated, Dec. 21, 2020, 12 pages.
Au Opposition, "Response to Directors Letter", in Australian Appl. No. 2015305271, dated Feb. 1, 2021, 6 pages.
AU Opposition, "Second Declaration of Donald McMahon, Ph.D.," in Australian Appln. No. 2015305271, dated Sep. 22, 2020, 3 pages.
AU Opposition, "Second Declaration of Tonya Schoenfuss, Ph.D.," in Australian Appln. No. 2015305271, dated Sep. 21, 2020, 5 pages.
Farrell Jr., et al., "Casein Micelle Structure: What Can Be Learned from Milk Synthesis and Structural Biology?" Curr. Opin. Colloid Interface Sci. 11:135-147, 2006.
Chatel et al., "Expression, Purification and Immunochemical Characterization of Recombinant Bovine Beta-Lactoglobulin, A Major Cow Milk Allergen," Molecular Immunology, Aug. 1996, 33(14):1113-1118.
Choi et al., "Expression and Purification of Glycosylated Bovine β-Casein(L70S/P71S) in Pichia pastoris," J. Agric. Food Chem., 2001, 49:1761-1766.
Conesa et al., "Recombinant human lactoferrin: A valuable protein for pharmaceutical products and functional foods," Biotechnology Advances, 2010, 28:831-838.
JP Notice of Opposition Number in Japanese Appln. No. 2017-529979, dated Aug. 30, 2022, 2 pages, (with English translation).
JP Opposition, Notice of Reasons for Revocation in Japanese Appln. No. 2017-529979, mailed Jan. 17, 2023, 32 pages (with English translation).
JP Opposition, Written Opposition, in Japanese Appl. No. 2017-529979, dated Oct. 27, 2022, 106 pages (with English Translation).
Kawai et al., "Transformation of *Saccharomyces cerevisiae* and other fungi," Bioengineered Bugs, 2010, 1(6):395-403.
Milk Proteins: From Expression To Food, 2009, Chapter 4, pp. 107-132.
Office Action in Canadian Appl. No. 2,958,858, dated Aug. 17, 2023, 3 pages.
Office Action in Chinese Application No. 202111188178.X, dated Jul. 6, 2023, 23 pages (with English Translation).
Office Action in Japanese Application No. 2021-155495, mailed Jul. 18, 2023, 7 pages (with English Translation).
Office Action in Japanese Application No. 2021-155495, mailed Nov. 22, 2022, 9 pages (with English translation).
Store.alishan.jp [online], "Dairy Free Margarine," Jul. 25, 2022, retrieved on Aug. 21, 2023, retrieved from URL<https://store.alishan.jp/en/product/dairy-freemargarine>, 10 pages (with English translation).
Totsuka et al., Expression and Secretion of Bovine β-Lactoglobulin in *Saccharomyces cerevisiae*, Agric. Biol. Chem., 1990, 54(12):3111-3116.
Khan et al., "Humanizing glycosylation pathways in eukaryotic expression systems", World J. Microbiol. Biotechnol. 2017, 33:4.
O'Connell et al., "The two-stage coagulation of milk proteins in the minimum of the heat coagulation time-pH profile pf milk: Effect of casein micelle size", J Diary Sci. 2000.
Stuff.co.nz, [online], "Milk made in laboratories to hit shelves," Jul. 12, 2014, retrieved on Sep. 3, 2021, retrieved from URL<https://www.stuff.co.nz/business/10258565/Milk-made-in-laboratories-to-hit-shelves>,3 pages.

(56) References Cited

OTHER PUBLICATIONS wired.com,[online], "Cow milk without the cow is coming to change food forever," Apr. 15, 2015, retrieved on Sep. 3, 2021 from URL< https://www.wired.com/2015/04/diy-biotech-vegan-cheese/ >, 7 pages.
Office Action in Canadian Appl. No. 2958858, dated Jul. 28, 2021, 4 pages.
[No Author Listed], "96th Annual Collegiate Dairy Products Evaluation Contest" Apr. 17, 2019, 10 pages.
Au Opposition, "Letter to The Commisioner of Patents—Applicants Response" in Australian Appl No. 2015305271, dated Jun. 17, 2021, 4 pages.
Declaration by Ravi Jhala, in Australian Patent Application No. 2015305271, dated Jun. 14, 2021, 12 pages.
Khan et al., "Humanizing glycosylation pathways in eukaryotic expression systems" World J. Microbiol. Biotechnol., 33:4, 2017.
Lorenzen et al., "A Comparative study of the gelation properties of whey protein concentrate and whey protein isolate" Le Lait 86(4):259-271, 2006.
Office Action in Australian Appln. No. 2015305271, dated Nov. 12, 2018, 5 pages.
Office Action in Brazilian Appln. No. BR112017003414-0, dated Aug. 21, 2015, 6 pages(with English translation).
Office Action in Brazilian Appln. No. BR122020004762-3, dated Aug. 21, 2015, 24 pages(with English translation).
Office Action in Brazilian Appln. No. BR122020004774-7, dated Nov. 11, 2021, 8 pages(with English translation).
Office Action in Canadian Appl. No. 2,958,858, dated Aug. 5, 2020, 3 pages.
Office Action in Canadian Appl. No. 2,958,858, dated Jul. 29, 2019, 3 pages.
Office Action in Chinese Appln. No. 201580057456.4, dated Jan. 15, 2020, 21 pages.
Office Action in Chinese Appln. No. 201580057456.4, dated Oct. 30, 2020, 23 pages.
Office Action in Indian Appln. No. 201737009683, dated Nov. 11, 2020, 8 pages.
Office Action in Japanese Appln. No. 2017-529979, dated Nov. 11, 2020, 12 pages, (with English translation).
Office Action in Japanese Appln. No. 2017-529979, dated Nov. 12, 2019, 16 pages (with English translation).
Office Action in Malaysian Appln. No. PI 2017000254, dated May 21, 2019, 4 pages.
Office Action in U.S. Appl. No. 15/438,273, dated Aug. 23, 2017, 10 pages.
Office Action in U.S. Appl. No. 15/505,557, dated Sep. 26, 2019, 25 pages.
Office Action in U.S. Appl. No. 16/002,818, dated Aug. 31, 2018, 14 pages.
Office Action in U.S. Appl. No. 16/002,818, dated May 8, 2019, 20 pages.
Saunois et al., "The Global Methane Budget 2000-2017" Earth Syst. Sci. Data, 12:1561-1623, 2020.
Third Declaration by Dr. Tonya Schoenfuss, PH.D, in Australian Patent Application No. 2015305271, dated Jun. 14, 2021, 20 pages.
Adapa et al., "Rheological Properties of Ice Cream Mixes and Frozen Ice Creams Containing Fat and Fat Replacers", Journal of Dairy Science, May 2000, 83:2224-2229.
Choi et al., "Studies on Physical and Sensory Properties of Premium Vanilla Ice Cream Distributed in Korean Market", Korean J. Food Sci. An., Dec. 2014, 34(6): 757-762.
Desai et al., "Sensory properties and drivers of liking for Greek yogurts", Journal of Diary Science, Oct. 28, 2013, 96(12): 7454-7466.
Firebaugh et al., "Emulsifying and Foaming Properties of a Derivatized Whey Protein Ingredient", International Journal of Food Properties, 2005, 8:243-253.
Kneifel et al., "Water-holding capacity of proteins with special regard to milk proteins and methodological aspects", Journal of Diary Science, 1991, 74:2027-2041.

Koc et al., "Physical properties of yoghurt powder produced by spray drying", Journal Food Science Technology, Jul. 2014, 51(7): 1377-1383.
Lee et al., "Impact of Gelation Conditions and Structural Breakdown on the Physical and Sensory Properties of Stirred Yogurts", Journal of Diary Science, Jul. 2006, 89:2374-2385.
Office Action in Brazilian Appln. No. BR122020004774-7, dated Jun. 4, 2022, 10 pages (with machine translation).
Office Action in Chinese Appln. No. 201580057456.4, dated May 17, 2021, 22 pages, ( with English translation).
Office Action in Japanese Appln. No. 2017-529979, dated May 25, 2021, 14 pages, (with English translation).
Lorenzen et al., "Comparative study of the gelation properties of whey protein concentrate and whey protein isolate" Le Lait 86(4):259-271, 2006.
Arora et al., "Variations in the fat unsaponifiable matter and cholesterol contents of goat milk," Ind. J. Dairy Sci., Sep. 1976, 29:191.
AU Opposition, "Declaration of Dr. Colin Robert South: "Declaration of Dr. Colin Robert South," In the Matter of Australian Patent Application 2015305271 in the name of Perfect Day, Inc. and in the Matter of an Opposition Thereto by Fonterra Co-operative Group Limited," Exhibit CS-2, Federal Court of Australia, Jun. 22, 2020, 3 pages.
AU Opposition, "Declaration of Dr. Stephen Richard Davis," In the Matter of Australian patent application 2015305271 in the name of Perfect Day, Inc. and In the Matter of an opposition thereto by Fonterra Co-operative Group Limited, dated Jun. 23, 2020, 16 pages.
AU Opposition, "Declaration of Dr. Steven Richard Davis: Expert witness in proceedings in the Federal Court of Australia," Exhibit SRD-2, Federal Court of Australia, Jun. 2020, 3 pages.
AU Opposition, "Second Declaration of Dr. Colin Robert South," In the Matter of Australian patent application 2015305271 in the name of Perfect Day, Inc. and In the Matter of an opposition thereto by Fonterra Co-operative Group Limited, dated Jun. 22, 2020, 10 pages.
AU Opposition, "Second Declaration of Dr. Colin Robert South:Comment on opposed patent, with patent specification as reviewed attached," Exhibit CS-6, Australian Appln No. 2015305271, dated Jun. 22, 2020, 225 pages.
AU Opposition, "Statement of Grounds and Particulars," in Australian Application No. 2015305271, dated Mar. 23, 2020, 14 pages.
AU Opposition, "Declaration of Dr. Stephen Richard Davis: AU 2015305271 Table comparing claim features with disclosure of U.S. Pat. No. 8,809,259(D1)," Exhibit SRD-9, Jun. 2020, 8 pages.
AU Patent Application No. 2015305271 Opposition, "Declaration of Dr. Colin Robert South," In the Matter of Australian Patent Application 2015305271 in the name of Perfect Day, Inc. and in the Matter of an Opposition Thereto by Fonterra Co-operative Group Limited, dated Jun. 22, 2020, 15 pages.
Beare-Rogers et al., "Lexicon of lipid nutration (IUPAC Technical Report)," Pure and Applied Chemistry 73(4):685-744, 2001.
Bill et al., "Play catch-up with *Escherichia coli*: using yeast to increase success rates in recombinant protein production experiments," Frontiers Microbiol., vol. 5, Article 85, 5 pages, 2014.
BR Office Action in Brazilian Appln. No. BR112017003414-0, dated Oct. 31, 2019, 5 pages (with English translation).
Brignon et al., "Preparation and amino acid sequences of human kappa-casein," FEBS Lett. 188(1):48-54, 1985.
CA Office Action in Canadian Appln. No. 2958858, dated Aug. 5, 2020, 4 pages.
CA Office Action in Canadian Appln. No. 2958858, dated Jul. 29, 2019, 3 pages.
Chapter 5, "Post-translational Modification of Caseins," in Milk Proteins from Expression to Food, Second Edition, Singh et al. (Eds), Elsevier, Boston, MA, pp. 141-162, 2014.
Choi and Jimenez-Flores, "Expression and purification of glycosylated bovine beta-casein (L70S/P71S) in *Pichia pastoris*," J. Agric. Food Chem. 49(4):1761-1766, 2001.
CN Office Action in Chinese Application No. 201580057456, dated Mar. 18, 2020, 5 pages.

(56) References Cited

OTHER PUBLICATIONS

CN Office Action in Chinese Appln. No. 201580057456.4, dated Jan. 15, 2020, 22 pages (with English translation).
CN Office Action in Chinese Appln. No. 201580057456.4, dated Oct. 30, 2020, 23 pages (with English Translation).
Deshpande et al., "Protein Glycosylation Pathways in Filamentus Fungi," Glycobiology 18(8):626-637, 2008.
European Office Action in Application No. 15/763,136.7, dated Jun. 5, 2019, 9 pages.
European Office Action in Application No. 15/763,136.7, dated Nov. 9, 2020, 10 pages.
Examination Report in Australian Patent Application No. 2015305271, dated Nov. 12, 2018.
Goda et al., "Production of Synthetic Methionine-Free and Synthetic Methionine-Limited Alpha Casein: Protein Foodstuff for Patients with Homocystinuria due to Cystathionine Beta-Synthase Deficiency," Protein J., 29: 44-49, 2010.
Greenberg et al., "Human beta-casein. Amino acid sequence and identification of phosphorylation sites," J. Biol. Chem., 1984, 259(8):5132-5138.
Hansson et al., "Expression of human milk beta-casein in *Escherichia coli*: comparison of recombinant protein with native isoforms," Protein Expr. Purif. 4(5):373-381, 1993.
Idiris et al., "Engineering of protein secretion in yeast: strategies and impact on protein production," Appl. Microbiol. Biotechnol. 86(2):403-417, 2010.
Imafidon et al., "Isolation, purification, and alteration of some functional groups of major milk proteins: a review," Crit. Rev. Food. Sci. Nutr. 37(7):663-689, 1997.
Indian Office Action in Application No. 201737009683, dated Nov. 24, 2020, 7 pages.
International Preliminary Report on Patentability in International Application No. PCT/US2015/046428, dated Feb. 21, 2017.
International Search Report for PCT/US2015/046428, mailed Feb. 5, 2016, 8 pages.
Jenness, "Composition and Characteristics of Goat Milk: Review 1968-1979," J. Dairy Sci., 1980, 63(10):1605-1630.
Jensen, "Bovine milk lipids," in Handbook of Milk Composition, Academic Press, 1995, 543-575.
Jimenez-Flores et al., "Expression of bovine B-casein in *Saccharomyces cerevisiae* and characterization of the protein produced in vivo," J. Agric. Food Chem., 36, 1134-1141, 1990.
JP Office Action in Japanese Appln No. 2017-529979, dated, Oct. 13, 2020, 14 pages (with Machine translation).
Juarez et al., "Physico-Chemical Characteristics Of Goat's Milk As Distinct From Those Of Cow's Milk," Int. Dairy Fed. Bulletin, 1986, 202: 54-67.
Kang et al., "Molecular cloning and expression of bovine k-casein in *Escherichia coli*," J. Dairy Sci., 71: 29-40, 1988.
Kawai et al., "Transformation of *Saccharomyces cerevisiae* and other fungi," Bioengineered Bugs, 2010, 1: 395-403.
Kim et al., "Production of human caseinomacropeptide in recombinant *Saccharomyces cerevisiae* and *Pichia pastoris*," Journal of Microbiology & Biotechnology; Official Journal of the Society for Industrial Microbiology, Springer, Berlin, DE, vol. 32, No. 9, pp. 402-408, 2005.
Kim et al., "High-Level Expression of Bovine β-Lactoglobulin in Pichia pastoris and Characterization of Its Physical Properties," Protein Engineering 10(11):1339-1345, 1997.
Li et al., "Cell culture processes for monoclonal antibody production," Landes Bioscience, 2010, 2: 466-477.
Lonnerdal, "Recombinant Human Milk Proteins—An Opportunity and a Challenge," Am. J. Clin. Nutr. 63(4):622S-626S, 1996; Abstract only.
Lonnerdal, "Recombinant Human Milk Proteins," Nestle Nutr. Workshop Ser. Pediatr. Program 58:207-217, 2006.
MacGibbon et al., "Compositions and structure of bovine milk lipids," in Advanced Dairy Chemistry, vol. 2 Lipids, Springer, US, pp. 1-42, 2006.
Mansson, "Fatty acids in bovine milk fat," Food & Nutrition Research, 2008, 52:1.
MY Office Action in Malaysian Appln. No. PI2017000254, dated May 21, 2019, 4 pages.
Park, "Bioreactive Components in Bovine Milk," in Bioactive Components in Milk and Dairy Products, Wiley-Blackwell, Danvers, MA, pp. 15-42, 2009.
Park, "Rheological characteristics of goat and sheep milk," Small Ruminant Res. 68(1-2):73-87, 2007.
Posati et al., "Composition of foods: dairy and egg products: raw, processed, and prepared," Agricultural Handbook—U.S. Dept. of Agriculture (USA), 1976, No. 8-1, 158 pages.
Rocha et al. "Expression and secretions of recombinant ovine β-lactoglobulin in *Saccharomyces cerevisiae* and *Kluveromyces lactis*," Biochem. J., Feb. 1996, 313:927-932.
Rosmaninho et al., "The effect of citrate on calcium phosphate deposition from simulated milk ultrafiltrate (SMUF)," J. Food Engineering 77(3):379-387, 2006.
Saito et al., "Secretion of Glycosylated a-Lacatalbumin in Yeast *Pichia pastori*," J. Biochemistry, Jul. 2002, 132:77-82.
Simons et al., "Overproduction of bovine beta-casein in *Escherichia coli* and engineering of its main chymosin cleavage site," Protein Eng. 6(7):763-770, 1993.
Smouse, "A Laboratory Continuous Deodorizer," Inform, 1997, 8:1176-1181.
Sood et al., "Colloidal Calcium Phosphate in the Reconstituted Milk Micelle May Direct Wild-type Recombinant Human [beta]-Casein to Fold Like the Native Protein," Journal of Protein Chemistry, Kluwer Academic Publishers—Plenum Publishers, NE, vol. 24, No. 6, pp. 379-384, 2005.
Su et al., "Heterologous gene expression in filamentous fungi," Adv Appl Microbiol., 81: 1-61, 2012.
Third Party Submission Under 37 C.F.R. § 1.290 and Concise Description of Relevance filed in U.S. Appl. No. 15/505,557 on Feb. 1, 2019, 46 pages.
Third Party Submission Under 37 C.F.R. § 1.290 Concise Description of Relevance filed in U.S. Appl. No. 15/505,557 on Feb. 1, 2019, 10 pages.
Third Party Submission Under 37 C.F.R. § 1.290 Concise Description of Relevance filed in U.S. Appl. No. 15/505,557 on Oct. 24, 2018, 13 pages.
Third Party Submission Under 37 C.F.R. § 1.290 Concise Description of Relevance filed in U.S. Appl. No. 15/505,557 on Oct. 24, 2018, 3 pages.
Totsuka et al., "Expression and Secretion of Bovine β-lactoglobulin in *Saccharomyces cerevisiae*," Agric. Biol. Chem., 54 (12) 3111-3116, 1990.
Viaene et al., "Efficient expression of bovine x-lactalbumin in *Saccharomyces cerevisiae*," Eur. J. Bichem., 202, 471-477, 1991.
Ward et al., "An inducible expression system for the production of human lactoferrin in *Aspergillus nidulans*," Gene, Aug. 1992, 122: 219-223.
Ward et al., "Production of Biologically Active Recombinant Human Lactoferrin in *Aspergillus oryzae*," Nature Biotechnology, Aug. 1992, 10:784-789.
Wilson et al., "Expression of recombinant wild type and mutant β-Lactoglobulins in the yeast *Pichia pastoris*," International J. Food Sci. Tech., Oct. 1999, 34:445-450.
Written Opinion of the International Searching Authority for PCT/US2015/046428, mailed Feb. 5, 2016, 10 pages.
Yu et al., "The Modification and Analysis of Vegetable Oil for Cheese Making," J. Am. Oil. Chem. Soc., 2000, 77:911-915.
Zhang et al., "Fermentation Strategies for Recombinant Protein Expression in the Methylotrophic Yeast *Pichia pastoris*," Biotechnol. Bioprocess Eng., 2000, 5:275-287.
Zhu, "Mammalian cell protein expression for biopharmaceutical production," Biotechnol. Adv. 30(5):1158-1170, 2012.

COMPOSITIONS COMPRISING A CASEIN AND METHODS OF PRODUCING THE SAME

CROSS-REFERENCE TO RELATED APPLICATION

This application is a continuation of U.S. patent application Ser. No. 15/505,557, filed Feb. 21, 2017, which is a national stage application filed under 35 U.S.C. § 371 of International Patent Application No. PCT/US2015/046428, filed Aug. 21, 2015, which claims priority to U.S. Provisional Patent Application Ser. No. 62/040,393, filed on Aug. 21, 2014, the entire contents of which are incorporated by reference.

FIELD OF THE INVENTION

The invention is directed to dairy substitutes, methods of manufacturing the same, and compositions comprising animal-free milk fats and proteins for food applications, such as milk, butter, cheese, yogurt, and cream.

BACKGROUND OF THE INVENTION

The global dairy market is estimated at $500 billion with an average annual growth rate of 4%. Bovine milk attributes to a significant portion of the market whereas plant-based alternatives account for $1 billion in the US and an estimated $700 million is estimated for lactose-intolerant milk. Bovine milk is known to have four specific caseins, α-s1-casein, α-s2-casein, β-casein, and κ-casein. Mammal- or mammalian-produced milk is a very complex fluid that includes several thousand components (e.g., if all triglycerides are identified). Mammal- or mammalin-produced milk includes water, variety of different lipids, sugar, a variety of different proteins, and a variety of different inorganic salts and compounds (see, e.g., Boland and Thompson (Eds), Milk Proteins from Expression to Food, Academic Press, 2014). Although mammal-produced milk, such as bovine milk, is considered by many to be an ideal source of nutrition, various milk alternatives to mammal- or mammalian-produced milk (e.g., bovine milk), such as plant- or nut-based milks, e.g., soy, almond, or coconut milk, have been pursued for reasons related to mammal- or mammalian-produced milk's allergenicity, lactose intolerance of certain components, personal preference, and the perceived environmental benefits of a reduced dairy industry.

For example, the environmental impact resulting from dairy effluent can result in significant levels of nitrate which has the potential to contaminate groundwater. Groundwater forms the main source of water supply for many towns and farms where surface water supplies are limited. In the US, half the population relies completely or partially on groundwater, and similar figures are available for Europe (see, e.g., the Victoria State Government Department of Environment and Primary Industries website at www.depi.vic.gov.au/agriculture-and-food/dairy/managing-effluent/dairy-effluent-protecting-groundwater). The presence of foodborne pathogens in milk is due to direct contact with contaminated sources in the dairy farm environment and to excretion from the udder of an infected animal. Outbreaks of disease in humans have been traced to the consumption of unpasteurized milk and have also been traced back to pasteurized milk. The major contaminants usually encountered in milk and milk products include pesticide residues, heavy metals, and aflatoxin M1 (Awasthi et al., Indian J. Public Health 56:95-99, 2012).

Existing dairy milk alternatives, such as soy, almond, or coconut milk fall short both in flavor and in functionality; moreover, a large part of the industrial and cultural significance of dairy milk stems from its usefulness in derivative products, such as cheese, yogurt, cream, or butter. Non-dairy plant-based milks, while addressing environmental and health concerns (and while providing adequate flavor for a small segment of the population), almost universally fail to form such derivative products when subjected to the same processes used for dairy milk.

What is needed, therefore, is a dairy substitute or composition that has desirable flavor and performance characteristics, e.g., a composition that replicates dairy flavors, minimizes foodborne pathogens, and has a lower environmental impact in production, while retaining the ability to be used for derivative or downstream applications of dairy milk and while providing a similar nutritional profile as a mammal- or mammalian-produced milk.

SUMMARY OF THE INVENTION

The present invention is based on the discovery that only a subset of components in mammal-produced milk can be used to generate a composition that has a similar flavor, a similar appearance, a similar nutritional value, a similar aroma, and a similar mouth feel of mammal-produced milk.

Provided herein are compositions including: about 0.3 g/L to about 1.1 g/L κ-casein protein; about 1.25 g/L to about 4.9 g/L β-casein protein; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %, where the composition does not include an animal-derived component.

Also provided are compositions that include: about 0.3 g/L to about 1.1 g/L κ-casein protein; about 1.25 g/L to about 4.9 g/L β-casein protein; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %, where the composition: does not include at least one component found in a mammal-produced milk; includes at least one component not present in a mammal-produced milk; and/or includes a higher or lower concentration of at least one component as compared to the concentration of the at least one component in a mammal-produced milk. In some embodiments of these compositions, the composition includes a higher concentration of at least one component selected from the group of: calcium, phosphate, B complex vitamins, vitamin A, vitamin D, vitamin E, and vitamin K, as compared to the concentration of the one or more components in a mammal-produced milk. In some embodiments of these compositions, the composition does not include at least one component found in a mammal-produced milk selected from the group of: lactose, bacteria, mycobacteria, allergens, viruses, prions, yeast, growth hormones, leukocytes, antibiotics, heavy metals, immunoglobulins, lactoferrin, lactoperoxidase, and lipase. In some embodiments of these compositions, wherein the composition includes at least one component not present in a mammal-produced milk selected from the group of an artificial sweetener, a plant-derived lipid, a β-casein protein that is non-glycosylated or has a non-mammalian glycosylation pattern, and a κ-casein protein that is non-glycosylated or has a non-mammalian glycosylation pattern.

Also provided are compositions including: about 0.3 g/L to about 1.1 g/L κ-casein protein that is unglycosylated or has a non-mammalian glycosylation pattern; about 1.25 g/L to about 4.9 g/L β-casein protein that is unglycosylated or has a non-mammalian glycosylation pattern; a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %.

Also provided are composition including a micelle including a κ-casein protein and a β-casein protein, where the micelle has a diameter of about 50 nm to about 350 nm, and the κ-casein protein and the β-casein protein are unglycosylated or have a non-mammalian glycosylation pattern. In some embodiments of these methods, the compositions include a final concentration of micelles of about 2.0 weight % to about 6 weight %. In some embodiments of these compositions, the ratio of the β-casein protein to the κ-casein protein in the micelle is about 3.5:1 to about 5.5:1 (e.g., about 4:1 to about 5:1). In some embodiments of these methods, the composition further includes: a final total concentration of one or more lipids of about 0 weight % to about 45 weight %; a final total concentration of one or more flavor compounds of about 0.01 weight % to about 6 weight %; a final total concentration of about 0.1 weight % to about 6 weight % of one or more sweetening agents; and a final total concentration of ash of about 0.15 weight % to about 1.5 weight %.

In some embodiments of any of the compositions described herein, the composition comprises about 0.27 weight % to about 0.75 weight % κ-casein protein and about 1.23 weight % to about 3.27 weight % β-casein. In some embodiments of any of the compositions described herein, the final total concentration of one or more lipids of about 0 weight % to about 4.5 weight %.

In some embodiments of any of the compositions described herein, the one or more lipids are selected from the group consisting of: sunflower oil, coconut oil, tributyrin, mono- and di-glycerides, free fatty acids, and phospholipids. In some embodiments of any of the compositions described herein, the composition includes one of more of: a final concentration of sunflower oil of about 1 weight % to about 28 weight %; a final concentration of coconut oil of about 0.5 weight % to about 14 weight %; a final concentration of tributyrin of about 0.05 weight to about 1.0 weight %; a final total concentration of monoglycerides and diglycerides of about 0.08 weight % to about 1.2 weight %; a final total concentration of free fatty acids of about 0.02 weight % to about 0.28 weight %; and a final total concentration of phospholipids of about 0.02 weight % to about 0.3 weight percent. In some embodiments of any of the compositions described herein, the free fatty acids comprise at least one fatty acid selected from the group of: butyric acid, caproic acid, caprylic acid, and capric acid. In some embodiments of any of the compositions described herein, the phospholipids are soy lecithin phospholipids, sunflower lecithin phospholipids, cotton lecithin phospholipids, or rapeseed lecithin phospholipids. In some embodiments of any of the compositions described herein, the monoglycerides and diglycerides are plant-derived monoglycerides and diglycerides, or are bacteria-derived monoglycerides and diglycerides.

In some embodiments of any of the compositions described herein, the flavor compounds include at least one flavor compound selected from the group consisting of: δ-decalactone, ethyl butyrate, 2-furyl methyl ketone, 2,3-pentanedione, γ-undecalactone, and δ-undecalactone. In some embodiments of any of the compositions described herein, the one or more sweetening agents is a saccharide. In some embodiments of any of the compositions described herein, the saccharide is selected from the group consisting of: glucose, mannose, maltose, fructose, galactose, lactose, sucrose, monatin, and tagatose. In some embodiments of any of the compositions described herein, the one or more sweetening agents is an artificial sweetener. In some embodiments of any of the compositions described herein, the artificial sweetener is selected from the group of: stevia, aspartame, cyclamate, saccharin, sucralose, mogrosides, brazzein, curculin, erythritol, glycyrrhizin, inulin, isomalt, lacitol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000.

In some embodiments of any of the compositions described herein, the ash includes one or more of: calcium, phosphorus, potassium, sodium, citrate, and chloride. In some embodiments of any of the compositions described herein, the ash comprises one or more (e.g., one, two, or three) of $CaCl_2$), $KH_2PO_4$, and $Na_3$ citrate. In some embodiments of any of the compositions described herein, the $CaCl_2$) has a final concentration of about 0.05 g/L to about 0.2 g/L; the $KH_2PO_4$ has a final concentration of about 0.2 g/L to about 0.4 g/L; and the $Na_3$ citrate has a final concentration of about 0.1 g/L to about 0.3 g/L.

In some embodiments of any of the compositions described herein, the κ-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In some embodiments of any of the compositions described herein, the β-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein.

In some embodiments of any of the compositions described herein, the composition further includes: a final concentration of α-lactalbumin protein of about 0.4 g/L weight % to about 2.5 weight %; and/or a final concentration of β-lactoglobulin protein of about 2.5 weight % to about 4.5 weight %. In some embodiments of any of the methods described herein, the α-lactalbumin protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. In some embodiments of any of the compositions described herein, the β-lactoglobulin protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein.

In some embodiments of any of the compositions described herein, the composition further includes: a final concentration of α-S1-casein protein of about 11 weight % to about 16 weight %; and/or a final concentration of α-S2-casein protein of about 2 weight % to about 5 weight %. In some embodiments of any of the compositions described herein, the α-S1-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein; and/or the α-S2-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein.

In some embodiments of any of the compositions described herein, the composition further includes one or more of: serum albumin, lactoferrin, and transferrin. In some embodiments of any of the compositions described herein, the serum albumin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin; the lactoferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin; and/or the transferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein.

Some embodiments of any of the compositions described herein, further include one or more color balancing agents. In some embodiments of any of the compositions described herein, the one or more color balancing agents is β-carotene or annatto. In some embodiments of any of the compositions described herein, the composition has a pH of about 6.2 to about 7.2 (e.g., about 6.2 to about 6.8).

Also provided are compositions including: a mammalian-produced milk or a processed mammal-produced milk; and one or both of a κ-casein protein that is unglycosylated or has an non-mammalian glycosylation pattern, and a β-casein protein that is unglycosylated or has an non-mammalian glycosylation pattern. In some embodiments of these methods, the final concentration of the κ-casein protein that is unglycosylated or has a non-mammalian glycosylation pattern in the composition is 0.02 weight % to about 3.0 weight %. In some embodiments of these methods, the final concentration of the β-casein protein that is unglycosylated or has a non-mammalian glycosylation pattern in the composition is 0.02 weight % to about 3.0 weight %. In some embodiments of these methods, the final concentration of the κ-casein protein that is unglycosylated and/or has a non-mammalian glycosylation pattern in the composition is about 0.02 weight % to about 0.6 weight %; and the final concentration of the β-casein that is unglycosylated and/or has a non-mammalian glycosylation pattern in the composition is about 0.02 weight % to about 2.5 weight %.

Also provided are powder compositions that include: a final concentration of κ-casein protein of about 3.6 weight % to about 5.4 weight %; a final concentration of β-casein protein of about 16.3 weight % to about 24.5 weight %; a final concentration of a sweetening agent of about 35 weight % to about 40 weight %; a final concentration of one or more lipids of about 25 weight % to about 30 weight %; a final concentration of ash of about 5 weight % to about 7 weight %; and a final concentration of water of about 2 weight % to about 5 weight %, where the κ-casein protein is an unglycosylated and/or has a non-mammalian glycosylation pattern, and/or the β-casein protein is an unglycosylated and/or has a non-mammalian glycosylation pattern.

Also provided are nucleic acids that include: a promoter; a sequence encoding a signal sequence; a sequence encoding a milk protein; and a yeast termination sequence, where the promoter is operably linked to the signal sequence, the signal sequence is operably linked to the sequence encoding the milk protein, and the terminal sequence is operably linked to the sequence encoding the milk protein. In some embodiments of these nucleic acids, the promoter is a constitutive promoter. In some embodiments of these nucleic acids, the promoter is an inducible promoter. In some embodiments of these nucleic acids, the signal sequence is a signal sequence from the encoded milk protein or a different milk protein, or is a signal sequence from a yeast mating factor. In some embodiments of these nucleic acids, the encoded milk protein is selected from the group consisting of: β-casein, κ-casein, α-S1-casein, α-S2-casein, α-lactalbumin, β-lactoglobulin, lactoferrin, or transferrin. In some embodiments of these nucleic acids, the nucleic comprises a bacterial origin of replication. In some embodiments of these nucleic acids, the nucleic acid further includes a selection marker. In some embodiments of these nucleic acids, the selection marker is an antibiotic resistance gene.

Some embodiments of these nucleic acids further include: an additional promoter sequence; an additional sequence encoding a signal sequence; a sequence encoding an additional milk protein; and an additional yeast termination sequence, where the additional promoter sequence is operably linked to the additional sequence encoding a signal sequence, the sequence encoding the signal sequence is operably linked to the sequence encoding the additional milk protein, and the sequence encoding the additional milk protein is operably linked to the additional yeast terminal sequence.

Also provided are host cells that include any of the nucleic acids described herein. In some embodiments of these host cells, the host cell is a yeast strain (e.g., a *Kluyveromyces* sp., *Pichia* sp., *Saccharomyces* sp., *Tetrahymena* sp., *Yarrowia* sp., *Hansenula* sp., *Blastobotrys* sp., *Candida* sp., *Zygosaccharomyces* sp., or *Debaryomyces* sp.).

Also provided herein are methods of producing a recombinant milk protein that is unglycosylated or has a non-mammalian glycosylation pattern, the method including: culturing any of the host cells described herein in a culture medium under conditions sufficient to allow for secretion of the milk protein that is unglycosylated or has a non-mammalian glycosylation pattern; and harvesting the milk protein that is unglycosylated or has a non-mammalian glycosylation pattern from the culture medium.

Also provided are methods of producing a micelle including a β-casein that is unglycosylated or has a non-mammalian glycosylation pattern and a κ-casein that is unglycosylated or has a non-mammalian glycosylation pattern, that include: culturing any of the host cells provided herein in a culture medium under conditions sufficient to allow for release of the micelle from the host cell, where the host cell includes nucleic acid including a sequence that encodes a β-casein and a sequence that encodes a κ-casein.

Also provided are methods of supplementing a mammal-produced milk that include: providing a mammalian-produced milk or a processed mammalian-produced milk; and mixing into the milk at least one of: a β-casein protein that is unglycosylated or has a non-mammalian glycosylation pattern; a κ-casein protein that is unglycosylated or has a non-mammalian glycosylation pattern; and a micelle including a β-casein protein that is unglycosylated or has a non-mammalian glycosylation pattern, and a κ-casein protein that is unglycosylated or has a non-mammalian glycosylation pattern.

Also provided are methods of producing a composition that include: sonicating a liquid including a protein mixture comprising β-casein protein and casein κ protein, or comprising micelles comprising β-casein protein and κ-casein protein; mixing ash into the liquid; adding to the liquid a mixture of one or more lipids, one or more flavor compounds, and one or more color balancing agents, and sonicating the liquid; and adding to the liquid one or more sweetening agents, thereby producing the composition. In some embodiments of these methods, the β-casein protein is unglycosylated or has a non-mammalian glycosylation pattern, and/or the κ-casein protein is unglycosylated or has a non-mammalian glycosylation pattern. In some embodiments of these methods, the ash includes one or more of: calcium, phosphorus, potassium, sodium, citrate, and chloride. In some embodiments of these methods, the ash added includes one or more (e.g., one, two, or three) of $CaCl_2$), $KH_2PO_4$, and $Na_3$ citrate. In some embodiments of these methods, the one or more lipids comprises at least one of: sunflower oil, coconut oil, tributyrin, mono- and di-glycerides, free fatty acids, and phospholipids. In some embodiments of these methods, the free fatty acids comprise at least one fatty acid selected from the group of: butyric acid, caproic acid, caprylic acid, and capric acid. In some embodiments of these methods, the phospholipids are soy lecithin phospholipids, sunflower lecithin phospholipids, cotton lecithin phospholipids, or rapeseed lecithin phospholipids. In some embodiments of these methods, the monoglycerides and diglycerides are plant-derived monoglycerides and diglycerides, or are bacteria-derived monoglycerides and diglycerides. In some embodiments of these methods, the flavor compounds include at least one flavor compound selected from the group consisting of: 6-decalactone, ethyl butyrate, 2-furyl methyl ketone, 2,3-pentanedione, γ-undecalactone, and 6-undecalactone. In some embodiments of these methods, the one or more coloring balancing agent is β-carotene or annatto. In some embodiments of these methods, the one or more sweetening agents is a saccharide. In some embodiments of these methods, the saccharide is selected from the group consisting of: glucose, mannose, maltose, fructose, galactose, lactose, sucrose, monatin, and tagatose. In some embodiments of these methods, the one or more sweetening agents is an artificial sweetener. In some embodiments of these methods, the artificial sweetener is selected from the group consisting of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame sodium cyclamate, dulcin, glucin, neohesperidin dihyrdochalcone, neotame, and P-4000. In some embodiments of these methods, the pH of the liquid is between about 6.2 and about 7.4 (e.g., about 6.4 to about 6.8). In some embodiments of these methods, the β-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein; and/or the κ-casein protein is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In some embodiments of these methods, the protein mixture further includes one or more proteins selected from the group of: α-lactalbumin, β-lactoglobulin, α-S1-casein, α-S2-casein, lactoferrin, transferrin, and serum albumin.

Also provided is a composition produced by any of the methods described herein.

Also provided is a method of making butter, cheese, caseinate, or yogurt that include: providing any of the compositions described herein; and producing the butter, cheese, caseinate, or yogurt using any of the compositions described herein as a starting material.

Also provided are kits that include: (a) a mixture of one or more milk proteins, one or more fats, and one or flavor compounds; and (b) a mixture of ash and at least one sweetening agent. In some embodiments of these kits, the one or more milk proteins are selected from the group of: β-casein, κ-casein, α-lactalbumin, β-lactoglobulin, α-S1-casein, α-S2-casein, lactoferrin, transferrin, and serum albumin. In some embodiments of these kits, the one or more milk proteins are cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth milk proteins. In some embodiments of these kits, the one or more fats are selected from the group consisting of: sunflower oil, coconut oil, tributyrin, mono- and di-glycerides, free fatty acids, and phospholipids. In some embodiments of these kits, the free fatty acids include at least one fatty acid selected from the group of: butyric acid, caproic acid, caprylic acid, and capric acid. In some embodiments of these kits, the phospholipids are soy lecithin phospholipids, sunflower lecithin phospholipids, cotton lecithin phospholipids, or rapeseed lecithin phospholipids. In some embodiments of these kits, the monoglycerides and diglycerides are plant-derived monoglycerides and diglycerides, or are bacteria-derived monoglycerides and diglycerides. In some embodiments of these kits, the flavor compounds comprise at least one flavor compound selected from the group consisting of: δ-decalactone, ethyl butyrate, 2-furyl methyl ketone, 2,3-pentanedione, γ-undecalactone, and δ-undecalactone. In some embodiments of these kits, the mixture in (a) further includes one or more color balancing agent. In some embodiments of these kits, the one or more color balancing agent is β-carotene or annatto. In some embodiments of these kits, the one or more sweetening agents is a saccharide (e.g., a saccharide selected from the group of: glucose, mannose, maltose, fructose, galactose, lactose, sucrose, monatin, and tagatose). In some embodiments of these kits, the one or more sweetening agents is an artificial sweetener (e.g., an artificial sweetener selected from the group of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000). In some embodiments of any of these kits, the ash includes one or more of: calcium, phosphorus, potassium, sodium, citrate, and chloride. In some embodiments of these kits, the ash includes one or more (e.g., one, two, or three) of $CaCl_2$), $KH_2PO_4$, and $Na_3$ citrate. Some embodiments of these kits further include instructions for making any of the compositions described herein.

Also provided are kits that include at least one of the nucleic acids described herein.

Also provided herein are dairy substitute food products including one or more isolated milk protein components, fats, carbohydrates, and ash. In some embodiments of these dairy substitute food products, the food product is non-animal derived. In some embodiments of these substitute food product, the food product includes milk, butter, cheese, caseinare, yogurt, and cream. In some embodiments of these dairy substitute food products, the isolated milk protein components include casein and whey proteins. In some embodiments of these dairy substitute food products, the casein protein further includes alpha-s1, alpha-s2, beta, and kappa-casein. In some embodiments of these dairy substitute food products, the casein protein further includes alpha-s1, beta, and kappa. In some embodiments of these dairy substitute food products, the casein protein further includes components for micelle formation. In some embodiments of these dairy substitute food products, the casein protein exhibits curdling properties at pH 4.0-6.0. In some embodiments of these dairy substitute food products, the casein protein is at least or equal to 2.5% (w/v) and less than or equal to 10% (w/v). In some embodiments of these dairy substitute food products, the whey protein further includes beta-lactoglobulin and alpha-lactalbumin. In some embodiments of these dairy substitute food products, the whey protein forms a polymer matrix gel. In some embodiments of these dairy substitute food products, the whey protein is at least 0.1% (w/v) and less than or equal to 1% (w/v). In some embodiments of these dairy substitute food products, the one or more milk protein components is isolated from microbes. In some embodiments of any of these dairy substitute food products, the one or more milk protein components is isolated from recombinant microbes. In some embodiments of these dairy substitute food products, the one or more milk protein components is synthesized in eukaryotic microbes. In some embodiments of these dairy substitute food products, the eukaryotic microbes include yeast. In some embodiments of these dairy substitute food products, the yeast include *Kleuyveromyces* sp., *Pichia* sp., *Saccharomyces* sp. and *Tetrahymena* sp.

In some embodiments of these substitute food products, the fats include triglycerides. In some embodiments of these dairy substitute food products, the fats comprise high-oleic oil. In some embodiments of these dairy substitute food products, the high-oleic oil further includes one or more of monounsaturates, oleic, linoleic, linolenic and saturates. In some embodiments of these dairy substitute food products, the fats comprise short chain fatty acids. In some embodiments of these dairy substitute food products, the short chain fatty acids include butanoic, hexanoic, octanoic, and decanoic acids. In some embodiments of these dairy substitute food products, one or more of the fats comprised trans-esterified fatty acids. In some embodiments of these dairy substitute food products, one or more of the fats are isolated from plants. In some embodiments of these dairy substitute food products, the plant is selected from one or more of the following: sunflower, corn, olive, soy, peanut, walnut, almond, sesame, cottonseed, canola, safflower, flax seed, palm, palm kernel, palm fruit, coconut, babassu, shea butter, mango butter, cocoa butter, wheat germ and rice bran oil. In some embodiments of these dairy substitute food products, the sugars comprise of galactose, sucrose, glucose, fructose and maltose. In some embodiments of these dairy substitute food products, the dairy substitute food product is essentially free of lactose. In some embodiments of these dairy substitute food products, the ash includes minerals. In some embodiments of these dairy substitute food products, the minerals further include one or more of the following: sodium, potassium, calcium, magnesium, phosphorus, iron, copper, zinc, chloride, manganese, selenium, iodine, retinol, carotene, vitamins, vitamin D, vitamin E, vitamin B12, thiamin and riboflavin. In some embodiments of these dairy substitute food products, the ash includes anions. In some embodiments of these dairy substitute food products, the minerals further include one or more of the following: phosphate, citrate, sulfate, carbonate, and chloride.

Also provided are methods of making a dairy substitute food product including the step of contacting one or more isolated milk protein components, interesterified fats, carbohydrates and ash. Some embodiments of these methods, further include the step of isolating one or more milk protein components is from a lower eukaryote.

Also provided are methods of altering a flavor profile of a dairy substitute product that include modulating a combination of fatty acids in a mixture including milk protein components, carbohydrates, and ash. In some embodiments of these methods, the step of modulating includes triglyceride comprising three oleic acids and short-chain triglyceride comprising butyric, one hexanoic, and one octanoic acid. In some embodiments of these methods, the step of modulating comprises increasing or decreasing one or more fatty acids comprising butyric acid, caprioc acid, caprylic acid, and capric acid. In some embodiments of these methods, the flavor profile of a dairy substitute product mimics the flavor profile of one or more dairy product. In some embodiments of these methods, the flavor profile of one or more dairy food product includes bovine milk, goat milk, soy milk, almond milk and coconut milk. In some embodiments of these methods, the flavor profile includes one or more sensory impressions selected from: buttery, nutty, sweet, sour, fruity, floral, bitter, woody, earthy, beany, spicy, metallic, sweet, musty, oily and vinegary.

Disclosed herein are methods and compositions to produce dairy substitutes. In some embodiments, methods and compositions are provided for a dairy substitute food product comprising one or more isolated milk protein components, fats, carbohydrates and ash. In certain embodiments, methods and compositions are provided for dairy substitute composition comprising casein protein and whey protein wherein the composition is essentially free of animal products and wherein the casein protein to whey protein are in a preferred (w/v) ratio. In certain other embodiments, methods are provided to modulate a flavor profile of a dairy substitute food product comprising modulating a fatty acid content in a mixture comprising milk protein components, fats, carbohydrates, and ash. Preferred steps of modulating comprises increasing or decreasing one or more fatty acids comprising butyric acid, caproic acid, caprylic acid, and capric acid. In additional embodiments, methods and compositions of the present invention provide milk protein components and fats in a desired (w/v) ratio.

In various aspects, the methods and compositions of the present invention provide for dairy substitutes that still retain their functional characteristics and organoleptic properties. In some embodiments, the core functionalities can be, but are not limited to achieving a nutritional profile similar to a conventional dairy product, and replicates one or more, if not all, of the core functionalities thereof.

In other embodiments, the core functionalities can be, but are not limited to replicating sensory characteristics that are identical or similar to the traditional dairy-based products, which include but are not limited to taste, appearance, handling and mouthfeel, desired density, structure, texture, elasticity, springiness, coagulation, binding, leavening, aeration, foaming, creaminess, and emulsification.

Preferred methods and compositions provide dairy substitute products such as milk, butter, cheese, yogurt, and cream. Provided herein are formulations for a non-dairy milk substitute comprising (3.3%) one or more isolated milk protein components, (4.0%) fats, (2.4%) carbohydrates and (0.7%) ash (w/v). Varying the fat content through modulating triglyceride levels and the fatty acid composition of the triglycerides enhances the flavor profile of the non-dairy milk substitute.

Advantages in the methods and dairy substitute compositions include reduction or removal of antibiotic residues, heavy metals, bacteria and adulterations commonly found in natural dairy products as well as reducing environmental impact.

Accordingly, certain aspects of the present invention provide animal-free dairy substitute that has desirable flavor characteristics, e.g., replicates dairy flavors, minimizes foodborne pathogens and has a lower environmental impact, while retaining the downstream applications of dairy milk.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, dairy processing, biochemistry, enzymology, molecular and cellular biology, microbiology, genetics and protein and nucleic acid chemistry and hybridization described herein are those well-known and commonly used in the art.

Methods and materials are described herein for use in the present invention; other, suitable methods and materials known in the art can also be used. The materials, methods, and examples are illustrative only and not intended to be limiting.

All publications, patents, patent applications, sequences, database entries, and other references mentioned herein are incorporated by reference to the same extent as if each individual publication, patent, patent application, sequence, database entry, or other reference was specifically and individually indicated to be incorporated by reference. In case of conflict, the present specification, including definitions, will control.

Other features and advantages of the invention will be apparent from the following detailed description and figures, and from the claims.

The terminology and description used herein is for the purpose of describing particular embodiments only and is not intended to limit the invention. As used herein, the singular forms "a," "an," and "the" can be intended to include the plural forms as well, unless the context clearly indicates otherwise. The terms "including," "includes," "having," "has," "with," or variants thereof are intended to be inclusive in a manner similar to the term "comprising".

An "isolated" RNA, DNA or a mixed polymer is one which is substantially separated from other cellular components that naturally accompany the native polynucleotide in its natural host cell, e.g., ribosomes, polymerases, and genomic sequences with which it is naturally associated.

As used herein, an "isolated" organic molecule (e.g., a fatty acid or a SCFA) is one which is substantially separated from the cellular components (membrane lipids, chromosomes, proteins) of the host cell from which it originated. As used herein, the term "isolated" with respect to protein indicates that the preparation of protein is at least 60% pure, e.g., greater than 65%, 70%, 75%, 80%, 85%, 90%, 95%, or 99% pure. The term does not require that the biomolecule has been separated from all other chemicals, although certain isolated biomolecules may be purified to near homogeneity.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, or double-stranded, or circular.

The term "SCFA" is abbreviated for short-chain fatty acids, the term "HOSO" is abbreviated for high oleic sunflower oil, "SCTG" is abbreviated for short-chain triglycerides.

The term "milk protein component" refers to proteins or protein equivalents and variants found in milk such as casein, whey or the combination of casein and whey, including their subunits, which are derived from various sources and as further defined herein.

The term "milk protein" means a protein that is found in a mammal-produced milk or a protein having a sequence that is at least 80% identical (e.g., at least 85%, at least 90%, at least 95%, at least 96%, at least 97%, at least 98%, or at least 99% identical) to the sequence of a protein that is found in a mammal-produced milk. Non-limiting examples of milk proteins include: β-casein, κ-casein, α-S1-casein, α-S2-casein, α-lactalbumin, β-lactoglobulin, lactoferrin, transferrin, and serum albumin. Additional milk proteins are known in the art.

The term "casein protein" is art-known and represents a family of proteins that is present in mammal-produced milk and is capable of self-assembling with other proteins in the family to form micelles and/or precipitate out of an aqueous solution at an acidic pH. Non-limiting examples of casein proteins include: β-casein, κ-casein, α-S1-casein, and α-S2-casein. Non-limiting examples of sequences for casein protein from different mammals are provided herein. Additional sequences for other mammalian caseins are known in the art.

The term "mammal-produced milk" is art known and means a milk produced by a mammal.

The term "processed mammal-produced milk" means a mammal-produced milk that is processed using one or more steps known in the dairy industry (e.g., homogenization, pasteurization, irradiation, or supplementation).

The term "mammal-derived component" means a molecule or compound (e.g., a protein, a lipid, or a nucleic acid) obtained from the body of a mammal or a molecule obtained from a fluid or solid produced by a mammal.

The term "component of milk" or "milk component" is a molecule, compound, element, or an ion present in a mammal-produced milk.

The term "non-mammalian glycosylation pattern" means one of a difference in one or more location(s) of glycosylation in a protein, and/or a difference in the amount of and/or type of glycosylation at one or more location(s) in a protein produced and posttranslational modified in a non-mammalian cell (e.g., a yeast cell, an insect cell, or a bacterial cell) as compared to a reference protein (e.g., the same protein produced and post-translationally modified in a mammalian cell, e.g., a CHO cell, a MEK cell, or a mammalian udder cell).

The term "lipids" means one or more molecules (e.g., biomolecules) that include a fatty acyl group (e.g., saturated or unsaturated acyl chains). For example, the term lipids includes oils, phospholipids, free fatty acids, phospholipids, monoglycerides, diglycerides, and triglycerides. Non-limiting examples of lipids are described herein. Additional examples of lipids are known in the art.

The term "plant-derived lipid" means a lipid obtained from and/or produced by a plant (e.g., monocot or dicot).

The term "sweetening agent" means a saccharide (e.g., a monosaccharide, a disaccharide, or a polysaccharide) or an artificial sweetener (e.g., a small molecule artificial sweetener or a protein artificial sweetener) that, when added to a composition, makes the composition taste sweet when ingested by a mammal, such as a human. Non-limiting examples of sweetening agents are described herein. Additional examples of sweetening agents are known in the art.

The term "ash" is an art-known term and represents one or more ions, elements, minerals, and/or compounds that can be found in a mammal-produced milk. Non-limiting ions, elements, minerals, and compounds that are found in a mammal-produced milk are described herein. Additional ions, elements, minerals, and compounds that are found in a mammal-produced milk are also known in the art.

The term "color balancing agent" or "coloring agent" means an agent added to a composition to modulate the color of the composition, e.g., to make the color of the composition appear more similar to a mammalian-produced milk. Non-limiting examples of color balancing agents or coloring agents include β-carotene and annatto. Other examples of coloring balancing agents are known in the art. A color balancing agent or a coloring agent can be produced by or obtained from a plant.

The term "micelle" means is a generally (or roughly) spherical supramolecular structure that exists as a dispersion within a composition. A micelle can have, e.g., a surface that is composed of a charged outer layer. A micelle can encapsulate one or more biomolecules. For example, a micelle can encapsulate two or more proteins (e.g., a β-casein protein and a κ-casein protein). A micelle can have diameter of between about 10 nm and about 350 nm. Additional aspects and characteristics of micelles are known in the art.

The phrase "concentration of a component in a mammal-produced milk" means the concentration of a component in the milk produced by a mammal or the mean concentration of a component in milk produced by a population of mammals of the same species.

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion: The removal of one or more nucleotides from a nucleic acid molecule or one or more amino acids from a protein, the regions on either side being joined together.

Knock-Out: A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "synthetic milk substitute" refers to a composition that resembles, is similar to, is to equivalent to, or is nearly identical to a dairy milk.

The term "flavor" refers to the taste and/or the aroma of a food or drink.

The term "recombinant" is an art known-term. When referring to a nucleic acid (e.g., a gene), the term "recombinant" can be used, e.g., to describe a nucleic acid that has been removed from its naturally occurring environment, a nucleic acid that is not associated with all or a portion of a nucleic acid abutting or proximal to the nucleic acid when it is found in nature, a nucleic acid that is operatively linked to a nucleic acid which it is not linked to in nature, or a nucleic acid that does not occur in nature. The term "recombinant" can be used, e.g., to describe cloned DNA isolates, or a nucleic acid including a chemically-synthesized nucleotide analog. When "recombinant" is used to describe a protein, it can refer to, e.g., a protein that is produced in a cell of a different species or type, as compared to the species or type of cell that produces the protein in nature.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion, or a point mutation introduced artificially, e.g., by human intervention. A "recombinant nucleic acid" also includes a nucleic acid integrated into a host cell chromosome at a heterologous site and a nucleic acid construct present as an episome.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap, or Bestfit, which are programs in Wisconsin Package Version 10.0, Genetics Computer Group (GCG), Madison, Wis. FASTA provides alignments and percent sequence identity of the regions of the best overlap between the query and search sequences. See, e.g., Pearson, *Methods Enzymol.* 183:63-98, 1990 (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410, 1990; Gish and States, *Nature Genet.* 3:266-272, 1993; Madden et al., *Meth. Enzymol.* 266:131-141, 1996; Altschul et al., *Nucleic Acids Res.* 25:3389-3402, 1997; Zhang and Madden, *Genome Res.* 7:649-656, 1997, especially blastp or tblastn (Altschul et al., *Nucleic Acids Res.* 25:3389-3402, 1997.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y., page 9.51, 1989, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Examples of modified nucleotides are described in Malyshev et al., *Nature* 509:385-388, 2014; and Li et al., *J. Am. Chem. Soc.* 136:826-829, 2014. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted, or changed compared to a reference nucleic acid sequence. A single alteration may be made at a locus (a point mutation) or multiple nucleotides may be inserted, deleted, or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique* 1:11-15, 1989, and Caldwell and Joyce, *PCR Methods Applic.* 2:28-33, 1992); and "oligonucleotide-directed mutagenesis" (a process which enables the generation of site-specific mutations in any cloned DNA segment of interest; see, e.g., Reidhaar-Olson and Sauer, *Science* 241: 53-57, 1988).

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

Promoters useful for expressing the recombinant genes described herein include both constitutive and inducible/repressible promoters. Examples of inducible/repressible promoters include galactose-inducible promoters (e.g., PLAC4-PBI). Where multiple recombinant genes are expressed in an engineered yeast, the different genes can be controlled by different promoters or by identical promoters in separate operons, or the expression of two or more genes may be controlled by a single promoter as part of an operon.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events, and translation of nucleic acid sequences. Expression control sequences include appropriate transcription initiation, termination, promoter and enhancer sequences; efficient RNA processing signals, such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", "transfection", "transfecting," and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

The term "yeast and filamentous fungi" include, but are not limited to any *Kluyveromyces* sp., such as *Kluyveromyces lactis, Kluyveromyces marxianus, Saccharomyces* sp., such as *Saccharomyces cerevisiae, Pichia* sp., such as *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Hansenula polymorpha, Candida albicans*, any *Aspergillus* sp., such as *Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens*, and *Neurospora crassa*.

As used herein, the term "predominantly" or variations thereof will be understood to mean, for instance, a) in the context of fats the amount of a particular fatty acid composition relative to the total amount of fatty acid composition; b) in the context of protein the amount of a particular protein composition (e.g., β-casein) relative to the total amount of protein composition (e.g., α-, β-, and κ-casein).

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

The phrase "essentially free of" is used to indicate the indicated component, if present, is present in an amount that does not contribute, or contributes only in a de minimus fashion, to the properties of the composition. In various embodiments, where a composition is essentially free of a particular component, the component is present in less than a functional amount. In various embodiments, the component may be present in trace amounts. Particular limits will vary depending on the nature of the component, but may be, for example, selected from less than 10% by weight, less than 9% by weight, less than 8% by weight, less than 7% by weight, less than 6% by weight, less than 5% by weight, less than 4% by weight, less than 3% by weight, less than 2% by weight, less than 1% by weight, or less than 0.5% by weight.

As used herein, the term "essentially free of" a particular carbohydrate, such as lactose is used to indicate that the food composition is substantially devoid of carbohydrate residues. Expressed in terms of purity, essentially free means that the amount of carbohydrate residues do not exceed 10%, and preferably is below 5%, more preferably below 1%, most preferably below 0.5%, wherein the percentages are by weight or by mole percent. Thus, substantially all of the carbohydrate residues in a food composition according to the present invention are free of, for example, lactose.

Unless indicated otherwise, percentage (%) of ingredients refer to total % by weight.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

DETAILED DESCRIPTION OF THE INVENTION

Figure 1:
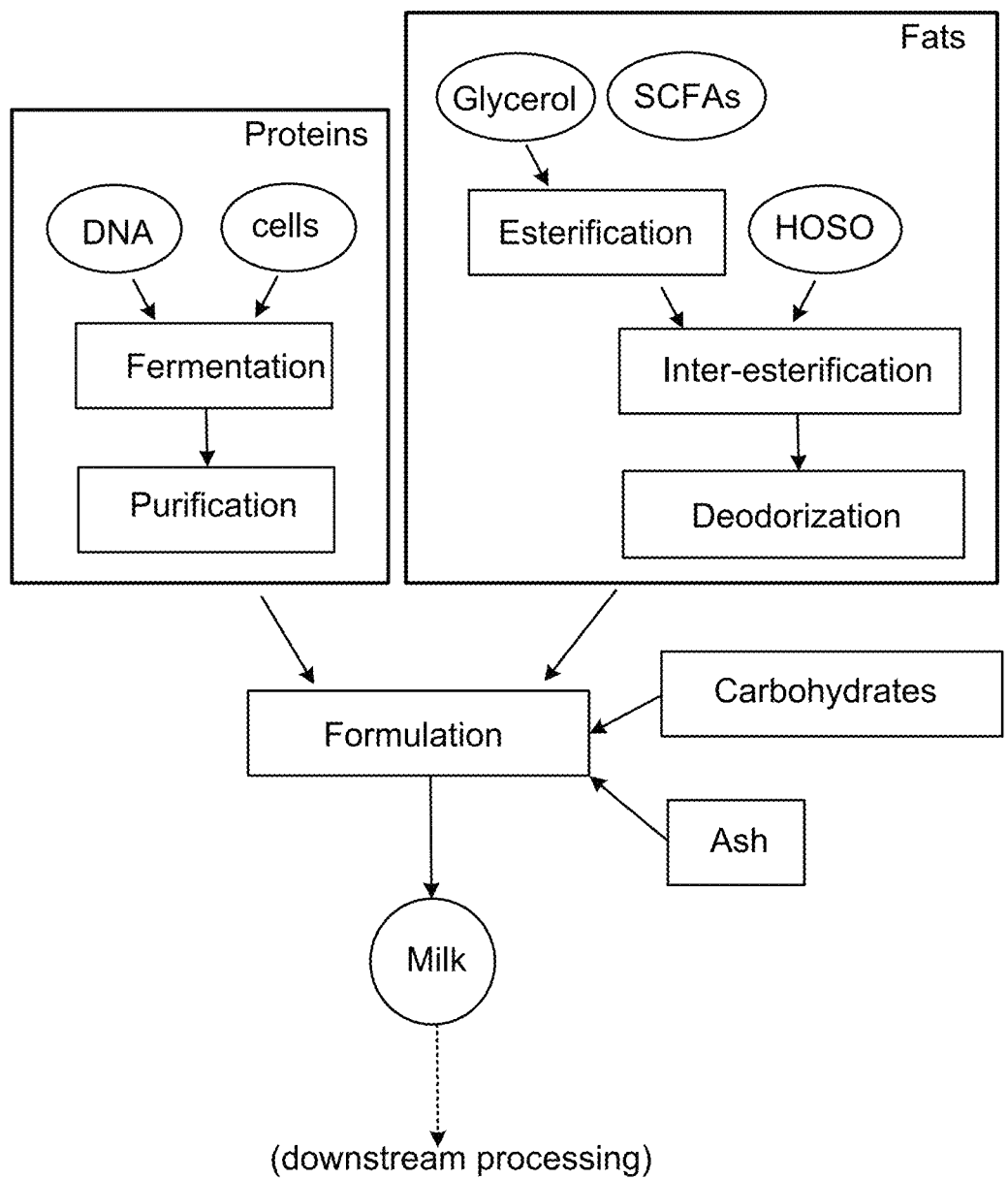
FIG. 1 represents a flow diagram representative of an exemplary process to produce synthetic milk substitute.

The invention is based on the discovery that only a few components present in a mammal-produced milk provide for the texture and taste of a mammal-produced milk, and the development of compositions that have a similar taste, aroma, and mouth feel as compared to a mammal-produced milk. In view of this discovery, provided herein are such compositions, methods of making the compositions, and kits including these compositions and mixtures useful for making these compositions.

The compositions provided herein provide for compositions that have a similar taste, mouth feel, aroma, and nutritional value as compared to a mammal-produced milk, but lack one or more of the components of a mammal-produced milk that may be considered to be undesirable (e.g., allergens, lactose, antibiotics, hormones (e.g., stress hormones and/or growth hormones), heavy metals, bacteria (e.g., *E. coli*), viruses, and prions). The compositions provided herein also have an improved shelf-life as compared to mammal-produced milk, and can have an improved aroma profile as compared to a mammal-produced milk.

Also provided herein are methods and compositions for dairy substitute food product comprising one or more isolated milk protein components, fats, carbohydrates and ash. In certain aspects the methods and compositions comprise milk or milk-like protein equivalents. Preferably, the milk protein component is essentially free of impurities. In some embodiments, the milk protein component comprises microbially derived or produced casein, whey or a combination thereof. More preferably, a method is provided to introduce an engineered nucleic acid sequence encoding one or more milk protein components. Even more preferably, the milk protein component is not animal derived. In other preferred embodiments, the recombinant milk protein component is modified to express the same phosphate groups or lack phosphate groups and/or carbohydrate groups attached to the casein proteins. By having recombinant β-casein and κ-casein having the same phosphate groups as the same proteins present in a mammal-produced milk, the recombinant β-casein and the recombinant κ-casein are able to form micelles.

The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y., 1989; Ausubel et al., Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

Exemplary materials and methods for use in any of the methods and compositions are described below, and can be used in any combination. Additional materials and methods that can be used in any of the methods and compositions are also known in the art.

Casein Proteins

Casein proteins include a variety of different proteins found in mammalian milk. Non-limiting examples of casein proteins include: β-casein, κ-casein, α-S2-casein, and α-S1-casein.

As an alternative to obtaining casein proteins from mammals or mammal-produced milk for us in dairy product manufacture, the present invention provides methods and composition for the production of recombinant casein proteins. In various aspects of the present invention, methods and compositions are provided for non-animal derived casein that has similar solubility and similar turbidity, and heat stability suitable for incorporation into various food products. Preferably, the non-animal derived casein has excellent solubility similar turbidity and heat stability suitable for incorporation into various dairy substitute products. Additionally, further characterization of the protein includes less or no aggregation or precipitation during such heat treatment and is suitable for procedures such as pasteurization, concentration, etc.

Difference in function of the non-animal derived casein in milk can be characterized in terms of viscosity of the liquid; the ability of the proteins to withstand heat; the ability of the proteins to form micelles; and the ability of the proteins to hold different minerals & vitamins.

β-Casein

The primary structure of human β-casein as determined by Greenberg et al. (*J. Biol. Chem.* 259:5132-5138, 1984) was shown to be a phosphorylated protein with phosphorylation sites at specific seryl and threonyl residues located near the amino terminus. A comparison of human and bovine β-caseins showed 47% identity.

Non-limiting examples of β-casein proteins are SEQ ID Nos: 25, 27, 29, 31, 33, 35, 36, 38, 40, 42, 44, and 46. Non-limiting examples of nucleic acid sequences encoding a β-casein protein are SEQ ID NOs: 26, 28, 30, 32, 34, 37, 39, 41, 43, 45, 47, and 144. A β-casein protein can be a β-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein. Additional sequences for different β-casein proteins and nucleic acids encoding different β-casein proteins are known in the art.

A β-casein protein can also be a proteins that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype β-casein protein (e.g., SEQ ID Nos: 25, 27, 29, 31, 33, 35, 36, 38, 40, 42, 44, or 46). A nucleic acid encoding a β-casein protein can encode a protein that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype β-casein protein (e.g., SEQ ID Nos: 25, 27, 29, 31, 33, 35, 36, 38, 40, 42, 44, or 46).

Methods known for isolating β-casein from genetically engineered bacterial cells typically involve precipitating the β-casein from a supernatant derived from lysed or fractionated cells. For example, Simons, et al., *Protein Eng.* 6: 763-770 (1993), used genetically engineered *E. coli* to express bovine β-casein. The protein, which accumulated in the periplasmic spaces of the bacteria, was released into a cell suspension by osmotic shock. After centrifugation of the suspension, the β-casein in the pellet was resuspended in a cold water wash and centrifuged again. The β-casein, present in the supernatant, was precipitated by acidification with acetic acid, filtered, and further purified by HPLC. Similarly, Hansson, et al., *Protein Express. Purif.* 4:373-381, 1993, used genetically engineered *E. coli* to express β-casein. The β-casein, present in a cell lysate, was precipitated with ammonium sulfate, dissolved in ethanolamine and 6M urea, and further purified by ion-exchange chromatography. See, e.g., U.S. Pat. No. 6,121,421.

Additionally, methods for isolating recombinantly produced β-casein in yeast that are simpler and more effective than known techniques are also known. Choi et al., *J. Agric. Food Chem.* 49(4):1761-1766, 2001. Expression and purification of glycosylated bovine β-casein (L70S/P71S) in *Pichia pastoris*, resulted in the observation that the majority of bovine β-casein was not being hyperglycosylated in *P. pastoris*, and its molecular weight was estimated to be 33.6 kDa. Glycosylated bovine β-casein was normally phosphorylated to the same degree as native bovine β-casein.

K-Casein

Kappa-casein is both phosphorylated and glycosylated. The sequence of human κ-casein was determined by Brignon et al. (Fed. Eur. Biol. Soc. Lett. 188:48-54, 1985). See, e.g., U.S. Pat. No. 5,710,044.

Non-limiting examples of κ-casein proteins are SEQ ID Nos: 1, 3, 5, 7, 9, 11, 13, 15, 17, 19, 21, and 23. Non-limiting examples of nucleic acid sequences encoding a κ-casein protein are SEQ ID NOs: 2, 4, 6, 8, 10, 12, 14, 16, 18, 20, 22, 24, and 148. A κ-casein protein can be a κ-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. Additional sequences for different κ-casein proteins and nucleic acids encoding different κ-casein proteins are known in the art.

A κ-casein protein can also be a proteins that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype κ-casein protein (e.g., SEQ ID Nos: 1, 3, 5, 7, 9, 11, 13, 15, 17, 19, 21, or 23). A nucleic acid encoding a κ-casein protein can encode a protein that is at least 50% (e.g., at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5%) identical to a wildtype κ-casein protein (e.g., SEQ ID Nos: 1, 3, 5, 7, 9, 11, 13, 15, 17, 19, 21, or 23).

α-S1-Casein

Non-limiting examples of α-S1-casein proteins are SEQ ID Nos: 48, 50, 52, 54, 56, 57, 59, 61, 63, 64, 66, 68, 70, 72, 74, and 76. Non-limiting examples of nucleic acid sequences encoding an α-S1-casein protein are SEQ ID NOs: 49, 51, 53, 55, 58, 60, 62, 65, 67, 69, 71, 73, 75, 77, and 147. A α-S1-casein protein can be an α-S1-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein. Additional sequences for different α-S1-casein proteins and nucleic acids encoding different α-S1-casein proteins are known in the art.

An α-S1-casein protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S1-casein protein (e.g., SEQ ID Nos: 48, 50, 52, 54, 56, 57, 59, 61, 63, 64, 66, 68, 70, 72, 74, or 76). A nucleic acid encoding an α-S1-casein protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S1-casein protein (e.g., SEQ ID Nos: 48, 50, 52, 54, 56, 57, 59, 61, 63, 64, 66, 68, 70, 72, 74, or 76).

α-S2-Casein

Non-limiting examples of α-S2-casein proteins are SEQ ID Nos: 78, 80, 82, 84, 86, 88, and 90. Non-limiting examples of nucleic acid sequences encoding an α-S2-casein protein are SEQ ID NOs: 79, 81, 83, 85, 87, 89, 91, 145, and 146. A α-S2-casein protein can be an α-S2-casein protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein. Additional sequences for different α-S2-casein proteins and nucleic acids encoding different α-S2-casein proteins are known in the art.

An α-S2-casein protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S2-casein protein (e.g., SEQ ID Nos: 78, 80, 82, 84, 86, 88, or 90). A nucleic acid encoding an α-S2-casein protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-S2-casein protein (e.g., SEQ ID Nos: 78, 80, 82, 84, 86, 88, or 90).

Micelles Including Casein Proteins

In bovine milk, casein or casein micelles usually makes up 2.5% of the entire mixture in suspension. If sufficient casein is not present the micelles, which are very important for the optimum behavior of milk, will not form. Too much protein does not go into solution properly resulting in an undesirable mixture. The casein micelle can include water and salts—mainly calcium and phosphorous. Casein micelles are easily separated and removed by centrifugation. Separation from whey is easily done by precipitating casein with an acid to lower the pH to around 4.6.

In some embodiments, a micelle can include a β-casein protein (e.g., any of the β-casein proteins described herein) and κ-casein protein (e.g., any of the κ-casein proteins described herein). In some examples, the ratio of β-casein protein to κ-casein protein in the micelle is about 2.0:1 to about 5.5:1, 2.0:1 to about 5.0:1, 2.0:1 to about 4.5:1, about 2.0:1 to about 4.0:1, about 2.0:1 to about 3.5:1, about 2.0:1 to about 3.0:1, about 2.0:1 to about 2.5:1, about 2.5:1 to about 5.0:1, about 2.5:1 to about 4.5:1, about 2.5:1 to about 4.0:1, about 2.5:1 to about 3.5:1, about 2.5:1 to about 3.0:1, 3.0:1 to about 5.0:1, about 3.0:1 to about 4.5:1, about 3.0:1 to about 4.0:1, about 3.0:1 to about 3.5:1, about 3.5:1 to about 5.0:1, about 3.5:1 to about 4.5:1, about 3.5:1 to about 4.0:1, about 4.0:1 to about 5.0:1, about 4.0:1 to about 4.5:1, or about 4.5:1 to about 5.0:1.

In some examples, the micelle has a diameter (or a population of micelles have an average diameter) of about 20 nm to about 350 nm, about 320 nm, about 300 nm, about 280 nm, about 260 nm, about 240 nm, about 220 nm, about 200 nm, about 180 nm, about 160 nm, about 140 nm, about 120 nm, about 100 nm, about 80 nm, about 60 nm, or about 40 nm; about 40 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, about 100 nm, about 80 nm, or about 60 nm; about 60 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, or about 100 nm; about 80 nm to about 350 nm, about 340 nm, about 320 nm, about 300 nm, about 280 nm, about 260 nm, about 240 nm, about 220 nm, about 200 nm, about 180 nm, about 160 nm, about 140 nm, about 120 nm, or about 100 nm; about 100 nm to about 350 nm, about 340 nm, about 320 nm, about 300 nm, about 280 nm, about 260 nm, about 240 nm, about 220 nm, about 200 nm, about 180 nm, about 160 nm, about 140 nm, or about 120 nm; about 120 nm to about 350 nm, about 340 nm, about 320 nm, about 300 nm, about 280 nm, about 260 nm, about 240 nm, about 220 nm, about 200 nm, about 180 nm, about 160 nm, or about 140 nm; about 140 nm to about 350 nm, about 340 nm, about 320 nm, about 300 nm, about 280 nm, about 260 nm, about 240 nm, about 220 nm, about 200 nm, about 180 nm, or about 160 nm; about 160 nm to about 350 nm, about 340 nm, about 320 nm, about 300 nm, about 280 nm, about 260 nm, about 240 nm, about 220 nm, about 200 nm, or about 180 nm; about 180 nm to about 350 nm, about 340 nm, about 320 nm, about 300 nm, about 280 nm, about 260 nm, about 240 nm, about 220 nm, or about 200 nm; about 200 nm to about 350 nm, about 340 nm, about 320 nm, about 300 nm, about 280 nm, about 260 nm, about 240 nm, or about 220 nm; about 220 nm to about 350 nm, about 340 nm, about 320 nm, about 300 nm, about 280 nm, about 260 nm, or about 240 nm; about 240 nm to about 350 nm, about 340 nm, about 320 nm, about 300 nm, about 280 nm, or about 260 nm; about 260 nm to about 350 nm, about 340 nm, about 320 nm, about 300 nm, or about 280 nm; about 280 nm to about 350 nm, about 340 nm, about 320 nm, or about 300 nm; about 300 nm to about 350 nm or about 325 nm; or about 325 nm to about 350 nm.

Whey Proteins

Whey is commonly known as the by-product of cheese and is also known to be one cause for milk allergies. A typical whey composition comprises a mixture of β-lactoglobulin, α-lactalbumin, serum albumin, immunoglobulins, lactoferrin, and transferrin. Whey proteins do not contain phosphorus, and remain in solution at low pH whereas casein proteins do not. In one embodiment, a select combination of whey proteins comprising β-lactoglobulin and α-lactalbumin are used as the primary component or at least a part of the milk protein component or composition. Non-limiting examples of different whey proteins are provided below.

α-Lactalbumin

Non-limiting examples of α-lactalbumin proteins are SEQ ID Nos: 92, 94, 96, and 98. Non-limiting examples of nucleic acid sequences encoding an α-lactalbumin protein are SEQ ID NOs: 93, 95, 97, 99, and 157. An α-lactalbumin protein can be an α-lactalbumin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. Additional sequences for different α-lactalbumin proteins and nucleic acids encoding different α-lactalbumin proteins are known in the art.

An α-lactalbumin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-lactalbumin protein (e.g., SEQ ID Nos: 92, 94, 96, or 98). A nucleic acid encoding an α-lactalbumin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype α-lactalbumin protein (e.g., SEQ ID Nos: 92, 94, 96, or 98).

β-Lactoglobulin

Non-limiting examples of β-lactoglobulin proteins are SEQ ID Nos: 100, 102, 104, and 106. Non-limiting examples of nucleic acid sequences encoding a β-lactoglobulin protein are SEQ ID NOs: 101, 103, 105, 107, and 143. A β-lactoglobulin protein can be a β-lactoglobulin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein. Additional sequences for different β-lactoglobulin proteins and nucleic acids encoding different β-lactoglobulin proteins are known in the art.

A β-lactoglobulin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype β-lactoglobulin protein (e.g., SEQ ID Nos: 100, 102, 104, or 106). A nucleic acid encoding a β-lactoglobulin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype β-lactoglobulin protein (e.g., SEQ ID Nos: 100, 102, 104, or 106).

Lactoferrin

Non-limiting examples of lactoferrin proteins are SEQ ID Nos: 108, 110, 112, and 114. Non-limiting examples of nucleic acid sequences encoding a lactoferrin protein are SEQ ID NOs: 109, 111, 113, and 115. A lactoferrin protein can be a lactoferrin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin protein. Additional sequences for different lactoferrin proteins and nucleic acids encoding different lactoferrin proteins are known in the art.

A lactoferrin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype lactoferrin protein (e.g., SEQ ID Nos: 108, 110, 112, or 114). A nucleic acid encoding a lactoferrin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype lactoferrin protein (e.g., SEQ ID Nos: 108, 110, 112, or 114).

Transferrin

Non-limiting examples of transferrin proteins are SEQ ID Nos: 116 and 118. Non-limiting examples of nucleic acid sequences encoding a transferrin protein are SEQ ID NOs: 117 and 119. A transferrin protein can be a transferrin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein. Additional sequences for different transferrin proteins and nucleic acids encoding different transferrin proteins are known in the art.

A transferrin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype transferrin protein (e.g., SEQ ID Nos: 116 or 118). A nucleic acid encoding a transferrin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype transferrin protein (e.g., SEQ ID Nos: 116 or 118).

Serum Albumin

Non-limiting examples of serum albumin proteins are SEQ ID Nos: 120, 122, 124, and 126. Non-limiting examples of nucleic acid sequences encoding a serum albumin protein are SEQ ID NOs: 121, 123, 125, and 127. A serum albumin protein can be a serum albumin protein from any mammalian species, e.g., a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin protein. Additional sequences for different serum albumin proteins and nucleic acids encoding different serum albumin proteins are known in the art.

A serum albumin protein can also be a proteins that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype serum albumin protein (e.g., SEQ ID Nos: 20, 122, 124, or 126). A nucleic acid encoding a serum albumin protein can encode a protein that is at least 80% (e.g., at least 85%, at least 90%, at least 91%, at least 92%, at least 93%, at least 94%, at least 95%, at least 96%, at least 97%, at least 98%, at least 99%, or at least 99.5%) identical to a wildtype serum albumin protein (e.g., SEQ ID Nos: 20, 122, 124, or 126).

Lipids in Mammal-Produced Milk

Milk fat contains approximately 400 different fatty acids, which makes it the most complex of all natural fats. The milk fatty acids are derived almost equally from two sources, the feed and the microbial activity in the rumen of the cow and the lipids in bovine milk are mainly present in globules as an oil-in-water emulsion. Fat is present in all natural dairy products and is critical for sensory characteristics such as flavor, mouthfeel and consistency. In addition, fats provide nutrition and health benefits. The milk fat consists mainly of triglycerides, approximately 98%, while other milk lipids are diacylglycerol (about 2% of the lipid fraction), cholesterol (less than 0.5%), phospholipids (about 1%) and free fatty acids (FFA) (about 0.1%) Jensen R G, Newburg D S. Bovine milk lipids, Handbook of milk composition. Jensen R G London: Academic Press; 1995. 543-75. In addition, there are trace amounts of ether lipids, hydrocarbons, fat-soluble vitamins, flavor compounds and compounds introduced by the feed (Lindmark Mansson H., Food & Nutrition Research 2008. DOI: 10.3402/fnr.v52i0.1821)

Milk fat triglycerides are synthesized from more than 400 different fatty acids, which makes milk fat the most complex of all natural fats. Nearly all fatty acids in milk are present in trace quantities and only about 15 acids at the 1% level or higher. Many factors are associated with the variations in the amount and fatty acid composition of bovine milk lipids. They may be of animal origin, i.e. related to genetics (breed and selection), stage of lactation, mastitis and ruminal fermentation, or they may be feed-related factors, i.e. related to fibre and energy intake, dietary fats, and seasonal and regional effects. The fatty acids in the milk fat are arranged in the triglycerides in accordance with a pattern that appears to be universal among ruminants. The percent unsaturated fatty acids (e.g., oleic and linolenic) in goats do not differ from the average found for cow's milk. A major difference between the milk fat of the goat and the cow is the percentage distribution among specific short chain fatty acids. Goats have an appreciably higher proportion of capric, caprylic and caproic acids. The high amounts of these specific fatty acids are responsible for the characteristic flavor and odor associated with goat's milk. John C. Bruhn, FST, UC Davis, Davis, CA 95616-8598; Seewww.drinc.uc-davis.edu/goat1.htm; www.ncbi.nlm.nih.gov/pmc/articles/PMC2596709/#_ffn_sectitle; Food Nutr Res. 2008; 52: 10.3402/fnr.v52i0.1821. Published online Jun. 11, 2008. doi: 10.3402/fnr. v52i0.1821.

The milk fatty acids are derived almost equally from two sources, the feed and the microbial activity in the rumen of the cow. The fatty acid synthesizing system in the mammary gland of the cow produces fatty acids with even number of carbons of 4-16 carbons in length and accounts for approximately 60 and 45% of the fatty acids on a molar and weight basis, respectively. This de novo synthesis in the mammary gland is of the 4:0-14:0 acids together with about half of the 16:0 from acetate and p-hydroxybutyrate. Acetate and butyric acid are generated in the rumen by fermentation of feed components. The butyric acid is converted to p-hydroxybutyrate during absorption through the rumen epithelium.

Medium- and long-chain fatty acids, but mainly 18:0, may be desaturated in the mammary gland to form the corresponding monosaturated acids.

Fatty acids are not randomly esterified at the three positions of the triacylglycerol molecule (MacGibbon AHK, Taylor M W. Composition and structure of bovine milk lipidsAdvanced dairy chemistry. Fox PFMcSweeney PLH-New York: Springer; 2006. 1-42). The short-chain acids butyric (4:0) and caproic (6:0) are esterified almost entirely at sn-3. Medium-chain fatty acids (8:0-14:0) as well as 16:0 are preferentially esterified at positions sn-1 and sn-2. Stearic acid (18:0) is selectively placed at position sn-1, whereas oleic acid (18:1) shows preference for positions sn-1 and sn-3 (Lindmark 2008).

Milk replacers with a fat component formulated to selected fatty acid profiles exist, however, such triglycerides are not interesterified into long-chain monounsaturated fatty acid triglycerides such as found in vegetable oils. U.S. Patent Appl. No. 20140147548 discloses milk replacers for young animals with by adding medium chain triglyceride, specifically caproic, caprylic, capric and lauric fatty acid or a combination thereof.

Lipids in the Present Compositions

The lipids in any of the compositions or used in any of the methods described herein can include: one or more fats, one or more oils, one or more monoglycerides, diglycerides, and/or triglycerides, one or more free fatty acids, and one or more phospholipids. Exemplary oils, monoglycerides, diglycerides, free fatty acids, and phospholipids are described below. Additional examples of fats, oils, monoglycerides, diglycerides, triglycerides, free fatty acids, and phospholipids are known in the art.

Oils

Oils used in the present compositions or methods can include, e.g., plant-derived oils. Non-limiting examples of plant-based oils include sunflower oil, coconut oil, peanut oil, corn oil, cottonseed oil, olive oil, palm oil, rapeseed oil, safflower oil, sesame oil, soybean oil, almond oil, beech nut oil, brazil nut oil, cashew oil, hazelnut oil, macadamia nut oil, mongongo nut oil, pecan oil, pine nut oil, pistachio nut oil, walnut oil, and avocado oil.

Monoglycerides and Diglycerides

Monoglycerides and diglycerides that can be used in the present invention can be plant-derived monoglycerides and diglycerides. For example, monoglycerides and diglycerides can be derived from sunflowers, coconuts, peanuts, cottonseed, olives, palm, rapeseed, safflowers, sesame seed, soybeans, almonds, beech nuts, brazil nuts, cashews, hazelnuts, macadameia nuts, mongongo nuts, pecans, pine nuts, pistachios, walnuts, and avocados. The monoglycerides and diglycerides can include the acyl chain of any of the free fatty acids listed herein. Additional examples of monoglycerides and diglycerides are known in the art.

Free Fatty Acids

The compositions described herein can include and the methods described herein can include the use of one or more free fatty acids. Non-limiting examples of free fatty acids include butyric acid, caproic acid, caprylic acid, and capric acid. Additional examples of fatty acids include lauric acid, myristic acid, palmitic acid, stearic acid, arachidic acid, behenic acid, lignoceric acid, cerotic acid, myristoleic acid, pamitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, omega-3 fatty acids, and omega-6 fatty acids. In some examples, the free fatty acid is saturated. In some examples, the free fatty acid is unsaturated. In some embodiments, the free fatty acids are not derived from or produced by a mammal. Additional examples of free fatty acids are known in the art.

Phospholipids

The compositions described herein and the methods described herein can include the use of one or more phospholipids. Non-limiting examples of phospholipids include lecithin phospholipids (e.g., soy lecithin phospholipids, sunflower lecithin phospholipids, cotton lecithin phospholipids, rapeseed lecithin phospholipids. rice bran lecithin phospholipids, and corn lecithin phospholipids). In some embodiments, the phospholipids are not derived from or produced by a mammal. Additional aspects of phospholipids are known in the art.

Flavor Compounds

Any of the compositions or methods described herein can include or include the use of one or more different flavor compounds. Non-limiting examples of flavor compounds include δ-decalactone, ethyl butyrate, 2-furyl methyl ketone, 2,3-pentanedione, γ-undecalactone, and δ-undecalactone. Additional examples of flavor compounds include artificial flavors, e.g., chocolate, coffee, strawberry, almond, hazelnut, vanilla, green tea, Irish cream, and coconut flavoring. Additional examples of flavor compounds are known in the art.

Ash

Any of the compositions or methods described herein can include or include the use of ash. Ash can, e.g., include one or more (two, three, four, five, six, seven, eight, nine, ten, eleven, twelve, thirteen, fourteen fifteen, sixteen, seventeen, eighteen, nineteen, or twenty) of: calcium, phosphorous, potassium, sodium, citrate, chloride, phosphate, magnesium, iron, molybdenum, manganese, copper, thiamin (vitamin B1), riboflavin (vitamin B2), niacin (vitamin B3), pantothenic acid (vitamin B5), vitamin B6 (pyridoxine), vitamin B12 (cobalamin), vitamin C, folate, vitamins A, vitamin D, vitamin E, and vitamin K. In some examples, the ash includes one or more (two or three) of $CaCl_2$, $KH_2PO_4$, and $Na_3$ citrate. Ash can be provided as a powder or as a solution. Additional components in and aspects of ash are known in the art. In some embodiments, the ash is not derived from or produced by mammal.

Color Balancing Agents

A variety of different color balancing agents are known in the art. For example, a color balancing agent can be a compound from obtained from a plant (e.g., a monocot or a dicot). In some examples, the color balancing agent is a synthetic compound. In some examples, the color balancing agent is not obtained from or produced by a mammal or a mammalian cell. Non-limiting examples of color balancing agents include β-carotene and annatto.

Sweetening Agents

A sweetening agent can be a saccharide (e.g., a monosaccharide, a disaccharide, or a polysaccharide) or an artificial sweetener. Non-limiting examples of sweetening agents that are saccharides include glucose, mannose, maltose, fructose, galactose, lactose, sucrose, monatin, and tagatose. Additional examples of saccharides that can be used as a sweetening agent in any of the compositions or methods described herein are known in the art.

Non-limiting examples of sweetening agents that are artificial sweeteners include stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, and P-4000. Additional artificial sweeteners that can be used as sweetening agents in any of the compositions or methods described herein are known in the art.

Compositions

Provided herein are compositions including: about 0.3 g/L to about 1.1 g/L (e.g., about 0.3 g/L to about 1.0 g/L, about 0.3 g/L to about 0.9 g/L, about 0.3 g/L to about 0.8 g/L, about 0.3 g/L to about 0.7 g/L, about 0.3 g/L to about 0.6 g/L, about 0.3 g/L to about 0.5 g/L, about 0.3 g/L to about 0.4 g/L, about 0.4 g/L to about 1.1 g/L, about 0.4 g/L to about 1.0 g/L, about 0.4 g/L to about 0.9 g/L, about 0.4 g/L to about 0.8 g/L, about 0.4 g/L to about 0.7 g/L, about 0.4 g/L to about 0.6 g/L, about 0.4 g/L to about 0.5 g/L, about 0.5 g/L to about 1.1 g/L, about 0.5 g/L to about 1.0 g/L, about 0.5 g/L to about 0.9 g/L, about 0.5 g/L to about 0.8 g/L, about 0.5 g/L to about 0.7 g/L, about 0.5 g/L to about 0.6 g/L, about 0.6 g/L to about 1.1 g/L, about 0.6 g/L to about 1.0 g/L, about 0.6 g/L to about 0.9 g/L, about 0.6 g/L to about 0.8 g/L, about 0.6 g/L to about 0.7 g/L, about 0.7 g/L to about 1.1 g/L, about 0.7 g/L to about 1.0 g/L, about 0.7 g/L to about 0.9 g/L, about 0.7 g/L to about 0.8 g/L, about 0.8 g/L to about 1.1 g/L, about 0.8 g/L to about 1.0 g/L, about 0.8 g/L to about 0.9 g/L, about 0.9 g/L to about 1.1 g/L, about 0.9 g/L to about 1.0 g/L, about 1.0 g/L to about 1.1 g/L, or about 0.27 weight % to about 0.75 weight %) κ-casein protein (e.g., any of the κ-casein proteins described herein); about 1.25 g/L to about 4.9 g/L (e.g., about 1.25 g/L to about 4.6 g/L, about 1.25 g/L to about 4.4 g/L, about 1.25 g/L to about 4.2 g/L, about 1.25 g/L to about 4.0 g/L, about 1.25 g/L to about 3.8 g/L, about 1.25 g/L to about 3.6 g/L, about 1.25 g/L to about 3.4 g/L, about 1.25 g/L to about 3.2 g/L, about 1.25 g/L to about 3.0 g/L, about 1.25 g/L to about 2.8 g/L, about 1.25 g/L to about 2.6 g/L, about 1.25 g/L to about 2.4 g/L, about 1.25 g/L to about 2.2 g/L, about 1.25 g/L to about 2.0 g/L, about 1.25 g/L to about 1.8 g/L, about 1.25 g/L to about 1.6 g/L, about 1.25 g/L to about 1.4 g/L, about 1.4 g/L to about 4.9 g/L, about 1.4 g/L to about 4.6 g/L, about 1.4 g/L to about 4.4 g/L, about 1.4 g/L to about 4.2 g/L, about 1.4 g/L to about 4.0 g/L, about 1.4 g/L to about 3.8 g/L, about 1.4 g/L to about 3.6 g/L, about 1.4 g/L to about 3.4 g/L, about 1.4 g/L to about 3.2 g/L, about 1.4 g/L to about 3.0 g/L, about 1.4 g/L to about 2.8 g/L, 1.4 g/L to about 2.6 g/L, about 1.4 g/L to about 2.4 g/L, about 1.4 g/L to about 2.2 g/L, about 1.4 g/L to about 2.0 g/L, about 1.4 g/L to about 1.8 g/L, about 1.4 g/L to about 1.6 g/L, about 1.6 g/L to about 4.9 g/L, about 1.6 g/L to about 4.6 g/L, about 1.6 g/L to about 4.4 g/L, about 1.6 g/L to about 4.2 g/L, about 1.6 g/L to about 4.0 g/L, about 1.6 g/L to about 3.8 g/L, about 1.6 g/L to about 3.6 g/L, about 1.6 g/L to about 3.4 g/L, about 1.6 g/L to about 3.2 g/L, about 1.6 g/L to about 3.0 g/L, about 1.6 g/L to about 2.8 g/L, 1.6 g/L to about 2.6 g/L, about 1.6 g/L to about 2.4 g/L, about 1.6 g/L to about 2.2 g/L, about 1.6 g/L to about 2.0 g/L, about 1.6 g/L to about 1.8 g/L, about 1.8 g/L to about 4.9 g/L, about 1.8 g/L to about 4.6 g/L, about 1.8 g/L to about 4.4 g/L, about 1.8 g/L to about 4.2 g/L, about 1.8 g/L to about 4.0 g/L, about 1.8 g/L to about 3.8 g/L, about 1.8 g/L to about 3.6 g/L, about 1.8 g/L to about 3.4 g/L, about 1.8 g/L to about 3.2 g/L, about 1.8 g/L to about 3.0 g/L, about 1.8 g/L to about 2.8 g/L, 1.8 g/L to about 2.6 g/L, about 1.8 g/L to about 2.4 g/L, about 1.8 g/L to about 2.2 g/L, about 1.8 g/L to about 2.0 g/L, about 2.0 g/L to about 4.9 g/L, about 2.0 g/L to about 4.6 g/L, about 2.0 g/L to about 4.4 g/L, about 2.0 g/L to about 4.2 g/L, about 2.0 g/L to about 4.0 g/L, about 2.0 g/L to about 3.8 g/L, about 2.0 g/L to about 3.6 g/L, about 2.0 g/L to about 3.4 g/L, about 2.0 g/L to about 3.2 g/L, about 2.0 g/L to about 3.0 g/L, about 2.0 g/L to about 2.8 g/L, 2.0 g/L to about 2.6 g/L, about 2.0 g/L to about 2.4 g/L, about 2.0 g/L to about 2.2 g/L, about 2.2 g/L to about 4.9 g/L, about 2.2 g/L to about 4.6 g/L, about 2.2 g/L to about 4.4 g/L, about 2.2 g/L to about 4.2 g/L, about 2.2 g/L to about 4.0 g/L, about 2.2 g/L to about 3.8 g/L, about 2.2 g/L to about 3.6 g/L, about 2.2 g/L to about 3.4 g/L, about 2.2 g/L to about 3.2 g/L, 2.2 g/L to about 3.0 g/L, about 2.2 g/L to about 2.8 g/L, 2.2 g/L to about 2.6 g/L, about 2.2 g/L to about 2.4 g/L, 2.4 g/L to about 4.9 g/L, about 2.4 g/L to about 4.6 g/L, about 2.4 g/L to about 4.4 g/L, about 2.4 g/L to about 4.2 g/L, about 2.4 g/L to about 4.0 g/L, about 2.4 g/L to about 3.8 g/L, about 2.4 g/L to about 3.6 g/L, about 2.4 g/L to about 3.4 g/L, about 2.4 g/L to about 3.2 g/L, about 2.4 g/L to about 3.0 g/L, about 2.4 g/L to about 2.8 g/L, 2.4 g/L to about 2.6 g/L, about 2.6 g/L to about 4.9 g/L, about 2.6 g/L to about 4.6 g/L, about 2.6 g/L to about 4.4 g/L, about 2.6 g/L to about 4.2 g/L, about 2.6 g/L to about 4.0 g/L, about 2.6 g/L to about 3.8 g/L, about 2.6 g/L to about 3.6 g/L, about 2.6 g/L to about 3.4 g/L, about 2.6 g/L to about 3.2 g/L, about 2.6 g/L to about 3.0 g/L, about 2.6 g/L to about 2.8 g/L, about 2.8 g/L to about 4.9 g/L, about 2.8 g/L to about 4.6 g/L, about 2.8 g/L to about 4.4 g/L, about 2.8 g/L to about 4.2 g/L, about 2.8 g/L to about 4.0 g/L, about 2.8 g/L to about 3.8 g/L, about 2.8 g/L to about 3.6 g/L, about 2.8 g/L to about 3.4 g/L, about 2.8 g/L to about 3.2 g/L, about 2.8 g/L to about 3.0 g/L, about 3.0 g/L to about 4.9 g/L, about 3.0 g/L to about 4.6 g/L, about 3.0 g/L to about 4.4 g/L, about 3.0 g/L to about 4.2 g/L, about 3.0 g/L to about 4.0 g/L, about 3.0 g/L to about 3.8 g/L, about 3.0 g/L to about 3.6 g/L, about 3.0 g/L to about 3.4 g/L, about 3.0 g/L to about 3.2 g/L, about 3.2 g/L to about 4.9 g/L, about 3.2 g/L to about 4.6 g/L, about 3.2 g/L to about 4.4 g/L, about 3.2 g/L to about 4.2 g/L, about 3.2 g/L to about 4.0 g/L, about 3.2 g/L to about 3.8 g/L, about 3.2 g/L to about 3.6 g/L, about 3.2 g/L to about 3.4 g/L, about 3.4 g/L to about 4.9 g/L, about 3.4 g/L to about 4.6 g/L, about 3.4 g/L to about 4.4 g/L, about 3.4 g/L to about 4.2 g/L, about 3.4 g/L to about 4.0 g/L, about 3.4 g/L to about 3.8 g/L, about 3.4 g/L to about 3.6 g/L, about 3.6 g/L to about 4.9 g/L, about 3.6 g/L to about 4.6 g/L, about 3.6 g/L to about 4.4 g/L, about 3.6 g/L to about 4.2 g/L, about 3.6 g/L to about 4.0 g/L, about 3.6 g/L to about 3.8 g/L, about 3.8 g/L to about 4.9 g/L, about 3.8 g/L to about 4.6 g/L, about 3.8 g/L to about 4.4 g/L, about 3.8 g/L to about 4.2 g/L, about 3.8 g/L to about 4.0 g/L, about 4.0 g/L to about 4.9 g/L, about 4.0 g/L to about 4.6 g/L, about 4.0 g/L to about 4.4 g/L, about 4.0 g/L to about 4.2 g/L, about 4.2 g/L to about 4.9 g/L, about 4.2 g/L to about 4.6 g/L, about 4.2 g/L to about 4.4 g/L, about 4.4 g/L to about 4.9 g/L, about 4.4 g/L to about 4.6 g/L, about 4.6 g/L to about 4.9 g/L, or about 1.23 weight % to about 3.27 weight %) β-casein protein (e.g., any of the β-casein proteins described herein); a final total concentration of one or more lipids (e.g., any one or more of the lipids described herein) of about 0 weight % to about 45 weight % (e.g., 0 weight %; about 0 weight % to about 4.5 weight %; about 0.5 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, about 3 weight %, about 2 weight %, or about 1 weight %; about 1.0 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, about 3 weight %, or about 2 weight %; about 2 weight % to about 40 weight %, about 35 weight %, about 30 weight %, about 25 weight %, about 20 weight %, about 15 weight %, about 10 weight %, about 8 weight %, about 6 weight %, about 5 weight %, about 4 weight %, or about 3 weight %; about 3 weight % to about 40 weight %, about 35 weight %, about 30 weight %, about 25 weight %, about 20 weight %, about 15 weight %, about 10 weight %, about 8 weight %, about 6 weight %, about 5 weight %, or about 4 weight %; about 4 weight % to about 40 weight %, about 35 weight %, about 30 weight %, about 25 weight %, about 20 weight %, about 15 weight %, about 10 weight %, about 8 weight %, about 6 weight %, or about 5 weight %; about 5 weight % to about 40 weight %, about 35 weight %, about 30 weight %, about 25 weight %, about 20 weight %, about 15 weight %, about 10 weight %, about 8 weight %, or about 6 weight %; about 6 weight % to about 40 weight %, about 35 weight %, about 30 weight %, about 25 weight %, about 20 weight %, about 15 weight %, about 10 weight %, or about 8 weight %; about 8 weight % to about 40 weight %, about 35 weight %, about 30 weight %, about 25 weight %, about 20 weight %, about 15 weight %, or about 10 weight %; about 10 weight % to about 40 weight %, about 35 weight %, about 30 weight %, about 25 weight %, about 20 weight %, or about 15 weight %; about 15 weight % to about 40 weight %, about 35 weight %, about 30 weight %, about 25 weight %, or about 20 weight %; about 20 weight % to about 40 weight %, about 35 weight %, about 30 weight %, or about 25 weight %; about 25 weight % to about 40 weight %, about 35 weight %, or about 30 weight %; about 30 weight % to about 40 weight %, or about 35 weight %; or about 35 weight % to about 40 weight %); a final total concentration of one or more flavor compounds (e.g., any of one or more of the flavor compounds described herein) of about 0.01 weight % to about 6 weight % (e.g., about 0.1 weight % to about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, about 1.0 weight %, or about 0.5 weight %; about 0.5 weight % to about 6 weight %, about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, or about 1.0 weight %; about 1.0 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, or about 1.5 weight %; about 1.5 weight % to about 6.0 weight %, about 5.5 weight %, about 5.0 weight %, about 4.5 weight %, about 4.0 weight %, about 3.5 weight %, about 3.0 weight %, about 2.5 weight %, or about 2.0 weight %; about 2.0 weight % to about 6.0 weight %, about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, about 4.5 weight %; about 4.5 weight % to about 6.0 weight %, about 5.5 weight %, or about 5.0 weight %; about 5.0 weight % to about 6.0 weight % or about 5.5 weight %; or about 5.5 weight % to about 6.0 weight %); a final total concentration of about 0.1 weight % to about 6 weight % (e.g., about 0.1 weight % to about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, about 1.0 weight %, or about 0.5 weight %; about 0.5 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, about 1.5 weight %, or about 1.0 weight %; about 1.0 weight % to about 6.0 weight %, about 5.5 weight %, about 5.0 weight %, about 4.5 weight %, about 4.0 weight %, about 3.5 weight %, about 3.0 weight %, about 2.5 weight %, about 2.0 weight %, or about 1.5 weight %; about 1.5 weight % to about 6.0 weight %, about 5.5 weight %, about 5.0 weight %, about 4.5 weight %, about 4.0 weight %, about 3.5 weight %, about 3.0 weight %, about 2.5 weight %, or about 2.0 weight %; about 2.0 weight % to about 6.0 weight %, about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, or about 4.5 weight %; about 4.5 weight % to about 6.0 weight %, about 5.5 weight %, or about 5.0 weight %; about 5.0 weight % to about 6.0 weight %, or about 5.5 weight %; or about 5.5 weight % to about 6.0 weight %) of one or more sweetening agents (e.g., any one or more of the sweetening agents described herein); and a final total concentration of ash of about 0.15 weight % to about 1.5 weight % (e.g., about 0.15 weight % to about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, about 0.4 weight %, about 0.3 weight %, or about 0.2 weight %; about 0.2 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, about 0.4 weight %, or about 0.3 weight %; about 0.3 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, about 0.5 weight %, or about 0.4 weight %; about 0.4 weight % to about 1.5 weight %, about 1.4 weight %, about 1.3 weight %, about 1.2 weight %, about 1.1 weight %, about 1.0 weight %, about 0.9 weight %, about 0.8 weight %, about 0.6 weight %, or about 0.5 weight %; about 0.5 weight % to about 1.5 weight %, about 1.4 weight %, about 1.3 weight %, about 1.2 weight %, about 1.1 weight %, about 1.0 weight %, about 0.9 weight %, about 0.8 weight %, or about 0.6 weight %; about 0.6 weight % to about 1.5 weight %, about 1.4 weight %, about 1.3 weight %, about 1.2 weight %, about 1.1 weight %, about 1.0 weight %, about 0.9 weight %, or about 0.8 weight %; about 0.8 weight % to about 1.4 weight %, about 1.3 weight %, about 1.2 weight %, about 1.1 weight %, about 1.0 weight %, or about 0.9 weight %; about 0.9 weight % to about 1.5 weight %, about 1.4 weight %, about 1.3 weight %, about 1.2 weight %, about 1.1 weight %, or about 1.0 weight %; about 1.0 weight % to about 1.5 weight %, about 1.4 weight %, about 1.3 weight %, about 1.2 weight %, or about 1.1 weight %; about 1.1 weight % to about 1.5 weight %, about 1.4 weight %, about 1.3 weight %, or about 1.2 weight %; about 1.2 weight % to about 1.5 weight %, about 1.4 weight %, or about 1.3 weight %; about 1.3 weight % to about 1.5 weight % or about 1.4 weight %; or about 1.4 weight % to about 1.5 weight %), where the composition does not comprise an animal-derived component.

Also provided are compositions including: about 0.3 g/L to about 1.1 g/L (e.g., any of the subranges of about 0.3 g/L to about 1.1 g/L described in the above paragraph) κ-casein protein (e.g., any of the κ-casein proteins described herein); about 1.25 g/L to about 4.9 g/L (e.g., any of the subranges of about 1.25 g/L to about 4.9 g/L described in the above paragraph) β-casein protein (e.g., any of the β-casein proteins described herein); a final total concentration of one or more lipids (e.g., any of the one or more lipids described herein) of about 0 weight % to about 45 weight % (e.g., any of the subranges of about 0 weight % to about 45 weight % described in the above paragraph); a final total concentration of one or more flavor compounds (e.g., any of the one or more flavor compounds described herein) of about 0.01 weight % to about 6 weight % (e.g., any of the subranges of about 0.01 weight % to about 6 weight % described in the above paragraph); a final total concentration of about 0.1 weight % to about 6 weight % (e.g., any of the subranges of about 0.1 weight % to about 6 weight % described herein) of one or more sweetening agents (e.g., any one or more sweetening agents described herein); and a final total concentration of ash (e.g., any of the exemplary ash described herein) of about 0.15 weight % to about 1.5 weight % (e.g., any of the subranges of about 0.15 weight % to about 1.5 weight % described in the above paragraph), where: the composition: does not include at least one component found in a mammal-produced milk; includes at least one component not present in a mammal-produced milk; and/or includes a higher or lower concentration of at least one component as compared to the concentration of the at least one component in a mammal-produced milk. In some examples of these compositions, the composition includes a higher concentration of at least one component selected from the group of: calcium, phosphate, B complex vitamins, vitamin A, vitamin D, vitamin E, and vitamin K, as compared to the concentration of the one or more components in a mammal-produced milk. In some embodiments of these compositions, the composition does not include at least one component found in a mammal-produced milk selected from the group of: lactose, bacteria, mycobacteria, allergens, viruses, prions, yeast, growth hormones, leukocytes, antibiotics, heavy metals, immunoglobulins, lactoferrin, lactoperoxidase, and lipase. In some examples of these compositions, the composition includes at least one component not present in a mammal-produced milk selected from the group of an artificial sweetener, a plant-derived lipid, a β-casein protein that is non-glycosylated or has a non-mammalian glycosylation pattern, and a κ-casein protein that is non-glycosylated or has a non-mammalian glycosylation pattern.

Also provided are compositions including: about 0.3 g/L to about 1.1 g/L (e.g., any of the subranges of about 0.3 g/L to about 1.1 g/L described in this section) κ-casein protein (e.g., any of the κ-casein proteins described herein) that is unglycosylated or has a non-mammalian glycosylation pattern; about 1.25 g/L to about 4.9 g/L (e.g., any of the subranges of about 1.25 g/L to about 4.9 g/L described in this section) β-casein protein (e.g., any of the β-casein proteins described herein) that is unglycosylated or has a non-mammalian glycosylation pattern; a final total concentration of one or more lipids (e.g., any of the one or more lipids described herein) of about 0 weight % to about 45 weight % (e.g., any of the subranges of about 0 weight % to about 45 weight % described in this section); a final total concentration of one or more flavor compounds (e.g., any of the one or more flavor compounds described herein) of about 0.01 weight % to about 6 weight % (e.g., any of the subranges of about 0.01 weight % to about 6 weight % described in this section); a final total concentration of about 0.1 weight % to about 6 weight % (e.g., any of the subranges of about 0.1 weight % to about 6 weight % described in this section) of one or more sweetening agents (e.g., any of the one or more sweetening agents described herein); and a final total concentration of ash (e.g., any of the ash described herein) of about 0.15 weight % to about 1.5 weight % (e.g., any of the subranges of about 0.15 weight % to about 1.5 weight % described in this section).

Also provided are compositions including a micelle including a κ-casein protein (e.g., any of the κ-casein proteins described herein) and a β-casein protein (e.g., any of the β-casein proteins described herein), where the micelle has a diameter of about 50 nm to about 350 nm (e.g., any of the subranges of the diameter of a micelle described herein), and the κ-casein protein and the β-casein protein are unglycosylated or have a non-mammalian glycosylation pattern. In some embodiments, the composition includes a final concentration of micelles of about 2.0 weight % to about 6 weight % (e.g., about 2.0 weight % to about 5.5 weight %, about 5.0 weight %, about 4.5 weight %, about 4.0 weight %, about 3.5 weight %, about 3.0 weight %, or about 2.5 weight %; about 2.5 weight % to about 6.0 weight %, about 5.5 weight %, about 5.0 weight %, about 4.5 weight %, about 4.0 weight %, about 3.5 weight %, or about 3.0 weight %; about 3.0 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, about 4.0 weight %, or about 3.5 weight %; about 3.5 weight % to about 6.0 weight %, about 5.5 weight %, about 5.0 weight %, about 4.5 weight %, or about 4.0 weight %; about 4.5 weight % to about 6.0 weight %, about 5.5 weight %, about 5.0 weight %, about 4.5 weight %, or about 4.0 weight %; about 4.0 weight % to about 6.0 weight %, about 5.5 weight %, about 5.0 weight %, or about 4.5 weight %; about 4.5 weight % to about 5.5 weight %, or about 5.0 weight %; about 5.0 weight % to about 6.0 weight % or 5.5 weight %; or about 5.5 weight % to about 6.0 weight %). In some embodiments of these compositions, the ratio of the β-casein protein to the κ-casein protein in the micelle is about 2.0:1 to about 5.5:1 (e.g., any of the subranges of the ratios about 2.0:1 to about 5.5:1 described for the micelle herein). In some embodiments, these compositions further include: a final total concentration of one or more lipids (e.g., any of the one or more lipids described herein) of about 0 weight % to about 45 weight % (e.g., any of the subranges of about 0 weight % to about 45 weight percent described in this section); a final total concentration of one or more flavor compounds (e.g., any of the one or more flavor compounds described herein) of about 0.01 weight % to about 6 weight % (e.g., any of the subranges of 0.01 weight % to about 6 weight % described in this section); a final total concentration of about 0.1 weight % to about 6 weight % (e.g., any of the subranges of about 0.1 weight % to about 6 weight % described in this section) of one or more sweetening agents (e.g., any one or more of the sweetening agents described herein); and a final total concentration of ash (e.g., any of the ash described herein) of about 0.15 weight % to about 1.5 weight % (e.g., any of the subranges of about 0.15 weight % to about 1.5 weight % described in this section).

In some embodiments of any of the compositions described herein, the one or more lipids are selected from the group consisting of: sunflower oil, coconut oil, tributyrin, mono- and di-glycerides, free fatty acids, and phospholipids. Some examples of any of the compositions described herein further include one or more of: a final concentration of sunflower oil of about 1 weight % to about 28 weight % (e.g., about 1 weight % to about 26 weight %, about 24 weight %, about 22 weight %, about 20 weight %, about 18 weight %, about 16 weight %, about 14 weight %, about 12 weight %, about 10 weight %, about 8 weight %, about 6 weight %, about 4 weight %, or about 2 weight %; about 2 weight % to about 28 weight %, about 26 weight %, about 24 weight %, about 22 weight %, about 20 weight %, about 18 weight %, about 16 weight %, about 14 weight %, about 12 weight %, about 10 weight %, about 8 weight %, about 6 weight %, or about 4 weight %; about 4 weight % to about 28 weight %, about 26 weight %, about 24 weight %, about 22 weight %, about 20 weight %, about 18 weight %, about 16 weight %, about 14 weight %, about 12 weight %, about 10 weight %, or about 8 weight %; about 8 weight % to about 28 weight %, about 26 weight %, about 24 weight %, about 22 weight %, about 20 weight %, about 18 weight %, about 16 weight %, about 14 weight %, about 12 weight %, or about 10 weight %; about 10 weight % to about 28 weight %, about 26 weight %, about 24 weight %, about 22 weight %, about 20 weight %, about 18 weight %, about 16 weight %, about 14 weight %, or about 12 weight %; about 12 weight % to about 28 weight %, about 26 weight %, about 24 weight %, about 22 weight %, about 20 weight %, about 18 weight %, about 16 weight %, or about 14 weight %; about 14 weight % to about 28 weight %, about 26 weight %, about 24 weight %, about 22 weight %, about 20 weight %, about 18 weight %, or about 16 weight %; about 16 weight % to about 28 weight %, about 26 weight %, about 24 weight %, about 22 weight %, about 20 weight %, about 18 weight %; about 18 weight % to about 28 weight %, about 26 weight %, about 24 weight %, about 22 weight %, or about 20 weight %; about 20 weight % to about 28 weight %, about 26 weight %, about 24 weight %, about 22 weight %; about 22 weight % to about 28 weight %, about 26 weight %, about 24 weight %; about 24 weight % to about 28 weight % or about 26 weight %; or about 28 weight % to about 30 weight %); a final concentration of coconut oil of about 0.5 weight % to about 14 weight % (e.g., about 0.5 weight % to about 12 weight %, about 10 weight %, about 8 weight %, about 6 weight %, about 4 weight %, about 2 weight %, or about 1 weight %; about 1 weight % to about 14 weight %, about 12 weight %, about 10 weight %, about 8 weight %, about 6 weight %, about 4 weight %, or about 2 weight %; about 2 weight % to about 12 weight %, about 10 weight %, about 8 weight %, about 6 weight %, or about 4 weight %; about 4 weight % to about 14 weight %, about 12 weight %, about 10 weight %, about 8 weight %, or about 6 weight %; about 6 weight % to about 14 weight %, about 12 weight %, about 10 weight %, or about 8 weight %; about 8 weight % to about 14 weight %, about 12 weight %, or about 10 weight %; about 10 weight % to about 14 weight % or 12 weight %; or about 12 weight % to about 14 weight %); a final concentration of tributyrin of about 0.05 weight to about 1.0 weight % (e.g., between about 0.05 weight % to about 0.9 weight %, about 0.8 weight %, about 0.7 weight %, about 0.6 weight %, about 0.5 weight %, about 0.4 weight %, about 0.3 weight %, or about 0.2 weight %; 0.1 weight % to about 1.0 weight %, about 0.9 weight %, about 0.8 weight %, about 0.7 weight %, about 0.6 weight %, about 0.5 weight %, about 0.4 weight %, about 0.3 weight %, or about 0.2 weight %; about 0.3 weight %, or about 0.2 weight %; about 0.2 weight % to about 1.0 weight %, about 0.9 weight %, about 0.8 weight %, about 0.7 weight %, about 0.6 weight %, about 0.5 weight %, or about 0.4 weight %; about 0.4 weight % to about 1.0 weight %, about 0.9 weight %, about 0.8 weight %, about 0.7 weight %, about 0.6 weight %, or about 0.5 weight %; about 0.5 weight % to about 1.0 weight %, about 0.9 weight %, about 0.8 weight %, about 0.7 weight %, or about 0.6 weight %; about 0.6 weight % to about 1.0 weight %, about 0.9 weight %, about 0.8 weight %, or about 0.7 weight %; about 0.7 weight % to about 1.0 weight %, about 0.9 weight %, or about 0.8 weight %; about 0.8 weight % to about 1.0 weight % or about 0.9 weight %; or about 0.9 weight % to about 1.0 weight %); a final total concentration of monoglycerides and diglycerides (e.g., any one or more of the monoglycerides or diglycerides described herein) of about 0.08 weight % to about 1.2 weight % (e.g., 0.08 weight % to about 1.0 weight %, about 0.8 weight %, about 0.6 weight %, about 0.4 weight %, or about 0.2 weight %; about 0.2 weight % to about 1.2 weight %, about 1.0 weight %, about 0.8 weight %, about 0.6 weight %, or about 0.4 weight %; about 0.4 weight % to about 1.2 weight %, about 1.0 weight %, about 0.8 weight %, or about 0.6 weight %;

about 0.6 weight % to about 1.2 weight %, about 1.0 weight %, or about 0.8 weight %; about 0.8 weight % to about 1.2 weight % or about 1.0 weight %; or about 1.0 weight % to about 1.2 weight %); and a final total concentration of free fatty acids of about 0.02 weight % to about 0.28 weight %; and a final total concentration of phospholipids (e.g., any one or more of the phospholipids described herein) of about 0.02 weight % to about 0.3 weight % (e.g., about 0.02 weight % to about 0.25 weight %, about 0.20 weight %, about 0.15 weight %, or about 0.10 weight %; about 0.05 weight % to about 0.3 weight %, about 0.25 weight %, about 0.20 weight %, about 0.15 weight %, or about 0.10 weight %; about 0.10 weight % to about 0.30 weight %, about 0.25 weight %, about 0.20 weight %, or about 0.15 weight %; about 0.15 weight % to about 0.30 weight %, about 0.25 weight %, or about 0.20 weight %; about 0.20 weight % to about 0.30 weight % or about 0.25 weight %; or about 0.25 weight % to about 0.30 weight %).

In some embodiments of any of the compositions, the free fatty acids include at least one (e.g., two, three, or four) fatty acid selected from the group of: butyric acid, caproic acid, caprylic acid, and capric acid. In some embodiments of any of the compositions, the phospholipids are soy lecithin phospholipids, sunflower lecithin phospholipids, cotton lecithin phospholipids, or rapeseed lecithin phospholipids. In some examples of any of the compositions described herein, the flavor compounds include at least one flavor compound selected from the group of: δ-decalactone, ethyl butyrate, 2-furyl methyl ketone, 2,3-pentanedione, γ-undecalactone, and δ-undecalactone. In some embodiments of any of the compositions described herein, the one or more sweetening agents is a saccharide (e.g., glucose, mannose, maltose, fructose, galactose, lactose, sucrose, monatin, or tagatose). In some examples of any of the compositions described herein, the one or more sweetening agents is an artificial sweetener (e.g., stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

In some examples of any of the compositions described herein, the ash includes one or more (e.g., two, three, four, five, or six) of: calcium, phosphorus, potassium, sodium, citrate, and chloride. In some embodiments of any of the compositions described herein, the ash comprises one or more (e.g., two or three) of $CaCl_2$), $KH_2PO_4$, and $Na_3$ citrate. Some embodiments of the compositions described herein include: a final concentration of $CaCl_2$) of about 0.05 g/L to about 0.2 g/L (e.g., about 0.05 g/L to about 0.15 g/L, about 0.05 g/L to about 0.10 g/L, about 0.10 g/L to about 0.20 g/L, about 0.10 g/L to about 0.15 g/L, or about 0.15 g/L to about 0.2 g/L); a final concentration of $KH_2PO_4$ of about 0.2 g/L to about 0.4 g/L (e.g., about 0.2 g/L to about 0.35 g/L, about 0.2 g/L to about 0.30 g/L, about 0.2 g/L to about 0.25 g/L, about 0.25 g/L to about 0.4 g/L, about 0.25 g/L to about 0.30 g/L, about 0.30 g/L to about 0.40 g/L, or about 0.30 g/L to about 0.35 g/L, or about 0.35 g/L to about 0.40 g/L); and/or a final concentration of $Na_3$ citrate of about 0.1 g/L to about 0.3 g/L (e.g., 0.1 g/L to about 0.25 g/L, about 0.1 g/L to about 0.20 g/L, about 0.1 g/L to about 0.15 g/L, about 0.15 g/L to about 0.30 g/L, about 0.15 g/L to about 0.25 g/L, about 0.15 g/L to about 0.20 g/L, about 0.20 g/L to about 0.30 g/L, about 0.20 g/L to about 0.25 g/L, or about 0.25 g/L to about 0.30 g/L).

In any of the composition described herein, the κ-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein. In any of the compositions described herein, the β-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein.

In some examples of any of the compositions described herein can further include: a final concentration of α-lactalbumin protein (e.g., any of the α-lactalbumin proteins described herein) of about 0.4 weight % to about 2.5 weight % (e.g., about 0.4 weight % to about 2.0 weight %, about 1.5 weight %, or about 1.0 weight %; about 1.0 weight % to about 2.5 weight %, about 2.0 weight %, or about 1.5 weight %, about 1.5 weight % to about 2.5 weight % or 2.0 weight %; or about 2.0 weight % to about 2.5 weight %), and/or a final concentration of β-lactoglobulin protein (e.g., any of the 0-lactoglobulin proteins described herein) of about 2.5 weight % to about 4.5 weight %. In some embodiments of any of the compositions described herein, the α-lactalbumin protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-lactalbumin protein. In some embodiments of any of the compositions described herein, the β-lactoglobulin protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-lactoglobulin protein.

Some embodiments of any of the compositions described herein further include: a final concentration of α-S1-casein protein (e.g., any of the α-S1-casein proteins described herein) of about 11 weight % to about 16 weight % (e.g., about 11 weight % to about 15 weight %, about 14 weight %, about 13 weight %, or about 12 weight %; about 12 weight % to about 16 weight %, about 15 weight %, about 14 weight %, or about 13 weight %; about 13 weight % to about 16 weight %, about 15 weight %, or about 14 weight %; about 14 weight % to about 16 weight % or 15 weight %; or about 15 weight % to about 16 weight %); and/or a final concentration of α-S2-casein protein (e.g., any of the α-S2-casein proteins described herein) of about 2 weight % to about 5 weight % (e.g., about 2 weight % to about 4.5 weight %, about 4.0 weight %, about 3.5 weight %, about 3.0 weight %, or about 2.5 weight %; about 2.5 weight % to about 5.0 weight %, about 4.5 weight %, about 4.0 weight %, about 3.5 weight %, or about 3.0 weight %; about 3.0 weight % to about 5.0 weight %, about 4.5 weight %, about 4.0 weight %, or about 3.5 weight %; about 3.5 weight % to about 5 weight %, about 4.5 weight %, or about 4.0 weight %; about 4.0 weight % to about 5.0 weight % or 4.5 weight %; or about 4.5 weight % to about 5.0 weight %).

In some examples of any of the compositions described herein, the α-S1-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S1-casein protein; and/or the α-S2-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth α-S2-casein protein.

Some examples of any of the compositions described herein further include one or more (e.g., two or three) of serum albumin (e.g., any of the serum albumin proteins described herein), lactoferrin (e.g., any of the lactoferrin proteins described herein), and transferrin (e.g., any of the transferrin proteins described herein). In some examples of any of the compositions described herein, the serum albumin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin; the lactoferrin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin; and/or the transferrin can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein.

In some examples of any of the compositions described herein, the composition further includes one or more color balancing agents (e.g., any of the coloring agents described herein, e.g., β-carotene or annatto).

Any of the compositions described herein can have a pH of about 6.2 to about 7.2 (e.g., about 6.2 to about 7.0, about 6.2 to about 6.8, about 6.2 to about 6.6, about 6.2 to about 6.4, about 6.4 to about 7.2, about 6.4 to about 7.0, about 6.4 to about 6.8, about 6.4 to about 6.6, about 6.6 to about 7.2, about 6.6 to about 7.0, about 6.6 to about 6.8, about 6.8 to about 7.2, about 6.8 to about 7.0, or about 7.0 to about 7.2).

In various embodiments, the milk protein components comprise about 0.5% about 1%, about 1.5%, about 2%, about 2.5%, about 3%, about 3.5%, about 4%, about 4.5%, about 5%, about 6% milk protein by dry weight or total weight. In some embodiments, the compositions can comprise about 0.5-2.5%, about 1-2%, about 2-3%, or about 4-10% protein by dry weight or total weight. In particular embodiments, the compositions can comprise about 10-15% protein by dry weight or total weight.

A wide range of caseins including casein with substantial homology to the wildtype casein, variants, mutants of casein are expressed and incorporated as a component of milk protein.

Dry Compositions

Also provided are powder compositions including: a final concentration of κ-casein protein (e.g., any of the α-casein proteins described herein) of about 3.6 weight % to about 5.4 weight % (e.g., about 3.6 weight % to about 5.2 weight %, about 5.0 weight %, about 4.8 weight %, about 4.6 weight %, about 4.4 weight %, about 4.2 weight %, about 4.0 weight %, or about 3.8 weight %; about 3.8 weight % to about 5.4 weight %, about 5.2 weight %, about 5.0 weight %, about 4.8 weight %, about 4.6 weight %, about 4.4 weight %, about 4.2 weight %, or about 4.0 weight %; about 4.0 weight % to about 5.4 weight %, about 5.2 weight %, about 5.0 weight %, about 4.8 weight %, about 4.6 weight %, about 4.4 weight %, or about 4.2 weight %; about 4.2 weight % to about 5.2 weight %, about 5.2 weight %, about 5.0 weight %, about 4.8 weight %, about 4.6 weight %, or about 4.4 weight %; about 4.8 weight % to about 5.4 weight %, about 5.2 weight %, or about 5.0 weight %; about 5.0 weight % to about 5.4 weight % or about 5.2 weight %; or about 5.2 weight % to about 5.4 weight %); a final concentration of β-casein protein (e.g., any of the β-casein proteins described herein) of about 16.3 weight % to about 24.5 weight %; 16.3 weight % to about 22 weight %, about 20 weight %, or about 18 weight %; about 18 weight % to about 24.5 weight %, about 22 weight %, or about 20 weight %; about 20 weight % to about 24.5 weight % to about 22 weight %; or about 22 weight % to about 24.5 weight %); a final concentration of a sweetening agent (e.g., any one or more of the sweetening agents described herein) of about 35 weight % to about 40 weight % (e.g., about 35 weight % to about 39 weight %, about 38 weight %, about 37 weight %, or about 36 weight %; about 36 weight % to about 40 weight %, about 39 weight %, about 38 weight %, or about 37 weight %; about 37 weight % to about 40 weight %, about 39 weight %, or about 38 weight %; about 38 weight % to about 40 weight % or 39 weight %; or about 39 weight % to about 40 weight %); a final concentration of one or more lipids (e.g., any of the one or more lipids described herein) of about 25 weight % to about 30 weight % (e.g., about 25 weight % to about 29 weight %, about 28 weight %, about 27 weight %, or about 26 weight %; about 26 weight % to about 30 weight %, about 29 weight %, about 28 weight %, or about 27 weight %; about 27 weight % to about 30 weight %, about 29 weight %, or about 28 weight %; about 28 weight % to about 30 weight % or about 29 weight %; or about 29 weight % to about 30 weight %); a final concentration of ash (e.g., any of the ash described herein) of about 5 weight % to about 7 weight % (e.g., about 5 weight % to about 6.5 weight %, about 6.0 weight %, or about 5.5 weight %; about 5.5 weight % to about 7.0 weight %, about 6.5 weight %, or about 6.0 weight %; about 6.0 weight % to about 7.0 weight % or about 6.5 weight %; or about 6.5 weight % to about 7.0 weight %); and a final concentration of water of about 2 weight % to about 5 weight % (e.g., about 2 weight % to about 4 weight % or about 3 weight %; about 3 weight % to about 5 weight % or about 4 weight %; or about 4 weight % to about 5 weight %), where the κ-casein protein is an unglycosylated and/or has a non-mammalian glycosylation pattern, and/or the β-casein protein is an unglycosylated and/or has a non-mammalian glycosylation pattern.

Any of the powder compositions can contain any of the components described in any of the compositions described herein (e.g., one or more of any of the color matching agents, α-S1-casein proteins, α-S2-casein proteins, α-lactalbumin proteins, 0-lactoglobulin proteins, lactoferrin proteins, transferrin proteins, and serum albumin protein described herein at any of the concentrations described herein for each component, respectively).

Supplemented Milk Compositions

Also provided herein are compositions including: a mammalian-produced milk or a processed mammal-produced milk; and one or more (e.g., two or three) of a κ-casein protein that is unglycosylated or has an non-mammalian glycosylation pattern; a β-casein protein that is unglycosylated or has an non-mammalian glycosylation pattern; or a micelle including a κ-casein protein that is unglycosylated or has an non-mammalian glycosylation pattern and a β-casein protein that is unglycosylated or has an non-mammalian glycosylation pattern.

In some examples, the composition includes a mammal-produced milk or a processed mammalian-produced milk and a κ-casein protein that is unglycosylated or has a non-mammalian glycosylation pattern. In some examples, the composition includes a mammal-produced milk or a processed mammalian-produced milk and a β-casein protein that is unglycosylated or has a non-mammalian glycosylation pattern. In other examples, the composition includes a mammal-produced milk or a processed mammalian-produced milk and a micelle including a κ-casein protein that is unglycosylated or has a non-mammalian glycosylation pattern and a β-casein protein that is unglycosylated or has a non-mammalian glycosylation pattern.

In some examples, the final concentration of the κ-casein protein that is unglycosylated or has a non-mammalian glycosylation pattern or the final concentration of the β-casein protein that is unglycosylated or has a non-mammalian glycosylation pattern in the composition is: 0.02 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, about 0.2 weight %, or about 0.1 weight %; about 0.1 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.8 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, or about 1.2 weight %; about 1.2 weight % to about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 3.0 weight %, about 2.8 weight %, about 2.6 weight %, about 2.4 weight %, about 2.2 weight %, about 2.0 weight %, about 1.8 weight %, or about 1.6 weight %; about 1.6 weight % to about 3.0 weight %, about 2.8 weight %, about 2.6 weight %, about 2.4 weight %, about 2.2 weight %, about 2.0 weight %, or about 1.8 weight %; about 1.8 weight % to about 3.0 weight %, about 2.8 weight %, about 2.6 weight %, about 2.4 weight %, about 2.2 weight %, or about 2.0 weight %; about 2.0 weight % to about 3.0 weight %, about 2.8 weight %, about 2.6 weight %, about 2.4 weight %, or about 2.2 weight %; about 2.2 weight % to about 3.0 weight %, about 2.8 weight %, about 2.6 weight %, or about 2.4 weight %; about 2.4 weight % to about 3.0 weight %, about 2.8 weight %, or about 2.6 weight %; about 2.6 weight % to about 3.0 weight % or about 2.8 weight %; or about 2.8 weight % to about 3.0 weight % (of the final composition).

In some compositions, the final concentration of the κ-casein protein that is unglycosylated and/or has a non-mammalian glycosylation pattern in the composition is about 0.02 weight % to about 0.6 weight % (e.g., about 0.02 weight % to about 0.5 weight %, about 0.02 weight % to about 0.4 weight %, about 0.02 weight % to about 0.3 weight %, about 0.02 weight % to about 0.2 weight %, about 0.02 weight % to about 0.1 weight %, about 0.1 weight % to about 0.5 weight %, about 0.1 weight %, to about 0.4 weight %, about 0.1 weight % to about 0.3 weight %, about 0.1 weight % to about 0.2 weight %, about 0.2 weight % to about 0.5 weight %, about 0.2 weight % to about 0.4 weight %, about 0.2 weight % to about 0.3 weight %, about 0.3 weight % to about 0.5 weight %, about 0.3 weight % to about 0.4 weight %, or about 0.4 weight % to about 0.5 weight %); and the final concentration of β-casein that is unglycosylated and/or has a non-mammalian glycosylation pattern in the composition is about 0.02 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.4 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, or about 0.6 weight %; about 0.6 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, or about 0.8 weight %; about 0.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, or about 1.2 weight %; about 1.2 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, about 1.8 weight %, or about 1.6 weight %; about 1.6 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, about 2.0 weight %, or about 1.8 weight %; about 1.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, or about 2.0 weight %; about 1.8 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, about 2.2 weight %, or about 2.0 weight %; about 2.0 weight % to about 4.0 weight %, about 3.8 weight %, about 3.6 weight %, about 3.4 weight %, about 3.2 weight %, about 3.0 weight %, about 2.8 weight %, about 2.6 weight %, about 2.4 weight %, or about 2.2 weight %; about 2.2 weight % to about 4.0 weight %, about 3.8 weight %, about 3.6 weight %, about 3.4 weight %, about 3.2 weight %, about 3.0 weight %, about 2.8 weight %, about 2.6 weight %, or about 2.4 weight %; about 2.4 weight % to about 4.0 weight %, about 3.8 weight %, about 3.6 weight %, about 3.4 weight %, about 3.2 weight %, about 3.0 weight %, about 2.8 weight %, or about 2.6 weight %; about 2.6 weight % to about 4.0 weight %, about 3.8 weight %, about 3.6 weight %, about 3.4 weight %, about 3.2 weight %, about 3.0 weight %, or about 2.8 weight %; about 2.8 weight % to about 4.0 weight %, about 3.8 weight %, about 3.6 weight %, about 3.4 weight %, about 3.2 weight %, or about 3.0 weight %; about 3.0 weight % to about 4.0 weight %, about 3.8 weight %, about 3.6 weight %, about 3.4 weight %, or about 3.2 weight %; about 3.2 weight % to about 4.0 weight %, about 3.8 weight %, about 3.6 weight %, or about 3.4 weight %; about 3.4 weight % to about 4.0 weight %, about 3.8 weight %, or about 3.6 weight %; about 3.6 weight % to about 4.0 weight % or about 3.8 weight %; or about 3.8 weight % to about 4.0 weight %.

In some examples, the final concentration of micelles including a κ-casein protein that is unglycosylated or has an non-mammalian glycosylation pattern and a β-casein protein that is unglycosylated or has an non-mammalian glycosylation pattern in the composition is: 0.02 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, about 0.2 weight %, or about 0.1 weight %; about 0.1 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, about 0.4 weight %, or about 0.2 weight %; about 0.2 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, about 1.0 weight %, about 0.8 weight %, about 0.6 weight %, or about 0.4 weight %; about 0.8 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, about 1.2 weight %, or about 1.0 weight %; about 1.0 weight % to about 3.0 weight %, about 2.8 weight %, about 2.6 weight %, about 2.4 weight %, about 2.2 weight %, about 2.0 weight %, about 1.8 weight %, about 1.6 weight %, about 1.4 weight %, or about 1.2 weight %; about 1.2 weight % to about 3.0 weight %, about 2.8 weight %, about 2.6 weight %, about 2.4 weight %, about 2.2 weight %, about 2.0 weight %, about 1.8 weight %, about 1.6 weight %, or about 1.4 weight %; about 1.4 weight % to about 3.0 weight %, about 2.8 weight %, about 2.6 weight %, about 2.4 weight %, about 2.2 weight %, about 2.0 weight %, about 1.8 weight %, or about 1.6 weight %; about 1.6 weight % to about 3.0 weight %, about 2.8 weight %, about 2.6 weight %, about 2.4 weight %, about 2.2 weight %, about 2.0 weight %, or about 1.8 weight %; about 1.8 weight % to about 3.0 weight %, about 2.8 weight %, about 2.6 weight %, about 2.4 weight %, about 2.2 weight %, or about 2.0 weight %; about 2.0 weight % to about 3.0 weight %, about 2.8 weight %, about 2.6 weight %, about 2.4 weight %, or about 2.2 weight %; about 2.2 weight % to about 3.0 weight %, about 2.8 weight %, about 2.6 weight %, or about 2.4 weight %; about 2.4 weight % to about 3.0 weight %, about 2.8 weight %, or about 2.6 weight %; about 2.6 weight % to about 3.0 weight % or about 2.8 weight %; or about 2.8 weight % to about 3.0 weight % (of the final composition).

Nucleic Acids and Vectors

Also provided are nucleic acids (e.g., vectors) that include: a promoter (e.g., a yeast, bacterial, or a mammalian promoter); a sequence encoding a signal sequence; a sequence encoding a milk protein (e.g., any of the exemplary sequences described herein); and a yeast termination sequence, where the promoter is operably linked to the signal sequence, the signal sequence is operably linked to the sequence encoding the milk protein, and the terminal sequence is operably linked to the sequence encoding the milk protein. In some examples of these nucleic acids, the promoter is a constitutive promoter or an inducible promoter. Non-limiting examples of promoters are described herein. Additional promoters that can be used in these nucleic acids are known in the art.

The signal sequence in any of the vectors described herein can be a signal sequence from the encoded milk protein or a different milk protein, or is a signal sequence from a yeast mating factor (e.g., any alpha mating factor). In some examples, the encoded milk protein is selected from the group of: β-casein (e.g., any of the β-casein proteins described herein), κ-casein (e.g., any of the κ-casein proteins described herein), α-S1-casein (e.g., any of the α-S1-casein proteins described herein), α-S2-casein (e.g., any of the α-S2-casein proteins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), or transferrin (e.g., any of the transferrin proteins described herein). Additional signal sequences that can be used in the present vectors are known in the art.

Any of the nucleic acids described herein can further include a bacterial origin of replication. Any of the nucleic acids described herein can further include a selection marker (e.g., an antibiotic resistance gene). The sequences of bacterial origin of replication are known in the art. Non-limiting examples of antibiotic resistance genes are described herein. Additional examples of resistance genes are known in the art.

Non-limiting examples of termination sequences are described herein. Additional examples of termination sequences are known in the art.

Some embodiments of the nucleic acids provided herein further include: an additional promoter sequence (e.g., any of the exemplary promoters described herein); an additional sequence encoding a signal sequence (e.g., any of the exemplary signal sequences described herein); a sequence encoding an additional milk protein (e.g., any of the exemplary sequences encoding a milk protein described herein); and an additional yeast termination sequence (e.g., any of the exemplary yeast termination sequences described herein), where the additional promoter sequence is operably linked to the additional sequence encoding a signal sequence, the sequence encoding the signal sequence is operably linked to the sequence encoding the additional milk protein, and the sequence encoding the additional milk protein is operably linked to the additional yeast terminal sequence. The additional milk protein can be, e.g., β-casein (e.g., any of the β-casein proteins described herein), κ-casein (e.g., any of the κ-casein proteins described herein), α-S1-casein (e.g., any of the α-S1-casein proteins described herein), α-S2-casein (e.g., any of the α-S2-casein proteins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), or transferrin (e.g., any of the transferrin proteins described herein). In some embodiments, the nucleic acid includes a sequence encoding a β-casein and a sequence encoding a κ-casein. The promoter and the additional promoter can be the same or different. The yeast termination sequence and the additional yeast terminal sequence can be the same or different. The signal sequence and the additional signal sequence can be the same or different.

The present invention also encompasses a vector containing the isolated DNA sequence encoding casein or whey polypeptide and host cells comprising the vector. The vector may further comprise an isolated DNA sequence comprising a nucleotide sequence encoding a casein, wherein the nucleotide sequence is operably linked to a promoter, a nucleotide sequence encoding an alpha mating factor, or a variant thereof, a nucleotide sequence encoding a bacterial resistance marker and a transcription terminator. One or more of suitable promoters are utilized for expression of the genes encoding casein or whey proteins may be any promoter which is functional in the host cell and is able to elicit expression of the product encoded by the gene. Suitable promoters include, for example, $P_{LAC4-PB1}$, T7, Ptac, Pgal, λPL, λPR, bla, spa, Adh, CYC, TDH3, ADH1 and CLB1.

Introducing Nucleic Acids into a Cell

Methods of introducing nucleic acids (e.g., any of the nucleic acids described herein) into a cell to generate a host cell are well-known in the art. Non-limiting examples of techniques that can be used to introduce a nucleic acid into a cell include: calcium phosphate transfection, dendrimer transfection, liposome transfection (e.g., cationic liposome transfection), cationic polymer transfection, electroporation, cell squeezing, sonoporation, optical transfection, protoplast fusion, impalefection, hyrodynamic delivery, gene gun, magnetofection, and viral transduction.

One skilled in the art would be able to select one or more suitable techniques for introducing the nucleic acids into a cell based on the knowledge in the art that certain techniques for introducing a nucleic acid into a cell work better for different types of host cells. Exemplary methods for introducing a nucleic acid into a yeast cell are described in Kawai et al., Bioeng. Bugs 1:395-403, 2010.

Host Cells

Also provided herein a host cells including any of the nucleic acids (e.g., vectors) described herein. In some examples, the nucleic acid described herein is stably integrated within the genome (e.g., a chromosome) of the host cell. In other examples, the nucleic acid described herein is not stably integrated within the genome of the host cell.

In some embodiments, the host cell is a yeast strain or a bacterial strain. In some embodiments, the host cell can be, e.g., a yeast strain selected from the group of: a Kluyveromyces sp., Pichia sp., Saccharomyces sp., Tetrahymena sp., Yarrowia sp., Hansenula sp., Blastobotrys sp., Candida sp., Zygosaccharomyces sp., and Debaryomyces sp. Additional non-limiting examples of yeast strains that can be used as the host cell are Kluyveromyces lactis, Kluyveromyces marxianus, Saccharomyces cerevisiae, and Pichia pastoris. Additional species of yeast strains that can be used as host cells are known in the art.

In some examples, the host cell can be a protozoa, such as, e.g., Tetrahymena thermophile, T. hegewischi, T. hyperangularis, T. malaccensis, T. pigmentosa, T. pyriformis, and T. vorax.

It is an object of the invention to isolate milk protein components by recombinantly expressing them in any of the host cells provided herein.

Methods of Producing a Recombinant Milk Protein and Methods of Making a Micelle

Also provided are methods of producing a recombinant milk protein (e.g., one or more of any of the milk proteins described herein) that is unglycosylated or has a non-mammalian glycosylation pattern that include: culturing any of the host cells described herein in a culture medium under conditions sufficient to allow for secretion of the milk protein that is unglycosylated or has a non-mammalian glycosylation pattern; and harvesting the milk protein that is unglycosylated or has a non-mammalian glycosylation pattern from the culture medium. Suitable culture medium for use in these methods are known in the art. Culture conditions sufficient to allow for secretion of a milk protein are also known in the art. The host cells used in these methods can be any of the host cells described herein. The host cells can include any of the nucleic acids described herein. The recombinant milk protein produced can be one or more of: β-casein (e.g., any of the β-casein proteins described herein), κ-casein (e.g., any of the κ-casein proteins described herein), α-S1-casein (e.g., any of the α-S1 caseins described herein), α-S2-casein (e.g., any of the α-S2-caseins described herein), α-lactalbumin (e.g., any of the α-lactalbumin proteins described herein), β-lactoglobulin (e.g., any of the β-lactoglobulin proteins described herein), lactoferrin (e.g., any of the lactoferrin proteins described herein), transferrin (e.g., any of the transferrin proteins described herein), and serum albumin (e.g., any of the serum albumin proteins described herein). Some of these methods further include isolating (e.g., purifying) the recombinant milk protein from the culture medium. Methods of isolating (e.g., purifying) a recombinant milk protein from a liquid are well-known in the art. Exemplary methods for isolating (e.g., purifying) recombinant milk proteins are described in Imafidon et al., Crit. Rev. Food Sci. Nutrition 37:663-669, 1997).

Also provided are methods of producing a micelle including a β-casein (e.g., any of the β-casein proteins described herein) that is unglycosylated or has a non-mammalian glycosylation pattern and a κ-casein (e.g., any of the κ-casein proteins described herein) that is unglycosylated or has a non-mammalian glycosylation pattern, that include: culturing any of the host cells described herein in a culture medium under conditions sufficient to allow for release of the micelle from the host cell, where the host cell comprises nucleic acid including a sequence that encodes a β-casein and a sequence that encodes a κ-casein; and harvesting the micelle from the culture medium. Suitable culture medium for use in these methods are known in the art. The host cells used in these methods can be any of the host cells described herein. The host cells can include any of the nucleic acids described herein. The micelles produced can be any of the micelles described herein (and can have any of the physical characteristics of micelles described herein). Some of these methods further include isolating (e.g., purifying) the micelle from the culture medium. Methods of isolating (e.g., purifying) a micelle from a liquid are well-known in the art (e.g., ultracentrifigation).

Exemplary details of culturing yeast host cells are described in Idiris et al., *Appl. Microbiol. Biotechnol.* 86:403-417, 2010; Zhang et al., *Biotechnol. Bioprocess. Eng.* 5:275-287, 2000; Zhu, *Biotechnol. Adv.* 30:1158-1170, 2012; Li et al., *MAbs* 2:466-477, 2010.

It is an object of the invention to express one or more different forms of casein for application into various types of dairy substitute products. Casein subunits such as α-s1-casein, α-s2-casein, β-casein and κ-casein differ by one or more amino acid changes. In certain embodiments, the methods and compositions comprise incorporation of bovine casein such as α-s1-casein, α-s2-casein, β-casein and κ-casein. In other embodiments, the methods and compositions comprise incorporation of human casein such as β-casein and κ-casein. See U.S. Pat. No. 5,942,274. In alternative embodiments, casein is selected from one or more following sources including but not limited to: bovine, human, buffalo, camel, goat, sheep, horse, dolphin, whale, mountain goat and pig.

Also provided are methods for producing the milk protein components that can include, e.g., using a plasmid or construct of the invention as described in Example 1. This method comprises preparing the plasmid of interest, inserting the plasmid into an appropriate host cell, culturing the host cell for a suitable time and under suitable conditions such that the protein of interest is expressed, and then purifying the protein.

Proteins can be separated on the basis of their molecular weight, for example, by size exclusion chromatography, ultrafiltration through membranes, or density centrifugation. In some embodiments, the proteins can be separated based on their surface charge, for example, by isoelectric precipitation, anion exchange chromatography, or cation exchange chromatography. Proteins also can be separated on the basis of their solubility, for example, by ammonium sulfate precipitation, isoelectric precipitation, surfactants, detergents or solvent extraction. Proteins also can be separated by their affinity to another molecule, using, for example, hydrophobic interaction chromatography, reactive dyes, or hydroxyapatite. Affinity chromatography also can include using antibodies having specific binding affinity for the protein, nickel NTA for His-tagged recombinant proteins, lectins to bind to sugar moieties on a glycoprotein, or other molecules which specifically binds the protein.

Generally, centrifugation at an optimum pH yields purification efficiency >95%. Isoelectric point for the native caseins and whey proteins are known. In nature, the pH is 4.91 for bovine α-s1-casein, pH 4.1 for bovine α-s2-casein, pH 4.5 for bovine β-casein, pH 4.1 for bovine κ-casein, pH 4.2 for bovine α-lactalbumin, and pH 5.2 for bovine β-lactoglobulin. The recombinantly produced casein and whey can differ in terms of its phosphate groups and sugar groups. Other methods for protein purification include membrane filtration to remove any potential bacteria or contaminants, followed by lyophilization for protein isolation.

Preferably, the methods and compositions provide for a production cost that is competitive at or below $1,000/kg, $500/kg, $10/kg, $1.0/kg, $0.10/kg, $0.010/kg or $0.0010/kg of milk protein component. In more preferred embodiments, the cost is below $0.009, $0.007, $0.006, $0.005/kg of milk protein component.

Methods of Supplementing a Mammal-Produced Milk

Also provided herein are methods of supplementing a mammal-produced milk that include providing a mammalian-produced milk or a processed mammalian-produced milk; and mixing into the milk at least one of: a β-casein protein (e.g., any of the β-casein proteins described herein) that is unglycosylated or has a non-mammalian glycosylation pattern; a κ-casein protein (e.g., any of the κ-casein proteins described herein) that is unglycosylated or has a non-mammalian glycosylation pattern; and a micelle (e.g., any of the micelles described herein) comprising a β-casein protein (e.g., any of the β-casein proteins described herein) that is unglycosylated or has a non-mammalian glycosylation pattern, and a κ-casein protein (e.g., any of the casein proteins described herein) that is unglycosylated or has a non-mammalian glycosylation pattern.

One or more of the β-casein protein, the κ-casein protein, and the micelles can be mixed into the milk to achieve any of the exemplary final concentrations of the β-casein protein, the κ-casein protein, and the micelles in a composition described in the section called "Supplemented Milk Compositions" herein. Methods of mixing are well known in the art. As one of skill in the art can appreciate, additional components described herein can also be mixed into the milk (e.g., any component described herein without limitation).

Methods of Making a Composition

Also provided are methods of producing a composition that include: sonicating a liquid including a protein mixture comprising β-casein protein (e.g., any of the β-casein proteins described herein) and casein κ protein (e.g., any of the κ-casein proteins described herein), or including micelles comprising β-casein protein (e.g., any of the 3-casein proteins described herein) and κ-casein protein (e.g., any of the κ-casein proteins described herein); mixing ash (e.g., any of the ash described herein) into the liquid; adding to the liquid a mixture of one or more lipids (e.g., any of the one or more liquids described herein), one or more flavor compounds (e.g., any of the one or more flavor compounds described herein), and one or more color balancing agents (e.g., any of the one or more color balancing agents described herein), and sonicating the liquid; and adding to the liquid one or more sweetening agents (e.g., one or more of any of the sweetening agents described herein), thereby producing the composition.

In some examples of these methods, the β-casein protein is unglycosylated or has a non-mammalian glycosylation pattern, and/or the κ-casein protein is unglycosylated or has a non-mammalian glycosylation pattern. In some examples of these methods, the ash includes one or more of: calcium, phosphorus, potassium, sodium, citrate, and chloride. In some examples of any of these methods, the ash added includes one or more (e.g., two or three) of $CaCl_2$), $KH_2PO_4$, and $Na_3$ citrate.

In some examples of these methods, the one or more lipids comprises at least one (e.g., two, three, four, five, six, or seven) of: sunflower oil, coconut oil, tributyrin, mono- and di-glycerides, free fatty acids, and phospholipids. In some examples of these methods, the free fatty acids comprise at least one fatty acid selected from the group of: butyric acid, caproic acid, caprylic acid, and capric acid. In some examples of these methods, the phospholipids are soy lecithin phospholipids, sunflower lecithin phospholipids, cotton lecithin phospholipids, or rapeseed lecithin phospholipids. In some embodiments of these methods, the flavor compounds include at least one (e.g., two, three, four, five, or six) flavor compound selected from the group of: δ-decalactone, ethyl butyrate, 2-furyl methyl ketone, 2,3-pentanedione, γ-undecalactone, and δ-undecalactone.

In some examples of these methods, the one or more coloring balancing agent is β-carotene or annatto. In some embodiments of these methods, the one or more sweetening agents is a saccharide (e.g., glucose, mannose, maltose, fructose, galactose, lactose, sucrose, monatin, or tagatose) or an artificial sweetener (e.g., stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

The pH of the resulting composition can be between about pH 6.2 and about pH 7.4 (e.g., about 6.2 to about 7.2; about 6.2 to about 7.0, about 6.2 to about 6.8, about 6.2 to about 6.6, about 6.2 to about 6.4, about 6.4 to about 7.2, about 6.4 to about 7.0, about 6.4 to about 6.8, about 6.4 to about 6.6, about 6.6 to about 7.2, about 6.6 to about 7.0, about 6.6 to about 6.8, about 6.8 to about 7.2, about 6.8 to about 7.0, or about 7.0 to about 7.2).

In any of these methods, the β-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth β-casein protein; and/or the κ-casein protein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth κ-casein protein.

In some embodiments of these methods, the protein mixture further comprises one or more proteins selected from the group of: α-lactalbumin (e.g., any of the α-lactalbumin proteins described herein), β-lactoglobulin (e.g., any of the β-lactoglobulin proteins described herein), α-S1-casein (e.g., any of the α-S1-casein proteins described herein), α-S2-casein (e.g., any of the α-S2-casein proteins described herein), lactoferrin (e.g., any of the lactoferrin proteins described herein), transferrin (e.g., any of the transferrin proteins described herein), and serum albumin (e.g., any of the serum albumin proteins described herein).

As one of skill in the art can appreciate, the amount of each component used in these methods can be calculated in order to produce any of the compositions described herein.

Methods of Making Butter, Cheese, Caseinate, or Yogurt

Also provided herein are methods of making butter, cheese, caseinate, or yogurt that include providing any of the compositions provided herein; and producing the butter, cheese, caseinate, or yogurt using any of the composition provided herein as a starting material.

Methods for making butter, cheese, caseinate, or yogurt are well-known in the art. See, e.g., Scott, Cheesemaking Practice, Kluwer Academic/Plenum Publishers, New York, NY, 1998; U.S. Pat. No. 4,360,535 (which describes methods of making creams); U.S 285,878 (which described methods of making butter);

Kits

Also provided are kits that include: (a) a mixture of one or more milk proteins (e.g., any of the milk proteins described herein, including any one or more of the β-casein proteins, κ-casein proteins, α-S1-proteins, α-S2-proteins, α-lactalbumin proteins, 0-lactoglobulin proteins, lactoferrin proteins, transferrin proteins, and serum albumin proteins described herein), one or more lipids (e.g., any of one or more of the lipids described herein), and one or flavor compounds (e.g., any one or more of the flavor compounds described herein); and (b) a mixture of ash (e.g., any of the ash described herein) and at least one sweetening agent (e.g., any one or more of the sweetening agents described herein). In some examples of these kits, the one or more milk proteins are cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth milk proteins.

In some examples of these kits, the one or more fats are selected from the group of: sunflower oil, coconut oil, tributyrin, mono- and di-glycerides, free fatty acids, and phospholipids. The fatty acids present in the kit can include at least one fatty acid selected from the group of: butyric acid, caproic acid, caprylic acid, and capric acid. The phospholipids in the kit can be soy lecithin phospholipids, sunflower lecithin phospholipids, cotton lecithin phospholipids, or rapeseed lecithin phospholipids.

The flavor compounds in the kit can include at least one flavor compound selected from the group of: δ-decalactone, ethyl butyrate, 2-furyl methyl ketone, 2,3-pentanedione, γ-undecalactone, and δ-undecalactone.

In some embodiments of the kit, the mixture in (a) further includes one or more color balancing agent (e.g., any of the color balancing agents described herein, e.g., 3-carotene or annatto).

In some examples of the kits, the one or more sweetening agents is a saccharide (e.g., glucose, mannose, maltose, fructose, galactose, lactose, sucrose, monatin, or tagatose) or an artificial sweetener (e.g., stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihyrdochalcone, neotame, or P-4000).

The kits can include an ash including one or more of: calcium, phosphorus, potassium, sodium, citrate, and chloride. In some examples, the ash in the kit includes one or more (e.g., two or three) of $CaCl_2$, $KH_2PO_4$, and $Na_3$ citrate.

In some embodiments of the kits, the mixture in (a) is provided in a light-sealed and airtight package (e.g., a metal foil, e.g., an aluminum foil), and/or the mixture in (b) is provided in an airtight package (e.g., a sealed plastic bag).

Some examples of the kits further include instructions for making any of the compositions described herein.

Also provided herein are kits including at least one nucleic acid described herein.

Modulating Flavor Profiles

Sensory impressions such as "feed," "barny," or "unclean," are described as flavor descriptions that are absorbed from the food ingested by the cow and from the odours in its surroundings. Others develop through microbial action due to growth of bacteria in large numbers. Chemical changes can also take place through enzyme action, contact with metals (such as copper), or exposure to sunlight or strong fluorescent light. Quality-control directors are constantly striving to avoid off-flavors in milk and other dairy foods. It is, therefore, an object of the invention to reduce, eliminate or even mask the undesirable flavors and odor of various dairy products.

In certain preferred aspects of the present invention, varying the fat content can alter the flavors and odor of various dairy substitute products. For example, increasing the butyric acid content can change a flavor profile of a non-dairy cheese to a flavor profile similar to parmesan cheese. In other embodiments, modulating the triglycerides such caproic, capric, and/or caprylic acid results in a flavor profile similar to goat cheese. Accordingly, modulating the triglycerides with the ratios of fatty acid components provides different flavor profiles that can be fine-tuned to resemble those of various desirable dairy-food products.

Similarly, the methods and compositions provide for minimizing one or more undesirable aromas by modulating various triglycerides incorporated into the dairy substitute products.

In certain aspects flavor profile is modulated by incorporating synthetic short-chain triglycerides combined with plant-based oils e.g., sunflower oil, in desired combinations. For example a mixture of [C18 C18 C6] and [C18 C6 C18] provides a different flavor profile than a mixture of [C18 C4 C4] and [C18 C10 C10].

Dairy Substitute Products

A wide variety of dairy substitute products can be made using the methods and compositions of the present invention. Such products include without limitation, milk, whole milk, buttermilk, skim milk, infant formula, condensed milk, dried milk, evaporated milk, butter, clarified butter, cream and various types of cheese.

The dairy substitute products can also be incorporated into various food applications as a replacement for dairy products, which include the following ice cream, frozen custard, frozen yogurt, cookies, cakes, cottage cheese, cream cheese, creme fraiche, curds and yogurt.

In certain aspects, the present invention provides one or more subunits of casein selected from α-s1-casein, α-s2-casein, β-casein and κ-casein for the milk protein component in a dairy substitute product. A select combination of casein subunits are used as the primary or at least a part of the milk protein component. In preferred embodiments, the casein composition comprises the following amounts of casein subunits such that about 12-15 g/L α-s1-casein, about 3-4 g/L α-s2-casein, about 9-11 g/L β-casein and about 2-4 g/L κ-casein represent the total casein in a synthetic milk product.

In various embodiments, the casein compositions can comprise about 0.5% about 1%, about 1.5%, about 2%, about 2.5%, about 3%, about 3.5%, about 4%, about 4.5%, about 5%, about 6%, protein by dry weight or total weight.

In some embodiments, the casein compositions can comprise about 0.5-2.5%, about 1-2%, about 2-3%, or about 4-10% casein protein by dry weight or total weight. In particular embodiments, the casein compositions can comprise about 1.5-10% protein by dry weight or total weight.

In certain aspects, the methods and compositions of the dairy substitute products are essentially free of one or more serum proteins. Serum proteins typically comprise, among other proteins, enzymes, hormones, growth factors, nutrient transporters and disease resistance factors. In additional embodiments, the methods and compositions of the dairy substitute products are essentially free of one or more immunoglobulins, which may induce an undesirable immune response.

In some embodiments, whey compositions can comprise about 0.001%, about 0.05%, about 0.1%, about 0.5%, about 1%, about 1.5%, about 2%, about 2.5%, about 3%, about 3.5%, about 4% whey protein by dry weight or total weight. In some embodiments, the compositions can comprise about 0.1-1%, about 1-2%, about 2-3%, or about 0.1-2.3% protein by dry weight or total weight. In particular embodiments, the compositions can comprise about 10-15% protein by dry weight or total weight.

In various embodiments, carbohydrates are incorporated into the dairy substitute products. These carbohydrates provide a bland sweetness to the flavor profile of the product and additionally serve as a fast-acting energy and nutrition source. Carbohydrates include but are not limited to sugars such as galactose, sucrose, glucose, fructose and maltose. Dairy-free sources of sugars include but are not limited to sugar beet and other plants such as celery, basil, honey, cherries, corn, spinach, plums, kiwis and peas.

Lactose intolerance is common for many milk consumers. Accordingly, in preferred embodiments, carbohydrates such as lactose are omitted from the dairy substitute composition. In preferred embodiments, methods and compositions of the dairy substitute composition essentially free of lactose.

In some embodiments, the carbohydrate compositions can comprise about 1%, about 1.5%, about 2%, about 2.5%, about 3%, about 3.5%, about 4%, about 4.5%, about 5% carbohydrate by dry weight or total weight. In some embodiments, the compositions can comprise about 1-3%, about 2-4%, or about 10-30% carbohydrate by dry weight or total weight. In particular embodiments, the compositions can comprise about 2-5% carbohydrate by dry weight or total weight.

Ash attributes to the structure and stability of casein micelles. Ash is important for holding the emulsion that is milk or cream together. The calcium and phosphate present in the ash interact with the fat globules and the casein micelles to maintain an emulsified mixture.

The ash also affects the sensory characteristics such as mouthfeel, consistency, and to a certain extent, the flavor of the milk.

In some embodiments, the ash compositions can comprise about 0.1%, about 0.2%, about 0.3%, about 0.4%, about 0.5%, about 0.6%, about 0.7%, about 0.8%, about 0.9%, about 1%, about 2% or about 3% ash by dry weight or total weight. In some embodiments, the compositions can comprise about 0.1-0.3%, about 0.5-0.7%, about 0.7-1%, or about 1-2% ash by dry weight or total weight. In particular embodiments, the compositions can comprise about 0.6-0.8% protein by dry weight or total weight.

Additional ingredients for various animal-free dairy products include vitamins, flavoring agents, natural or artificial sweeteners, coloring agents, salt, pH adjustment agents, binders, buffers, stabilizers, essential amino acids, anti-caking agents, anti-foaming agents, and mixtures thereof.

In some embodiments, the remaining ingredient compositions can comprise about 0%, about 0.01%, about 0.1%, about 0.5%, about 1%, about 2%, about 3%, about 4% or about 5% additives by dry weight or total weight. In some embodiments, the compositions can comprise about 0.001-0.01%, about 0.01-1%, about 0.01-2%, or about 1-5% additives by dry weight or total weight. In particular embodiments, the compositions can comprise about 0-10% additives by dry weight or total weight.

In some aspects, the present invention provides methods and compositions for dairy substitutes with fat comprising varying levels of triglyceride content. In preferred embodiments, isolated triglycerides from various plant sources are incorporated with milk protein components, carbohydrates and ash. It is an object of the present invention to modulate the fatty acids isolated in plants and transesterified in a dairy substitute to resemble the percentage of fatty acids found in natural dairy products, and/or to develop novel flavor profiles with improved flavor not found in nature. In some embodiments, modulating specific short-to-medium chain fatty acids including but not limited to s butyric, capric, caprylic, caproic and lauric acids provides the desired flavor profile in a dairy substitute.

In some embodiments, the fat compositions in synthetic milk comprises about 0%, about 1%, about 2%, about 3%, about 3.5%, about 4% fat by dry weight or total weight. In some embodiments, the compositions can comprise about 1-2%, about 2-3%, about 34% fat by dry weight or total weight. In particular embodiments, the compositions can comprise about 34% fat by dry weight or total weight. In alternative embodiments, fat compositions in cream can comprise about 10%, about 20%, about 30%, about 40%, about 50% or even 60%. Preferably, fat compositions in cream is typically about 40 to about 50%.

In some aspects, the short-chain triglycerides are combined with longer chain oil to produce transesterified fatty acid esters. Preferably, the longer chain oils are selected from: sunflower, corn, olive, soy, peanut, walnut, almond, sesame, cottonseed, canola, safflower, flax seed, palm, palm kernel, palm fruit, coconut, babassu, shea butter, mango butter, cocoa butter, wheat germ and rice bran oil. More preferably, the longer chain oils comprise engineered sunflower varieties, which overexpress oleic acid by 400%.

Longer chain oil can also provide to the flavor profile, for example, reduce or even remove sharpness and mellow out the overall flavor profile of the desired end product.

In some embodiments, the fat component of the dairy substitute comprises select triglycerides that are transesterified into longer chain oil such as high-oleic sunflower oil (Example 2). It is contemplated that the same four short chain fatty acids give milk and derivative products such as cheese their particular flavors such as robustness and richness. Various combinations of triglycerides and longer chain oils are incorporated to create a number of different flavor profiles. In one embodiment, triglyceride with three oleic acids and synthetic short-chain triglyceride with, in this case, one butyric, one hexanoic, and one octanoic acid, yields a desired synthetic "milk fat" triglyceride. Additional embodiments include incorporating various short-chain triglycerides to tune slightly different flavor profiles, for instance, short-chain triglyceride comprising hexanoic acid; short-chain triglyceride comprising hexanoic acid and butyric acid; short-chain triglyceride comprising hexanoic acid and decanoic acid. Accordingly, methods and compositions provide for various combinations of synthetic short-chain triglycerides with the sunflower oil triglycerides resulting in different flavor profiles.

Synthetic Milk

An exemplary embodiment of synthetic milk formulation comprising microbially derived proteins of the present invention is illustrated in Example 4. For example, the present formulation incorporates all four subunits of bovine casein: α-s1-casein, α-s2-casein, β-casein and κ-casein and two whey proteins α-lactalbumin and β-lactoglobulin as the predominant milk protein components in the formulation. The exemplary synthetic milk formulation further comprises plant-based interesterified fats as shown in FIG. 1. Additional components include carbohydrates and ash. The resulting milk substitute exhibits characteristics that looks, functions, tastes, smells, and feels like natural milk. As one of key facets of the present invention, modifying the formulations for synthetic milk can exhibit different sensory impressions such as flavoring by modulating the oil content, namely the types of triglycerides added to mimic milk of different flavors.

As described in Young W. Park, Bioactive Components in Milk and Dairy Products, Technology & Engineering, pp 60, 2009, sterols are a minor fraction of total lipids in milk, the main sterol being cholesterol (300 mg/100 g fat, equivalent to 10 mg/100 mL bovine milk) (Park et al., *Small Rumin. Res.* 68: 88-113, 2007). Goat milk has been shown to contain less cholesterol than other milk but generally contains higher total fat than cow milk. See, Posati et al., 1976. Composition of Foods. Agric. Handbook No. 8-1. ARS, USDA, Washington, D.C., 1976; Jenness, *J. Dairy Sci.* 63:1605-1630, 1980; and Juarez et al., Intl. Dairy Fed. Bull. No. 202. pp. 54-67, 1986, have shown that goat milk has greater palmitic and oleic acid fractions than cows. Cholesterol content was significantly varied among different breeds and most cholesterol in goat milk was in free state, with only a small fraction in ester form 52 mg/100 g fat. See, e.g., Arora et al., Ind. J. Dairy Sci. 29: 191.

In certain embodiments, the methods and composition of the present invention provide synthetic milk product that has less cholesterol, or is cholesterol free or has the same cholesterol content in comparison to the dairy milk by modulating the oil content, namely the types of triglycerides. In other embodiments, the amount of saturated and unsaturated fats is also modulated in dairy substitutes to at least less or the same amount of fats in comparison to the dairy milk. In preferred embodiments the synthetic milk product of the present invention is very low in saturated fat but smells and tastes like dairy milk. The long chain fatty acids, which are typically saturated fatty acids in milk, are instead monounsaturated acids such as oleic acid, in the preferred embodiments of the invention.

The present invention may not require or at least minimizes pasteurization, as each component can be rendered sterile separately, before combining through the formulation process. In other embodiments of the invention, synthetic milk product of the present invention can undergo pasteurization.

Homogenization is optional for the methods and compositions of the present invention as is the case for natural milk. When sold as a standalone liquid beverage, the synthetic milk product of the present invention can be sold in homogenized form.

Differences between the milk substitute of the present invention with dairy milk include flavor, nutritional value and storage stability. Flavorings can be adjusted to a desired sensory impression based on triglycerides as well as other natural or artificial flavors that can impart in blandness or sharpness or a different aroma such as cow, goat, coconut, almond or soy.

Synthetic Cheese

In other aspects of the present invention, methods and compositions comprising one or more isolated milk protein components, fats, carbohydrates and ash are provided to produce various types of cheese products. Generally, the cheese is made from the milk protein components of the present invention. One or more sensory impressions are incorporated into the cheese product through modulating the triglycerides. Accordingly, cheese with desired organoleptic characteristics with distinct appearance, aroma, taste and texture can be produced. For some cheese varieties, in addition to modulating the triglycerides, one or more bacteria is employed in the cheese making process for fermentation where fermentative products and by-products such as lactic acid, carbon dioxide, alcohols, aldehydes and ketones are produced. Types of cheese include whey cheese such as ricotta and mozzarella, semi-soft cheese include Havarti and Munster, medium-hard cheese such as Swiss and Jarlsberg, hard cheese such as Cheddar and soft ripened cheese such as Brie and Camembert.

Synthetic Cream

Directly usable cream substitutes should preferably comprise from about 50 to 90% by weight water, and more preferably from about 65 to 80% by weight water, with the base being dispersed within the water. The base for a substitute cream should advantageously contain (all percentages computed using the total weight of the base taken as 100%) from about 22 to 87% by weight carbohydrate (more preferably from about 30 to 64%), from about 12 to 70% by weight of particulate fat (most preferably from about 28 to 60%), and from about 0.4 to 8% by weight of a selected emulsifier or group thereof (most preferably from about 1 to 4%).

In preferred embodiments, the products of the invention are stable in aqueous emulsion. As used herein, a dried, liquid fat-containing non-dairy food product is said to be "stable" when the following minimum criteria are met: reconstituted emulsion stability, whitening capability, oiling or oil separation, feathering-precipitation. See U.S. Pat. No. 4,310,561.

Synthetic Butter

Commercial butter is 80-82% milk fat, 16-17% water, and 1-2% milk solids other than fat (sometimes referred to as curd).

Advantages of Dairy Substitute Products or the Compositions Provided Herein

Desirable advantages of the present invention are environmental in nature such as 8 times more energy efficient, 260 times more water efficient than conventional milk product. Other environmental advantages include less water usage than conventional milk production, which is estimated to be about 1000 L/L and reduced land usage for conventional milk production typically requires grazing, crop land, ability to reduce the 600 billion kg of carbon dioxide per year that is emitted from conventional milk production. The present invention also provides reduction or elimination of costs of feed, operations, labor, animal and marketing. Preferably, substantially reduce feed cost by a factor of 8.

Advantages in food safety include reduction or removal of antibiotic residues, heavy metals, bacteria, adulterations. Accordingly, certain aspects of the present invention provide animal-free milk that is bacteria-free, requires no pasteurization or cold shipping yet has an increased shelf-life and exhibit a number of characteristics such as taste, appearance, handling and mouth feel properties which are identical or at least closely similar to their traditional dairy counterparts. Preferably, the dairy substitute products are essentially free of bacteria such as Brucella, Camplyobacter, Listeria, Mycobacterium, Salmonella, Shigella, Yersinia, Giardia and noroviruses, and, thus are safer for consumption. Further advantage include minimal or no pasteurization and/or homogenization. More preferably, the dairy substitute is shelf stable for relatively long periods (e.g., at least three weeks and preferably longer) for production and distribution. Even more preferably, the dairy substitute products has a lower environmental impact.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods.

EXAMPLES

Example 1

Vectors

Protein sequences bovine α-S1 casein (UniProt accession #P02662), bovine α-2 casein (UniProt accession #P02663), bovine β-casein (UniProt accession #P02666), bovine κ-casein (UniProt accession #P02668), bovine α-lactalbumin (UniProt accession #B6V3I5) and bovine β-lactoglobulin (UniProt accession #P02754) were obtained on Uniprot.org and altered with the following changes: removed 15 or 21-residue signal peptide from N-terminal end; added XhoI (CTC GAG) endonuclease recognition sequence and KEX endopeptidase recognition sequence (AAA AGA) to 5' end of DNA; and added SalI (GTC GAC) endonuclease recognition sequence to 3' end of DNA. An additional combination sequence was made by combining the sequences for the four caseins in the order shown above, separating each sequence with the following DNA phrase:

(SEQ ID NO: 128)
GGC TCA GGA TCA GGG TCG AAA AGA GGC TCA GGA TCA
GGG TCG.

Here the non-underlined segments encode a (GS)$_6$ linker sequence for adequate posttranslational spacing and accessibility to the KEX protease, and the underlined segment encodes the KEX endopeptidase sequence which cleaves the proteins apart post-translation. As above, the entire cassette is flanked on the 5' end by XhoI and on the 3' end by SalI for ligation into pKLAC2 (New England Biolabs, Beverly, MA). DNA was synthesized by either Gen9, Inc. (Cambridge, MA) or IDT (Coralville, IA). The plasmid used had, among other things, a multiple cloning site, a Lac promoter, an Acetamide based reporter gene and the alpha-mating factor gene, used as a fusion protein for secretion of exogenous proteins.

Yeast Transfection

Transfection of the yeast was accomplished by thawing a tube of 0.5 mL competent cells containing 25% glycerol on ice and adding 0.62 mL yeast transfection reagent. The mixture was then warmed at 30° C. for 30 minutes, heat shocked at 37° C. for 1 hour. The cells were then pelleted at 7000 rpm & washed twice with 1.0 mL of YPGal medium.

The cell mixture was then transferred to a sterile culture tube and incubated at 30° C. for 3 hours, with constant shaking at 300 rpm. The cell mixture was then transferred to a sterile 1.5 mL microcentrifuge tube and pelleted the cells at 7000 rpm for 2 minutes, and resuspended in 1 mL sterile 1×PBS. 10, 50 and 100 µL of the cell suspension was placed into separate fresh sterile 1.5 mL microcentrifuge tubes each containing 50 µL of sterile deionized water. Tubes were mixed briefly and spread onto separate yeast carbon base agar (YCB Agar) plates containing 5 mM acetamide for selection. Plates were then incubated, inverted, at 30° C. for 4 days until colonies form. 15 individual colonies were then streaked onto fresh YCB Agar plates containing 5 mM acetamide and incubated at 30° C. for 2 days.

DNA encoding alpha-lactalbumin and beta-lactoglobulin, two key whey proteins, was designed in-house and ordered for synthesis from IDT and was transfected into competent *K. lactis* cells from the New England Biolabs kit (Catalog #E1000S) according to the vendor-supplied protocol.

High-Throughput Transfectant Selection

From each YCB Agar plate, once the colonies had grown sufficiently, each of the 30 plates was tested for successful integration of the vector plasmid. This was followed by PCR analysis of each plate to test for special cells with multiple integrants of the vector. Once isolated, the highest producing individual culture was used for scale up. This process can be iterated with successively higher concentrations of selective pressure in order to force colonies to develop higher copy numbers of our engineered plasmid.

Five transfection events were performed and plated on 5 separate plates consisting of nitrogen-free yeast carbon base medium. (Any observed growth on these plates therefore implied successful uptake of the plasmid, if not uptake of the exogenous DNA itself). Of these 5 plates, 100% showed positive growth. 30 individual colonies from the 5 plates were chosen for scale-up, and each was grown in a separate YCB agar plate to create a homozygous culture plate to allow for easy characterization and management. After a 3 day growth period, a single colony from each plate was initially added to a 10 ml glass culture tube, containing 2 ml YPGal media, to test for protein expression. After a growth period of two days, the cells were pelleted out and the supernatant was run on an SDS PAGE gel to check for protein expression. The strains which provided the best protein expression were scaled up to a 10 ml, 100 ml, 500 ml, and ultimately 1 L culture vessel. From each whey protein, two liters of culture were grown. Approximately one gram of protein was harvested from the total, suggesting a non-optimized yield/productivity of 0.5 g/L.

Scale-Up in 1 L Shake Flask Culture

Cultures are scaled up and seeded in a 1 L shake flask at split ratios of at least 1:10. Prior to seeding, inoculation flasks are grown for 24 hours in production media without acetamide supplementation. On the starting day of a fed-batch production run, the reactor is charged with 90% of the target starting volume and heated to the run temperature. For now, the temperature is set at 30° C. in order to save on energy costs associated with heating the reactor. Additional parameters can be explored in the process optimization phase. When the reactor reaches 30° C., the inoculation flask is added to the reaction vessel dropwise using a peristaltic pump. The reactor is maintained using vendor supplied software at a target pH. Twice daily samples are taken of the reactor broth in order to quantify the amount of glucose and electrolyte usage by the cells, and as a doublecheck for the reactor's pH and dissolved gas measurements. After each measurement, bolus glucose is added to maintain a target glucose concentration 10% to start, although this may also be altered in process development. When cells reach maximum density, protein production is triggered by the addition of galactose, which triggers the promoter on our pKLAC2 plasmid. Galactose is supplemented until the end of the run. Optimum run length can be determined in process development as well, but is set as a 5-day fedbatch. After a full run, yeast cells are removed from the reactor and the proteins are purified as discussed below.

Casein Protein Purification

The following casein proteins α-s1casein, α-s2casein, and β-casein are inherently hydrophobic, which precipitate out when secreted from the yeast and come into contact with water. Purification from the reactor media involves collection of the protein from the surface of the media, followed by drying to isolate pure protein. Kappa-casein is inherently hydrophilic and purification of the κ-caseins involves the change in pH of the solution to 4.6, followed by centrifugation at 10,000 rcf Combined casein cassette works the same way as κ-casein.

Whey Protein Purification

Alpha-lactalbumin: The isoelectric point of alpha-lactalbumin is 4.2. When the pH of the bioreactor media solution is lowered to 4.2, the solubility of the protein is at its lowest. This knocks the protein out of solution and allows for collection by centrifugation. Beta-lactoglobulin: Similar to the purification of the alpha-lactalbumin, the pH of the solution is lowered to 5.2 the isoelectric point of beta-lactoglobulin. This neutralizes the charge of the protein and allows its collection by centrifugation at 14,000 rcf.

Protein Purification

Figure 2A:
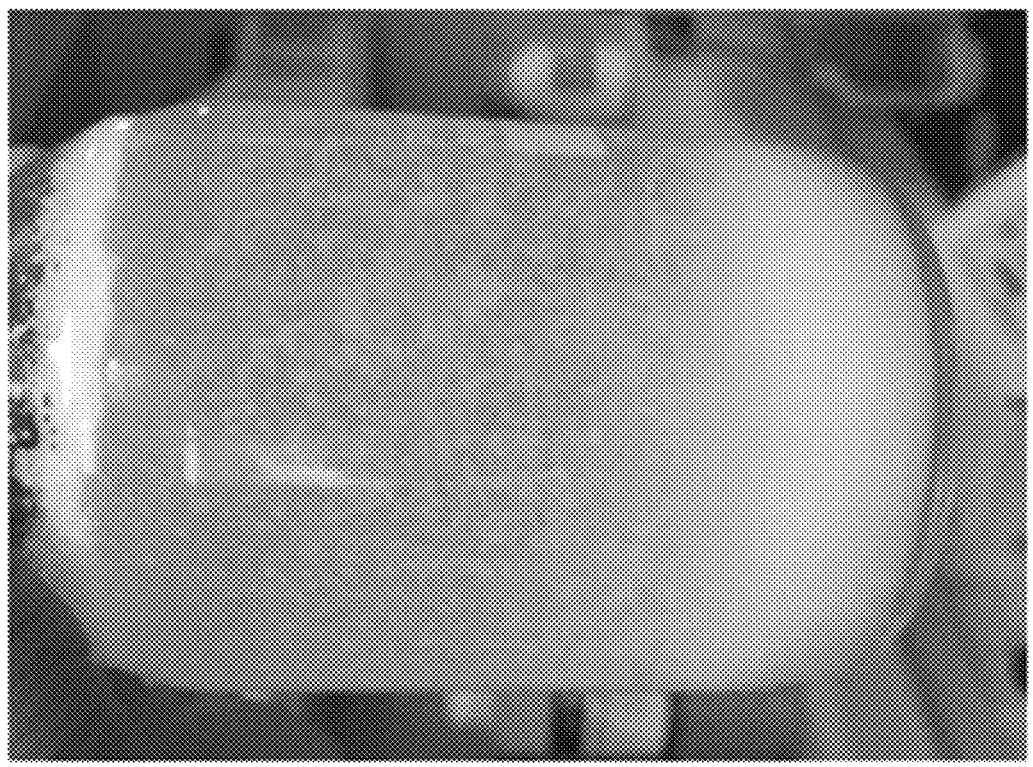
FIG. 2A represents a picture depicting precipitate of an exemplary milk protein component.
Figure 2B:
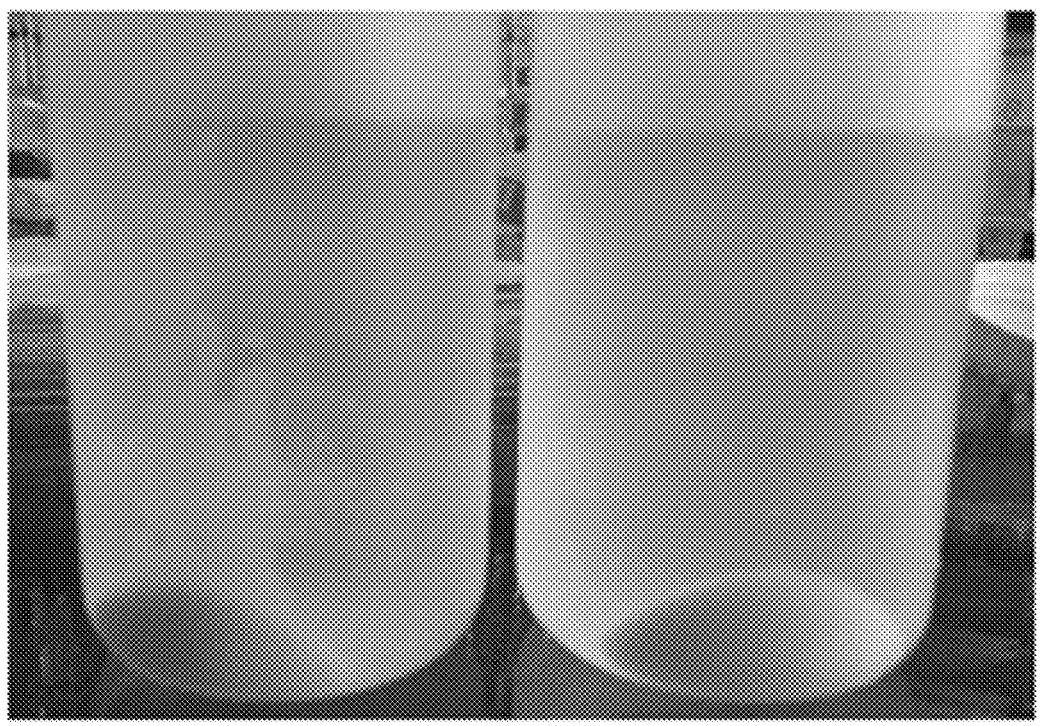
FIG. 2B represents a picture depicting a pellet of an exemplary milk protein component.

The 2 L of culture media was spun at 3,000 g in a floor centrifuge to pellet out the yeast cells. The pellet was discarded, and the supernatant was transferred into a new vessel & the pH of the solution was lowered to 4.2 for the alpha-lactalbumin and 5.2 for the beta-lactoglobulin (FIG. 2A). This was followed by incubation of the supernatant at 35° C. for 30 mins in a shaker flask, centrifugation at 14,000 g in a floor centrifuge to pellet out the protein mixture (FIG. 2B).

Protein Characterization

Figure 3:
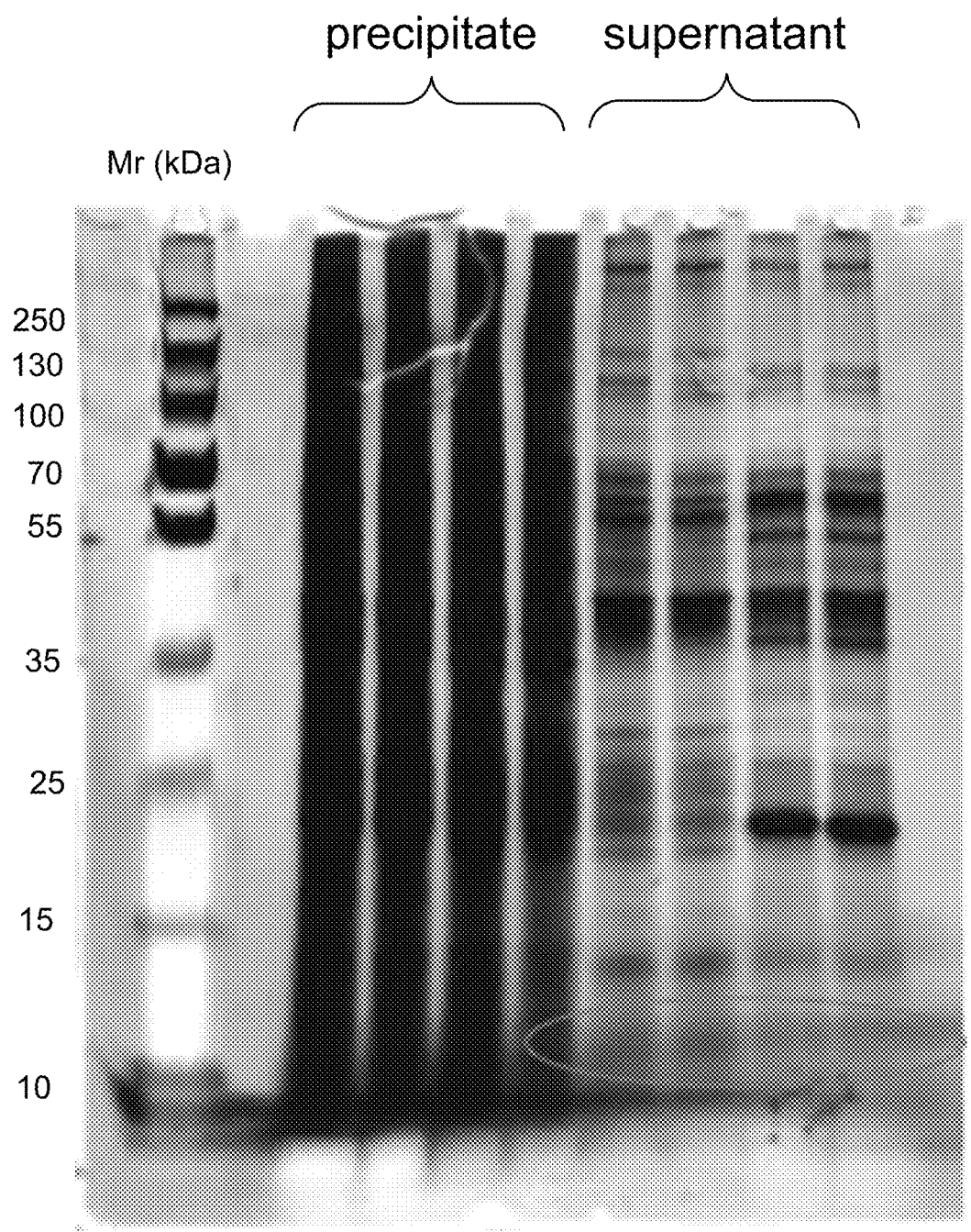
FIG. 3 represents an image of a silver stain SDS-PAGE gel to visualize the milk protein components.

After separation of the protein by centrifugation, the solid pellet and the supernatant solution were run on a 14% SDA-PAGE gel to check for protein expression. A positive band was observed at 14 kDa and at 18 kDa (FIG. 3), which correlates to the size of alpha-lactalbumin and beta-lactoglobulin of bovine origin, respectively. Further characterization is done to confirm equivalence in terms of primary sequence, glycosylation and phosphorylation.

Example 2

Triglyceride Synthesis

Milk fat triglycerides were made by transesterifying short-chain triglycerides into high oleic sunflower oil, the oil from a custom engineered variant of sunflowers which express the following ratios of fatty acid esters as described in Table 1:

TABLE 1

| Fatty Acids | Sunflower† | NuSun Mid-Oleic Sunflower‡ | High-Oleic Sunflower† |
|---|---|---|---|
| C6:0 | ND | ND | ND |
| C8:0 | ND | ND | ND |

TABLE 1-continued

| Fatty Acids | Sunflower† | NuSun Mid-Oleic Sunflower‡ | High-Oleic Sunflower† |
|---|---|---|---|
| C10:0 | ND | ND | ND |
| C12:0 | ND-0.1 | ND | ND |
| C14:0 | ND-0.2 | 0.4-0.8 | ND-0.1 |
| C16:0 | 2.0-7.6 | 4.0-5.5 | 2.6-5.0 |
| C16:1 | ND-0.3 | ND-0.05 | ND-0.1 |
| C17:0 | ND-0.2 | ND-0.05 | ND-0.1 |
| C17:1 | ND-0.1 | ND-0.06 | ND-0.1 |
| C18:0 | 1.0-6.5 | 2.1-5.0 | 2.9-6.2 |
| C18:1 | 14-39.4 | 43.1-71.8 | 75-90.7 |
| C18:2 | 46.3-74.0 | 18.7-45.3 | 2.1-17.0 |
| C18:3 | ND-0.3 | ND-0.1 | ND-0.3 |
| C20:0 | 0.1-0.5 | 0.2-0.4 | 0.2-0.5 |
| C20:1 | ND-0.3 | 0.2-0.3 | 0.1-0.5 |
| C20:2 | ND | ND | ND |
| C22:0 | 0.3-1.5 | 0.6-1.1 | 0.5-1.6 |
| C22:1 | ND-0.3 | ND | ND-0.3 |
| C22:2 | ND-0.3 | ND-0.09 | ND |
| C24:0 | ND-0.5 | 0.3-0.4 | ND-0.5 |
| C24:1 | ND | ND | ND |

ND = not detectable (ND defined as <0.05%)
†From Codex Almentarius (2001)
‡From Table 3 www.sunflowernsa.com/uploads/resources/51/warner_.pdf

Short-Chain Triglyceride Preparation

The short-chain fatty acids which are principally responsible for rich flavor in milk and cream are the molecules with even numbers of carbons between 4 and 10, and are mixed in the following ratios as described in Table 2:

TABLE 2

Table 1. Fatty acid compositon expressed as percent by weight of total fatty acids in Swedish dairy milk in 2001, given as weighted means with standard deviations (SD) and as the minimum and maximum weighted means. The estimation of the weighted mean values was based on the proportion of milk delivered to each dairy or dairy company at each sampling occasion (seven dairies at four sampling occasions during 2001). The lowest and highest values observed and p-values for geographical and seasonal variation are also given

| Fatty acid | Weighted mean 2001 | SD | Lowest value observed | Highest value observed | Seasonal variation |
|---|---|---|---|---|---|
| 4:0 | 4.4 | 0.1 | 4.0 | 5.1 | n.s. |
| 6:0 | 2.4 | 0.1 | 2.1 | 2.9 | n.s. |
| 8:0 | 1.4 | 0.1 | 1.2 | 1.9 | n.s. |
| 10:0 | 2.7 | 0.2 | 2.4 | 3.5 | * |
| 12:0 | 3.3 | 0.2 | 3.0 | 4.1 | ** |
| 14:0 | 10.9 | 0.5 | 10.0 | 12.1 | *** |
| 15:0 | 0.9 | 0.0 | 0.8 | 1.1 | n.s. |
| 16:0 | 30.6 | 0.9 | 28.7 | 34.1 | ** |
| 17:0 | 0.4 | 0.0 | 0.4 | 0.5 | ** |
| 18:0 | 12.2 | 0.4 | 10.3 | 13.3 | n.s. |
| 20:0 | 0.2 | 0.0 | 0.2 | 0.2 | n.s. |
| Saturated fatty acids total | 69.4 | 1.7 | 67.1 | 74.4 | *** |
| 10:1 | 0.3 | 0.0 | 0.2 | 0.4 | n.s. |
| 14:1 | 0.8 | 0.4 | 0.4 | 1.3 | ** |
| 16:1 | 1.0 | 0.0 | 0.9 | 1.8 | n.s. |
| 17:1 | 0.1 | 0.0 | <0.1 | 0.3 | n.s. |
| 18:1 | 22.8 | 1.0 | 19.7 | 24.7 | *** |
| Mono-unsaturated fatty acids, cis, total | 25.0 | 1.0 | 22.2 | 26.7 | ** |
| 18:2 | 1.6 | 0.1 | 1.4 | 1.8 | n.s. |
| 18:3 | 0.7 | 0.0 | 0.6 | 0.9 | ** |
| Poly-unsaturated fatty acids, cis, total | 2.3 | 0.1 | 2.0 | 2.5 | n.s. |
| 16:1t | 0.4 | 0.1 | 0.3 | 0.4 | *** |
| 18:1t | 2.1 | 0.7 | 2.0 | 3.3 | *** |
| 18:2t | 0.2 | 0.0 | 0.1 | 0.5 | n.s. |
| Trans fatty acids total | 2.7 | 0.7 | 0.6 | 3.9 | *** |
| CLA | 0.4 | 0.1 | 0.3 | 0.5 | *** | n.s.: Not significant; *p < 0.05; p < 0.01; *p < 0.001.

www.ncbi.nlm.nih.gov/pmc/articles/PMC2596709/pdf/FNR-52-1821.pdf

TABLE 3

| Chain Length | Names | Mass Fraction in Mixture (%) |
|---|---|---|
| 4 | Butanoic/butyric acid | 40 |
| 6 | Hexanoic/caproic acid | 26 |
| 8 | Octanoic/caprylic acid | 11 |
| 10 | Decanoic/capric acid | 22 |

The fractions in Table 3 are based upon the relative prevalence of these species in cow's milk, but can be altered during process development both in order to design a better tasting product and in order to design milks of other species, such as buffalo or goat. Short-chain fatty acids in the mass ratios shown above are combined with toluene, paratoluenesulfonic acid, and glycerol in a Dean-Stark water trap, commonly used for esterification reactions in order to remove water produced in the condensation reaction. The reaction is carried out in a fume hood for several hours, until the level of water entering the water trap is observed as unchanging for more than 30 minutes. The vessel is allowed to cool and the mixture is removed from the reaction flask. The mixture is washed twice with a 5% sodium carbonate solution and five times with plain water. Brine (a 10% solution of NaCl in water) is added periodically in order to disrupt an emulsion which forms in the separating funnel. The washed mixture of short-chain triglycerides, water, toluene, and impurities is dried in a rotary evaporator at 90° C. and under a 54 mbar atmosphere for one hour, until it has proceeded well past excess in order to minimize the chance of food contamination.

Transesterification

The short-chain triglyceride mixture is combined with high-oleic sunflower oil at a volumetric ratio of 1:8. A mass of sodium methoxide equal to 1% of the oil mixture mass is added in order to catalyze the transesterification, and the reaction vessel is heated to 65° C., stirring continuously, under an inert Argon atmosphere, for six hours. A 5% acetic acid mixture is added to quench the reaction, then the oil is washed five times with deionized water and dried in a rotary evaporator for one hour at >90° C. The finished milk fat is autoclaved to ensure sterility and is thence suitable for use in milk or cream as described above.

Example 3

Milk Formulation

One non-limiting milk composition formulation is described below.

TABLE 4

| Components | % (w/v) Range | Amount (g/L) |
|---|---|---|
| Casein proteins | 1-10 | 10-100 |
| Whey proteins | 0-1 | 0-10 |
| Plant-based milk fats | 0-8 | 0-80 ml/L |
| Sugar | 0-5 | 0-50 |
| Ash | 0.1-1 | 1-10 |
| Calcium | 0.1-0.5 | 1-L |
| X (Functional additive) | 0-1 | 0-10 L |

Following Table 4, milk formulation is achieved through the following procedure, per 1 liter of milk. 26 grams of casein, 3.5 grams of whey and 5 grams of ash are combined and mixed well. 40 mL of triglycerides are thawed & heated to 55° C. Protein mixture is poured slowly into triglycerides and vortexed at high speed for five minutes. In the meantime, 3.5 grams of whey and 24 grams of galactose are added to 850 mL deionized water; mixture is heated to 37° C. Triglyceride/protein/ash mixture is moved into Waring commercial blender and blended at low speed. Whey/galactose/water mixture is poured slowly into blender; cap placed on blender. Mixture is blended at high speed for ten minutes. Deionized water is added to a final volume of 1000 mL. Milk can optionally be homogenized using existing methods. The above protocol can be altered for cream or arbitrary milk formulations by altering the ratios of solids; however, our preliminary research suggests that the presence of ash in the protein mixture and the separation of a significant proportion of the whey can greatly affect the quality of the emulsion.

Example 4

Synthetic Milk Formulation

As a preliminary proof of concept, in order to determine whether the key components of milk could be recombined to form milk, dry food-grade purified casein and research grade whey was purchased. Irish cream was obtained from a local source and pure fat was isolated from it by centrifuging the cream at 14,000 g. Finally, all minerals used were purchased from Sigma Aldrich.

Terms:

C-roux=roux made by mixing casein proteins & fat together while maintaining the temperature of the mixture at 37° C.

W-roux=roux made by mixing whey proteins & fat together while maintaining the temperature of the mixture at 37° C.

CW-roux=roux made by mixing casein & whey proteins together in a mixture first, adding fat and mixing at 37° C.

TABLE 5

| Experiment | Result |
|---|---|
| Casein + Fat + Water | A pale yellow liquid with bad taste, precipitation of protein, and bad mouthfeel (watery). |
| Casein + Water + Fat | A pale yellow liquid with bad taste, precipitation of protein, and bad mouthfeel (watery). |
| (Casein + Fat) to make a roux. roux + Water | A pale yellow liquid with average taste and bad mouthfeel (watery). Low protein precipitation was observed. |

Hypothesized that the bad mouthfeel (e.g., wateriness) was due to the lack of whey protein.

TABLE 6

| Experiment | Result |
|---|---|
| Casein + Whey + Fat + Water | Pale yellow-white liquid with bad taste, precipitation of protein, and bad mouthfeel. |
| C-roux + Whey + Water | Pale yellow-white liquid with average taste, low precipitation of protein, and bad mouthfeel |
| W-roux + Casein + Water | Pale yellow-white liquid with average taste, low precipitation of protein, and bad mouthfeel. |
| CW-roux + Water | Pale yellow-white liquid with average taste and bad mouthfeel. Zero protein precipitation. |

Hypothesized that bad mouth feel was because of bad casein micelle formation, that addition of Ca would allow the micelle to reform.

TABLE 7

| Experiment | Result |
|---|---|
| CW-roux + Water + Calcium phosphate (optimum amount of Ca was figured out by trial & error) | White liquid with normal mouth feel. Zero protein precipitation. Average taste |

To improve taste, different sugars were added in different concentrations to the above mixture.

TABLE 8

| Sugar | 2.4% | 3.0% | 3.6% | 4.2% | 4.8% |
|---|---|---|---|---|---|
| Glucose | Good | Too Sweet | Too Sweet | Too Sweet | Too Sweet |
| Galactose | Bland | Excellent | Average | Excellent | Too Sweet |
| Sucrose | Bad | Bad | Bad | Bad | Bad |
| Maltose | Bland | Excellent | Excellent | Too Sweet | Too Sweet |

All additional ions found in cow milk was incorporated to recreate the ionic environment found in nature.

Reference: R. Rosmaninho, L. F. Melo/Journal of Food Engineering 73 (2006) 379-387

TABLE 9

| Reagent | Composition (mM) |
|---|---|
| $KH_2PO_4$ | 11.60 |
| $K_3$ Citrate $H_2O^a$ | 3.7 |
| $Na_3$ Citrate $2H_2O$ | 6.1 |
| $K_2SO_4$ | 1.03 |
| $K_2CO_3$ | 2.17 |
| KCL | 8.0 |
| $CaCL_2 \cdot 2H_2O$ | 8.98 |

End result was a liquid which was bright white in color, likely because the ionic environment kept the solids present in milk from joining together and increased the overall refractive index of the solution. Taste was excellent, but it had an average mouthfeel (e.g., a certain amount of chalkiness was observed in the liquid). Exact mineral composition as described in Table 9 can provide excellent mouthfeel.

Milk Fat Synthesis

Synthetic milk fat was made by interesterifying short-chain fatty acids among the large-chain fatty acids present in high-oleic sunflower oil triglycerides. The four short-chains used were:

40% C4: Butyric acid. found in milk, especially goat, sheep and buffalo milk, butter, Parmesan cheese, and as a product of anaerobic fermentation (including in the colon and as body odor). It has an unpleasant smell and acrid taste, with a sweetish aftertaste (similar to ether). Butyric acid is present in, and is the main distinctive smell of, human vomit.

26% C6: Caproic acid. a colorless oily liquid with an odor that is fatty, cheesy, waxy, and like that of goats or other barnyard animals.

11% C8: Caprylic acid. It is an oily liquid that is minimally soluble in water with a slightly unpleasant rancid-like smell and taste.

22% C10: Capric acid. Not much said about the flavor, and with longer carbon chains you start to get less flavors. This is in coconut oil so it is not a milk fat flavor per se as much as the other ones.

Iterations include lauric acid (C12), as it is present at 2.9% of total fatty acid content in cow's milk (Beare-Rogers, J.; Dieffenbacher, A.; Holm, J. V. (2001). "Lexicon of lipid nutrition (IUPAC Technical Report)". Pure and Applied Chemistry 73 (4): 685-744. doi:10.1351/pac200173040685.)

The following procedure as described Yu et al., The modification an analysis of vegetable oil for cheese making. *J. Am. Oil Chem. Soc.*, 77:911 (2000) was followed in, at quarter of the amounts specified below:

A mixture of butyric, caproic, caprylic, and capric acids (Sigma Chemical Co., St. Louis, MO) at the same ratios found for a milk fat sample [see above] and totaling 7.26 mol, 21.42 g of p-toluenesulfonic acid (Sigma Chemical Co.), 2.305 mol of glycerol (Sigma Chemical Co.), and 458 mL of toluene (Fisher Scientific) was refluxed with a Dean-Stark water trap for 6 h. The reaction was considered complete when no more water dripped into the trap. The SCTG were washed once with 5% sodium carbonate solution and several times with water. Then, the SCTG were heated at 85° C. in a rotary evaporator to remove water and toluene.

SCTG from both commercial and natural sources are interesterified with HOSO (Trisun 80, RBD; AC Humko, Memphis, TN) at a SCTG/HOSO ratio of 1:8.82 in order to produce a fat that has the same percentage of SCFA as that of milk fat. SCTG from the commercial source are also interesterified at a SCTG/HOSO ratio of 1:7.19 to produce a fat that has a level of SCFA equal to 120% of that in milk fat. Sodium methoxide (Aldrich Chemical Company, St. Louis, MO) is used as a catalyst at 0.5% of total oil weight. The reaction is carried out at 65° C. under nitrogen with stirring for 6 h. Next, 5% acetic acid (Fisher Scientific) is added to neutralize the catalyst, and the oil is then washed several times with distilled water and dried on a rotary evaporator for 30 min at 90° C.

A pilot-scale continuous deodorizer similar to the one described by Smouse (Smouse, T. H., A Laboratory Continuous Deodorizer, inform 8:1176-1181 (1997)) is used to deodorize the interesterified oils. The oil flow rate is 600 mL/h, the column temperature is 180° C., pressure at 0.5 Torr, and the steam rate 12.6 mL/h. Each batch of deodorized oil is tasted by to ensure the flavor. The deodorized oil is stored at 4° C. until used for cheese making.

Example 5

Modulation of Fatty Acids

Sunflower oil triglycerides with three oleic acids are transesterified with four short chain fatty acids containing one butyric acid, one hexanoic acid, and one octanoic acid as part of the fat composition in a mixture of synthetic milk product. This array or combination of fat is expected to result in a synthetic milk fat providing its rich flavor as compared to natural dairy milk. The ability to control the composition of one or more triglycerides is likely to enhance or change flavor profiles of synthetic dairy products. Accordingly, a matrix of long-chain and short-chain can yield in flavor profiles including, but not limited to, multiple aromatic compounds associated with buttery, nutty, sweet, sour, fruity, floral, bitter, woody, earthy, beany, spicy, metallic, sweet, musty, oily and vinegary sensory impressions. Additionally, increase in texture such as creaminess, improvements in melting characteristics or tolerance and increase in stretching ability relative to a corresponding dairy product can be exhibited.

Example 6. Recombinant Production of Milk Proteins

Alpha-lactalbumin, β-lactoglobulin, α-S1-casein, α-S2-casein, β-casein, and κ-casein were produced in recombinant yeast strain (*Pichia pastoris*) strains. As the glycosylation enzymes in yeast are different than mammalian cells, the proteins producted by the yeast will either be non-glycosylated or have a non-mammalian glycosylation pattern. The produced proteins can be used as a component in any of the compositions described herein.

Plasmids

Plasmids were constructed for the expression of each protein. Each plasmid included the following components: an inducible promoter (e.g., AOX1 promoter) or a consecutive (GAP promotor or PGK promoter) promoter, for each protein being expressed; a sequence encoding a signal peptide for each protein being expressed, derived either from the native bovine protein sequence or one from a yeast protein sequence (alpha mating factor or OST1); a sequence encoding the milk protein(s) to be expressed; a yeast transcription termination sequence (e.g., AOX1, AOD, or CYC1) for each protein being expressed; a bacterial origin of replication from pUC19 to enable replication of the plasmid in *E. coli*; and a selectable marker cassette (e.g., karR or zeocinR) to enable selection in bacteria and yeast with antibiotics.

The different plasmids used to produce the different proteins are listed in Table 10 below.

TABLE 10

Expression Plasmids (SEQ ID NO)

| Plasmid name | Select marker | Prom 1 | Signal peptide 1 | ORF 1 | Terminant 1 | Prom 2 | Signal pept 2 | ORF 2 | Term 2 |
|---|---|---|---|---|---|---|---|---|---|
| pJAG-nat-LAA | Amp (bacteria), G418 | P_AOX1 (153) | SP_lactalbumin (156) | α-lactalbumin (157) | TT_AOX1 (158) | | | | |

TABLE 10-continued

Expression Plasmids (SEQ ID NO)

| Plasmid name | Select marker | Prom 1 | Signal peptide 1 | ORF 1 | Terminant 1 | Prom 2 | Signal pept 2 | ORF 2 | Term 2 |
|---|---|---|---|---|---|---|---|---|---|
| pJAG-MFa-LAA | Ampicilin (bacteria), G418 (yeast) (159) | P_AOX1 (153) | SP_MFα (154) | α-lactalbumin (157) | TT_AOX1 (158) | | | | |
| pJAG-OST-LAA | Ampicilin (bacteria), G418 (yeast) (159) | P_AOX1 (153) | SP_OST (155) | α-lactalbumin (157) | TT_AOX1 (158) | | | | |
| pLH37 | Zeocin (151) | P_AOX1 (129) | S_MFαT (132) | β-lactoglobulin (143) | TT_AOX1 (149) | | | | |
| pLH0044 | Zeocin (151) | P_GAP1 (130) | SP_MFαT (132) | β-lactoglobulin (143) | TT_AOX1 (149) | | | | |
| pLH0045 | Zeocin (151) | P_PGK1 (131) | SP_MF alphaT (132) | β-lactoglobulin (143) | TT_AOX1 (149) | | | | |
| pLH46 | Zeocin (151) | P_GAP1 (130) | SP_β_casein (135) | β-casein (144) | TT_CYC1 (150) | P_PGK1 (131) | SP_αS1_casein (137) | αS1-casein (147) | TT_AOX1 (149) |
| pLH47 | Kanamycin (bacteria), G418 (yeast) (152) | P_GAP1 (130) | SP_αS2_casein (133) | αS2-casein (145) | TT_CYC1 (150) | P_PGK1 (131) | SP_κ_casein (138) | κ-casein (148) | TT_AOX1 (149) |
| pLH48 | Zeocin (151) | P_GAP1 (130) | SP_OST (134) | β-casein (144) | TT_CYC1 (150) | P_PGK1 (131) | SP_OST (134) | αS1-casein (147) | TT_AOX1 (149) |
| pLH49 | Kanamycin (bacteria), G418 (yeast) (152) | P_GAP1 (130) | SP_OST (136) | αS2-casein (145) | TT_CYC1 (150) | P_PGK1 (131) | SP_OST (134) | κ-casein (148) | TT_AOX1 (149) |
| pLH50 | Zeocin (151) | P_GAP1 (130) | SP_OST (136) | β-casein (144) | TT_CYC1 (150) | P_PGK1 (131) | SP_αS1_casein (137) | αS1-casein (147) | TT_AOX1 (149) |
| pLH51 | Zeocin (151) | P_GAP1 (130) | SP_β_casein (135) | β-casein (144) | TT_CYC1 (150) | P_PGK1 (131) | SP_OST (134) | αS1-casein (147) | TT_AOX1 (149) |
| pLH52 | Kanamycin (bacteria), G418 (yeast) (152) | P_GAP1 (130) | SP_αS2_casein (133) | αS2-casein K113E (146) | TT_CYC1 (150) | P_PGK1 (131) | SP κ_casein (138) | κ-casein (148) | TT_AOX1 (149) |
| pLH53 | Kanamycin (bacteria), G418 (yeast) (152) | P_GAP1 (130) | SP_OST (136) | αS2-casein K113E (146) | TT_CYC1 (150) | P_PGK1 (131) | SP_OST (134) | κ-casein (148) | TT_AOX1 (149) |
| pLH54 | Kanamycin (bacteria), G418 (yeast) (152) | P_GAP1 (130) | SP_OST (136) | αS2-casein (145) | TT_CYC1 (150) | P_PGK1 (131) | SP_κ_casein (138) | κ-casein (148) | TT_AOX1 (149) |
| pLH55 | Kanamycin (bacteria), G418 (yeast) (152) | P_GAP1 (130) | SP_αS2_casein (133) | αS2-casein (145) | TT_CYC1 (150) | P_PGK1 (131) | SP_OST1 (134) | κ-casein (148) | TT_AOX1 (149) |

(Synthetic)

[1]SEQ ID NO: 159

```
ATGGGTAAGGAAAAGACTCACGTTTCCAGACCAAGATTGAACTCTAACAT

GGACGCTGACTTGTACGGTTACAAGTGGGCTAGAGACAACGTTGGTCAAT

CTGGTGCTACTATTTACAGATTGTACGGTAAGCCAGACGCTCCAGAGTTG

TTCTTGAAGCACGGTAAGGGTTCTGTTGCTAACGACGTTACTGACGAGAT

GGTTAGATTGAACTGGTTGACTGAGTTCATGCCATTGCCAACTATTAAGC
```

-continued

```
ACTTCATTAGAACTCCAGACGACGCTTGGTTGTTGACTACTGCTATTCCA

GGTAAGACTGCTTTCCAAGTTTTGGAGGAGTACCCAGACTCTGGTGAGAA

CATTGTTGACGCTTTGGCTGTTTTCTTGAGAAGATTGCACTCTATTCCAG

TTTGTAACTGTCCATTCAACTCTGACAGAGTTTTCAGATTGGCTCAAGCT

CAATCCAGAATGAACAACGGTTTGGTTGACGCTTCTGACTTCGACGACGA

GAGAAACGGTTGGCCAGTTGAGCAAGTTTGGAAGGAGATGCACAAGTTGT

TGCCATTCTCTCCAGACTCTGTTGTTACTCACGGTGACTTCTCTTTGGAC

AACTTGATTTTCGACGAGGGTAAGTTGATTGGTTGTATTGACGTTGGTAG

AGTTGGTATTGCTGACAGATACCAAGACTTGGCTATTTTGTGGAACTGTT

TGGGTGAGTTCTCTCCATCTTTGCAAAAGAGATTGTTCCAAAAGTACGGT

ATTGACAACCCAGACATGAACAAGTTGCAATTCCACTTGATGTTGGACGA

GTTCTTCTAA
```

These plasmids were then integrated into wildtype *P. pastoris* for expression. The production of the proteins was detected by SDS-PAGE, ELISA, and Western blot.

Alpha-Lactalbumin

Strain Construction

Three plasmids were created, placing the expression of bovine alpha-lactalbumin (bvLAA) under the control of the methanol-induced promoter $P_{AOX1}$, with either the native LAA signal peptide (pJAG-nat-LAA), the full length alpha mating factor signal peptide (pJAG-aMF-LAA), or the OST1 signal peptide (pJAG-OST-LAA).

Prior to transformation, 20 µg each plasmid was linearized by digestion with the restriction enzyme SacI. The digested plasmids were then concentrated by ethanol precipitation, and resuspended in 10 µl distilled water.

Competent *Pichia pastoris* cells were prepared as follows: A culture of *P. pastoris* was grown to log phase (OD600 ~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 µL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 µL 1 M sorbitol.

The cells were combined with the linearized plasmid DNA in a chilled 2 mm electroporation cuvette, and subjected to a 1.5 kV pulse (25 &F, 200Ω). The cells were transferred to a culture tube with 200 µL cold 1:1 YPD:1 M sorbitol, and allowed to recover for 2 hours at 30° C. (300 rpm). Finally, the cells were plated onto YPD agar plates containing zeocin and grown for two days at 30° C.

Protein Expression

Colonies were picked from the agar plates and grown in 750 µL BMD1% (0.2M Potassium Phosphate buffer, 13.4 g/l Yeast Nitrogen Base, 0.4 mg/ml biotin, 1.1% glucose) at 30° C., 300 rpm. After 48 hours, 900 µL of culture was used to inoculate 750 µL BMM2 (0.2M Potassium Phosphate buffer, 13.4 g/l Yeast Nitrogen Base, 0.4 mg/ml Biotin, 1% methanol). After 24 hours, 150 µL BMM10 (BMM10: 0.2M Potassium Phosphate buffer, 13.4 g/l Yeast Nitrogen Base, 0.4 mg/ml Biotin, 5% methanol), and samples were harvested for analysis after one additional day.

Analysis

Protein expression was analyzed in samples of culture that were centrifuged to remove the cell mass. The clarified supernatant was then evaluated by SDS-PAGE, ELISA, and western blot.

Figure 4:
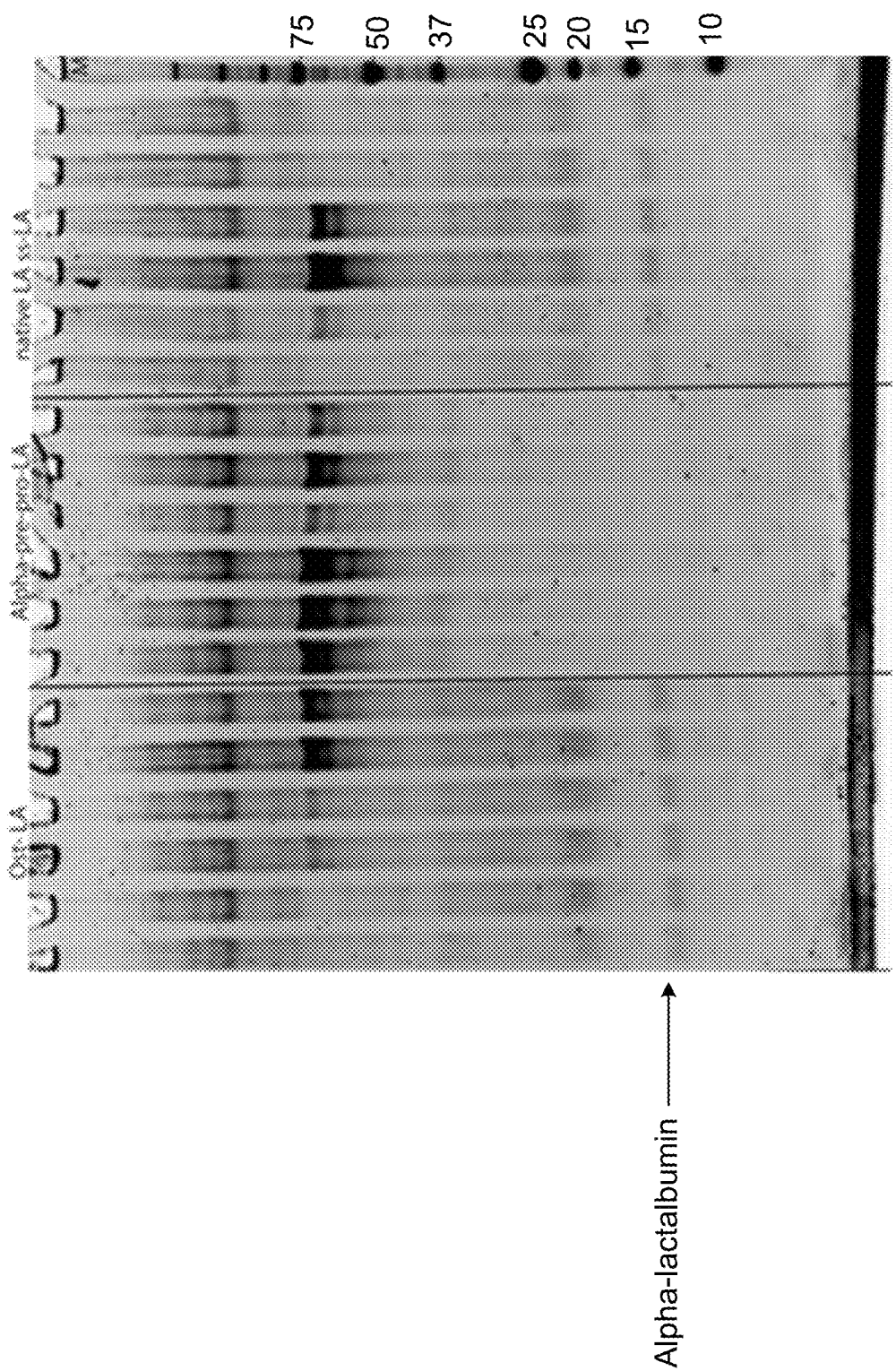
FIG. 4 is a SYPRO Ruby-stained SDS-PAGE gel showing the levels of secretion of α-lactalbumin mediated by the OST signal sequence, the native α-lactalbumin signal sequence, and the α mating factor signal sequence as described in Example 6.

To visualize total protein via SDS-PAGE, cell-free supernatant was treated with SDS-PAGE sample buffer, boiled, and run on a 10% polyacrylamide gel. The gel was stained with SYPRO Ruby stain (Life Technologies). The resulting gel shows that secretion of α-lactalbumin occurs using the OST1 or the native lactalbumin signal peptide (FIG. 4).

Figure 5:
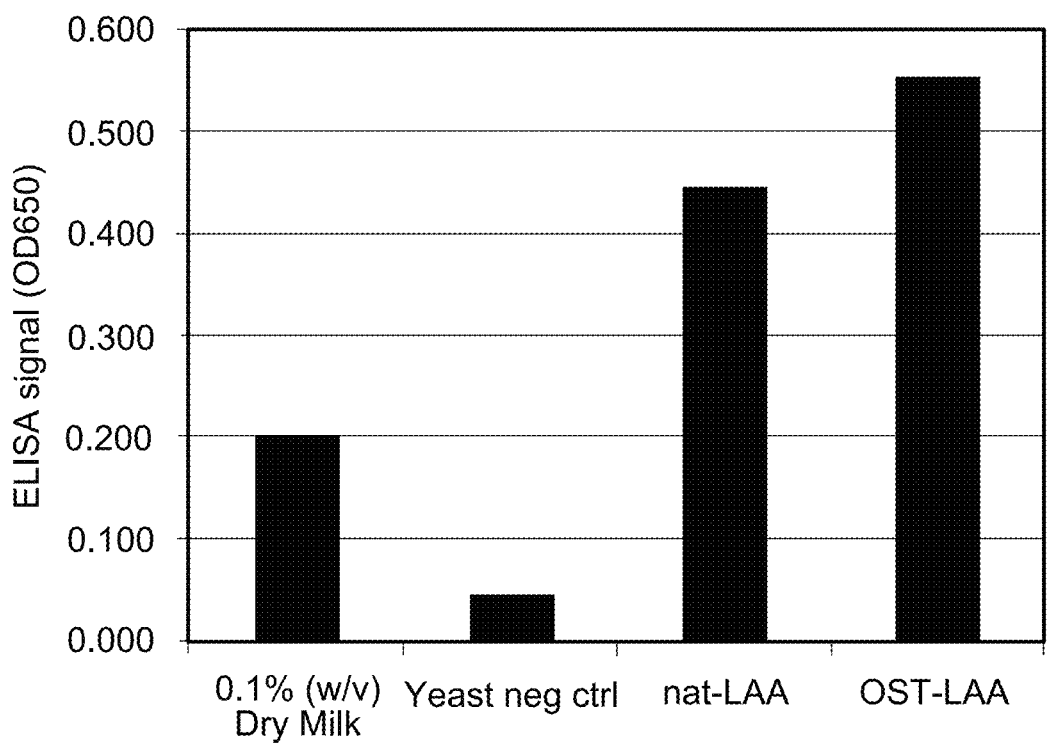
FIG. 5 is shows the levels of secretion of α-lactalbumin by wildtype yeast cells or yeast cells expressing α-lactalbumin using the native α-lactalbumin signal peptide or a OST1 signal peptide (as determined by an ELISA assay as described in Example 6).

To measure protein titers via ELISA, 25 µL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The resulting data show that α-lactalbumin was secreted using the native α-lactalbumin signal peptide or the OST1 signal peptide (FIG. 5).

To analyze samples via Western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water.

Beta-Lactoglobulin

Strain Constructions

Three plasmids were assembled, placing the expression of bovine beta-lactoglobulin (bvLGB) under the control of either a methanol-induced promoter ($P_{AOX1}$ in pLH37) or one of two constitutive promoters ($P_{GAP}$ in pLH44, or $P_{PGK}$ in pLH45).

Prior to transformation, 20 µg pLH37 was linearized by digestion with the restriction enzyme SacI. The same amounts of pLH44 and pLH45 were linearized with the enzyme ApaLI. The digested plasmids were then concentrated by ethanol precipitation, and resuspended in 10 µl distilled water.

Competent *Pichia pastoris* cells were prepared as follows: A culture of *P. pastoris* was grown to log phase (OD600 ~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 µL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 µL 1 M sorbitol.

The cells were combined with the linearized plasmid DNA in a chilled 2 mm electroporation cuvette, and subjected to a 1.5 kV pulse (25 µF, 200Ω). The cells were transferred to a culture tube with 200 µL cold 1:1 YPD:1 M sorbitol, and allowed to recover for 2 hours at 30° C. (300 rpm). Finally, the cells were plated onto YPD agar plates containing zeocin and grown for two days at 30° C.

Protein Expression

To evaluate expression in clones transformed with the plasmid containing a methanol-inducible promoter (pLH37), individual clones were grown in 750 µL BMD1% (0.2M Potassium Phosphate buffer, 13.4 g/l Yeast Nitrogen Base, 0.4 mg/ml biotin, 1.1% glucose) at 30° C., 300 rpm. After 48 hours, 900 µL of culture was used to inoculate 750 µL BMM2 (0.2M Potassium Phosphate buffer, 13.4 g/l Yeast Nitrogen Base, 0.4 mg/ml Biotin, 1% methanol). After 24 hours, 150 µL BMM10 (BMM10: 0.2M Potassium Phosphate buffer, 13.4 g/l Yeast Nitrogen Base, 0.4 mg/ml Biotin, 5% methanol), and samples were harvested for analysis after one additional day.

To evaluate expression in clones transformed with a plasmid supporting constitutive expression (pLH44 or pLH45), individual clones were grown overnight in PG media (20 g/L peptone, 2% glycerol) at 30° C. with shaking at 300 rpm. The cultures were diluted 1:10 in minimal sulfate media:

| | |
|---|---|
| Glucose | 20 g/L |
| Calcium Chloride (CaCl2) | 1 g/L |
| Sodium phosphate (Na2PO4) | 24 g/L |
| Potassium sulfate (K2SO4) | 18.2 g/L |
| Magnesium sulfate (MgSO4—7H2O) | 14.9 g/L |
| Ammonium sulfate (NH4)2SO4 | 9 g/L |
| EDTA (Ethylenediaminetetraacetic acid) | 65.25 mg/L |
| FeSO4—7H2O (Iron Sulfate heptahydrate) | 12.18 g/L |
| ZnSO4—7H2O (Zinc sulfate heptahydrate) | 25.0125 g/L |
| CaCl2—2H2O (Calcium chloride dihydrate) | 12.615 g/L |
| CuSO4—5H2O (Copper sulfate pentahydrate) | 2.175 g/L |
| NaMoO4—2H2O (Sodium molybdate dihydrate) | 2.088 g/L |
| CoCl2—6H2O (Cobalt chloride hexahydrate) | 2.0445 g/L |
| MnCl2—4H2O (Manganese chloride tetrahydrate) | 1.392 g/L |
| Biotin | 0.2175 g/L |

After 48 hours, samples were harvested for analysis.

Analysis

Protein expression was analyzed in samples of culture that were centrifuged to remove the cell mass. The clarified supernatant was then evaluated by ELISA and Western blot.

Figure 6:
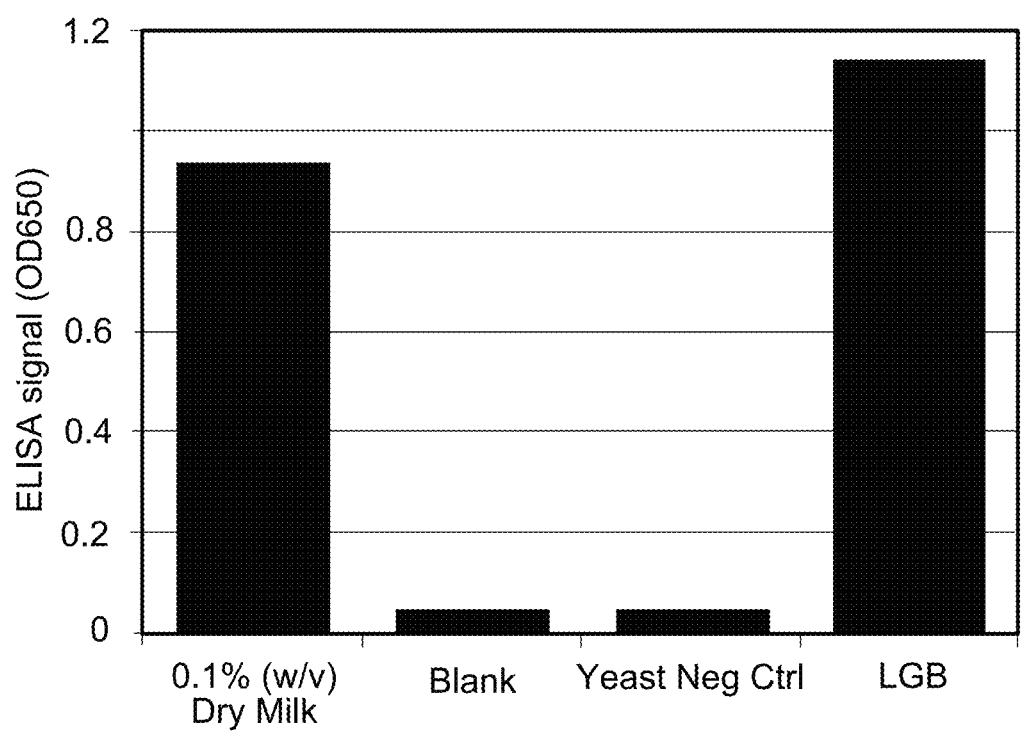
FIG. 6 is shows the levels of secretion of β-lactoglobulin by wildtype yeast cells and yeast cells including a vector as described in Example 6 (using SDS-PAGE).

To measure protein titers via ELISA, 25 µL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The resulting data show the secretion of β-lactoglobulin (FIG. 6).

Figure 7:
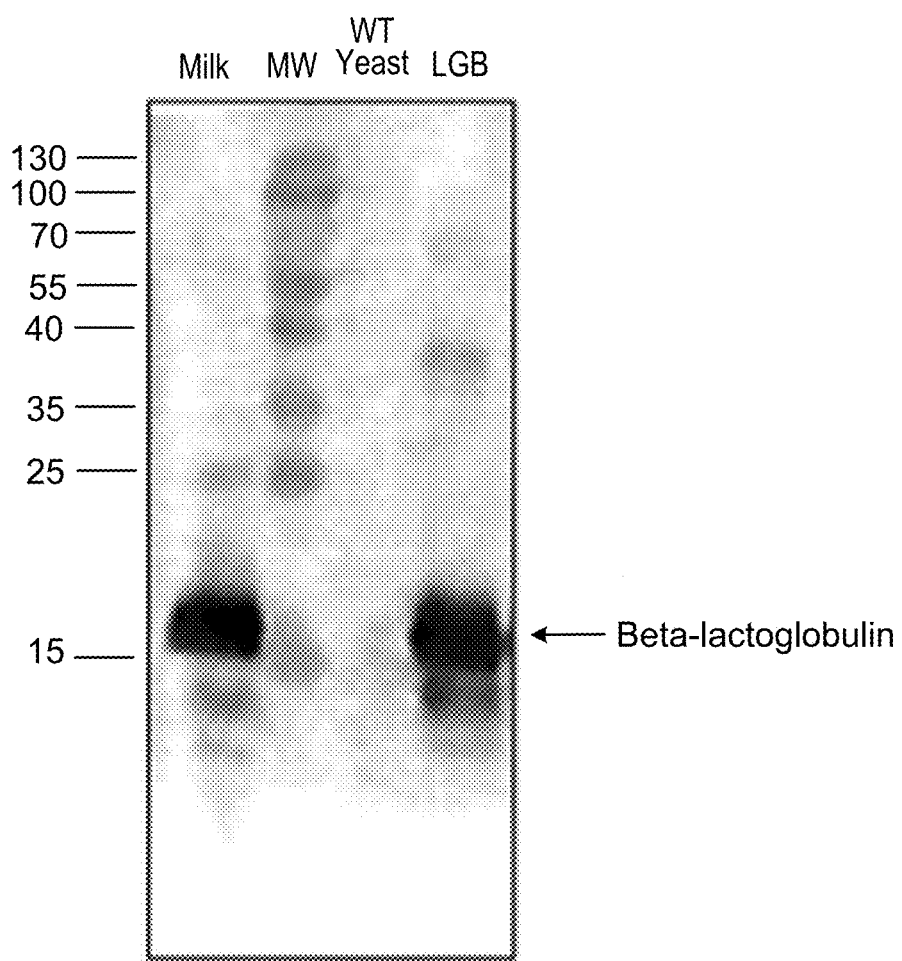
FIG. 7 is a Western blot showing the level of secretion of β-lactoglobulin from wildtype yeast and yeast cells including a vector as described in Example 6.

To analyze samples via western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water. The resulting Western blot shows that β-lactoglobulin was secreted from the recombinant yeast (FIG. 7).

Bovine Caseins

Dual expression plasmids were built, to support expression of α-S1-casein with β-casein in one plasmid, and α-S2-casein with kappa-casein in another plasmid. These pairings were chosen because the molar ratio of α-S1:α-S2:β:κ in fluid milk is approximately 5.5:1.5:4.0:1.5; it is therefore desirable to have a similar number of copies of α-S1-casein and beta-casein, and a similar number of copies of α-S2-casein and kappa-casein.

Beta-casein and α-S2-casein were placed under the control of the constitutive PGAP promoter in their respective plasmids, while α-S1-casein and κ-casein were placed under the control of the constitutive $P_{PGK}$ promoter.

In order to direct the proteins into the secretory pathway, the proteins were expressed with either their native signal peptide (pLH46 and pLH47), or the OST1 signal peptide (pLH48 and pLH49). In addition, plasmids were made in which one protein was expressed with its native signal peptide, and the other protein with the OST1 signal peptide:

pLH0050 OST1-beta, native-α-S1
pLH0051 native-β, OST1-α-S1
pLH0054 OST1-α-S2, native-κ
pLH0055 native-α-S2, OST1-κ

To generate strains expressing all four casein proteins, yeast cells were first transformed with the plasmid encoding beta-casein and α-S1-casein. Prior to transformation, 20 µg of each plasmid was linearized with the enzyme ApaLI. The digested plasmids were then concentrated by ethanol precipitation, and resuspended in 10 µl distilled water.

Competent *Pichia pastoris* cells were prepared as follows: A culture of *P. pastoris* was grown to log phase (OD600 ~1.0) in YPD media (10 g/L yeast extract, 20 g/L peptone, 20 g/L dextrose). A 1.5 mL aliquot was harvested by centrifugation, then resuspended in 1 mL of a 1:1 mixture of YPD+20 mM HEPES (pH 8):1M lithium acetate. After adding 10 µL 1 M dithiothreitol, the cells were incubated for 15 min at 30° C. in a shaker at 300 rpm. The cells were pelleted by centrifugation and washed three times in 1 mL ice cold 1 M sorbitol. After the final wash, the cells were resuspended in 50 µL 1 M sorbitol.

The cells were combined with the linearized plasmid DNA in a chilled 2 mm electroporation cuvette, and subjected to a 1.5 kV pulse (25 &F, 200Ω). The cells were transferred to a culture tube with 200 µL cold 1:1 YPD:1 M sorbitol, and allowed to recover for 2 hours at 30° C. (300 rpm). Finally, the cells were plated onto PG agar (20 g/L peptone, 2% (v/v) glycerol, 2% agar) plates containing zeocin and grown for two days at 30° C.

Six clones from the beta+alphaS1 plates were then grown in culture, and made competent for DNA uptake using the procedure described above. They were then transformed with the linearized alphaS2+kappa plasmids, and grown for two days at 30° C. on PG plates containing G418.

Expression

To evaluate the production of bovine casein proteins, five clones expressing casein and a wildtype yeast negative control were grown overnight in PG media (20 g/L peptone, 2% glycerol) at 30° C. with shaking at 300 rpm. All five of the casein-expressing clones expressed alphaS2- and κ-casein with the respective native casein signal peptides. Clones sLH115, 116, 117, and 118 expressed β-casein and α-S1-casein with the respective native signal peptides; clone sLH122 expressed beta-casein and α-S1-casein with the OST1 signal peptide. The cultures were diluted 1:10 in minimal sulfate media:

| | |
|---|---|
| Glucose | 20 g/L |
| Calcium Chloride (CaCl2) | 1 g/L |
| Sodium phosphate (Na2PO4) | 24 g/L |
| Potassium sulfate (K2SO4) | 18.2 g/L |
| Magnesium sulfate (MgSO4—7H2O) | 14.9 g/L |
| Ammonium sulfate (NH4)2SO4 | 9 g/L |
| EDTA (Ethylenediaminetetraacetic acid) | 65.25 mg/L |
| FeSO4—7H2O (Iron Sulfate heptahydrate) | 12.18 g/L |
| ZnSO4—7H2O (Zinc sulfate heptahydrate) | 25.0125 g/L |
| CaCl2—2H2O (Calcium chloride dihydrate) | 12.615 g/L |
| CuSO4—5H2O (Copper sulfate pentahydrate) | 2.175 g/L |
| NaMoO4—2H2O (Sodium molybdate dihydrate) | 2.088 g/L |
| CoCl2—6H2O (Cobalt chloride hexahydrate) | 2.0445 g/L |
| MnCl2—4H2O (Manganese chloride tetrahydrate) | 1.392 g/L |
| Biotin | 0.2175 g/L |

After 48 hours, samples were harvested for analysis.

Analysis

Protein expression was analyzed in samples of culture that were centrifuged to remove the cell mass. The clarified supernatant was then evaluated by ELISA and western blot.

Figure 8:
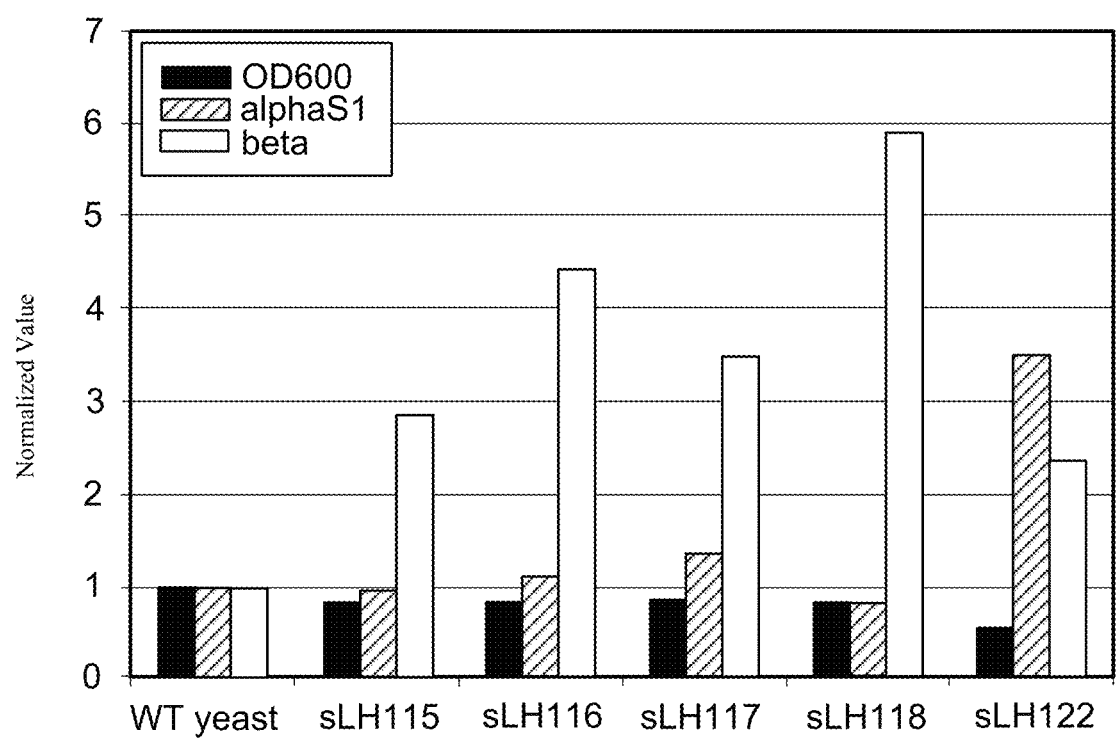
FIG. 8 is a graph showing the level of secreted β-casein and secreted α-S1-casein produced by wildtype yeast and yeast cells including the vectors described in Example 6.

To measure protein titers via ELISA, 25 µL of each sample were placed in a half-area 96 well microtiter plate, and allowed to bind overnight at 4° C. After removing the samples, the binding surface was blocked by filling each well with 1% (w/v) bovine serum albumin (BSA) dissolved in Tris Buffered Saline (50 mM Tris, pH 7.6, 150 mM NaCl) and incubating for 1 hour at room temperature. The samples were then incubated for 1.5 hr in primary antibody that was diluted in 1% BSA/TBS+0.1% (v/v) Tween-20. Following three washes in TBS+Tween, the samples were incubated with secondary antibody conjugated with horseradish peroxidase (HRP) for an additional hour. After three final washes in TBS+Tween, a chromogenic substrate (TMB Single Solution, Life Technologies) was added, and the absorbance at 650 nm was measured. The ELISA data show that the different yeast strains can secrete α-S1 casein and β-casein into the culture medium (FIG. 8).

To analyze samples via western blot, one volume of sample was combined with an equal volume of SDS-PAGE sample buffer and run on a 10% polyacrylamide gel. The proteins were transferred to a nitrocellulose membrane, which was blocked by treating with 1% BSA/TBS for 1 hr. After incubating for 1.5 hr with primary antibody diluted in 1% BSA/TBS+Tween, the blot was washed three times in TBS+Tween. The blot was then incubated with secondary antibody conjugated with horseradish peroxidase (HRP) for an additional hour. After three final washes in TBS+Tween, a chromogenic substrate (1-Step Ultra TMB Blotting Solution, Thermo Fisher) was added. After staining was completed, the blot was washed in distilled water.

The data in this Example show that the different expression vectors described herein can be used to generate transgenic yeast strains that secrete the different milk proteins.

Example 7. Method of Making a Composition

An exemplary composition described herein was generated using the specific method described below. A schematic diagram of this method is shown in FIG. 9.

To prepare the milk product, laboratory equipment such as mixers, stirring plates, and sonicators are employed. For large scale production, standard fluid milk processing equipment should be used.

Figure 9:
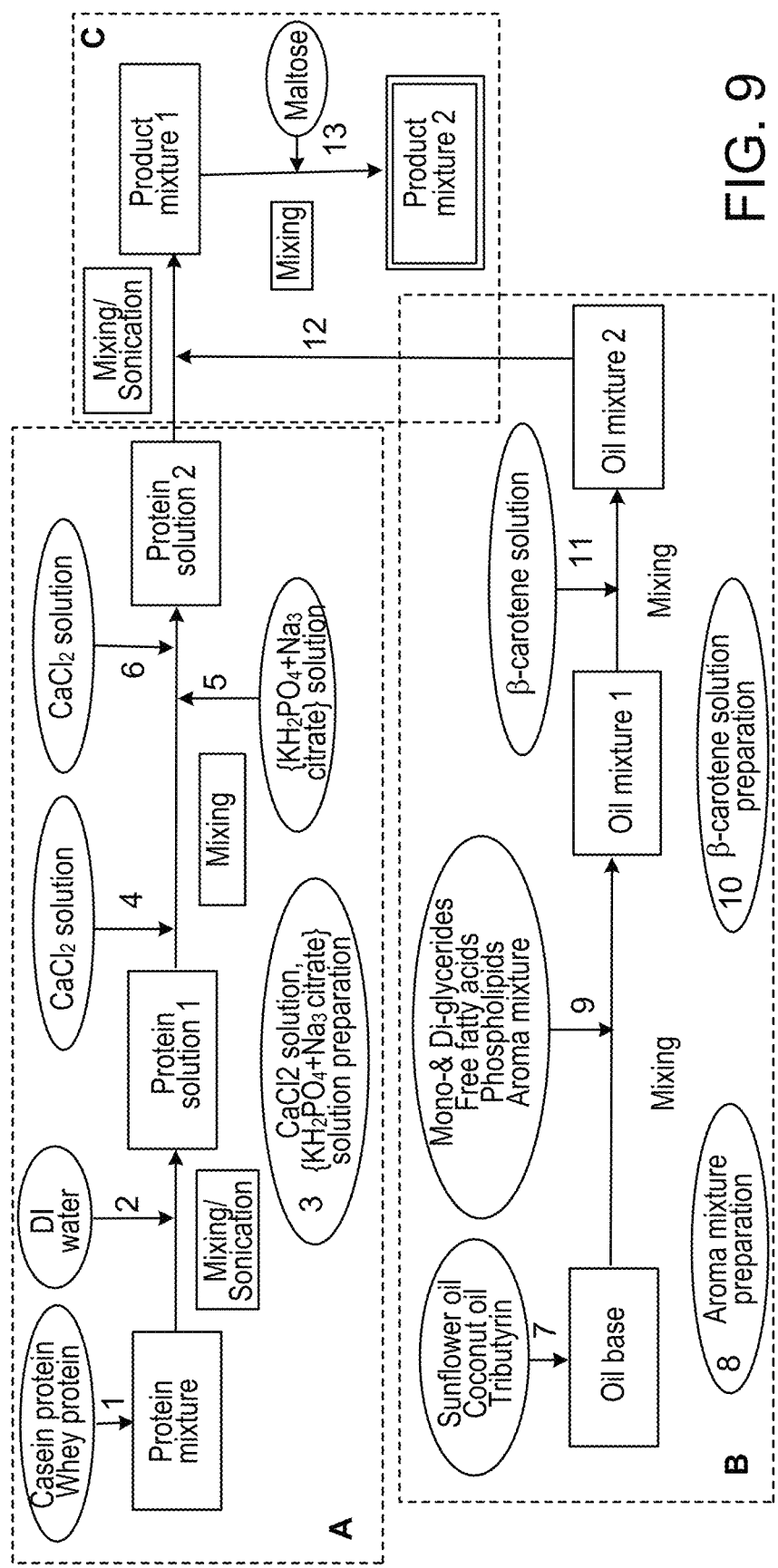
FIG. 9 is a schematic showing the steps in the process described in Example 7.

As FIG. 9 shows, there are three main components to this method of making a composition. These steps include:
A. Preparation of the protein solution
B. Preparation of the oil mixture
C. Reconstitution of the milk solids In step A, powdered micellar casein protein and whey protein are combined and blended (step 1) and subsequently mixed with deionized (DI) water (step 2) to obtain the protein solution 1. Typically, this contains 2.8% powered micellar casein, 0.7% powered whey protein, and 85.5% water in this solution. The mixing vessel is covered to prevent evaporation of water. This mixing is performed by mixers, stirring plates, or a sonicator in a sufficient period of time (approximately 30 minutes). This mixing time ensures all proteins are dispersed in the water. The mixing speed has been optimized as medium which provides enough force to disperse the proteins and avoids the entrapment of air in the solution. The water content can be adjusted according to the usage of other ingredients.

In step 3, separate solutions of $CaCl_2$), $KH_2PO_4$, and $Na_3$ citrate in water are the mineral sources utilized to prepare similar mineral profile as native bovine milk. In a typical instance, $CaCl_2$) solution concentration is 0.1 g/mL, $KH_2PO_4$ is 0.27 g/mL, and $Na_3$citrate solution is 0.21 g/ml $Na_3$citrate. The water used to prepare $KH_2PO_4$ with $Na_3$citrate solution is usually warm to make sure the complete dissolution of $KH_2PO_4$. During the mixing of protein solution 1, 0.015% $CaCl_2$) is added slowly (step 4). The volume of $CaCl_2$) solution used is adjusted according to the weight percent of $CaCl_2$) needed. The mixing continues for approximately 30 minutes to allow the complete interaction between proteins and $Cm^2$ ions. Subsequently, 0.27% $KH_2PO_4$ and 0.21% $Na_3$citrate are divided to 5 portions and each portion is added slowly into the mixing solution at an interval time of 5 to 10 minutes (step 5). 0.085% $CaCl_2$) is divided to 4 portions and each portion is added slowly into the mixing solution at an interval time of 5-10 minutes (step 6). The mixing continues for at least 30 minutes, preferably 1-2 hours, to obtain the protein solution 2.

In the process B, low speed mixing is sufficient to achieve the homogeneous mixing of different oil ingredients. The percent of each component used below for preparing the oil mixture 1 is based on the total oil mixture 1 weight. Initially, 65% sunflower oil, 29% coconut oil, and 2% tributyrin are mixed together form the oil base (step 7). The sunflower oil and coconut oil is deodorized to prevent an unwanted aroma. The combination of sunflower oil, coconut oil, and tributyrin can mimic a similar fatty acid profile as the native milk. The oil base ingredient and its content can be adjusted according to different needs (different types of products). The aroma mixture is prepared by mixing different the aroma components in the sunflower oil (step 8). The compounds used to mimic the aroma contain, but are not limited to ethyl butyrate, δ-decalactone, 2-furyl methyl ketone, 2,3-pentanedione, γ-undecalactone, δ-undecalactone, acetoin, furfuryl alcohol, furfural, 2-methylfurfural, and 2-methylpyrazine. Their contents can be adjusted by different applications and preference. 2.5% mono- and di-glycerides, 0.6% free fatty acids, 0.5% phospholipids, and 0.4% aroma mixture are added to prepare the oil mixture 1 with mixing (step 9). In a typical instance, free fatty acids contain 0.15% butyric acid and 0.45% hexanoic acid. Soy lecithin is used as the phospholipid source. Soy lecithin is readily available and is inexpensive. A β-carotene solution is prepared in sunflower oil at a concentration of 0.5 mg/g (step 10). 4% of oil mixture 1 and 0.06% the β-carotene solution are mixed together to obtain the oil mixture 2 (step 11). The usage of β-carotene is adjusted to achieve different color levels of the milk. The usage of oil mixture 1 can also be adjusted according to different milk product applications.

In the process C, oil mixture 2 is added slowly to protein solution 2 and mixed thoroughly to prepare product mixture 1 (step 12). The mixing can be performed by mixers or sonicators. In a typical instance, oil mixture 2 and protein solution 2 are mixed under medium to high speed to ensure sure the oil is uniformly dispersed in the aqueous solution. Subsequently, sonication is applied to break down the oil globules into smaller size, which leads to an increase of their stability in the solution. It is necessary to prevent the entrapment of air bubbles in the solution during mixing. A mixing time of least 20 minutes is utilized to stir the oil mixture 2 into the aqueous solution and allow the thorough dispersion. A 4% maltose solution is added into product mixture 1 and was mixed continuously for an additional 30 minutes to yield product mixture 2 (step 13). The sweetness can be adjusted by the sugar content according to different applications. The source of the sugar can also be adjusted according to requests. Extra DI water may be required to make up the final total weight to 100%.

No intensive homogenization, pasteurization, and sterilization is included in this process. However, it will be necessary to apply these steps to prepare the product mixture in the process C for a scale-up production.

Equipment Used
- Mixer: IKA-Labortechnik RW16 Basic, speed level (4-6)
- Tip sonicator: Qsonica Model CL-188, Amplitude 70%
- Water bath sonicator: Bransonic Model 1510R-MT Example 8. Example Formulations Example formulations compositions that have a similar taste and texture profile as whole milk, cream, high protein milk, fat-free milk, and sugar-free milk are provided in Tables 11-15 below.

As can be appreciated in the art, the compositions listed in Tables 11-15 are made by making the necessary modifications to the process described in Example 7.

TABLE 11

Composition like Whole Milk
Total Sample Weight 100 g

|  | Wt % | Amount in Section | Weight Percent in 100 g Sample |
|---|---|---|---|
| Protein Component 3 g | | | |
| Micellular Casein | 80% | 2.4 g | 2.40% |
| Whey Protein | 20% | 0.6 g | 0.60% |
| Fat 3.9 g | | | |
| Sunflower Oil | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid) | 0.60% | 0.023 g | 0.023% |
| Phospholipids | 0.50% | 0.020 g | 0.2% |
| Aroma Compounds 0.4% | 0.40% | 0.016 g | 0.016% |

TABLE 11-continued

Composition like Whole Milk
Total Sample Weight 100 g

|  | Wt % | Amount in Section | Weight Percent in 100 g Sample |
|---|---|---|---|
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 88.56 g | 88.56% |
| Aroma Compounds List | | | |
| δ-Decalactone | | | |
| Ethyl butyrate | | | |
| 2-furyl methyl ketone | | | |
| 2,3-pentanedione | | | |
| γ-Undecalactone | | | |
| δ-Undecatactone | | | |

TABLE 12

Composition like Cream
Total Sample Weight 100 g

|  | Wt % | Amount in Section | Weight Percent in 100 g Sample |
|---|---|---|---|
| Protein Component 3 g | | | |
| Micellular Casein | 80% | 2.4 g | 2.40% |
| Whey Protein | 20% | 0.6 g | 0.60% |
| Fat 40 g | | | |
| Sunflower Oil | 65% | 26 g | 26.0% |
| Coconut Oil | 29% | 11.6 g | 11.6% |
| Tributyrin | 2% | 0.8 g | 0.8% |
| Mono and Di Glycerides | 2.50% | 1 g | 1.0% |
| Free fatty acids (butyric and hexanoic acid) | 0.60% | 0.24 g | 0.24% |
| Phospholipids | 0.50% | 0.2 g | 0.2% |
| Aroma Compounds 0.4% | 0.40% | 0.16 g | 0.16% |
| Minerals 0.54 g | | | |
| Calcium | | 0.1005 g | 0.1005% |
| Phosphorus | | 0.09 g | 0.090% |
| Potassium | | 0.078 g | 0.078% |
| Sodium | | 0.0545 g | 0.0545% |
| Citrate | | 0.1493 g | 0.1493% |
| Chloride | | 0.064 g | 0.064% |
| Sugar 4 g | | | |
| Maltose | | 4 g | 4% |
| Water | | 52.46 g | 52.46% |
| Aroma Compounds List | | | |
| δ-Decalactone | | | |
| Ethyl butyrate | | | |
| 2-furyl methyl ketone | | | |
| 2,3-pentanedione | | | |
| γ-Undecalactone | | | |
| δ-Undecatactone | | | |

TABLE 13

Composition like Protein Rich Milk
Total Sample Weight 100 g

|  | Wt % | Amount in Section | Weight Percent in 100 g Sample |
|---|---|---|---|
| Protein Component 6 g |  |  |  |
| Micellular Casein | 80% | 4.8 g | 4.80% |
| Whey Protein | 20% | 1.2 g | 1.20% |
| Fat 3.9 g |  |  |  |
| Sunflower Oil | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid) | 0.60% | 0.023 g | 0.023% |
| Phospholipids | 0.50% | 0.020 g | 0.02% |
| Aroma Compounds 0.4% | 0.40% | 0.016 g | 0.016% |
| Minerals 0.54 g |  |  |  |
| Calcium |  | 0.1005 g | 0.1005% |
| Phosphorus |  | 0.09 g | 0.090% |
| Potassium |  | 0.078 g | 0.078% |
| Sodium |  | 0.0545 g | 0.0545% |
| Citrate |  | 0.1493 g | 0.1493% |
| Chloride |  | 0.064 g | 0.064% |
| Sugar 4 g |  |  |  |
| Maltose |  | 4 g | 4% |
| Water |  | 85.56 g | 85.56% |
| Aroma Compounds List |  |  |  |
| δ-Decalactone |  |  |  |
| Ethyl butyrate |  |  |  |
| 2-furyl methyl ketone |  |  |  |
| 2,3-pentanedione |  |  |  |
| γ-Undecalactone |  |  |  |
| δ-Undecatactone |  |  |  |

TABLE 14

Composition like Fat-Free Milk
Total Sample Weight 100 g

|  | Wt % | Amount in Section | Weight Percent in 100 g Sample |
|---|---|---|---|
| Protein Component 3 g |  |  |  |
| Micellular Casein | 80% | 2.4 g | 2.40% |
| Whey Protein | 20% | 0.6 g | 0.60% |
| Minerals 0.54 g |  |  |  |
| Calcium |  | 0.1005 g | 0.1005% |
| Phosphorus |  | 0.09 g | 0.090% |
| Potassium |  | 0.078 g | 0.078% |
| Sodium |  | 0.0545 g | 0.0545% |
| Citrate |  | 0.1493 g | 0.1493% |
| Chloride |  | 0.064 g | 0.064% |
| Sugar 4 g |  |  |  |
| Maltose |  | 4 g | 4% |
| Water |  | 92.46 g | 92.46% |
| Aroma Compounds List |  |  |  |
| δ-Decalactone |  |  |  |
| Ethyl butyrate |  |  |  |
| 2-furyl methyl ketone |  |  |  |
| 2,3-pentanedione |  |  |  |
| γ-Undecalactone |  |  |  |
| δ-Undecatactone |  |  |  |

TABLE 15

Composition like Sugar Free Milk
Total Sample Weight 100 g

|  | Wt % | Amount in Section | Weight Percent in 100 g Sample |
|---|---|---|---|
| Protein Component 3 g |  |  |  |
| Micellular Casein | 80% | 2.4 g | 2.40% |
| Whey Protein | 20% | 0.6 g | 0.60% |
| Fat 3.9 g |  |  |  |
| Sunflower Oil | 65% | 2.54 g | 2.54% |
| Coconut Oil | 29% | 1.13 g | 1.13% |
| Tributyrin | 2% | 0.08 g | 0.08% |
| Mono and Di Glycerides | 2.50% | 0.098 g | 0.098% |
| Free fatty acids (butyric and hexanoic acid) | 0.60% | 0.023 g | 0.023% |
| Phospholipids | 0.50% | 0.020 g | 0.02% |
| Aroma Compounds 0.4% | 0.40% | 0.016 g | 0.016% |
| Minerals 0.54 g |  |  |  |
| Calcium |  | 0.1005 g | 0.1005% |
| Phosphorus |  | 0.09 g | 0.090% |
| Potassium |  | 0.078 g | 0.078% |
| Sodium |  | 0.0545 g | 0.0545% |
| Citrate |  | 0.1493 g | 0.1493% |
| Chloride |  | 0.064 g | 0.064% |
| Sugar 4 g |  |  |  |
| Stevia |  | 4 g | 4% |
| Water |  | 88.56 g | 88.56% |
| Aroma Compounds List |  |  |  |
| δ-Decalactone |  |  |  |
| Ethyl butyrate |  |  |  |
| 2-furyl methyl ketone |  |  |  |
| 2,3-pentanedione |  |  |  |
| γ-Undecalactone |  |  |  |
| δ-Undecatactone |  |  |  |

Example 9. Exemplary Composition

Figure 10:
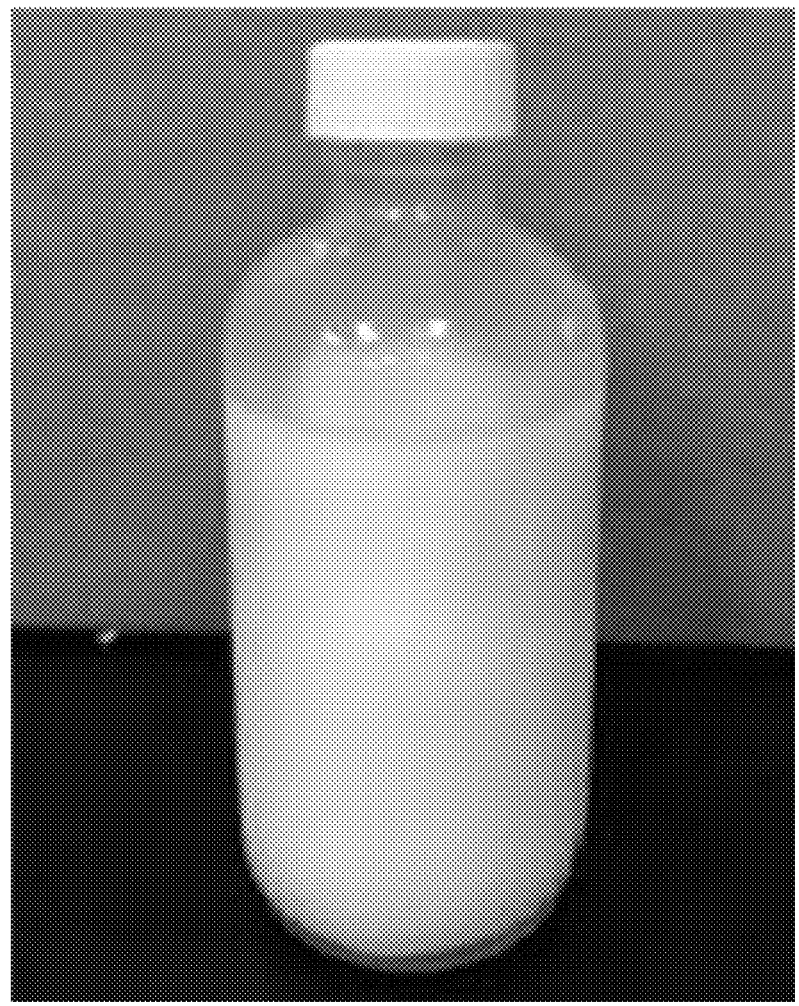
FIG. 10 is an image of a composition made by a method described herein.

An exemplary composition made by the presently described methods is shown in FIG. 10. The composition in FIG. 10 has a similar look (color), viscosity, foaming property, flavor, and nutritional value as a mammal-produced milk. The composition shown in FIG. 10 comprises mammal-derived proteins.

What is claimed is:

1. A substitute dairy food composition, wherein:
   (a) the substitute dairy food composition comprises one or more identified recombinant milk proteins;
   (b) the substitute dairy food composition is essentially free of milk proteins other than the one or more identified recombinant milk proteins;
   (c) the one or more identified recombinant milk proteins are:
      i. a recombinant β-lactoglobulin protein, a recombinant I-lactalbumin protein, a recombinant β-casein protein, a recombinant I-S1-casein protein, a recombinant I-S2-casein protein, and a recombinant P-casein protein;
      ii. a recombinant β-lactoglobulin protein, a recombinant I-lactalbumin protein, and a recombinant β-casein protein;
      iii. a recombinant β-casein protein and a recombinant I-S1-casein protein;
      iv. a recombinant β-lactoglobulin protein, a recombinant I-lactalbumin protein, and a recombinant P-casein protein; or
      v. a recombinant β-casein, a recombinant I-S1-casein protein, and a recombinant I-S2-casein protein;
   (d) the one or more identified recombinant milk proteins confer on the substitute dairy food composition one or more characteristics of a dairy product selected from the group consisting of: taste, flavor, aroma, appearance, mouthfeel, density, structure, texture, elasticity, springiness, coagulation, binding, leavening, aeration, foaming, creaminess, and emulsification.

2. The substitute dairy food composition of claim 1, wherein the one or more identified recombinant milk proteins are essentially free of milk impurities.

3. The substitute dairy food composition of claim 1, wherein at least one of the one or more identified recombinant milk proteins comprises an amino acid sequence that is at least 80% identical to an amino acid sequence of a cow milk protein, sheep milk protein, horse milk protein, or goat milk protein.

4. The substitute dairy food composition of claim 1, wherein at least one of the one or more identified recombinant milk proteins comprises an amino acid sequence that is at least 90% identical to an amino acid sequence of a cow milk protein, sheep milk protein, horse milk protein, or goat milk protein.

5. The substitute dairy food composition of claim 1, wherein at least one of the one or more identified recombinant milk proteins comprises an amino acid sequence that is at least 95% identical to an amino acid sequence of a cow milk protein, sheep milk protein, horse milk protein, or goat milk protein.

6. The substitute dairy food composition of claim 1, wherein at least one of the one or more identified recombinant milk proteins comprises an amino acid sequence that is at least 98% identical to an amino acid sequence of a cow milk protein, sheep milk protein, horse milk protein, or goat milk protein.

7. The substitute dairy food composition of claim 1, wherein at least one of the one or more identified recombinant milk proteins comprises an amino acid sequence that is at least 90% identical to an amino acid sequence of a cow milk protein.

8. The substitute dairy food composition of claim 1, wherein at least one of the one or more identified recombinant milk proteins is produced by a fungal cell.

9. The substitute dairy food composition of claim 8, wherein the fungal cell is *Aspergillus* or *Trichoderma*.

10. The substitute dairy food composition of claim 1, wherein at least one of the one or more identified recombinant milk proteins is produced by a bacterial cell.

11. The substitute dairy food composition of claim 1 further comprising one or more of calcium, potassium, sodium, citrate, thiamin (vitamin B1), riboflavin (vitamin B2), niacin (vitamin B3), pantothenic acid (vitamin B5), vitamin B6 (pyridoxine), vitamin B12 (cobalamin), vitamin C, folate, vitamins A, vitamin D, vitamin E, and vitamin K.

12. The substitute dairy food composition of claim 1 further comprising one or more sweetening agents selected from the group consisting of brazzein, curculin, mabinlin, miraculin, monelin, pentadin, and thaumatin.

13. The substitute dairy food composition of claim 12, wherein the one or more sweetening agents comprise brazzein.

14. The substitute dairy food composition of claim 1 further comprising one or more lipids derived from a plant.

15. The substitute dairy food composition of claim 14, wherein the plant is selected from the group consisting of: soy, sunflower, coconut, peanut, cottonseed, olive, palm, rapeseed, safflower, sesame seed, soybean, almond, beech nut, brazil nut, cashew, hazelnut, macadamia nut, mongongo nut, pecans, pine nut, pistachio, walnut, avocado, corn, canola, safflower, flax seed, palm kernel, palm fruit, babassu, shea butter, mango, cocoa, wheat, and rice.

16. The substitute dairy food composition of claim 1 further comprising one or more monoglycerides, diglycerides, triglycerides, and/or phospholipids comprising a short chain fatty acid selected from the group consisting of butyric acid, caproic acid, caprylic acid, and capric acid.

17. The substitute dairy food composition of claim 16, wherein at least one of the one or more monoglycerides, diglycerides, triglycerides, and/or phospholipids is a plant-based trans-esterified monoglyceride, diglyceride, triglyceride, and/or phospholipid.

18. The substitute dairy food composition of claim 16, wherein the one or more monoglycerides, diglycerides, triglycerides, and/or phospholipids comprise fatty acyl chains in a percentage that resembles a percentage of the fatty acyl chains found in a mammal-derived milk or dairy product.

19. The substitute dairy food composition of claim 1, wherein the substitute dairy food composition comprises a plurality of micelles comprising at least one of the identified recombinant milk proteins.

20. The substitute dairy food composition of claim 1, wherein the substitute dairy food composition comprises a polymer matrix gel comprising at least one of the identified recombinant milk proteins.

21. The substitute dairy food composition of claim 1, wherein the one or more identified recombinant milk proteins are a recombinant β-lactoglobulin protein, a recombinant α-lactalbumin protein, a recombinant β-casein protein, a recombinant α-S1-casein protein, a recombinant α-S2-casein protein, and a recombinant κ-casein protein.

22. The substitute dairy food composition of claim 1, wherein the one or more identified recombinant milk proteins are a recombinant β-lactoglobulin protein, a recombinant α-lactalbumin protein, and a recombinant β-casein protein.

23. The substitute dairy food composition of claim 1, wherein the one or more identified recombinant milk proteins are a recombinant β-casein protein and a recombinant α-S1-casein protein.

24. The substitute dairy food composition of claim 1, wherein the one or more identified recombinant milk proteins are a recombinant β-lactoglobulin protein, a recombinant α-lactalbumin protein, and a recombinant κ-casein protein.

25. The substitute dairy food composition of claim 1, wherein the one or more identified recombinant milk proteins are a recombinant β-casein, a recombinant α-S1-casein protein, and a recombinant α-S2-casein protein.

26. The substitute dairy food composition of claim 1, wherein the substitute dairy food composition is substitute ice cream.

27. The substitute dairy food composition of claim 1, wherein the substitute dairy food composition is a powder composition.

28. The substitute dairy food composition of claim 1, wherein the substitute dairy food composition is substitute cream.

29. The substitute dairy food composition of claim 1, wherein the substitute dairy food composition is substitute milk.

30. The substitute dairy food composition of claim 1, wherein the substitute dairy food composition is substitute cream cheese.

31. The substitute dairy food composition of claim 1, wherein the substitute dairy food composition is substitute cottage cheese.

32. The substitute dairy food composition of claim 1, wherein the substitute dairy food composition is a nutritional supplement composition.

33. The substitute dairy food composition of claim 1, wherein the substitute dairy food composition is substitute yogurt.

34. The substitute dairy food composition of claim 1, wherein the substitute dairy food composition is substitute cheese.

35. The substitute dairy food composition of claim 1, wherein the substitute dairy food composition is substitute crème fraiche.

36. The substitute dairy food composition of claim 1, wherein the substitute dairy food composition is substitute buttermilk.

37. The substitute dairy food composition of claim 1, wherein the substitute dairy food composition is substitute butter.

38. The substitute dairy food composition of claim 1, wherein the substitute dairy food composition is substitute frozen custard.

39. The substitute dairy food composition of claim 1, wherein the substitute dairy food composition is substitute curd.

40. The substitute dairy food composition of claim 1, wherein the one or more characteristics of a dairy product consist of at least taste.

41. The substitute dairy food composition of claim 1, wherein the one or more characteristics of a dairy product consist of at least flavor and/or aroma.

42. The substitute dairy food composition of claim 1, wherein the one or more characteristics of a dairy product consist of at least appearance.

43. The substitute dairy food composition of claim 1, wherein the one or more characteristics of a dairy product consist of at least mouthfeel, texture, and/or creaminess.

44. The substitute dairy food composition of claim 1, wherein the one or more characteristics of a dairy product consist of at least density.

45. The substitute dairy food composition of claim 1, wherein the one or more characteristics of a dairy product consist of at least structure, elasticity, and/or springiness.

46. The substitute dairy food composition of claim 1, wherein the one or more characteristics of a dairy product consist of at least coagulation.

47. The substitute dairy food composition of claim 1, wherein the one or more characteristics of a dairy product consist of at least binding.

48. The substitute dairy food composition of claim 1, wherein the one or more characteristics of a dairy product consist of at least leavening, aeration, and/or foaming.

49. The substitute dairy food composition of claim 1, wherein the one or more characteristics of a dairy product consist of at least emulsification.

50. The substitute dairy food composition of claim 1, wherein the substitute dairy food composition has an improved storage stability compared to a corresponding dairy food composition.

* * * * *

SEQUENCE LISTING

<160> NUMBER OF SEQ ID NOS: 159

<210> SEQ ID NO 1
<211> LENGTH: 190
<212> TYPE: PRT
<213> ORGANISM: Bos taurus
<220> FEATURE:
<221> NAME/KEY: VARIANT
<222> LOCATION: (0)...(0)
<223> OTHER INFORMATION: Casein k

<400> SEQUENCE: 1

Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Arg Cys
            20                  25                  30

Glu Lys Asp Glu Arg Phe Phe Ser Asp Lys Ile Ala Lys Tyr Ile Pro
        35                  40                  45

Ile Gln Tyr Val Leu Ser Arg Tyr Pro Ser Tyr Gly Leu Asn Tyr Tyr
    50                  55                  60

Gln Gln Lys Pro Val Ala Leu Ile Asn Asn Gln Phe Leu Pro Tyr Pro
65                  70                  75                  80

Tyr Tyr Ala Lys Pro Ala Ala Val Arg Ser Pro Ala Gln Ile Leu Gln
            85                  90                  95

Trp Gln Val Leu Ser Asn Thr Val Pro Ala Lys Ser Cys Gln Ala Gln
            100                 105                 110

Pro Thr Thr Met Ala Arg His Pro His Pro His Leu Ser Phe Met Ala
        115                 120                 125

Ile Pro Pro Lys Lys Asn Gln Asp Lys Thr Glu Ile Pro Thr Ile Asn
    130                 135                 140

Thr Ile Ala Ser Gly Glu Pro Thr Ser Thr Pro Thr Ile Glu Ala Val
145                 150                 155                 160

Glu Ser Thr Val Ala Thr Leu Glu Ala Ser Pro Glu Val Ile Glu Ser
            165                 170                 175

Pro Pro Glu Ile Asn Thr Val Gln Val Thr Ser Thr Ala Val
        180                 185                 190

<210> SEQ ID NO 2
<211> LENGTH: 573
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein k cDNA

<400> SEQUENCE: 2
atgatgaaga gttttttcct agttgtgact atcctagcat taaccctgcc attttttgggt      60 gcccaagagc aaaaccaaga acaaccaata cgctgtgaga agatgaaag attcttcagt      120 gacaaaatag ccaaatatat cccaatccag tatgtgctga gtaggtatcc tagttatgga      180
ctcaattact accaacagaa accagttgca ctaattaata tcaatttct gccatacccca      240 tattatgcaa agccagctgc agttaggtca cctgcccaaa ttcttcaatg gcaagttttg      300
tcaaatactg tgcctgccaa gtcctgccaa gcccagccaa ccaccatggc acgtcaccca      360
cacccacatt tatcatttat ggccattcca ccaaagaaaa atcaggataa aacagaaatc      420
cctaccatca taccattgc tagtggtgag cctacaagta cacctaccat cgaagcagta      480
gagagcactg tagctactct agaagcttct ccagaagtta ctgagagccc acctgagatc      540
aacacagtcc aagttacttc aaccgcggtc taa                573

<210> SEQ ID NO 3
<211> LENGTH: 192
<212> TYPE: PRT
<213> ORGANISM: Capra hircus
<220> FEATURE:
<221> NAME/KEY: VARIANT
<222> LOCATION: (0)...(0)
<223> OTHER INFORMATION: Casein k

<400> SEQUENCE: 3

```
Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Pro Ile Cys Cys
            20                  25                  30

Glu Lys Asp Glu Arg Phe Phe Asp Asp Lys Ile Ala Lys Tyr Ile Pro
        35                  40                  45

Ile Gln Tyr Val Leu Ser Arg Tyr Pro Ser Tyr Gly Leu Asn Tyr Tyr
    50                  55                  60

Gln Gln Arg Pro Val Ala Leu Ile Asn Asn Gln Phe Leu Pro Tyr Pro
65                  70                  75                  80

Tyr Tyr Ala Lys Pro Val Ala Val Arg Ser Pro Ala Gln Thr Leu Gln
                85                  90                  95

Trp Gln Val Leu Pro Asn Thr Val Pro Ala Lys Ser Cys Gln Asp Gln
            100                 105                 110

Pro Thr Thr Leu Ala Arg His Pro His Pro His Leu Ser Phe Met Ala
        115                 120                 125

Ile Pro Pro Lys Lys Asp Gln Asp Lys Thr Glu Val Pro Ala Ile Asn
    130                 135                 140

Thr Ile Ala Ser Ala Glu Pro Thr Val His Ser Thr Pro Thr Thr Glu
145                 150                 155                 160

Ala Ile Val Asn Thr Val Asp Asn Pro Glu Ala Ser Ser Glu Ser Ile
                165                 170                 175

Ala Ser Ala Ser Glu Thr Asn Thr Ala Gln Val Thr Ser Thr Glu Val
            180                 185                 190
```

<210> SEQ ID NO 4
<211> LENGTH: 579
<212> TYPE: DNA
<213> ORGANISM: Capra hircus
<220> FEATURE:
<221> NAME/KEY: misc_feature
<222> LOCATION: (0)...(0)
<223> OTHER INFORMATION: Casein k cDNA

<400> SEQUENCE: 4
atgatgaaga gttttttcct agttgtgact atcctggcat taaccctgcc attttttgggt    60 gcccaggagc aaaaccagga acagccgata tgctgtgaga agatgaaaag attcttcgat   120
gacaaaatag ccaaatatat cccaattcag tatgtgctga gtaggtatcc tagttatgga   180
ctcaattact atcaacagag accagttgca ctaattaata tcaatttct gccataccca    240 tattatgcaa agccagttgc agttaggtca cctgcccaaa ctcttcaatg gcaagttttg    300
ccaaatactg tgcctgccaa gtcctgccaa gaccagccaa ctaccctggc acgtcaccca    360
cacccacatt tatcatttat ggccattcca ccaaagaaag atcaggataa acagaagtc    420 cctgccatca ataccattgc tagtgctgag cctacagtac acagtacacc taccaccgaa    480

```
gcaatagtga acactgtaga taatccagaa gcttcctcag aatcgattgc gagtgcatct    540
gagaccaaca cagcccaagt tacttcaacc gaggtctaa                          579
```

<210> SEQ ID NO 5
<211> LENGTH: 182
<212> TYPE: PRT
<213> ORGANISM: Felis catus
<220> FEATURE:
<221> NAME/KEY: VARIANT
<222> LOCATION: (0)...(0)
<223> OTHER INFORMATION: Casein k

<400> SEQUENCE: 5

```
Met Lys Thr Phe Phe Leu Val Val Asn Ile Leu Ala Leu Thr Leu Pro
1               5                   10                  15

Phe Leu Gly Ala Gln Val Gln Asn Gln Glu Gln Pro Thr Cys Arg Glu
            20                  25                  30

Asn Asp Glu Arg Leu Leu Asn Gln Lys Thr Ala Lys Tyr Ile Pro Val
        35                  40                  45

His Tyr Val Leu Ser Asn Tyr Pro His Tyr Glu Pro Ser Tyr Tyr Pro
    50                  55                  60

His Lys Pro Ala Val Pro Val Asn Asn Gln Tyr Met Pro Tyr Pro Tyr
65                  70                  75                  80

Tyr Ala Lys Pro Val Ala Val Arg Pro His Val Gln Ile Pro Gln Trp
                85                  90                  95

Gln Val Leu Pro Asn Thr Tyr Thr Pro Thr Val Val Arg His Pro His
            100                 105                 110

Leu Pro Ala Ser Phe Ile Ala Ile Pro Pro Lys Lys Ile Gln Asp Lys
        115                 120                 125

Thr Gly Asn Pro Thr Ile Asn Thr Ile Ala Thr Ala Glu Leu Thr Leu
    130                 135                 140

Thr Pro Thr Thr Glu Pro Ile Val Asn Thr Val Val Thr Thr Glu Ala
145                 150                 155                 160

Ser Ser Glu Phe Thr Ile Thr Ser Thr Pro Glu Thr Thr Thr Val Pro
                165                 170                 175

Val Ala Ser Thr Met Val
            180
```

<210> SEQ ID NO 6
<211> LENGTH: 549
<212> TYPE: DNA
<213> ORGANISM: Felis catus
<220> FEATURE:
<221> NAME/KEY: misc_feature
<222> LOCATION: (0)...(0)
<223> OTHER INFORMATION: Casein k cDNA

<400> SEQUENCE: 6

```
atgaagactt ttttcctagt tgtgaatatc cttgcattaa ccttgccatt tttgggtgca    60
caggtgcaaa accaagaaca accaacttgc cgtgaaaatg atgaaagatt gcttaatcag   120
aaaactgcca agtatatccc agttcattat gtactgagta actatcctca ctatgagccc   180
agttactacc cgcataaacc agctgtacca gttaataatc aatatatgcc ctatccatat   240
tatgcaaaac cagttgcagt taggccacat gtccaaattc ctcagtggca agtcctgcca   300
aataccacta cacccactgt ggtacgtcac ccacacctac ctgcgtcatt tattgccatt   360
cccccaaaga aaattcagga taagacaggc aaccctacca tcaataccat tgctactgct   420
gagcttacac ttactcctac cactgaacca atagtgaaca ctgtagtcac tacagaagca   480
```
tcctcagaat tcaccatcac aagcacacct gagactacca cagttccagt ggcttcaacc    540
atggtctaa                                                           549

<210> SEQ ID NO 7
<211> LENGTH: 196
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Casein k

<400> SEQUENCE: 7

Met Arg Ala Asn Ala Asn Val Ala Asp Ala Gln Ser Ala Ile Met Lys
1               5                   10                  15

Ser Phe Leu Leu Val Val Asn Ala Leu Ala Leu Thr Leu Pro Phe Leu
            20                  25                  30

Ala Val Glu Val Gln Asn Gln Lys Gln Pro Ala Cys His Glu Asn Asp
        35                  40                  45

Glu Arg Pro Phe Tyr Gln Lys Thr Ala Pro Tyr Val Pro Met Tyr Tyr
    50                  55                  60

Val Pro Asn Ser Tyr Pro Tyr Tyr Gly Thr Asn Leu Tyr Gln Arg Arg
65                  70                  75                  80

Pro Ala Ile Ala Ile Asn Asn Pro Tyr Val Pro Arg Thr Tyr Tyr Ala
                85                  90                  95

Asn Pro Ala Val Val Arg Pro His Ala Gln Ile Pro Gln Arg Gln Tyr
            100                 105                 110

Leu Pro Asn Ser His Pro Pro Thr Val Val Arg Arg Pro Asn Leu His
        115                 120                 125

Pro Ser Phe Ile Ala Ile Pro Pro Lys Lys Ile Gln Asp Lys Ile Ile
    130                 135                 140

Ile Pro Thr Ile Asn Thr Ile Ala Thr Val Glu Pro Thr Pro Ala Pro
145                 150                 155                 160

Ala Thr Glu Pro Thr Val Asp Ser Val Val Thr Pro Glu Ala Phe Ser
                165                 170                 175

Glu Ser Ile Ile Thr Ser Thr Pro Glu Thr Thr Thr Val Ala Val Thr
            180                 185                 190

Pro Pro Thr Ala
        195

<210> SEQ ID NO 8
<211> LENGTH: 591
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Casein k cDNA

<400> SEQUENCE: 8
atgagggcaa atgcaaatgt agctgatgcg caaagtgcaa taatgaagag ttttcttcta     60
gttgtcaatg ccctggcatt aaccctgcct tttttggctg tggaggttca aaaccagaaa    120
caaccagcat gccatgagaa tgatgaaaga ccattctatc agaaaacagc tccatatgtc    180
ccaatgtatt atgtgccaaa tagctatcct tattatggaa ccaatttgta ccaacgtaga    240
ccagctatag caattaataa tccatatgtg cctcgcacat attatgcaaa cccagctgta    300
gttaggccac atgcccaaat tcctcagcgg caatacctgc caaatagcca cccacccact    360

```
gtggtacgtc gcccaaacct gcatccatca tttattgcca tccccccaaa gaaaattcag    420
gataaaataa tcatccctac catcaatacc attgctactg ttgaacctac accagctcct    480
gccactgaac caacggtgga cagtgtagtc actccagaag ctttttcaga gtccatcatc    540
acgagcaccc ctgagacaac cacagttgca gttactccac ctacggcata a            591
```

<210> SEQ ID NO 9
<211> LENGTH: 178
<212> TYPE: PRT
<213> ORGANISM: Loxodonta Africana
<220> FEATURE:
<221> NAME/KEY: VARIANT
<222> LOCATION: (0)...(0)
<223> OTHER INFORMATION: Casein k

<400> SEQUENCE: 9

```
Met Lys Gly Phe Leu Leu Val Val Asn Ile Leu Leu Leu Pro Leu Pro
1               5                   10                  15

Phe Leu Ala Ala Glu Val Gln Asn Gln Glu Glu Ser Arg Cys Leu Glu
            20                  25                  30

Lys Asp Glu Arg Trp Phe Cys Gln Lys Ala Val Lys Tyr Ile Pro Asn
        35                  40                  45

Asp Tyr Val Leu Lys Ser Tyr Tyr Arg Tyr Glu Pro Asn Tyr Asn Gln
    50                  55                  60

Phe Arg Ala Ala Val Pro Ile Asn Asn Pro Tyr Leu Ile Tyr Leu Tyr
65                  70                  75                  80

Pro Ala Lys Gln Val Ala Val Arg Pro His Thr Gln Ile Pro Gln Trp
                85                  90                  95

Gln Val Pro Ser Asn Ile Tyr Pro Ser Pro Ser Val Pro His Thr Tyr
            100                 105                 110

Leu Lys Pro Pro Phe Ile Val Ile Pro Pro Lys Lys Thr Gln Asp Lys
        115                 120                 125

Pro Ile Ile Pro Pro Thr Gly Thr Val Ala Ser Ile Glu Ala Thr Val
    130                 135                 140

Glu Pro Lys Val Asn Thr Val Val Asn Ala Glu Ala Ser Ser Glu Phe
145                 150                 155                 160

Ile Ala Thr Asn Thr Pro Glu Ala Thr Thr Val Pro Val Ile Ser Pro
                165                 170                 175

Gln Ile
```

<210> SEQ ID NO 10
<211> LENGTH: 537
<212> TYPE: DNA
<213> ORGANISM: Loxodonta Africana
<220> FEATURE:
<221> NAME/KEY: misc_feature
<222> LOCATION: (0)...(0)
<223> OTHER INFORMATION: Casein k cDNA

<400> SEQUENCE: 10

```
atgaagggct ttctcttggt tgtgaacatc ctgttgttac ctttgccctt tttggctgca    60
gaggtgcaaa accaggagga gtcaagatgc cttgagaaag atgaaagatg gttctgtcag    120
aaagcagtca atatattcc aaatgattat gtgctgaaga gctattatcg ttatgaacca    180
aattataacc aatttagggc agctgtacca atcaataatc cataccctaat ttacctatat    240 cctgctaaac aggttgcagt taggccacat acacaaattc cgcaatggca agttccatca    300
aatatctacc catctccatc agtacctcac acataccctca aaccaccatt tattgtcatt    360
```

```
cccccaaaga aaactcagga taaacctata atccctccca ccggcaccgt tgcttctatt    420
gaagctaccg ttgagcctaa ggtgaacact gtcgtcaatg ctgaagcttc ctcagagttc    480
attgccacaa atacacctga ggctaccaca gtcccagtta tttcacccca gatctaa      537
```

```
<210> SEQ ID NO 11
<211> LENGTH: 175
<212> TYPE: PRT
<213> ORGANISM: Mammuthus primigenius
<220> FEATURE:
<221> NAME/KEY: VARIANT
<222> LOCATION: (0)...(0)
<223> OTHER INFORMATION: Casein k

<400> SEQUENCE: 11
```

```
Met Lys Gly Phe Leu Leu Val Val Asn Ile Leu Leu Pro Leu Phe
1               5                   10                  15

Leu Ala Ala Glu Val Gln Asn Gln Glu Glu Ser Arg Cys Leu Glu Lys
            20                  25                  30

Asp Glu Arg Trp Phe Cys Gln Lys Ala Val Lys Tyr Ile Pro Asn Asp
        35                  40                  45

Tyr Val Leu Lys Ser Tyr Tyr Arg Tyr Glu Pro Asn Tyr Asn Gln Phe
    50                  55                  60

Arg Ala Ala Val Pro Ile Asn Asn Pro Tyr Leu Ile Tyr Leu Tyr Pro
65                  70                  75                  80

Ala Lys Gln Val Ala Val Arg Pro His Thr Gln Ile Gln Trp Gln Val
                85                  90                  95

Pro Ser Asn Ile Tyr Pro Ser Pro Ser Val Pro His Thr Tyr Leu Lys
            100                 105                 110

Pro Pro Phe Ile Ile Pro Pro Lys Lys Thr Gln Asp Lys Pro Ile Ile
        115                 120                 125

Pro Pro Thr Gly Thr Val Ala Ser Ile Glu Ala Thr Val Glu Pro Lys
    130                 135                 140

Val Asn Thr Val Val Asn Ala Glu Ala Ser Ser Glu Phe Ile Ala Thr
145                 150                 155                 160

Asn Thr Pro Glu Ala Thr Thr Val Pro Val Ile Ser Pro Gln Ile
                165                 170                 175
```

```
<210> SEQ ID NO 12
<211> LENGTH: 546
<212> TYPE: DNA
<213> ORGANISM: Mammathus primigenius
<220> FEATURE:
<221> NAME/KEY: misc_feature
<222> LOCATION: (0)...(0)
<223> OTHER INFORMATION: Casein k cDNA

<400> SEQUENCE: 12
```

```
atgatgaagg gctttctctt ggttgtgaac atcctgttgt tacctttggc cttttttggct   60 gcagaggtgc aaaaccagga ggagtcaaga agctgttgcc ttgagaaaga tgaaagatgg   120
ttctgtcaga aagcagtcaa atatattcca atgattatg tgctgaagag ctattatcgt    180
tatgaaccaa attataacca atttagggca gctgtaccaa tcaataatcc atacctaatt   240
tacctatatc ctgctaaaca ggttgcagtt aggccacata cacaaattct gcaatggcaa   300
gttccatcaa atatctaccc atctccatca gtacctcaca catacctcaa accaccattt   360
attgccattc ccccaaagaa aactcaggat aaacctataa tccctcccac cggcaccgtt   420
gcttctattg aagctaccgt tgagcctaag gtgaacactg tcgtcaatgc tgaagcttcc   480
```

```
tcagagttca ttgccacaaa tacacctgag gctaccacag tcccagttat ttcaccccag    540
atctaa                                                               546
```

<210> SEQ ID NO 13
<211> LENGTH: 180
<212> TYPE: PRT
<213> ORGANISM: Oryctolagus cuniculus
<220> FEATURE:
<221> NAME/KEY: VARIANT
<222> LOCATION: (0)...(0)
<223> OTHER INFORMATION: Casein k

<400> SEQUENCE: 13

```
Met Met Lys His Phe Leu Leu Val Val Asn Ile Leu Ala Val Thr Leu
1               5                   10                  15

Pro Phe Leu Ala Ala Asp Ile Gln Asn Gln Glu Gln Thr Thr Cys Arg
            20                  25                  30

Glu Asn Glu Glu Arg Leu Phe His Gln Val Thr Ala Pro Tyr Ile Pro
        35                  40                  45

Val His Tyr Val Met Asn Arg Tyr Pro Gln Tyr Glu Pro Ser Tyr Tyr
    50                  55                  60

Leu Arg Arg Gln Ala Val Pro Thr Leu Asn Pro Phe Met Leu Asn Pro
65                  70                  75                  80

Tyr Tyr Val Lys Pro Ile Val Phe Lys Pro Asn Val Gln Val Pro His
                85                  90                  95

Trp Gln Ile Leu Pro Asn Ile His Gln Pro Lys Val Gly Arg His Ser
            100                 105                 110

His Pro Phe Phe Met Ala Ile Leu Pro Asn Lys Met Gln Asp Lys Ala
        115                 120                 125

Val Thr Pro Thr Thr Asn Thr Ile Ala Ala Val Glu Pro Thr Pro Ile
    130                 135                 140

Pro Thr Thr Glu Pro Val Val Ser Thr Glu Val Ile Ala Glu Ala Ser
145                 150                 155                 160

Pro Glu Leu Ile Ile Ser Pro Glu Thr Thr Glu Ala Thr Ala Ala
                165                 170                 175

Ser Ala Ala Ala
            180
```

<210> SEQ ID NO 14
<211> LENGTH: 543
<212> TYPE: DNA
<213> ORGANISM: Oryctolagus cuniculus
<220> FEATURE:
<221> NAME/KEY: misc_feature
<222> LOCATION: (0)...(0)
<223> OTHER INFORMATION: Casein k cDNA

<400> SEQUENCE: 14

```
atgatgaagc attttcttct agttgtgaac atcctggcag taaccttgcc ttttttggct    60
gcagacatac aaaaccagga acagacaacg tgccgtgaga atgaggaaag actgttccac   120
caggttacag ctccatatat cccagttcac tatgtgatga acagatatcc tcaatacgaa   180
cccagctact acctgcgcag acaagctgtt ccaactctta atccatttat gcttaaccca   240
tattatgtaa aaccaattgt atttaagcca aatgtccaag ttcctcactg gcaaatcctg   300
ccaaatatcc accagccaaa agtgggacgt cactcacatc cattttttat ggccattctc   360
ccgaataaaa tgcaggataa agcagtcacc cccaccacca acaccattgc tgctgtggag   420
```

```
cctaccccga ttcctaccac tgagccagtg gtgagcactg aagtgattgc agaggcttcc    480
ccagagctca tcatcagccc tgagactacc acggaagcaa ctgctgcatc agcggcagca    540
tga                                                                 543
```

```
<210> SEQ ID NO 15
<211> LENGTH: 192
<212> TYPE: PRT
<213> ORGANISM: Ovis aries
<220> FEATURE:
<221> NAME/KEY: VARIANT
<222> LOCATION: (0)...(0)
<223> OTHER INFORMATION: Casein k

<400> SEQUENCE: 15
```

Met Met Lys Ser Phe Phe Leu Val Val Thr Ile Leu Ala Leu Thr Leu
1               5                   10                  15

Pro Phe Leu Gly Ala Gln Glu Gln Asn Gln Glu Gln Arg Ile Cys Cys
                20                  25                  30

Glu Lys Asp Glu Arg Phe Phe Asp Asp Lys Ile Ala Lys Tyr Ile Pro
            35                  40                  45

Ile Gln Tyr Val Leu Ser Arg Tyr Pro Ser Tyr Gly Leu Asn Tyr Tyr
        50                  55                  60

Gln Gln Arg Pro Val Ala Leu Ile Asn Asn Gln Phe Leu Pro Tyr Pro
65                  70                  75                  80

Tyr Tyr Ala Lys Pro Val Ala Val Arg Ser Pro Ala Gln Thr Leu Gln
                85                  90                  95

Trp Gln Val Leu Pro Asn Ala Val Pro Ala Lys Ser Cys Gln Asp Gln
                100                 105                 110

Pro Thr Ala Met Ala Arg His Pro His Pro His Leu Ser Phe Met Ala
            115                 120                 125

Ile Pro Pro Lys Lys Asp Gln Asp Lys Thr Glu Ile Pro Ala Ile Asn
        130                 135                 140

Thr Ile Ala Ser Ala Glu Pro Thr Val His Ser Thr Pro Thr Thr Glu
145                 150                 155                 160

Ala Val Val Asn Ala Val Asp Asn Pro Glu Ala Ser Ser Glu Ser Ile
                165                 170                 175

Ala Ser Ala Pro Glu Thr Asn Thr Ala Gln Val Thr Ser Thr Glu Val
            180                 185                 190

```
<210> SEQ ID NO 16
<211> LENGTH: 579
<212> TYPE: DNA
<213> ORGANISM: Ovis aries
<220> FEATURE:
<221> NAME/KEY: misc_feature
<222> LOCATION: (0)...(0)
<223> OTHER INFORMATION: Casein k cDNA

<400> SEQUENCE: 16
atgatgaaga gttttttcct agttgtgact atcctggcat taaccctgcc attttttggt     60
gcccaggagc aaaaccaaga caacgaata tgctgtgaga agatgaaag attcttcgat     120 gacaaaatag ccaaatatat cccaattcag tatgtgctga gtaggtatcc tagttatgga    180
ctcaattact accaacagag accagttgca ctaattaata tcaatttct gccatacccca   240 tattatgcga agccagttgc agttaggtca cctgcccaaa ctcttcaatg gcaagttttg    300
ccaaatgctg tgcctgccaa gtcctgccaa gaccagccac tgccatggc acgtcaccca    360 caccccacatt tatcatttat ggccattcca ccaaagaaag atcaggataa aacagaaatc    420
```

```
cctgccatca ataccattgc tagtgctgag cctacagtac acagtacacc taccaccgaa    480
gcagtagtga acgctgtaga taatccagaa gcttcctcag aatcgattgc gagtgcacct    540
gagaccaaca cagcccaagt tacttcaacc gaggtctaa                           579
```

<210> SEQ ID NO 17
<211> LENGTH: 181
<212> TYPE: PRT
<213> ORGANISM: Physeter catodon
<220> FEATURE:
<221> NAME/KEY: VARIANT
<222> LOCATION: (0)...(0)
<223> OTHER INFORMATION: Casein k

<400> SEQUENCE: 17

```
Met Lys Ser Phe Leu Leu Val Val Thr Ile Leu Ala Leu Thr Leu Pro
1               5                   10                  15

Phe Leu Ser Ala Glu Gly Gln Asn Gln Glu Gln Ser Thr Arg Cys Glu
            20                  25                  30

Asn Asp Glu Arg Leu Phe Asn Lys Lys Thr Val Lys Tyr Ile Pro Ile
        35                  40                  45

His Tyr Val Leu Ser Arg Tyr Pro Ser Tyr Gly Leu Asn Tyr Tyr Gln
    50                  55                  60

His Arg Pro Val Ala Leu Ile Asn Asn Gln Phe Met Pro Tyr Leu Tyr
65                  70                  75                  80

Tyr Ala Lys Pro Val Val Val Ser Pro His Ala Gln Ile Pro Gln Trp
                85                  90                  95

Gln Phe Leu Pro Asn Ile His Pro Pro Thr Leu Ala His His Pro His
            100                 105                 110

Pro Arg Pro Ser Phe Thr Ala Ile Pro Pro Lys Lys Thr Gln Asp Lys
        115                 120                 125

Thr Ala Ile Pro Ile Ile Asn Thr Ile Ala Thr Val Glu Pro Thr Leu
    130                 135                 140

Ile Pro Thr Thr Glu Pro Ile Val Asn Thr Val Val Thr Pro Glu Ala
145                 150                 155                 160

Ser Ser Glu Phe Ile Thr Ser Thr Pro Glu Thr Thr Thr Val Gln Val
                165                 170                 175

Ala Ser Pro Val Ala
            180
```

<210> SEQ ID NO 18
<211> LENGTH: 546
<212> TYPE: DNA
<213> ORGANISM: Physeter catodon
<220> FEATURE:
<221> NAME/KEY: misc_feature
<222> LOCATION: (0)...(0)
<223> OTHER INFORMATION: Casein k cDNA

<400> SEQUENCE: 18

```
atgaagagtt ttttactagt tgtgactatc ctggcattaa ccctgccttt tttgagtgca    60
gaggggcaaa accaggaaca atcaacacgc tgtgagaatg atgaaagatt gttcaataaa    120
aaaacagtaa aatatatccc aattcattat gtgctgagta ggtatcctag ttatggactc    180
aattactacc agcacagacc agttgcacta attaataacc aatttatgcc ataccatat    240 tatgcaaagc cagttgtagt tagcccacat gcccaaattc ctcaatggca attcctgcca    300
aatatccacc cacctactct ggcacatcac ccacacccac gtccatcatt tactgccatc    360
```

```
ccaccaaaga aaactcagga taaaacagca atccctatca tcaataccat tgctactgtt      420
gagcctacac ttatacctac cactgaacca atagtgaaca ctgtagttac tccagaagct      480
tcctcagaat tcatcacgag tacacctgag accaccacag tccaagttgc ttcacctgtg      540
gcctaa                                                                546
```

```
<210> SEQ ID NO 19
<211> LENGTH: 165
<212> TYPE: PRT
<213> ORGANISM: Tachyglossus aculeatus
<220> FEATURE:
<221> NAME/KEY: VARIANT
<222> LOCATION: (0)...(0)
<223> OTHER INFORMATION: Casein k

<400> SEQUENCE: 19
```

Met Lys Thr Leu Leu Leu Val Gly Gly Ile Leu Val Met Thr Val Cys
1               5                   10                  15

Phe Ser Ala Ala Glu Asp Glu Glu Trp Lys Lys Val Asp Tyr Ser Glu
            20                  25                  30

Ser Glu Glu Arg Trp Leu Arg Leu Lys Arg Gln Pro Ser Phe Pro Phe
        35                  40                  45

Ser Phe Gln Gly Lys Pro Glu Arg Asn Ile Pro Arg Pro Tyr Tyr Pro
    50                  55                  60

Arg Pro Phe Leu Asn Ile Pro Arg Pro Tyr Thr Ile Asn Pro Glu His
65                  70                  75                  80

Gln Phe Ala Tyr Val Phe Pro Asn Leu Lys Phe Gln Ile Pro Ser Val
                85                  90                  95

Phe Pro Phe Pro Leu Glu Phe Leu Pro Pro Tyr Pro Phe Val His
            100                 105                 110

Pro Ile Tyr Tyr Gly Pro Gln Thr Ser Thr Pro Pro Arg Asn Pro Thr
        115                 120                 125

Val Thr Ser Gln Thr Pro Gln Pro Pro Val His Ser Ser Ala Asn Thr
    130                 135                 140

Pro Glu Ser Ala Thr Ala Ala Pro Val Thr Ala Thr Pro Met Ala Gln
145                 150                 155                 160

Thr Pro Leu Gln Pro
            165

```
<210> SEQ ID NO 20
<211> LENGTH: 498
<212> TYPE: DNA
<213> ORGANISM: Tachyglossus aculeatus
<220> FEATURE:
<221> NAME/KEY: misc_feature
<222> LOCATION: (0)...(0)
<223> OTHER INFORMATION: Casein k cDNA

<400> SEQUENCE: 20
atgaagactc tactactggt tggaggtatc ctggttatga ccgtttgctt ctccgcggca       60
gaggacgagg aatggaaaaa ggttgattac agcgagagtg aagaaagatg gttgaggctg      120
aagcgccagc caagctttcc ctttagcttc aaggcaaac  ctgagagaaa catcccacgt      180
ccttattacc ctcgaccatt tctaaatatt ccccgcccct acacgattaa ccctgagcac      240
caattcgcct atgttttttcc caacttgaag ttccaaatcc caagtgtatt tccatttccc      300
ctggaattcc tccacccttt ctatcccttt gttcatccca tctattatgg ccctcaaacc      360 tcaaccccctc ccagaaaatcc caccgtgacc agccaaactc cacagccccc tgtccattcc      420
```

```
tccgccaata cccccggagtc tgctactgct gccccgtga ctgctacccc catgggcccaa    480 actccccctcc aaccttaa                                                  498
```

<210> SEQ ID NO 21
<211> LENGTH: 178
<212> TYPE: PRT
<213> ORGANISM: Trichosurus Vulpecula
<220> FEATURE:
<221> NAME/KEY: VARIANT
<222> LOCATION: (0)...(0)
<223> OTHER INFORMATION: Casein k

<400> SEQUENCE: 21

```
Met Lys Val Leu Phe Leu Thr Val His Ile Leu Ala Val Met Val Cys
1               5                   10                  15

Phe Ser Thr Ala Asp Leu Asp Trp Glu Lys Trp Pro Cys Asp Lys Gln
            20                  25                  30

Asn Glu Arg Gln Ser Glu Leu Arg Gln Gln Pro Leu Arg Arg Ser Pro
        35                  40                  45

Val Gln Tyr Val Tyr Thr Pro Tyr Thr His Gln Ser Tyr Val Pro Val
    50                  55                  60

Ile Tyr Pro Pro Arg Ala Tyr Val Arg His Pro Tyr Phe Ser Arg Val
65                  70                  75                  80

Ala Trp Gln Lys Pro Tyr Pro Ser Tyr Met Pro Leu Leu Pro Ser Ile
                85                  90                  95

Tyr Pro Trp Ser Val Val Ser Arg Asn Leu His Pro Ala Phe Ala Phe
            100                 105                 110

Asn Pro Pro His Tyr Ala Gln Leu Pro Val Pro Ser Ser Pro Thr Asn
        115                 120                 125

Ser Pro Thr Thr Thr Ile Gln Thr Thr Asn Ile Pro Ile Thr Asn Pro
    130                 135                 140

Thr Ser Thr Ile Val Thr Pro Ala Val Ser Ser Lys Ser Ala Ala Thr
145                 150                 155                 160

Glu Asp Ser Ala Ala Ala Met Leu Thr Ser Pro Thr Ala Ala Gln
                165                 170                 175

Met Ala
```

<210> SEQ ID NO 22
<211> LENGTH: 537
<212> TYPE: DNA
<213> ORGANISM: Trichosurus Vulpecula
<220> FEATURE:
<221> NAME/KEY: misc_feature
<222> LOCATION: (0)...(0)
<223> OTHER INFORMATION: Casein k cDNA

<400> SEQUENCE: 22

```
atgaaggtcc tattcttgac tgtgcatatt ctggcagtaa tggtgtgctt ctcaactgct    60
gacttggact gggaaaaatg gccttgcgat aagcaaaatg aaagacagtc tgagctgaga   120
caacagccac tcagacggtc ccctgtccaa tatgtctaca ccccatatac acatcaatca   180
tacgtgccag tcatttatcc accaagggca tatgtacgtc atccatattt ctctagagta   240
gcatggcaga aaccatatcc ctcctatatg ccactgctgc ccagtatcta cccttggtct   300
gtggtttcta gaaacctaca ccctgcattc gcttttaatc cccctcatta tgcccagctt   360
ccagtaccat caagtccaac caacagcccc acaactacca ttcagactac aaacattccc   420
atcactaacc ccacaagcac tatagtcacc ccagctgtct cctccaagtc tgcggccaca   480
```

```
gaggatagcg cagctgctgc aatgttgact tccccaaccg ctgctcagat ggcataa      537
```

<210> SEQ ID NO 23
<211> LENGTH: 178
<212> TYPE: PRT
<213> ORGANISM: Monodelphis domestica
<220> FEATURE:
<221> NAME/KEY: VARIANT
<222> LOCATION: (0)...(0)
<223> OTHER INFORMATION: Casein k

<400> SEQUENCE: 23

```
Met Lys Val Leu Phe Leu Ile Gly His Ile Leu Leu Ala Met Val Cys
1               5                   10                  15

Phe Ser Thr Ala Glu Leu Asp Trp Arg Lys Trp Pro Cys Glu Lys Gln
            20                  25                  30

Met Glu Arg Pro Ser Glu Leu Glu Gln Gln Pro Gly Gln Pro Pro
        35                  40                  45

Val Gln Asp Val Tyr Thr Arg Tyr Thr Arg Gln Ile Tyr Val Pro Ile
    50                  55                  60

Leu Tyr Ala Pro Lys Thr Ser Ile Gln Tyr Pro Tyr Phe Ser Lys Leu
65                  70                  75                  80

Ala Trp Gln Arg Pro Tyr Ala Ala Tyr Ile Pro Leu Leu Ser Ser Arg
                85                  90                  95

Tyr Pro Trp Pro Val Ile Pro Arg Ser Pro His Pro Ser Phe Ala Phe
            100                 105                 110

Asn Pro Pro Gln Tyr Ala Arg Val Pro Ala Pro Ser Gly Pro Thr Ser
        115                 120                 125

Ser Pro Ala Ala Pro Met Glu Thr Thr Thr Ile Pro Ser Thr Ser Thr
    130                 135                 140

Val Ala Ala Thr Val Thr Pro Asp Ala Thr Ser Lys Phe Val Thr Thr
145                 150                 155                 160

Glu Tyr Ser Thr Thr Ala Thr Ile Pro Thr Ser Pro Ile Pro Glu Gln
                165                 170                 175

Gln Pro
```

<210> SEQ ID NO 24
<211> LENGTH: 537
<212> TYPE: DNA
<213> ORGANISM: Monodelphis domestica
<220> FEATURE:
<221> NAME/KEY: misc_feature
<222> LOCATION: (0)...(0)
<223> OTHER INFORMATION: Casein k cDNA

<400> SEQUENCE: 24

```
atgaaggtcc tgttcttgat tgggcatatt ctgttggcaa tggtgtgctt ctctactgct      60
gaactggact ggaggaaatg gccttgcgag aagcaaatgg aaagaccatc ggagctggaa     120
caacagccac ccggacagcc ccctgtccaa gacgtctaca cccgatacac ccgtcagatc     180
tacgtaccca tcttgtatgc acccaagact tccatccagt atccatattt ctctaagcta     240
gcctggcaga gaccatatgc tgcctacata ccactgctgt ccagtcgcta cccgtggcct     300
gtgattccta gaagcccaca cccttccttc gcttttaatc cccacaata tgcccggggtt     360 ccagccccat caggtcctac cagcagcccc gcagctccca tggagactac aaccattccc     420
agcacgagca ccgtagctgc gactgtcacc cccgacgcca cttctaaatt tgtaaccacc     480
gagtatagca caactgcaac aatcccaact tccccaatcc ctgaacagca accatga       537
```

-continued

```
<210> SEQ ID NO 25
<211> LENGTH: 224
<212> TYPE: PRT
<213> ORGANISM: Bos taurus
<220> FEATURE:
<221> NAME/KEY: VARIANT
<222> LOCATION: (0)...(0)
<223> OTHER INFORMATION: Casein beta

<400> SEQUENCE: 25

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
    210                 215                 220

<210> SEQ ID NO 26
<211> LENGTH: 780
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein beta cDNA

<400> SEQUENCE: 26
atgccattaa atactatata taaacaacca caaatcaga  tcattatcca ttcagctcct      60
ccttcacttc ttgtcctcta ctttggaaaa aaggaattga gagccatgaa ggtcctcatc    120
cttgcctgcc tggtggctct ggcccttgca agagagctgg aagaactcaa tgtacctggt    180
gagattgtgg aaagcctttc aagcagtgag gaatctatta cacgcatcaa taagaaaatt    240
gagaagtttc agagtgagga acagcagcaa acagaggatg aactccagga taaaatccac    300
ccctttgccc agacacagtc tctagtctat cccttccctg ggcccatccc taacagcctc    360
ccacaaaaca tccctcctct tactcaaacc cctgtggtgg tgccgccttt ccttcagcct    420
```

-continued

```
gaagtaatgg gagtctccaa agtgaaggag ctatggctc ctaagcacaa agaaatgccc    480
ttccctaaat atccagttga gcccttact  gaaagccaga gcctgactct cactgatgtt    540
gaaaatctgc accttcctct gcctctgctc cagtcttgga tgcaccagcc tcaccagcct    600
cttcctccaa ctgtcatgtt tcctcctcag tccgtgctgt cccttttctca gtccaaagtc   660 ctgcctgttc cccagaaagc agtgccctat ccccagagag atatgcccat tcaggccttt    720
ctgctgtacc aggagcctgt actcggtcct gtccggggac ccttccctat tattgtctaa    780
```

```
<210> SEQ ID NO 27
<211> LENGTH: 222
<212> TYPE: PRT
<213> ORGANISM: Capra hircus
<220> FEATURE:
<221> NAME/KEY: VARIANT
<222> LOCATION: (0)...(0)
<223> OTHER INFORMATION: Casein beta

<400> SEQUENCE: 27
```

Met Lys Val Leu Ile Leu Ala Cys Leu Val Ala Leu Ala Ile Ala Arg
1               5                   10                  15

Glu Gln Glu Glu Leu Asn Val Val Gly Glu Thr Val Glu Ser Leu Ser
            20                  25                  30

Ser Ser Glu Glu Ser Ile Thr His Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Ala Gln Ser Leu Val Tyr Pro Phe Thr Gly Pro
65                  70                  75                  80

Ile Pro Asn Ser Leu Pro Gln Asn Ile Leu Pro Leu Thr Gln Thr Pro
                85                  90                  95

Val Val Val Pro Pro Phe Leu Gln Pro Glu Ile Met Gly Val Pro Lys
            100                 105                 110

Val Lys Glu Thr Met Val Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Lys Leu His Leu Pro Leu Pro Leu Val Gln Ser Trp Met His
145                 150                 155                 160

Gln Pro Pro Gln Pro Leu Ser Pro Thr Val Met Phe Pro Pro Gln Ser
                165                 170                 175

Val Leu Ser Leu Ser Gln Pro Lys Val Leu Pro Val Pro Gln Lys Ala
            180                 185                 190

Val Pro Gln Arg Asp Met Pro Ile Gln Ala Phe Leu Leu Tyr Gln Glu
        195                 200                 205

Pro Val Leu Gly Pro Val Arg Gly Pro Phe Pro Ile Leu Val
    210                 215                 220

```
<210> SEQ ID NO 28
<211> LENGTH: 669
<212> TYPE: DNA
<213> ORGANISM: Capra hircus
<220> FEATURE:
<221> NAME/KEY: misc_feature
<222> LOCATION: (0)...(0)
<223> OTHER INFORMATION: Casein beta cDNA

<400> SEQUENCE: 28
```

```
atgaaggtcc tcatccttgc ctgtctggtg gctctggcca ttgcaagaga gcaggaagaa    60
ctcaatgtag tcggtgagac tgtggaaagc ctttcaagca gtgaggaatc tattacacac   120
atcaataaga aaattgagaa gtttcaaagt gaggaacaac agcaaacaga ggatgaactc   180
caggataaaa tccaccccct tgcccaggca cagtctctag tctatccctt cactgggccc   240
atccctaaca gcctcccaca aacatcctg cctcttactc aaaccctgt ggtggtgccg    300
cctttccttc agcctgaaat aatgggagtc cccaaagtga aggagactat ggttcctaag   360
cacaaagaaa tgcccttccc taaatatcca gttgagccct ttactgaaag ccagagcctg   420
actctcactg atgttgaaaa gctgcacctt cctctgcctc tggtccagtc ttggatgcac   480
cagcctcccc agcctctttc tccaaccgtc atgtttcctc ctcagtccgt gctgtccctt   540
tctcagccca agttctgcc tgttccccag aaagtagtgc cccagagaga tatgcccatc   600
caggcctttc tgctgtacca ggagcctgta cttggtcctg tccggggacc cttccctatt   660
cttgtctaa                                                           669
```

<210> SEQ ID NO 29
<211> LENGTH: 244
<212> TYPE: PRT
<213> ORGANISM: Felis catus
<220> FEATURE:
<221> NAME/KEY: VARIANT
<222> LOCATION: (0)...(0)
<223> OTHER INFORMATION: Casein beta

<400> SEQUENCE: 29

```
Met Lys Val Leu Ile Leu Ala Cys Leu Leu Ala Leu Ala Leu Ala Arg
1               5                   10                  15

Glu Lys Glu Glu Leu Thr Val Ser Thr Glu Thr Val Glu Ser Leu Ser
            20                  25                  30

Ser Ser Glu Glu Ser Ile Thr His Ile Asn Lys Gln Lys Leu Glu Asn
        35                  40                  45

Leu Lys Arg Glu Glu Gln Gln Arg Gln Glu Arg Gln Asn Lys
    50                  55                  60

Ile His Pro Val Phe Gln Pro Gln Pro Leu Val Tyr Pro Tyr Ala Glu
65                  70                  75                  80

Pro Ile Pro Tyr Pro Val Leu Pro Gln Asn Ile Leu Pro Leu Ala Gln
                85                  90                  95

Pro Ala Met Val Leu Pro Phe Leu Gln Pro Glu Ile Met Glu Ile Pro
            100                 105                 110

Lys Val Lys Glu Thr Ile Phe Pro Arg Arg Lys Val Met Pro Ile Leu
        115                 120                 125

Lys Ser Pro Val Val Pro Ser Leu Asp Ser Gln Ile Val Asn Leu Pro
    130                 135                 140

Asp Leu Glu Ser Leu His Leu Pro Leu Pro Leu Pro Leu Ser Leu Leu
145                 150                 155                 160

Gln Pro Leu Met His Gln Ile Pro Gln Pro Leu Pro Gln Thr Thr Met
                165                 170                 175

Leu Pro Pro Gln Pro Leu Leu Ser Ile Pro Gln Pro Lys Val Met Pro
            180                 185                 190

Phe Pro Gln Gln Ile Val Pro Tyr Leu Gln Arg Asp Met Pro Val Gln
        195                 200                 205

Thr Leu Leu Leu Tyr Gln Asp Ala Thr Arg Glu Ala Gln Pro Val Thr
    210                 215                 220

Ala Pro Ala Tyr Asn Pro Val Ile Val Ser Pro Asn Leu Ile Ile Pro
```

```
225                 230                 235                 240
Leu Ser His Leu

<210> SEQ ID NO 30
<211> LENGTH: 735
<212> TYPE: DNA
<213> ORGANISM: Felis catus
<220> FEATURE:
<221> NAME/KEY: misc_feature
<222> LOCATION: (0)...(0)
<223> OTHER INFORMATION: Casein beta cDNA

<400> SEQUENCE: 30
atgaaggtcc tcatcctcgc ctgcctgctg gctcttgctc ttgcaagaga gaaggaagaa      60
ctcactgtat ccactgagac tgtggaaagt ctttcaagca gtgaggaatc tattacacac     120
atcaacaagc agaaacttga gaatcttaaa cgtgaggagc agcagcagag acaggaggaa     180
cgccagaata aaatccaccc cgttttccag ccacagcctc tagtctatcc ttatgctgag     240
cccattcctt accctgttct tccacagaac atccttcccc ttgctcagcc tgctatggtg     300 ctgccttttcc ttcagcctga ataatggaa atccccaaag ttaaggagac catctttccc     360
aggcgcaaag tgatgcccat tctgaaatct ccagtagtgc cctctttgga cagccaaatc     420
gtgaatctcc ctgatcttga aagtctgcac ttgcctctgc ctctgcctct gtctctactc     480
cagcccctga tgcaccagat cccccagcct cttcctcaga ctaccatgct tcctcctcag     540
ccactgctgt ccatcccaca gcccaaagtc atgcctttc cccagcaaat tgtgccctac     600
ctccagagag acatgcccgt gcaaacccta ctgctgtacc aggatgccac ccgtgaggcc     660
caacctgtga ctgccccagc ttacaatcct gttattgtaa gtccaaactt aataattccg     720
ctgtctcact tatga                                                      735

<210> SEQ ID NO 31
<211> LENGTH: 225
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Casein beta

<400> SEQUENCE: 31

Met Lys Val Leu Ile Leu Ala Cys Leu Val Ala Leu Ala Leu Ala Arg
1               5                   10                  15

Glu Thr Ile Glu Ser Leu Ser Ser Ser Glu Glu Ser Ile Thr Glu Tyr
            20                  25                  30

Lys Lys Val Glu Lys Val Lys His Glu Asp Gln Gln Gln Gly Glu Asp
        35                  40                  45

Glu His Gln Asp Lys Ile Tyr Pro Ser Phe Gln Pro Gln Pro Leu Ile
    50                  55                  60

Tyr Pro Phe Val Glu Pro Ile Pro Tyr Gly Phe Leu Pro Gln Asn Ile
65                  70                  75                  80

Leu Pro Leu Ala Gln Pro Ala Val Val Leu Pro Val Pro Gln Pro Glu
                85                  90                  95

Ile Met Glu Val Pro Lys Ala Lys Asp Thr Val Tyr Thr Lys Gly Arg
            100                 105                 110

Val Met Pro Val Leu Lys Ser Pro Thr Ile Pro Phe Phe Asp Pro Gln
        115                 120                 125

Ile Pro Lys Leu Thr Asp Leu Glu Asn Leu His Leu Pro Leu Pro Leu
```

```
                    130                 135                 140
Leu Gln Pro Leu Met Gln Gln Val Pro Gln Pro Ile Pro Gln Thr Leu
145                 150                 155                 160

Ala Leu Pro Pro Gln Pro Leu Trp Ser Val Pro Gln Pro Lys Val Leu
                165                 170                 175

Pro Ile Pro Gln Gln Val Val Pro Tyr Pro Gln Arg Ala Val Pro Val
                180                 185                 190

Gln Ala Leu Leu Leu Asn Gln Glu Leu Leu Leu Asn Pro Thr His Gln
                195                 200                 205

Ile Tyr Pro Val Thr Gln Pro Leu Ala Pro Val His Asn Pro Ile Ser
        210                 215                 220

Val
225

<210> SEQ ID NO 32
<211> LENGTH: 678
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Casein beta cDNA

<400> SEQUENCE: 32
atgaaggtcc tcatcctcgc ctgcctggtg gctcttgctc ttgcaaggga gaccatagaa      60
agcctttcaa gcagtgagga atctattaca gaatacaaga agttgagaa ggttaaacat     120 gaggaccagc agcaaggaga ggatgaacac caggataaaa tctacccctc tttccagcca     180
cagcctctga tctatccatt cgttgaacct atccctatg gttttcttcc acaaaacatt      240
ctgcctcttg ctcagcctgc tgtggtgctg cctgtccctc agcctgaaat aatggaagtc     300
cctaaagcta agacactgt ctacactaag ggcagagtga tgcctgtcct taaatctcca      360 acgatacccct ttttgaccc tcaaatccca aaactcactg atcttgaaaa tctgcatctt     420
cctctgcctc tgctccagcc cttgatgcag caggtccctc agcctattcc tcagactctt     480
gcacttcccc ctcagcccct gtggtctgtt cctcagccca agtcctgcc tatccccag     540 caagtggtgc cctaccctca gagagctgtg cctgttcaag cccttctgct caaccaagaa     600
cttctactta accccaccca ccagatctac cctgtgactc agccacttgc cccagttcat     660
aaccccatta gtgtctaa                                                    678

<210> SEQ ID NO 33
<211> LENGTH: 263
<212> TYPE: PRT
<213> ORGANISM: Loxodonta Africana
<220> FEATURE:
<221> NAME/KEY: VARIANT
<222> LOCATION: (0)...(0)
<223> OTHER INFORMATION: Casein beta

<400> SEQUENCE: 33

Met Lys Val Phe Ile Leu Ala Cys Leu Val Ala Phe Ala Leu Gly Arg
1               5                   10                  15

Glu Thr Val Glu Asn Leu Ser Ser Ser Glu Ile Arg Gln Phe Tyr Ser
                20                  25                  30

Glu Gln Lys Pro Glu Gly Val Lys His Glu Glu Gln Gln Arg Glu Asp
            35                  40                  45

Glu His Gln Asn Lys Ile Gln Pro Leu Phe Gln Pro Gln Pro Leu Val
        50                  55                  60
```

Tyr Pro Phe Ala Glu Pro Ile Pro Tyr Thr Val Phe Pro Pro Asn Ala
65                  70                  75                  80

Ile Pro Leu Ala Gln Pro Ile Val Val Leu Pro Phe Pro Gln Pro Glu
                85                  90                  95

Val Lys Gln Leu Pro Glu Ala Lys Glu Ile Thr Phe Pro Arg Gln Lys
            100                 105                 110

Leu Met Ser Phe Leu Lys Ser Pro Val Met Pro Phe Phe Asp Pro Gln
        115                 120                 125

Ile Pro Asn Leu Gly Thr Asp Leu Glu Asn Leu His Leu Pro Leu Pro
    130                 135                 140

Leu Leu Gln Pro Leu Arg His Gln Leu His Gln Pro Leu Ala Gln Thr
145                 150                 155                 160

Pro Val Leu Pro Leu Pro Leu Ser Leu Pro Lys Val Leu Pro Val Pro
                165                 170                 175

Gln Gln Val Ile Pro Tyr Pro Gln Arg Gly Arg Pro Ile Gln Asn Leu
            180                 185                 190

Gln Leu Tyr Glu Glu Pro Leu Leu Asp Pro Thr Arg Lys Ile Tyr Pro
        195                 200                 205

Val Ala Gln Pro Leu Ala Pro Val Tyr Asn Pro Val Ala Tyr Met Ile
    210                 215                 220

Gly Ile Pro Cys Cys Ser Thr Leu Leu Thr Tyr Leu His Gln Ser Ser
225                 230                 235                 240

Arg Ser Gln Tyr Pro Ile Gln Asn Lys Leu Gly Tyr Leu Ile Ala Met
                245                 250                 255

Pro Lys Lys Val Arg Pro Thr
            260

<210> SEQ ID NO 34
<211> LENGTH: 792
<212> TYPE: DNA
<213> ORGANISM: Loxodonta Africana
<220> FEATURE:
<221> NAME/KEY: misc_feature
<222> LOCATION: (0)...(0)
<223> OTHER INFORMATION: Casein beta cDNA

<400> SEQUENCE: 34
atgaaggtct tcatccttgc ctgcctggtg gcttttgctc ttggaagaga gactgtagaa     60
aatctttcaa gcagtgagat aagacaattt tattcagagc aaaaacctga gggagttaag    120
catgaggaac agcaaagaga ggatgaacat cagaataaaa tccagcccct tttccagcca    180
cagcctctag tctatccttt cgctgagccc attccttata ctgtctttcc accaaacgcc    240
attcctcttg ctcagcctat tgtggtgctg ccttttccct cagcctgaagt aaagcaactc    300 cctgaagcta agaaaatcac ctttcctagg caaaaattga tgtccttcct aagtctcca    360 gtaatgccct tttttgatcc ccagatccca aatcttggga ccgatcttga aaatctgcac    420
cttcctctgc ctctgctcca gcccttaaga caccagctcc accagcctct tgctcagact    480
ccagtgcttc ctcttcctct atccttgccc aaagtcctgc ccgttcccca gcaggtgata    540
ccctatcccc agagaggtag acccatccaa aaccttcaac tgtacgaaga gcctctactt    600
gacccaaccc gtaagatcta cccagtggct caaccacttg ctccagttta taccctgtt    660 gcttacatga taggtattcc ctgttgctca acattgctca catacttaca ccagagcagt    720
aggagccagt atcccatcca gaataaactg ggttacttaa tagcaatgcc aaagaaagta    780
cgacctacat ga                                                        792

<210> SEQ ID NO 35
<211> LENGTH: 302
<212> TYPE: PRT
<213> ORGANISM: Macropus eugenii
<220> FEATURE:
<221> NAME/KEY: VARIANT
<222> LOCATION: (0)...(0)
<223> OTHER INFORMATION: Casein beta

<400> SEQUENCE: 35

Met Lys Leu Leu Ile Leu Thr Cys Leu Val Ala Leu Gly Phe Ala Arg
1               5                   10                  15

Pro Met Val Glu Lys Ile Ser Glu Ser Glu Tyr Val Asn Glu Val
            20                  25                  30

Pro Glu Lys Arg Leu Lys Arg Arg Phe Pro Val Lys Asn Glu His Gln
            35                  40                  45

Val Glu Ile Asn His His Leu Arg Pro Glu Ser Glu Met Met Ser Leu
    50                  55                  60

Tyr Tyr Gln Pro Phe Tyr Trp Ser Glu Glu Met Arg Asn Leu Lys Met
65                  70                  75                  80

Thr Ser Leu Pro Lys Asp Arg Arg Met Ala Val Leu Lys Ser Thr Val
                85                  90                  95

Ser Asp Glu Val Phe Pro Ser Leu Gln His Lys Ser Leu Ser Leu Pro
            100                 105                 110

Lys Ser Lys Val Gln Pro Leu Ser Arg Gln Gln Ile Leu Thr Phe His
            115                 120                 125

Thr Leu Gln Met Val Pro Leu Ser His Lys Leu Leu Thr Thr Pro Lys
    130                 135                 140

Arg Glu Met Leu Pro Ile Tyr Glu Arg Glu Arg Leu Pro Ala His Lys
145                 150                 155                 160

Arg Glu Ser Leu Leu Ala His Glu Arg Glu Ser Leu Leu Ala His Glu
                165                 170                 175

Arg Asp Ile Leu Val Pro Gln Arg Glu Met Ser Phe Val Pro Glu Arg
            180                 185                 190

Glu Phe Leu Phe Ala Ser Glu Arg Val Val Leu Pro Glu Gln Glu Lys
            195                 200                 205

Glu Ile Leu His Asn Asp Glu Arg Glu Val Leu Ala Val His Lys Lys
    210                 215                 220

Glu Ile Leu Pro Pro Phe Glu Lys Glu Lys Val Leu Pro Leu Leu Gln
225                 230                 235                 240

His Arg Val Val Pro Leu Pro Gln Arg Glu Ile Val Pro Pro Phe Gln
                245                 250                 255

Arg Glu Thr Leu Leu Pro Glu Glu Ile Leu Pro Val Asn Gln Trp Glu
            260                 265                 270

Leu Met Pro Glu Val Val Pro Phe Asp Pro Tyr Pro Phe Leu Gln Pro
            275                 280                 285

Val Ala Pro Phe Tyr Tyr Ser Thr Glu Leu Asn Glu Lys Asn
    290                 295                 300

<210> SEQ ID NO 36
<211> LENGTH: 263
<212> TYPE: PRT
<213> ORGANISM: Monodelphis domestica
<220> FEATURE:
<221> NAME/KEY: VARIANT
<222> LOCATION: (0)...(0)
<223> OTHER INFORMATION: Casein beta

<400> SEQUENCE: 36

Met Lys Leu Leu Ile Leu Ser Cys Leu Val Ala Leu Ala Val Ala Arg
1               5                   10                  15

Pro Met Val Glu Lys Ile Ser Glu Thr Glu Glu Phe Val Thr Val Ile
            20                  25                  30

Pro Glu Gln Gln Ile Arg Arg Glu Asp Val Pro Val Lys Asn Glu Arg
        35                  40                  45

His Pro Glu Ile Asn Arg Phe Ile Pro Leu Glu Ala Glu Thr Met Ser
    50                  55                  60

Phe Tyr Val Pro Val Tyr Trp Pro Glu Met Arg Asp Ala Lys Met
65                  70                  75                  80

Thr Ser Pro Leu Lys Glu Lys Arg Met Thr Leu Ala Asn Pro Ile Ala
                85                  90                  95

Pro Glu Glu Glu Leu Pro His Leu Gln His Lys Ser Leu Ser Leu Ala
            100                 105                 110

Lys Gln Arg Phe Leu Ala Ser Leu Arg Pro Lys Ala Ala Gln Pro Phe
        115                 120                 125

Tyr Ala Pro Arg Met Ala Pro Leu Pro His Lys Leu Phe Thr Met Pro
    130                 135                 140

Lys Glu Gln Ala Leu Pro Ile Ala Lys Arg Asp Met Leu Ser Ala Ala
145                 150                 155                 160

Glu Leu Val Ile Pro Ala Val His Glu Arg Val Ile Pro Ala Ile Asp
                165                 170                 175

Lys Arg Glu Pro Leu Pro Leu Leu Ala Arg Glu Met Pro Ala Leu Pro
            180                 185                 190

Asp Lys Glu Ile Gln Gln Leu Ala Val Pro Phe Val Arg Arg Glu Ser
        195                 200                 205

Ala Leu Pro His Gln Arg Ala Ile Val Pro Val Ala Thr Ala Ala Ala
    210                 215                 220

Ala Val Arg Glu Ser Leu Pro Leu Val Gln Gln Glu Val Val Pro Pro
225                 230                 235                 240

Ile Met Pro Leu Asp Val Tyr Leu Val Arg His Pro Glu Val Ser Phe
                245                 250                 255

Tyr Asn Pro Thr Glu Lys Tyr
            260

<210> SEQ ID NO 37
<211> LENGTH: 792
<212> TYPE: DNA
<213> ORGANISM: Monodelphis domestica
<220> FEATURE:
<221> NAME/KEY: misc_feature
<222> LOCATION: (0)...(0)
<223> OTHER INFORMATION: Casein beta cDNA

<400> SEQUENCE: 37

```
atgaagctcc tcatcctcag ctgccttgtg gctcttgctg ttgccaggcc tatggtggaa      60
aagatctcag aaactgagga atttgtcacc gtcatcccgg agcaacagat caggagagag     120
gacgtcccag taaagaacga gcgtcatcct gaaatcaacc gctttattcc ccttgaagct     180
gaaacgatga gctttacgt gcccgtttac tggcccgaag aaatgcgtga cgccaagatg     240
accagccctc taaagagaa gagaatgacc ctcgctaacc ctattgcccc ggaggaagag     300
ctccctcacc tgcagcacaa atctctgtct ctcgctaagc aaagattcct ggcttctctt     360
cgccccaagg cggcgcagcc cttctatgcc ccaaggatgg cccctctccc tcacaaactg     420
```

-continued

```
tttaccatgc ccaaggagca ggcgctgcct attgccaaga gagacatgct gtccgccgcc    480
gagctcgtca tccctgcagt gcacgagaga gtcattccag ccattgacaa gagagagccc    540
ctgccgcttc ttgcgagaga gatgccagct cttcccgaca aagagattca acaactggct    600
gtgcccttcg tccgcagaga gagcgcgctc cctcaccaga gagccatcgt gcctgtcgcc    660
accgccgccg ccgccgtgag ggagagcctg cctctggtcc agcaggaagt cgtgcctccc    720
atcatgcctc tcgatgtcta cctggtccgc cacccagagg tcagcttcta caatcccacc    780
gagaagtact aa                                                        792
```

<210> SEQ ID NO 38
<211> LENGTH: 260
<212> TYPE: PRT
<213> ORGANISM: Mammuthus primigenius
<220> FEATURE:
<221> NAME/KEY: VARIANT
<222> LOCATION: (0)...(0)
<223> OTHER INFORMATION: Casein beta

<400> SEQUENCE: 38

```
Met Lys Val Phe Ile Leu Ala Cys Leu Val Ala Phe Ala Leu Gly Arg
1               5                   10                  15

Glu Thr Val Glu Asn Leu Ser Ser Ser Glu Ile Arg Gln Phe Tyr Ser
            20                  25                  30

Glu Gln Lys Pro Glu Gly Val Lys His Glu Glu Gln Gln Arg Glu Asp
        35                  40                  45

Glu His Gln Asn Lys Ile Gln Pro Leu Phe Gln Pro Gln Pro Leu Val
    50                  55                  60

Tyr Pro Phe Ala Glu Pro Ile Pro Tyr Thr Val Phe Pro Pro Asn Ala
65                  70                  75                  80

Ile Pro Leu Ala Gln Pro Ile Val Val Leu Pro Phe Pro Gln Pro Glu
                85                  90                  95

Val Gln Leu Pro Glu Ala Lys Glu Ile Thr Phe Pro Arg Gln Lys Leu
            100                 105                 110

Met Ser Phe Leu Lys Ser Pro Val Met Pro Phe Phe Asp Pro Gln Pro
        115                 120                 125

Asn Leu Gly Thr Asp Leu Glu Asn Leu His Leu Pro Leu Pro Leu Leu
    130                 135                 140

Gln Pro Leu Arg His Gln Leu His Gln Pro Leu Ala Gln Thr Pro Val
145                 150                 155                 160

Leu Pro Leu Pro Leu Ser Leu Pro Lys Val Leu Pro Val Pro Gln Gln
                165                 170                 175

Val Ile Pro Tyr Pro Gln Arg Gly Arg Pro Ile Gln Asn Leu Leu Tyr
            180                 185                 190

Glu Glu Pro Leu Leu Asp Pro Thr Arg Lys Ile Tyr Pro Val Ala Gln
        195                 200                 205

Pro Leu Ala Pro Val Tyr Asn Pro Val Ala Tyr Met Ile Gly Ile Pro
    210                 215                 220

Cys Cys Ser Thr Leu Leu Thr Tyr Leu His Gln Ser Ser Arg Ser Gln
225                 230                 235                 240

Tyr Pro Ile Gln Asn Lys Leu Gly Tyr Leu Ile Ala Met Pro Lys Lys
                245                 250                 255

Val Arg Pro Thr
            260
```

```
<210> SEQ ID NO 39
<211> LENGTH: 717
<212> TYPE: DNA
<213> ORGANISM: Mammuthus primigenius
<220> FEATURE:
<221> NAME/KEY: misc_feature
<222> LOCATION: (0)...(0)
<223> OTHER INFORMATION: Casein beta cDNA

<400> SEQUENCE: 39
atgaaggtct tcatccttgc ctgcctggtg gcttttgctc ttggaagaga gaaggaagaa      60
attattgtat ctactgagac tgtagaaaat ctttcaagca gtgagataag gcaattttat     120
tcagaggaat ctgttacaca agtcaacaaa caaaaacctg agggagttaa gcatgaggaa     180
cagcaaagag aggatgaaca tcagaataaa atccagcccc ttttccagcc acagcctcta     240
gtctatcctt tcgctgagcc cattccttat actgtctttc caccaaacgc cattcctctt     300
gctcagccta ttgtggtgct gccttttcct cagcctgaag taatgcaact ccctgaagct     360
aaagaaatca cctttcctag gcaaaaattg atgtccttcc ttaagtctcc agtaatgccc     420
ttttttgacc cccagatgcc aaatcttggg accgatcttg aaaatctgca ccttcctctg     480
cctctactcc agcccttaag acaccagctc caccagcctc ttgctcagac tccagtgctt     540
cctcttcctc tatccttgcc caaagtcctg cccgttcccc agcaggtgat accctatccc     600
cagagaggta gacccatcca aaaccttcca ctgtacgaag agcctctact tgacccaacc     660
cgtaagatct acccagtggc tcaaccactt gctccagttt ataaccctgt tgctgta       717

<210> SEQ ID NO 40
<211> LENGTH: 228
<212> TYPE: PRT
<213> ORGANISM: Oryctolagus cuniculus
<220> FEATURE:
<221> NAME/KEY: VARIANT
<222> LOCATION: (0)...(0)
<223> OTHER INFORMATION: Casein beta

<400> SEQUENCE: 40

Met Lys Val Leu Ile Leu Ala Cys Leu Val Ala Leu Ala Leu Ala Arg
1               5                   10                  15

Glu Lys Glu Gln Leu Ser Val Pro Thr Glu Ala Val Gly Ser Val Ser
            20                  25                  30

Ser Ser Glu Glu Ile Thr His Ile Asn Lys Gln Lys Leu Glu Thr Ile
        35                  40                  45

Lys His Val Glu Gln Leu Leu Arg Glu Glu Lys Leu Gln Asp Lys Ile
    50                  55                  60

Leu Pro Phe Ile Gln Ser Leu Phe Pro Phe Ala Glu Arg Ile Pro Tyr
65                  70                  75                  80

Pro Thr Leu Pro Gln Asn Ile Leu Asn Leu Ala Gln Leu Asp Met Leu
                85                  90                  95

Leu Pro Leu Leu Gln Pro Glu Ile Met Glu Asp Pro Lys Ala Lys Glu
            100                 105                 110

Thr Ile Ile Pro Lys His Lys Leu Met Pro Phe Leu Lys Ser Pro Lys
        115                 120                 125

Thr Val Pro Phe Val Asp Ser Gln Ile Leu Asn Leu Arg Glu Met Lys
    130                 135                 140

Asn Gln His Leu Leu Leu Pro Gln Leu Leu Pro Phe Met His Gln Val
145                 150                 155                 160

Phe Gln Pro Phe Pro Gln Thr Pro Ile Pro Tyr Pro Gln Ala Leu Leu
                165                 170                 175
```

Ser Leu Pro Gln Ser Lys Phe Met Pro Ile Val Pro Gln Val Val Pro
                180                 185                 190

Tyr Pro Gln Arg Asp Met Pro Ile Gln Ala Leu Gln Leu Phe Gln Glu
            195                 200                 205

Leu Leu Phe Pro Thr His Gln Gly Tyr Pro Val Gln Pro Ile Ala
    210                 215                 220

Pro Val Asn Val
225

<210> SEQ ID NO 41
<211> LENGTH: 687
<212> TYPE: DNA
<213> ORGANISM: Oryctolagus cuniculus
<220> FEATURE:
<221> NAME/KEY: misc_feature
<222> LOCATION: (0)...(0)
<223> OTHER INFORMATION: Casein beta cDNA

<400> SEQUENCE: 41
atgaaggtcc tcattcttgc ctgcctggtg gctctcgctc ttgcaaggga gaaggaacaa        60
ctcagtgttc ccacagaggc tgtaggaagt gtttccagca gcgaggaaat tacacatatc      120
aacaagcaga aactcgagac gattaagcac gtggaacagc tgctaagaga ggagaaactc      180
caggataaaa tcctcccctt tattcaatca ctctttcctt ttgctgagcg catcccctac      240
cctactcttc cacagaacat cctgaacctt gctcaactcg acatgctgct acctctcctt      300
cagcctgaaa taatggaaga ccccaaggct aaagagacca ttatccctaa gcacaaactg      360
atgcccttcc ttaaatctcc aaagacggtc cctttgttg actctcaaat tctgaatctc       420
agggagatga aaaatcaaca ccttcttttg ccccagctcc tgcccttcat gcaccaggtc      480
ttccagcctt tccccagac tcccattcca tatcctcagg ccctcctctc tcttcctcag      540
tccaaattca tgcctattgt cccacaagtg gtgccctacc ctcaaaggga catgcctatc      600
caagcccttc agctgttcca agaactgctt ttccctaccc atcaaggcta ccctgtggtt      660
caaccaatag ccccagttaa tgtctaa                                          687

<210> SEQ ID NO 42
<211> LENGTH: 222
<212> TYPE: PRT
<213> ORGANISM: Ovis aries
<220> FEATURE:
<221> NAME/KEY: VARIANT
<222> LOCATION: (0)...(0)
<223> OTHER INFORMATION: Casein beta

<400> SEQUENCE: 42

Met Lys Val Leu Ile Leu Ala Cys Leu Val Ala Leu Ala Leu Ala Arg
1               5                   10                  15

Glu Gln Glu Glu Leu Asn Val Val Gly Glu Thr Val Glu Ser Leu Ser
            20                  25                  30

Ser Ser Glu Glu Ser Ile Thr His Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Ala Gln Ser Leu Val Tyr Pro Phe Thr Gly Pro
65                  70                  75                  80

Ile Pro Asn Ser Leu Pro Gln Asn Ile Leu Pro Leu Thr Gln Thr Pro
                85                  90                  95

```
Val Val Val Pro Pro Phe Leu Gln Pro Glu Ile Met Gly Val Pro Lys
            100                 105                 110
Val Lys Glu Thr Met Val Pro Lys His Lys Glu Met Pro Phe Pro Lys
        115                 120                 125
Tyr Pro Val Glu Pro Phe Thr Glu Ser Gln Ser Leu Thr Leu Thr Asp
    130                 135                 140
Val Glu Lys Leu His Leu Pro Leu Pro Leu Val Gln Ser Trp Met His
145                 150                 155                 160
Gln Pro Pro Gln Pro Leu Pro Pro Thr Val Met Phe Pro Pro Gln Ser
                165                 170                 175
Val Leu Ser Leu Ser Gln Pro Lys Val Leu Pro Val Pro Gln Lys Ala
        180                 185                 190
Val Pro Gln Arg Asp Met Pro Ile Gln Ala Phe Leu Leu Tyr Gln Glu
    195                 200                 205
Pro Val Leu Gly Pro Val Arg Gly Pro Phe Pro Ile Leu Val
    210                 215                 220
```

<210> SEQ ID NO 43
<211> LENGTH: 669
<212> TYPE: DNA
<213> ORGANISM: Ovis aries
<220> FEATURE:
<221> NAME/KEY: misc_feature
<222> LOCATION: (0)...(0)
<223> OTHER INFORMATION: Casein beta cDNA
<220> FEATURE:
<221> NAME/KEY: misc_feature
<222> LOCATION: 19
<223> OTHER INFORMATION: n = A,T,C or G

<400> SEQUENCE: 43

```
atgaaggtcc tcatccttnc ctgtctggtg gctctggccc ttgcaagaga gcaggaagaa      60
ctcaatgtag tcggtgagac tgtggaaagc ctttcaagca gtgaggaatc tattacacac     120
atcaataaga aaattgagaa gtttcaaagt gaggaacaac agcaaacaga ggatgaactc     180
caggataaaa tccaccccct tgcccaggca cagtctctag tctatccctt cactgggccc     240
atccctaaca gcctcccaca aaacatcctg cctcttactc aaacccctgt ggtggtgccg     300
cctttccttc agcctgaaat aatgggagtc cccaaagtga aggagactat ggttcctaag     360
cacaaggaaa tgcccttccc taaatatcca gttgagccct ttactgaaag ccagagcctg     420
actctcactg atgttgaaaa gctgcacctt cctctgcctc tggtccagtc ttggatgcac     480
cagcctcccc agcctcttcc tccaaccgtc atgtttcctc ctcagtccgt gctgtccctt     540
tctcagccca aagttctgcc tgttccccag aaagcagtgc cccagagaga tatgcccatc     600
caggcctttc tgctgtacca ggagcctgta cttggtcctg tccggggacc cttccctatt     660
cttgtctaa                                                            669
```

<210> SEQ ID NO 44
<211> LENGTH: 224
<212> TYPE: PRT
<213> ORGANISM: Physeter catodon
<220> FEATURE:
<221> NAME/KEY: VARIANT
<222> LOCATION: (0)...(0)
<223> OTHER INFORMATION: Casein beta

<400> SEQUENCE: 44

```
Met Lys Val Leu Ile Leu Ala Cys Leu Leu Ala Leu Ala Leu Ala Arg
1               5                   10                  15
```

```
Glu Lys Glu Glu Leu Asn Val Ser Gly Glu Thr Val Lys Ser Leu Ser
             20                  25                  30

Ser Ser Glu Glu Ser Val Thr His Met Asn Lys Lys Ile Gly Lys Phe
         35                  40                  45

Lys His Glu Glu Gln Gln Gln Thr Glu Asp Glu Arg Gln Asp Lys Ile
 50                  55                  60

His Arg Phe Ser Gln Pro Gln Pro Leu Val Tyr Ser Tyr Thr Gly Pro
 65                  70                  75                  80

Ile Pro Tyr Pro Ile Leu Pro Gln Asn Ile Leu Pro Leu Ala Gln Pro
                 85                  90                  95

Pro Val Leu Val Pro Phe Pro Gln Pro Gly Ile Met Glu Val Pro Lys
            100                 105                 110

Ala Lys Glu Thr Leu Leu Pro Lys His Lys Glu Met Pro Phe Pro Lys
        115                 120                 125

Ser Pro Val Glu Pro Phe Ile Glu Ser Gln Ser Leu Thr Leu Asn Asp
    130                 135                 140

Leu Glu Asn Leu His Leu Pro Leu Pro Leu Gln Ser Leu Met His
145                 150                 155                 160

Gln Pro Pro His Pro Leu Pro Thr Pro Met Phe Pro Pro Gln Pro
                165                 170                 175

Leu Gln Ser Leu Ser Gln Pro Lys Val Leu Pro Ile Pro Gln Gln Val
            180                 185                 190

Val Pro Tyr Leu Gln Arg Asp Met Pro Ile Gln Ala Leu Leu Leu Tyr
        195                 200                 205

Gln Glu Pro Val Leu Gly Pro Ile Arg Gly Leu Tyr Pro Val Ile Val
    210                 215                 220

<210> SEQ ID NO 45
<211> LENGTH: 675
<212> TYPE: DNA
<213> ORGANISM: Pyseter catodon
<220> FEATURE:
<221> NAME/KEY: misc_feature
<222> LOCATION: (0)...(0)
<223> OTHER INFORMATION: Casein beta cDNA

<400> SEQUENCE: 45
atgaaggtcc tcatccttgc ctgcttgttg gctcttgccc ttgcaagaga gaaagaagaa      60
ctcaatgtat ccggtgagac tgtgaaaagc ctttcaagca gtgaggaatc tgttacgcac     120
atgaacaaga aaattgggaa gtttaaacat gaggaacagc agcaaacaga ggatgaacgc     180
caggataaaa tccaccgctt ttcccagcca cagcctctag tctattccta cactgggcca     240
atcccttacc ctatccttcc acaaaacatc ctgcctcttg ctcagccccc tgtgctggtg     300
cctttccctc agcctggaat aatggaagtc cccaaagcta aggagactct ccttcctaag     360
cataaagaaa tgcccttccc taaatctcca gtagagccct ttattgaaag ccagagcctg     420
actctcaatg atcttgaaaa tctgcacctt cctctgcctc tgctccagtc cttgatgcac     480
cagcctcccc atcctcttcc tcctaccccc atgtttcctc ctcagcccct gcagtccctt     540
tctcagccca agtcctgcc tattcccag caagtggtgc cctacctcca gagagatatg     600
cccatccagg cccttctgct gtaccaggag cctgtacttg gtcctatccg ggggctctac     660
cctgttattg tctaa                                                      675

<210> SEQ ID NO 46
<211> LENGTH: 183
<212> TYPE: PRT
```

<213> ORGANISM: Tachyglossus aculeatus
<220> FEATURE:
<221> NAME/KEY: VARIANT
<222> LOCATION: (0)...(0)
<223> OTHER INFORMATION: Casein beta

<400> SEQUENCE: 46

Met Lys Val Phe Ile Leu Ala Cys Leu Val Ala Val Ala Met Ala Leu
1               5                   10                  15

Pro Lys Gln His Ser Ser Ser Ser Glu Glu Ser Asp Arg Leu
            20                  25                  30

Leu Val Lys Asp Ile Pro Thr Ala Phe Ser Ser Glu Glu His Ser Val
            35                  40                  45

Asp Pro Lys Glu Leu Tyr Glu Pro Arg Gln Ser Tyr Ser Tyr Pro Trp
        50                  55                  60

Gln Ser Val Arg Pro Ile Asn Thr Tyr Thr Tyr Pro Arg Ala Tyr Gln
65                  70                  75                  80

Ile Pro Ala Val Leu Pro Met Thr His Pro Gln Thr Leu Thr Tyr Leu
                85                  90                  95

Gln Pro Gln Phe Lys Pro Glu Asp Met Ser Ile Ser Gln Lys Gln Ile
            100                 105                 110

Pro Pro Tyr Val Gln Ala Val Val Met Pro Tyr Pro Gln Val Glu Ala
        115                 120                 125

Ile Pro Phe Pro Gly Ala Glu Phe Met Pro Tyr Ala Gln Pro Ile Thr
    130                 135                 140

Thr Pro Leu Leu Gln Pro Glu Val Phe Ser Ala Pro Phe Tyr Arg Glu
145                 150                 155                 160

Ala Val Phe Lys Pro Val Ile Tyr Gly Leu Pro Gln Ser Gln Pro Val
                165                 170                 175

Gln Lys Ile Pro Glu Thr Asp
            180

<210> SEQ ID NO 47
<211> LENGTH: 552
<212> TYPE: DNA
<213> ORGANISM: Tachyglossus aculeatus
<220> FEATURE:
<221> NAME/KEY: misc_feature
<222> LOCATION: (0)...(0)
<223> OTHER INFORMATION: Casein beta cDNA

<400> SEQUENCE: 47
atgaaggtct tcatcctcgc ctgcctagtg gctgttgcca tggcattgcc taaacaacac      60
agcagcagct cttccagtga ggaatctgac agactgctgg ttaaggacat tcctactgcc     120
ttctccagcg aggaacactc tgtggacccg aaggaactct acgagccccg tcagagctat     180
tcctacccat ggcaatcagt ccgtcccatc aacacctaca cttatcctcg cgcttaccaa     240
attccggctg tcctccccat gactcatcct cagaccctga cttatctcca gcctcaattc     300
aagcccgaag acatgtctat ttctcagaaa caaatcccgc cctacgtcca ggctgtagtc     360
atgccctacc cccaggttga agccattcct ttccccgggg ctgaattcat gccctacgct     420
caacccatca ccacgcctct acttcagcct gaggtcttct ccgccccatt ctacagagag     480
gccgtcttca agccagtgat ctacggcctt cctcaatctc aaccagttca gaagatccca     540
gaaaccgact ga                                                         552

<210> SEQ ID NO 48
<211> LENGTH: 214

```
<212> TYPE: PRT
<213> ORGANISM: Bos taurus
<220> FEATURE:
<221> NAME/KEY: VARIANT
<222> LOCATION: (0)...(0)
<223> OTHER INFORMATION: Casein alpha-S1

<400> SEQUENCE: 48

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
    50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
    130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Gly Lys
        195                 200                 205

Thr Thr Met Pro Leu Trp
    210

<210> SEQ ID NO 49
<211> LENGTH: 645
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein alpha-S1 cDNA

<400> SEQUENCE: 49
atgaaacttc tcatccttac ctgtcttgtg gctgttgctc ttgctaggcc taaacatcct      60
atcaagcacc aaggactccc tcaagaagtc ctcaatgaaa atttactcag gttttttgtg     120
gcaccttttc cagaagtgtt tggaaaggag aaggtcaatg aactgagcaa ggatattggg     180
agtgaatcaa ctgaggatca agccatggaa gatattaagc aaatggaagc tgaaagcatt     240
tcgtcaagtg aggaaattgt tcccaatagt gttgagcaga agcacattca aaaggaagat     300
gtgccctctg agcgttacct gggttatctg aacagcttct cagactgaa aaaatacaaa     360 gtaccccagc tggaaattgt tcccaatagt gctgaggaac gacttcacag tatgaaagag     420
ggaatccatg cccaacagaa agaacctatg ataggagtga atcaggaact ggcctacttc     480
```

```
taccctgagc ttttcagaca attctaccag ctggatgcct atccatctgg tgcctggtat      540
tacgttccac taggcacaca atacactgat gccccatcat tctctgacat ccctaatcct      600
attggctctg agaacagtga aaagactact atgccactgt ggtga                      645
```

```
<210> SEQ ID NO 50
<211> LENGTH: 222
<212> TYPE: PRT
<213> ORGANISM: Camelus dromedarius
<220> FEATURE:
<221> NAME/KEY: VARIANT
<222> LOCATION: (0)...(0)
<223> OTHER INFORMATION: Casein alpha-S1

<400> SEQUENCE: 50
```

```
Met Lys Leu Leu Ile Leu Thr Cys Leu Val Ala Val Ala Leu Ala Arg
1               5                   10                  15

Pro Lys Tyr Pro Leu Arg Tyr Pro Glu Val Phe Gln Asn Glu Pro Asp
            20                  25                  30

Ser Ile Glu Glu Val Leu Asn Lys Arg Lys Ile Leu Asp Leu Ala Val
        35                  40                  45

Val Ser Pro Ile Gln Phe Arg Gln Glu Asn Ile Asp Glu Leu Lys Asp
50                  55                  60

Thr Arg Asn Glu Pro Thr Glu Asp His Ile Met Glu Asp Thr Glu Arg
65                  70                  75                  80

Lys Glu Ser Gly Ser Ser Ser Glu Val Val Ser Ser Thr Thr
                85                  90                  95

Glu Gln Lys Asp Ile Leu Lys Glu Asp Met Pro Ser Gln Arg Tyr Leu
            100                 105                 110

Glu Glu Leu His Arg Leu Asn Lys Tyr Lys Leu Leu Gln Leu Glu Ala
        115                 120                 125

Ile Arg Asp Gln Lys Leu Ile Pro Arg Val Lys Leu Ser Ser His Pro
130                 135                 140

Tyr Leu Glu Gln Leu Tyr Arg Ile Asn Glu Asp Asn His Pro Gln Leu
145                 150                 155                 160

Gly Glu Pro Val Lys Val Val Thr Gln Pro Phe Pro Gln Phe Gln
                165                 170                 175

Leu Gly Ala Ser Pro Tyr Val Ala Trp Tyr Tyr Pro Gln Val Met
            180                 185                 190

Gln Tyr Ile Ala His Pro Ser Ser Tyr Asp Thr Pro Glu Gly Ile Ala
        195                 200                 205

Ser Glu Asp Gly Gly Lys Thr Asp Val Met Pro Gln Trp Trp
210                 215                 220
```

```
<210> SEQ ID NO 51
<211> LENGTH: 669
<212> TYPE: DNA
<213> ORGANISM: Camelus dromedarius
<220> FEATURE:
<221> NAME/KEY: misc_feature
<222> LOCATION: (0)...(0)
<223> OTHER INFORMATION: Casein alpha-S1 cDNA

<400> SEQUENCE: 51
```

```
atgaagcttc tcatccttac ctgccttgtg ctgttgcgc ttgccaggcc taaatatcct      60
ctcaggtacc cagaagtctt tcaaaatgaa ccagacagca tagaggaagt cctcaacaaa      120
agaaagattc ttgatttagc agtggtttca cccattcagt ttagacagga gaacatcgat      180
gaactgaagg atactaggaa cgaaccaacc gaagatcaca tcatggaaga cactgagcga      240
```

-continued

```
aaggaatctg gaagcagttc aagtgaggaa gttgtttcca gtaccactga gcagaaggac    300
attctcaagg aagatatgcc ctcccaacgc tatctggaag agcttcacag actgaacaaa    360
tacaaactac tccagctgga agctatccgt gaccagaaac ttattccaag agtgaagctg    420
tcctcccacc catatctgga acaactttac agaataaatg aggacaacca cccccaactg    480
ggggagcctg tgaaagtagt gactcagcct ttcccacaat tcttccagct tggtgcctct    540
ccctatgttg cttggtatta tcctccacaa gtcatgcaat atattgctca ccccctcatcc    600 tacgacaccc ctgaaggcat tgcctctgag gacggtggaa aaaccgacgt tatgccacag    660
tggtggtga                                                            669
```

```
<210> SEQ ID NO 52
<211> LENGTH: 213
<212> TYPE: PRT
<213> ORGANISM: Capra hircus
<220> FEATURE:
<221> NAME/KEY: VARIANT
<222> LOCATION: (0)...(0)
<223> OTHER INFORMATION: Casein alpha-S1

<400> SEQUENCE: 52
```

Met Lys Leu Leu Ile Leu Thr Cys Leu Val Val Ala Leu Ala Arg
1               5                   10                  15

Pro Lys His Pro Ile Asn His Gln Gly Leu Ser Pro Glu Val Leu Asn
            20                  25                  30

Glu Asn Leu Leu Arg Phe Val Val Ala Pro Phe Pro Glu Val Phe Arg
        35                  40                  45

Lys Glu Asn Ile Asn Glu Leu Ser Lys Asp Ile Gly Ser Glu Ser Thr
    50                  55                  60

Glu Asp Gln Ala Met Glu Asp Ala Lys Gln Met Lys Ala Gly Ser Ser
65                  70                  75                  80

Ser Ser Ser Glu Glu Ile Val Pro Asn Ser Ala Gln Lys Tyr Ile Gln
                85                  90                  95

Lys Glu Asp Val Pro Ser Glu Arg Tyr Leu Gly Tyr Leu Glu Gln Leu
            100                 105                 110

Leu Arg Leu Lys Lys Tyr Asn Val Pro Gln Leu Glu Ile Val Pro Lys
        115                 120                 125

Ser Ala Glu Glu Gln Leu His Ser Met Lys Glu Gly Asn Pro Ala His
    130                 135                 140

Gln Lys Gln Pro Met Ile Ala Val Asn Gln Glu Leu Ala Tyr Phe Tyr
145                 150                 155                 160

Pro Gln Leu Phe Arg Gln Phe Tyr Gln Leu Asp Ala Tyr Pro Ser Gly
                165                 170                 175

Ala Trp Tyr Tyr Leu Pro Leu Gly Thr Gln Tyr Thr Asp Ala Pro Ser
            180                 185                 190

Phe Ser Asp Ile Pro Asn Pro Ile Gly Ser Glu Asn Ser Gly Lys Thr
        195                 200                 205

Thr Met Pro Leu Trp
    210

```
<210> SEQ ID NO 53
<211> LENGTH: 642
<212> TYPE: DNA
<213> ORGANISM: Capra hircus
<220> FEATURE:
<221> NAME/KEY: misc_feature
<222> LOCATION: (0)...(0)
```

<223> OTHER INFORMATION: Casein alpha-S1 cDNA

<400> SEQUENCE: 53

```
atgaaacttc tcatccttac ctgtcttgtg gttgttgctc ttgccaggcc taaacatcct      60
atcaatcacc aaggactctc tccagaagtc ctcaatgaaa atttactcag gtttgttgtg     120
gcgccttttc agaagtgtt tagaaaggag aacatcaatg aactgagtaa ggatattggg      180
agtgaatcaa ctgaggatca agccatggaa gatgctaagc aaatgaaagc tggaagcagt     240
tcgtcaagtg aggaaattgt tcccaatagt gctcagaagt acattcaaaa ggaagatgtg     300
ccctctgagc gttacctggg ttatctggaa cagcttctca gactgaaaaa atacaacgtg     360
ccccagctgg aaattgttcc caaaagtgct gaggaacaac ttcacagtat gaaagaggga     420
aaccctgccc accagaaaca gcctatgata gcagtgaacc aggaactggc ctacttctac     480
cctcagcttt tcagacaatt ctaccagctg gacgcctatc atctggtgc ctggtactac      540
cttccactag gcacacaata cactgatgcc cctcattct ctgacatccc taatcccatt      600
ggctctgaga acagtggaaa gactactatg ccactgtggt ga                        642
```

<210> SEQ ID NO 54
<211> LENGTH: 212
<212> TYPE: PRT
<213> ORGANISM: Equus przewalskii
<220> FEATURE:
<221> NAME/KEY: CONFLICT
<222> LOCATION: (0)...(0)
<223> OTHER INFORMATION: Casein alpha-S1

<400> SEQUENCE: 54

```
Met Lys Leu Leu Ile Leu Thr Cys Leu Val Ala Val Ala Leu Ala Arg
1               5                   10                  15

Pro Lys Leu Pro His Arg Gln Pro Glu Ile Ile Gln Asn Lys Gln Asp
            20                  25                  30

Ser Arg Glu Lys Val Leu Lys Glu Arg Lys Phe Pro Ser Phe Ala Leu
        35                  40                  45

Glu Tyr Ile Asn Glu Leu Asn Arg Gln Arg Glu Leu Leu Lys Glu Lys
    50                  55                  60

Gln Lys Asp Glu His Lys Glu Tyr Leu Ile Glu Asp Pro Glu Gln Gln
65                  70                  75                  80

Glu Ser Ser Ser Thr Ser Ser Ser Glu Glu Val Val Pro Ile Asn Thr
                85                  90                  95

Glu Gln Lys Arg Ile Pro Arg Glu Asp Met Leu Tyr Gln His Thr Leu
            100                 105                 110

Glu Gln Leu Arg Arg Leu Ser Lys Tyr Asn Gln Leu Gln Leu Gln Ala
        115                 120                 125

Ile His Ala Gln Glu Gln Leu Leu Arg Met Lys Glu Asn Ser Gln Arg
    130                 135                 140

Lys Pro Met Arg Val Val Asn Gln Glu Gln Ala Tyr Phe Tyr Leu Glu
145                 150                 155                 160

Pro Phe Gln Pro Ser Tyr Gln Leu Asp Val Tyr Pro Tyr Ala Ala Trp
                165                 170                 175

Phe His Pro Ala Gln Ile Met Gln His Val Ala Tyr Ser Pro Phe His
            180                 185                 190

Asp Thr Ala Lys Leu Ile Ala Ser Glu Asn Ser Glu Lys Thr Asp Ile
        195                 200                 205

Ile Pro Glu Trp
    210
```

```
<210> SEQ ID NO 55
<211> LENGTH: 639
<212> TYPE: DNA
<213> ORGANISM: Equus przewalskii
<220> FEATURE:
<221> NAME/KEY: misc_feature
<222> LOCATION: (0)...(0)
<223> OTHER INFORMATION: Casein alpha-S1 cDNA

<400> SEQUENCE: 55
atgaagcttc tcatccttac ctgccttgtg gctgttgctc ttgccaggcc taaacttcct      60
catagacagc cagaaatcat tcagaataaa caggacagta gagagaaagt cctcaaagaa     120
agaaagtttc ccagttttgc tctagagtac atcaatgaac tgaacaggca gagagaactt     180
ctgaaagaaa aacagaaaga tgaacacaag gaatatctca tagaagaccc tgagcaacag     240
gaatctagca gcacttcatc aagcgaggaa gttgttccca ttaacactga gcagaagcgc     300
attccaaggg aagacatgct ctaccaacac actctggaac agcttcgcag actgagcaaa     360
tacaaccaac tccagctgca agccatccat gcccaggaac aacttctcag aatgaaggaa     420
aacagccaga gaaagcctat gagagtagtg aatcaggaac aggcctactt ctaccttgag     480
cctttccaac catcctacca gcttgatgtc tatccctatg ctgcttggtt tcatcctgcg     540
caaatcatgc aacatgttgc ttactcacca ttccatgaca ctgccaaact cattgcctct     600
gagaactcgg aaaaaactga cattatacca gagtggtga                            639

<210> SEQ ID NO 56
<211> LENGTH: 212
<212> TYPE: PRT
<213> ORGANISM: Equus asinus africanus
<220> FEATURE:
<221> NAME/KEY: VARIANT
<222> LOCATION: (0)...(0)
<223> OTHER INFORMATION: Casein alpha-S1

<400> SEQUENCE: 56

Met Lys Leu Leu Ile Leu Thr Cys Leu Val Ala Val Ala Leu Ala Arg
1               5                   10                  15

Pro Lys Leu Pro His Arg His Pro Glu Ile Ile Gln Asn Glu Gln Asp
            20                  25                  30

Ser Arg Glu Lys Val Leu Lys Glu Arg Lys Phe Pro Ser Phe Ala Leu
        35                  40                  45

Glu Tyr Ile Asn Glu Leu Asn Arg Gln Arg Glu Leu Leu Lys Glu Lys
    50                  55                  60

Gln Lys Asp Glu His Lys Glu Tyr Leu Ile Glu Asp Pro Glu Gln Gln
65                  70                  75                  80

Glu Ser Ser Ser Thr Ser Ser Ser Glu Glu Val Val Pro Ile Asn Thr
                85                  90                  95

Glu Gln Lys Arg Ile Pro Arg Glu Asp Met Leu Tyr Gln His Thr Leu
            100                 105                 110

Glu Ala Leu Arg Arg Leu Ser Lys Tyr Asn Gln Leu Gln Leu Gln Ala
        115                 120                 125

Ile Tyr Ala Gln Glu Gln Leu Leu Arg Met Lys Glu Asn Ser Gln Arg
    130                 135                 140

Lys Pro Met Arg Val Val Asn Gln Glu Gln Ala Tyr Phe Tyr Leu Glu
145                 150                 155                 160

Pro Phe Gln Pro Ser Tyr Gln Leu Asp Val Tyr Pro Tyr Ala Ala Trp
                165                 170                 175
```

```
Phe His Pro Ala Gln Ile Met Gln His Val Ala Tyr Ser Pro Phe His
        180                 185                 190

Asp Thr Ala Lys Leu Ile Ala Ser Glu Asn Ser Glu Lys Thr Asp Ile
        195                 200                 205

Ile Pro Glu Trp
    210

<210> SEQ ID NO 57
<211> LENGTH: 212
<212> TYPE: PRT
<213> ORGANISM: Equus caballus
<220> FEATURE:
<221> NAME/KEY: VARIANT
<222> LOCATION: (0)...(0)
<223> OTHER INFORMATION: Casein alpha-S1

<400> SEQUENCE: 57

Met Lys Leu Leu Ile Leu Thr Cys Leu Val Ala Val Ala Leu Ala Arg
1               5                   10                  15

Pro Lys Leu Pro His Arg Gln Pro Glu Ile Ile Gln Asn Glu Gln Asp
            20                  25                  30

Ser Arg Glu Lys Val Leu Lys Glu Arg Lys Phe Pro Ser Phe Ala Leu
        35                  40                  45

Glu Tyr Ile Asn Glu Leu Asn Arg Gln Arg Glu Leu Leu Lys Glu Lys
    50                  55                  60

Gln Lys Asp Glu His Lys Glu Tyr Leu Ile Glu Asp Pro Glu Gln Gln
65                  70                  75                  80

Glu Ser Ser Ser Thr Ser Ser Glu Glu Val Val Pro Ile Asn Thr
                85                  90                  95

Glu Gln Lys Arg Ile Pro Arg Glu Asp Met Leu Tyr Gln His Thr Leu
            100                 105                 110

Glu Gln Leu Arg Arg Leu Ser Lys Tyr Asn Gln Leu Gln Leu Gln Ala
        115                 120                 125

Ile His Ala Gln Glu Gln Leu Ile Arg Met Lys Glu Asn Ser Gln Arg
    130                 135                 140

Lys Pro Met Arg Val Val Asn Gln Glu Gln Ala Tyr Phe Tyr Leu Glu
145                 150                 155                 160

Pro Phe Gln Pro Ser Tyr Gln Leu Asp Val Tyr Pro Tyr Ala Ala Trp
            165                 170                 175

Phe His Pro Ala Gln Ile Met Gln His Val Ala Tyr Ser Pro Phe His
        180                 185                 190

Asp Thr Ala Lys Leu Ile Ala Ser Glu Asn Ser Glu Lys Thr Asp Ile
        195                 200                 205

Ile Pro Glu Trp
    210

<210> SEQ ID NO 58
<211> LENGTH: 640
<212> TYPE: DNA
<213> ORGANISM: Equus caballus
<220> FEATURE:
<221> NAME/KEY: misc_feature
<222> LOCATION: (0)...(0)
<223> OTHER INFORMATION: Casein alpha-S1 cDNA

<400> SEQUENCE: 58
catgaagctt ctcatcctta cctgccttgt ggctgttgct cttgccaggc ctaaacttcc      60
tcatagacag ccagaaatca ttcagaatga acaggacagt agagagaaag tcctcaaaga     120
```

```
aagaaagttt cccagttttg ctctagagta catcaatgaa ctgaacaggc agagagaact    180
tctgaaagaa aaacagaaag atgaacacaa ggaatatctc atagaagacc ctgagcaaca    240
ggaatctagc agcacttcat caagcgagga agttgttccc attaacactg agcagaagcg    300
cattccaagg gaagacatgc tctaccaaca cactctggaa cagcttcgca gactgagcaa    360
atacaaccaa ctccagctgc aagccatcca tgcccaggaa caacttatca gaatgaagga    420
aaacagccag agaaagccta tgagagtagt gaatcaggaa caggcctact tctaccttga    480
gcctttccaa ccatcctacc agcttgatgt ctatccctat gctgcttggt ttcatcctgc    540
gcaaatcatg caacatgttg cttactcacc attccatgac actgccaaac tcattgcctc    600
tgagaactcg gaaaaaactg acattatacc agagtggtga                         640
```

```
<210> SEQ ID NO 59
<211> LENGTH: 125
<212> TYPE: PRT
<213> ORGANISM: Felis catus
<220> FEATURE:
<221> NAME/KEY: VARIANT
<222> LOCATION: (0)...(0)
<223> OTHER INFORMATION: Casein alpha-S1

<400> SEQUENCE: 59
```

```
Met Glu Asp Pro Glu Gln Arg Glu Ile Ser Ser Ser Ser Ser Glu
1               5                   10                  15

Glu Ala Val Pro Asn Asn Thr Gln Gln Lys His Ile Ser Lys Glu Asp
            20                  25                  30

Ile Leu Ser Gln Arg Tyr Leu Glu Gln Leu His Arg Leu Ser Lys Tyr
        35                  40                  45

Asn Gln Leu Gln Leu Glu Ala Leu Arg Asp Gln Gln Leu Arg Arg
    50                  55                  60

Val Thr Glu Asn Asn His Ile Gln Leu Pro Phe Gln Gln Phe Tyr Gln
65                  70                  75                  80

Leu Asp Ala Tyr Pro Tyr Ala Val Trp Tyr Pro Pro Gln Val Met
                85                  90                  95

Gln Tyr Ile Ala Tyr Thr Pro Phe Tyr Asp Val Thr Lys Leu Thr Ala
            100                 105                 110

Pro Glu Asn Ala Glu Asn Val Gly Val Val Pro Glu Trp
        115                 120                 125
```

```
<210> SEQ ID NO 60
<211> LENGTH: 378
<212> TYPE: DNA
<213> ORGANISM: Felis catus
<220> FEATURE:
<221> NAME/KEY: misc_feature
<222> LOCATION: (0)...(0)
<223> OTHER INFORMATION: Casein alpha-S1 cDNA

<400> SEQUENCE: 60
```

```
atggaagacc ctgagcaaag ggaaattagc agcagttcat caagcgagga agctgttccc     60
aataacactc agcagaagca catttcaaag gaagatatac tctctcaacg ctatctggaa    120
cagcttcata gactgagcaa atacaaccaa ctgcaactgg aagctctccg tgaccagcaa    180
caactgcgca gagtgactga aaacaaccac atccaattgc ctttccaaca attctaccaa    240
cttgatgctt atccctatgc tgtgtggtat taccctccac aagtcatgca gtatattgct    300
tacacaccat tctatgacgt cactaaactt acggcccctg agaacgctga aaacgttggt    360
```

```
gttgtgccag agtggtag                                                      378
```

<210> SEQ ID NO 61
<211> LENGTH: 185
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Casein alpha-S1

<400> SEQUENCE: 61

```
Met Arg Leu Leu Ile Leu Thr Cys Leu Val Ala Val Ala Leu Ala Arg
1               5                   10                  15

Pro Lys Leu Pro Leu Arg Tyr Pro Glu Arg Leu Gln Asn Pro Ser Glu
            20                  25                  30

Ser Ser Glu Pro Ile Pro Leu Glu Ser Arg Glu Glu Tyr Met Asn Gly
        35                  40                  45

Met Asn Arg Gln Arg Asn Ile Leu Arg Glu Lys Gln Thr Asp Glu Ile
    50                  55                  60

Lys Asp Thr Arg Asn Glu Ser Thr Gln Asn Cys Val Val Ala Glu Pro
65                  70                  75                  80

Glu Lys Met Glu Ser Ser Ile Ser Ser Ser Glu Glu Met Ser Leu
                85                  90                  95

Ser Lys Cys Ala Glu Gln Phe Cys Arg Leu Asn Glu Tyr Asn Gln Leu
            100                 105                 110

Gln Leu Gln Ala Val His Ala Gln Glu Gln Ile Arg Arg Met Asn Glu
        115                 120                 125

Asn Ser His Val Gln Val Pro Phe Gln Gln Leu Asn Gln Leu Ala Ala
    130                 135                 140

Tyr Pro Tyr Ala Val Trp Tyr Tyr Pro Gln Ile Met Gln Tyr Val Pro
145                 150                 155                 160

Phe Pro Pro Phe Ser Asp Ile Ser Asn Pro Thr Ala His Glu Asn Tyr
                165                 170                 175

Glu Lys Asn Asn Val Met Leu Gln Trp
            180                 185
```

<210> SEQ ID NO 62
<211> LENGTH: 558
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Casein alpha-S1 cDNA

<400> SEQUENCE: 62

```
atgaggcttc tcattctcac ctgtcttgtg gctgttgctc ttgccaggcc taaacttcct     60
cttagatacc cagaacgcct tcagaatcca tcagagagca gtgagcctat accattagaa    120
tcaagagagg aatacatgaa tggtatgaac aggcagagaa acattctgag agaaaaacag    180
actgatgaaa tcaaggatac taggaatgag tctactcaga actgtgttgt ggcagagcct    240
gagaagatgg aatccagcat cagttcatcg agtgaggaaa tgtctctcag taagtgtgcg    300
aacagttttt gtagactgaa cgaatacaac caacttcagc tgcaagctgt ccatgcccag    360
gagcaaattc gcagaatgaa tgaaaacagc catgtccaag tgcctttcca gcagctcaac    420
caacttgctg cctacccta tgctgtttgg tactatccac aaatcatgca gtatgttcct    480
ttcccaccgt tttccgacat ctccaatccc actgctcatg aaaattatga aaaaaataac    540
```
gtcatgctac agtggtga                                                                                    558

<210> SEQ ID NO 63
<211> LENGTH: 237
<212> TYPE: PRT
<213> ORGANISM: Macropus eugenii
<220> FEATURE:
<221> NAME/KEY: VARIANT
<222> LOCATION: (0)...(0)
<223> OTHER INFORMATION: Casein alpha-S1

<400> SEQUENCE: 63

Met Lys Leu Leu Ile Phe Ser Cys Leu Val Thr Leu Ala Leu Ala Arg
1               5                   10                  15

Pro Asp Ala Leu Arg Leu Ser Ile Asp Arg His Phe Lys His Arg Glu
            20                  25                  30

Leu Glu Asn Arg Leu Asn Glu Asp Pro Ile Pro Val Ser Glu Ala Ser
        35                  40                  45

Ser Ser Glu Glu Ser Val His Gln Leu Asn Arg Asp Arg Arg Pro Leu
    50                  55                  60

Glu Lys Tyr Glu Leu Asp Lys Tyr Arg Glu Asp Leu Lys Thr Ser Ser
65                  70                  75                  80

Ser Glu Glu Phe Val Thr Pro Ser Thr Asn Glu Arg Val Arg Arg Gln
                85                  90                  95

Val Glu Tyr Asn Phe Asn Glu Glu Asp Ser Ser Ala Ser Arg Glu Arg
            100                 105                 110

Lys Ile Glu Asp Phe Ser Glu His Asp Arg Gln Tyr Leu Arg Arg Arg
        115                 120                 125

Val Glu Glu Arg Ala Leu Asn Leu Arg Tyr Leu Glu Pro Leu Tyr Tyr
    130                 135                 140

Ala Thr Glu Pro Glu Tyr Tyr Tyr Tyr Ala Tyr Val Pro Val Ser
145                 150                 155                 160

Ser His Asp Ile Pro Tyr Gln Gln Lys Pro Leu Ser Leu Leu Pro Ala
                165                 170                 175

Lys Ser His Tyr Leu Ile Ser Thr Gly Leu Leu Asn Glu Pro Leu Pro
            180                 185                 190

Ile Leu Arg Glu Arg Leu Gly Arg Gly Phe Gln Ser Pro Ser Leu Leu
        195                 200                 205

Ile Leu Val Leu Thr Glu Asn Ser Asn Leu Phe Met Gly Ser Val Phe
    210                 215                 220

Tyr Trp Cys Leu Gln Ile Ala His Pro Met Gln Glu Ile
225                 230                 235

<210> SEQ ID NO 64
<211> LENGTH: 189
<212> TYPE: PRT
<213> ORGANISM: Monodelphis domestica
<220> FEATURE:
<221> NAME/KEY: VARIANT
<222> LOCATION: (0)...(0)
<223> OTHER INFORMATION: Casein alpha-S1

<400> SEQUENCE: 64

Met Lys Leu Leu Ile Phe Ser Cys Leu Val Ala Leu Ala Leu Ala Arg
1               5                   10                  15

Pro Glu Ala Leu Asn Phe Ser Ala Arg Arg Val Lys His Gln Glu Ala
            20                  25                  30

Glu Ser Arg Leu Asn Glu Val Ile Ile Pro Ala Arg Ala Val Ser Ser

```
                35                  40                  45
Ser Glu Glu Thr Ser Gln Glu Ala Ile Glu Ile Arg Tyr Pro Leu Glu
 50                  55                  60

Gln Gln Val Leu Asp Lys Ala Arg Glu Glu Val Arg Arg Pro Val
 65                  70                  75                  80

Glu Tyr Ile Ile Glu Asp Asp Ser Ser Ala Leu Asn Glu Arg Lys Ile
                 85                  90                  95

Glu Asp Ala Arg Ala Tyr Asp Glu Gln Tyr Leu Arg Arg Pro Glu Glu
                100                 105                 110

Glu Arg Ala Val His Tyr Arg Glu Leu Arg Ala Phe Pro Thr Glu Ala
                115                 120                 125

Arg Lys Leu Lys Ala Tyr Arg Glu Pro Tyr Val Gln Pro Glu Ile Tyr
                130                 135                 140

Tyr Tyr Leu Ile Ser Val Pro Gln Pro Met Pro Tyr Pro Asp Glu Val
145                 150                 155                 160

Pro Leu Ala Tyr Thr Tyr Lys Phe Val Val Pro Ala Val Asn Arg Ala
                165                 170                 175

Asp Glu Ala Val Asn Thr Pro Val Glu Glu Lys Asn
                180                 185

<210> SEQ ID NO 65
<211> LENGTH: 570
<212> TYPE: DNA
<213> ORGANISM: Monodelphis domestica
<220> FEATURE:
<221> NAME/KEY: misc_feature
<222> LOCATION: (0)...(0)
<223> OTHER INFORMATION: Casein alpha-S1 cDNA

<400> SEQUENCE: 65
atgaagctgc tcatcttctc ctgccttgtg gctcttgctc tggccaggcc agaagccctc        60
aacttctctg ctaggcgtgt taaacaccaa gaagcagaaa gccgcctgaa tgaagttatc       120
attccagcaa gagcggtttc atcaagtgag gaaacttccc aggaggcaat cgaaatcaga       180
tatcccctgg agcagcaagt actcgacaaa gccagagagg aacgtgtccg cagaccggtc       240
gagtacatca tcgaggatga ttcttctgcc ttaaatgaga gaaagattga agatgcccgt       300
gcatacgacg agcagtacct gagaagacct gaggaagaga gagctgttca ctaccgggaa       360
cttcgcgctt ttcctactga ggcaagaaaa cttaaggctt acagagaacc ctacgtgcag       420
ccagaaatct actactatct catttccgtg ccacaaccca tgccttatcc agatgaggtc       480
cctcttgctt acacctacaa attcgtagta cctgctgtca acagggcaga tgaggcagtc       540
aatacccctg tggaagagga gaagaactaa                                         570

<210> SEQ ID NO 66
<211> LENGTH: 207
<212> TYPE: PRT
<213> ORGANISM: Microcebus murinus
<220> FEATURE:
<221> NAME/KEY: VARIANT
<222> LOCATION: (0)...(0)
<223> OTHER INFORMATION: Casein alpha-S1

<400> SEQUENCE: 66

Met Lys Leu Leu Ile Leu Thr Cys Leu Val Ala Val Ala Leu Ala Arg
 1               5                  10                  15

Pro Lys His Pro Leu Arg His Pro Glu Leu Ile Gln Asn Gln Pro Gly
                20                  25                  30
```

Ser Ser Glu Glu Ile Leu Lys Glu Arg Lys Phe Ser Ala Ile Ala Leu
            35                  40                  45

Ala Thr Pro Ile Glu Leu Arg Gln Glu Tyr Ile Asn Glu Leu Asn Arg
 50                  55                  60

Glu Gln His Val Ile Thr Glu Thr Glu Gln Ser Glu Ser Ser Ser Ser
 65                  70                  75                  80

Ser Ser Ser Glu Glu Val Ala Ser Gln Ser Ser Thr Glu Pro Lys Cys
                85                  90                  95

Ala Leu Asn Glu Asp Val Thr Asn Gln Cys Asn Gln Gln Leu His
                100                 105                 110

Arg Met Asn Lys Tyr Asn Gln Leu Gln Leu Glu Ala Ile His Ala Gln
                115                 120                 125

Glu Gln Leu Arg Arg Met Asn Glu Tyr Asn His Ala Gln Val Glu Glu
    130                 135                 140

Pro Val Arg Val Val Asn Gln Glu Gln Ala Gln Phe Tyr Pro Glu Pro
145                 150                 155                 160

Phe Pro Gln Val Tyr Gln Leu Asp Ala Thr Trp Tyr Tyr Phe Pro Gln
                165                 170                 175

Asn Met Gln Tyr Pro Ser Phe Leu Pro Ser Gln Asp Ile Ala Lys Gln
                180                 185                 190

Thr Ser Ala Glu Asn Asn Glu Lys Thr Asn Val Met Ala Gln Trp
                195                 200                 205

<210> SEQ ID NO 67
<211> LENGTH: 624
<212> TYPE: DNA
<213> ORGANISM: Microcebus murinus
<220> FEATURE:
<221> NAME/KEY: misc_feature
<222> LOCATION: (0)...(0)
<223> OTHER INFORMATION: Casein alpha-S1 cDNA

<400> SEQUENCE: 67
atgaagcttc tcatactcac ctgccttgtg gctgtcgctc ttgccagacc taaacatcct      60
cttagacacc cagaactcat tcaaaatcaa ccaggcagca gcgaggaaat cctcaaagaa     120
agaaagtttt cagcaattgc tctggccaca ccaatagaat taagacagga atacatcaat     180
gaactgaaca gggaacaaca tgtaataacc gagactgagc agagtgaatc tagcagcagt     240
tcatcaagcg aggaagttgc ttcccaaagc agcaccgagc caaaatgcgc tttaaatgaa     300
gatgtgacca accaatgcaa tcaggaacag cttcatagaa tgaacaaata caaccaactc     360
cagctggaag ctatccatgc tcaggagcaa cttcgcagaa tgaatgaata caaccatgct     420
caagtggaag agcccgtaag agtagtgaat caggaacagg cccaattcta ccctgagccc     480
ttccctcaag tctaccagct tgacgctact tggtactatt tcccacaaaa catgcagtac     540
ccatctttcc tgccatccca agacatcgct aagcaaactt ccgctgagaa caatgagaaa     600
actaatgtta tggcacagtg gtga                                             624

<210> SEQ ID NO 68
<211> LENGTH: 215
<212> TYPE: PRT
<213> ORGANISM: Oryctolagus cuniculus
<220> FEATURE:
<221> NAME/KEY: VARIANT
<222> LOCATION: (0)...(0)
<223> OTHER INFORMATION: Casein alpha-S1

<400> SEQUENCE: 68

```
Met Lys Leu Leu Ile Leu Thr Cys Leu Val Ala Thr Ala Leu Ala Arg
1               5                   10                  15

His Lys Phe His Leu Gly His Leu Lys Leu Thr Gln Glu Gln Pro Glu
            20                  25                  30

Ser Ser Glu Gln Glu Ile Leu Lys Glu Arg Lys Leu Leu Arg Phe Val
            35                  40                  45

Gln Thr Val Pro Leu Glu Leu Arg Glu Glu Tyr Val Asn Glu Leu Asn
        50                  55                  60

Arg Gln Arg Glu Leu Leu Arg Glu Lys Glu Asn Glu Glu Ile Lys Gly
65                  70                  75                  80

Thr Arg Asn Glu Val Thr Glu Glu His Val Leu Ala Asp Arg Glu Thr
                85                  90                  95

Glu Ala Ser Ile Ser Ser Ser Glu Glu Ile Val Pro Ser Ser Thr
            100                 105                 110

Lys Gln Lys Tyr Val Pro Arg Glu Asp Leu Ala Tyr Gln Pro Tyr Val
            115                 120                 125

Gln Gln Gln Leu Leu Arg Met Lys Glu Arg Tyr Gln Ile Gln Glu Arg
            130                 135                 140

Glu Pro Met Arg Val Val Asn Gln Glu Leu Ala Gln Leu Tyr Leu Gln
145                 150                 155                 160

Pro Phe Glu Gln Pro Tyr Gln Leu Asp Ala Tyr Leu Pro Ala Pro Trp
                165                 170                 175

Tyr Tyr Thr Pro Glu Val Met Gln Tyr Val Leu Ser Pro Leu Phe Tyr
                180                 185                 190

Asp Leu Val Thr Pro Ser Ala Phe Glu Ser Ala Glu Lys Thr Asp Val
            195                 200                 205

Ile Pro Glu Trp Leu Lys Asn
    210                 215
```

<210> SEQ ID NO 69
<211> LENGTH: 648
<212> TYPE: DNA
<213> ORGANISM: Oryctolagus cuniculus
<220> FEATURE:
<221> NAME/KEY: misc_feature
<222> LOCATION: (0)...(0)
<223> OTHER INFORMATION: Casein alpha-S1 cDNA

<400> SEQUENCE: 69

| | | | | | |
|---|---|---|---|---|---|
| atgaagcttc | tcatcctcac | ttgccttgtg | gctactgctc | ttgccaggca | taaatttcat | 60 |
| ttaggacacc | tgaaactcac | tcaggagcag | cctgagagca | gtgagcagga | aatcttaaaa | 120 |
| gaaagaaagc | tcctcaggtt | tgtccagaca | gtaccactag | aattaagaga | ggaatatgtc | 180 |
| aatgaactga | acaggcagag | agaacttctg | agagaaaaag | agaatgagga | aatcaaggga | 240 |
| actagaaatg | aagtaactga | ggaacatgtt | ttggcagacc | gtgagacaga | agctagcatc | 300 |
| agctcatcaa | gtgaggaaat | tgttcccagc | agcaccaagc | agaagtacgt | gccaagggaa | 360 |
| gacctggctt | accaacctta | cgtgcagcag | cagcttctca | gaatgaaaga | acgctaccaa | 420 |
| atccaggaga | gagagcctat | gagagtggtg | aatcaggaac | tggctcagct | ctatcttcag | 480 |
| cctttcgaac | aaccctacca | gcttgatgcc | tatctccctg | ctccttggta | ctatactccg | 540 |
| gaagtgatgc | agtatgttct | ttccccactg | ttctatgacc | tcgttacacc | cagtgccttt | 600 |
| gagagtgctg | aaaaaactga | cgttattcca | gagtggttga | agaattaa | | 648 |

<210> SEQ ID NO 70
<211> LENGTH: 214

```
<212> TYPE: PRT
<213> ORGANISM: Ovis aries
<220> FEATURE:
<221> NAME/KEY: VARIANT
<222> LOCATION: (0)...(0)
<223> OTHER INFORMATION: Casein alpha-S1

<400> SEQUENCE: 70

Met Lys Leu Leu Ile Leu Thr Cys Leu Val Ala Val Ala Leu Ala Arg
1               5                   10                  15

Pro Lys His Pro Ile Lys His Gln Gly Leu Ser Pro Glu Val Leu Asn
            20                  25                  30

Glu Asn Leu Leu Arg Phe Val Val Ala Pro Phe Pro Glu Val Phe Arg
        35                  40                  45

Lys Glu Asn Ile Asn Glu Leu Ser Lys Asp Ile Gly Ser Glu Ser Ile
50                  55                  60

Glu Asp Gln Ala Met Glu Asp Ala Lys Gln Met Lys Ala Gly Ser Ser
65                  70                  75                  80

Ser Ser Ser Glu Glu Ile Val Pro Asn Ser Ala Glu Gln Lys Tyr Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Asn Val Pro Gln Leu Glu Ile Val Pro
        115                 120                 125

Lys Ser Ala Glu Glu Gln Leu His Ser Met Lys Glu Gly Asn Pro Ala
130                 135                 140

His Gln Lys Gln Pro Met Ile Ala Val Asn Gln Glu Leu Ala Tyr Phe
145                 150                 155                 160

Tyr Pro Gln Leu Phe Arg Gln Phe Tyr Gln Leu Asp Ala Tyr Pro Ser
                165                 170                 175

Gly Ala Trp Tyr Tyr Leu Pro Leu Gly Thr Gln Tyr Thr Asp Ala Pro
            180                 185                 190

Ser Phe Ser Asp Ile Pro Asn Pro Ile Gly Ser Glu Asn Ser Gly Lys
        195                 200                 205

Ile Thr Met Pro Leu Trp
    210

<210> SEQ ID NO 71
<211> LENGTH: 645
<212> TYPE: DNA
<213> ORGANISM: Ovis aries
<220> FEATURE:
<221> NAME/KEY: misc_feature
<222> LOCATION: (0)...(0)
<223> OTHER INFORMATION: Casein alpha-S1 cDNA

<400> SEQUENCE: 71
atgaaacttc tcatccttac ctgtcttgtg gctgttgctc ttgccaggcc taaacatcct      60
atcaagcacc aaggactctc tccagaagtc ctcaatgaaa atttactcag gtttgttgtg     120
gcgccttttc cagaagtgtt tagaaaggag aacatcaatg aactgagtaa ggatattggg     180
agtgaatcaa ttgaggatca agccatggaa gatgctaagc aaatgaaagc tggaagcagt     240
tcgtcaagtg aggaaattgt tcccaatagt gctgagcaga gtacattca aaaggaagat      300 gtgccctctg agcgttacct gggttatctg aacagcttc tcagactgaa aaaatacaac      360
gtgccccagc tggaaattgt tcccaaaagt gctgaggaac aacttcatag tatgaaagag     420
ggaaaccctg cccaccagaa acagcctatg atagcagtga atcaggaact ggcctacttc     480
```

```
taccctcagc ttttcagaca attctaccag ctggacgcct atccatctgg tgcctggtat    540
taccttccac taggcacaca atacactgat gcccctcat  tctctgacat ccctaatccc    600
attggctctg agaacagtgg aaagattact atgccactgt ggtga                    645
```

<210> SEQ ID NO 72
<211> LENGTH: 199
<212> TYPE: PRT
<213> ORGANISM: Physeter catodon
<220> FEATURE:
<221> NAME/KEY: VARIANT
<222> LOCATION: (0)...(0)
<223> OTHER INFORMATION: Casein alpha-S1

<400> SEQUENCE: 72

```
Val Leu Thr Thr Met Lys Leu Leu Ile Leu Thr Cys Leu Val Thr Ala
1               5                   10                  15

Ala Leu Ala Lys Pro Asn Glu Pro Asp Ser Arg Glu Pro Leu Ser Glu
            20                  25                  30

Gln Leu Arg Glu Asp His Gly Met Glu Asp Pro Glu Gln Arg Gly Ser
        35                  40                  45

Gly Ser Ser Ser Ser Ser Glu Val Asn Arg Phe Asp Val Asn Ser Ala
    50                  55                  60

Ser Gln Leu Glu Asn Val Cys Glu Ser Leu Leu Tyr Gln Glu Gly Tyr
65                  70                  75                  80

Leu Ser Pro Lys Glu Val Pro Asn Gly Asn Glu Arg Lys His Ile
                85                  90                  95

Gln Gly Glu Asp Val Pro Ser Glu Arg Tyr Leu Arg Glu Pro Met Arg
            100                 105                 110

Val Val Asn Gln Pro Phe Gln Gln Phe Tyr Gln Leu Asp Val His Pro
        115                 120                 125

Tyr Ala Ala Trp Tyr Tyr Pro Pro Gln Val Thr Gln Tyr Ile Ala Ser
    130                 135                 140

Pro Ser Phe Phe Asp Ile Pro Lys Pro Ile Ala Ser Glu Asn Gly Gly
145                 150                 155                 160

Lys Thr Ile Met Pro Gln Trp Cys Phe Tyr His Met Ser Val Pro Asn
                165                 170                 175

Glu Ser Thr Glu His Ser Phe Thr Cys Cys Glu Ser Tyr Arg Asn Lys
            180                 185                 190

Ala Ile Asp Val Met Asn Ala
        195
```

<210> SEQ ID NO 73
<211> LENGTH: 600
<212> TYPE: DNA
<213> ORGANISM: Physeter catodon
<220> FEATURE:
<221> NAME/KEY: misc_feature
<222> LOCATION: (0)...(0)
<223> OTHER INFORMATION: Casein alpha-S1 partial cDNA

<400> SEQUENCE: 73

```
gtcttgacaa ccatgaaact tctcatcctt acctgccttg tgactgctgc tcttgccaag     60
cctaatgaac cagatagcag agagccttta tcagaacagc ttagagga  tcatggcatg     120 gaagaccctg agcaaagggg gtctggcagc agttcatcaa gtgaggtaaa tcgttttgat    180
gttaattcag catcccaatt agaaaatgtt tgtgaaagct tgttgtacca ggaaggttac    240
ctgtccccta aggaagttgt tcccaatggc aatgagcgga agcacattca agggaagat     300
```

```
gtgccctctg aacgctatct gagagagcct atgagagtag tgaatcaacc tttccaacaa      360
ttctatcagc ttgatgtcca tccttatgct gcttggtatt atcctccaca agtcacacaa      420
tatattgctt ctccatcatt cttcgacatc cctaaaccca ttgcctctga gaacggtgga      480
aaaacaatta tgccacagtg gtgcttctat catatgtcgg ttcccaacga atcaacagaa      540
cacagcttca cgtgttgtga atcctacagg aataaagcca tcgatgtaat gaatgcatga      600

<210> SEQ ID NO 74
<211> LENGTH: 183
<212> TYPE: PRT
<213> ORGANISM: Tachyglossus aculeatus
<220> FEATURE:
<221> NAME/KEY: VARIANT
<222> LOCATION: (0)...(0)
<223> OTHER INFORMATION: Casein alpha-S1

<400> SEQUENCE: 74

Met Lys Val Leu Ile Leu Ala Cys Leu Val Ala Phe Val Val Ala Met
1               5                   10                  15

Pro Glu Ser Pro Ser Ser Ser Ser Ser Glu Ala Ser Lys Ile
            20                  25                  30

Leu Thr Lys Lys Arg Val Gln Arg Asp Gln Glu Tyr Tyr Leu Pro His
        35                  40                  45

Gln Glu Glu Ser Val Ser Ser Ser Ser Glu Ser Thr Asp Arg
    50                  55                  60

Leu Lys Arg Arg Leu Leu Lys Asp Lys Pro Ile Phe Arg Leu Leu Lys
65                  70                  75                  80

Ala Thr Glu Ser Ser Ser Ser Glu Glu Ser Asp Ser Ala Ile Glu Lys
                85                  90                  95

Arg Ile Leu Arg Glu Arg Gln Tyr Tyr Gln Gln Lys Leu Asp Glu Leu
            100                 105                 110

Lys Glu Tyr Phe Arg Gln Phe Glu Pro Tyr Phe Tyr Pro Val Ala Tyr
        115                 120                 125

Gln Lys Lys Glu Val Met Pro Tyr Gln Leu Glu Tyr Phe Val Pro Gln
    130                 135                 140

Pro Glu Val Tyr Ser Ile Pro Gln Pro Val Tyr Arg Val Pro Gln Glu
145                 150                 155                 160

Val Thr Phe Pro Ser Leu Leu His Phe Arg Tyr Ala Phe Pro Gln Ser
                165                 170                 175

Thr Leu Pro Ile Glu Arg Lys
            180

<210> SEQ ID NO 75
<211> LENGTH: 552
<212> TYPE: DNA
<213> ORGANISM: Tachyglossus aculeatus
<220> FEATURE:
<221> NAME/KEY: misc_feature
<222> LOCATION: (0)...(0)
<223> OTHER INFORMATION: Casein alpha-S1 cDNA

<400> SEQUENCE: 75
atgaaggtcc tcatcctggc ctgcctggtg gcttttgtcg tggcaatgcc tgagtcaccc       60
agcagcagtt catccagcga ggaagcttcc aaaattctga caaaaaagcg tgtccaaaga      120
gaccaagaat actaccttcc ccatcaggag gaatccgtaa gcagctcatc cagtgaggaa      180
tcgaccgatc gactcaaaag acgtctcctg aaagacaaac ccatcttccg tctcctgaag      240
gctacagaga gctcttcaag tgaggaatct gacagtgcta ttgaaaagcg tattctgagg      300
```

```
gagagacagt actatcaaca gaagctggat gaactcaaag aatattttcg tcagtttgaa    360
ccctacttct accctgtggc ttatcagaaa aagaagtca tgccctacca gctggaatac     420
tttgttcctc aaccagaagt gtacagcatc cccaaccag tatataggt tcctcaagag      480 gtaaccttcc ccagtcttct ccatttccgc tacgcttttc ctcagtcaac cctccccatt   540
gagaggaagt aa                                                        552

<210> SEQ ID NO 76
<211> LENGTH: 230
<212> TYPE: PRT
<213> ORGANISM: Ailuropoda melanoleuca
<220> FEATURE:
<221> NAME/KEY: VARIANT
<222> LOCATION: (0)...(0)
<223> OTHER INFORMATION: Casein alpha-S1

<400> SEQUENCE: 76

Met Glu Ile Lys His Cys Pro Lys Asp Leu Lys Asp Gly Ser Leu Lys
1               5                   10                  15

Gln Cys Thr Gly Ser Gly His Lys Ala Ala Leu Ser Gln Glu Glu Gln
            20                  25                  30

Gly Ser Ser Ala Val Ile Glu His Gly Ser Ile Pro Arg Gly Gly Asn
        35                  40                  45

Asn Val His Arg Val Gly Gly Val Arg Ala Ser Cys Thr Leu Glu Ser
50                  55                  60

Thr Arg Arg Leu Leu Trp Met Cys Pro Ser Glu Lys Thr Ser Val Leu
65                  70                  75                  80

Ala Leu Thr Thr Met Lys Val Leu Ile Leu Thr Cys Leu Val Ala Val
                85                  90                  95

Ala Leu Ala Arg Pro Gly Gln Ala Val Glu Asp Pro Glu Gln Arg Gln
            100                 105                 110

Ser Ser Ser Ser Ser Ser Ser Glu Glu Val Val Pro Ser Thr Thr Glu
        115                 120                 125

Gln Lys Gln Ile Pro Arg Glu Asp Ile Leu Asn Gln Arg Tyr Leu Glu
130                 135                 140

Gln Leu Arg Arg Leu Ser Lys Tyr Asn Gln Gln Gln Gln Glu Thr Ile
145                 150                 155                 160

His Asp Gln Gln Gln Leu Arg Gly Val Asn Glu Asn Asn Leu Leu Gln
                165                 170                 175

Leu Pro Phe Gln Gln Phe Tyr Gln Leu Asp Ala Tyr Pro Phe Ala Ala
            180                 185                 190

Trp Tyr Tyr Leu Pro Gln Ile Met Gln Tyr Ile Gly Tyr Thr Pro Ser
        195                 200                 205

Tyr Asp Ile Ile Lys Pro Ile Ala Ser Glu Asn Ile Glu Asn Val Asp
    210                 215                 220

Val Val Pro Glu Trp Trp
225                 230

<210> SEQ ID NO 77
<211> LENGTH: 693
<212> TYPE: DNA
<213> ORGANISM: Ailuropoda melanoleuca
<220> FEATURE:
<221> NAME/KEY: misc_feature
<222> LOCATION: (0)...(0)
<223> OTHER INFORMATION: Casein alpha-S1 cDNA

<400> SEQUENCE: 77
```

```
atggaaatta aacactgtcc aaaagacctc aaagacgggt cacttaaaca gtgcacggga    60
agtggtcaca aggcagcgct aagccaggaa gagcagggaa gtagtgctgt aatagaacac   120
ggaagcattc cacgtggagg aaataacgtg catagggttg gaggagtaag agcttcatgc   180
actcttgaaa gcacaagaag attgttgtgg atgtgtcctt cagaaaagac gagtgtgctg   240
gccttgacaa ccatgaaggt tctcatcctt acctgccttg tggctgttgc tcttgccagg   300
cctggacagg ccgtggaaga ccctgagcaa aggcaatcta gcagcagttc gtcaagtgag   360
gaagttgttc ccagtaccac tgagcagaag caaattccaa gagaagacat actcaaccaa   420
cgctatctgg aacagcttcg tagactgagc aaatacaacc aacaacagca ggaaactatc   480
catgaccagc aacaacttcg cggagtgaat gaaaacaacc tcctccaact gcctttccaa   540
cagttctacc agcttgatgc ttatcccttt gctgcttggt attatcttcc acaaatcatg   600
cagtatattg gttatacacc atcctatgac atcattaaac ccattgcctc tgagaacatt   660
gaaaacgttg atgttgtgcc agagtggtgg taa                                693
```

```
<210> SEQ ID NO 78
<211> LENGTH: 222
<212> TYPE: PRT
<213> ORGANISM: Bos taurus
<220> FEATURE:
<221> NAME/KEY: VARIANT
<222> LOCATION: (0)...(0)
<223> OTHER INFORMATION: Casein alpha-S2

<400> SEQUENCE: 78
```

```
Met Lys Phe Phe Ile Phe Thr Cys Leu Leu Ala Val Ala Leu Ala Lys
 1               5                  10                  15

Asn Thr Met Glu His Val Ser Ser Ser Glu Glu Ser Ile Ile Ser Gln
             20                  25                  30

Glu Thr Tyr Lys Gln Glu Lys Asn Met Asp Ile Asn Pro Ser Lys Glu
         35                  40                  45

Asn Leu Cys Ser Thr Phe Cys Lys Glu Val Val Arg Asn Ala Asn Glu
     50                  55                  60

Glu Glu Tyr Ser Ile Gly Ser Ser Ser Glu Glu Ser Ala Glu Val Ala
 65                  70                  75                  80

Thr Glu Glu Val Lys Ile Thr Val Asp Asp Lys His Tyr Gln Lys Ala
                 85                  90                  95

Leu Asn Glu Ile Asn Gln Phe Tyr Arg Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
    130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
    210                 215                 220
```

<210> SEQ ID NO 79
<211> LENGTH: 669
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein alpha-S2 cDNA

<400> SEQUENCE: 79

```
atgaagttct tcatctttac ctgccttttg gctgttgccc ttgcaaagaa tacgatggaa      60
catgtctcct ccagtgagga atctatcatc tcccaggaaa catataagca ggaaaagaat     120
atggacatta atcccagcaa ggagaacctt gctccacat tctgcaagga agttgtaagg     180
aacgcaaatg aagaggaata ttctatcggc tcatctagtg aggaatctgc tgaagttgcc     240
acagaggaag ttaagattac tgtggacgat aagcactacc agaaagcact gaatgaaatc     300
aatcagtttt atcggaagtt cccccagtat ctccagtatc tgtatcaagg tccaattgtt     360
ttgaacccat gggatcaggt taagagaaat gctgttccca ttactcccac tctgaacaga     420
gagcagctct ccaccagtga ggaaaattca agaagaccg ttgacatgga atcaacagaa     480
gtattcacta agaaaactaa actgactgaa gaagaaaaga atcgcctaaa tttctctgaaa    540 aaaatcagcc agcgttacca gaaattcgcc ttgccccagt atctcaaaac tgtttatcag     600
catcagaaag ctatgaagcc atggattcaa cctaagacaa aggttattcc ctatgtgagg     660
taccttttaa                                                            669
```

<210> SEQ ID NO 80
<211> LENGTH: 223
<212> TYPE: PRT
<213> ORGANISM: Capra hircus
<220> FEATURE:
<221> NAME/KEY: VARIANT
<222> LOCATION: (0)...(0)
<223> OTHER INFORMATION: Casein alpha-S2

<400> SEQUENCE: 80

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asn
    50                  55                  60

Glu Glu Glu Tyr Ser Ile Arg Ser Ser Ser Glu Glu Ser Ala Glu Val
65                  70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg 165                 170                 175
Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220

<210> SEQ ID NO 81
<211> LENGTH: 672
<212> TYPE: DNA
<213> ORGANISM: Capra hircus
<220> FEATURE:
<221> NAME/KEY: misc_feature
<222> LOCATION: (0)...(0)
<223> OTHER INFORMATION: Casein alpha-S2 cDNA

<400> SEQUENCE: 81

```
atgaagttct tcattttac ctgccttttg gccgttgccc ttgcaaagca taagatggaa      60
catgtctcct ccagtgagga acctatcaat atcttccagg aaatatataa gcaggaaaag    120
aatatggcca ttcatcccag aaaggagaaa ctttgcacca catcctgtga ggaagttgta    180
aggaacgcaa atgaagagga atattctatc agatcatcta gtgaggaatc tgctgaagtt    240
gccccagagg aaattaagat tactgtggac gataagcact accagaaagc cctgaatgaa    300
atcaatcagt tttatcagaa gttcccccag tatctccagt atccgtatca aggtccaatt    360
gttttgaacc catgggatca ggttaagaga atgctggcc cctttactcc caccgtgaac     420
agagagcagc tctccaccag tgaggaaaat tcaaagaaga ccattgatat ggaatcaaca    480
gaagtattca ctaagaaaac taaactgact gaagaagaaa agaatcgcct aaattttctg    540
aaaaaaatca gccagtatta ccagaaattt gcctggcccc agtatctcaa gactgttgat    600
cagcatcaga aagctatgaa gccatggact caacctaaga caaatgctat tccctatgtg    660
aggtaccttt aa                                                        672
```

<210> SEQ ID NO 82
<211> LENGTH: 239
<212> TYPE: PRT
<213> ORGANISM: Felis catus
<220> FEATURE:
<221> NAME/KEY: VARIANT
<222> LOCATION: (0)...(0)
<223> OTHER INFORMATION: Casein alpha-S2

<400> SEQUENCE: 82

Met Ser Gly Ala Glu Ala Val Asp Trp Glu Val Ser Glu Lys Lys Leu
1               5                   10                  15

His Ile Cys Arg Leu Ser Arg Gly Cys Gly Val Ser Pro Arg Val Thr
            20                  25                  30

Met Asn Phe Leu Leu Phe Thr Cys Leu Leu Ala Val Ala Leu Ala Lys
        35                  40                  45

His Glu Leu Lys Gln Leu Ser Ser Glu Glu Ser Ala Thr Ser Ser
    50                  55                  60

Ser Ser Gln Glu Thr Gly Asp Val Pro Thr Asp Thr Ile Glu Leu Thr
65                  70                  75                  80

Glu Glu Glu Lys Val Tyr Leu Asn Gln Leu Ser Lys Ile Asn Gln Phe
            85                  90                  95

Tyr Gln Ala Trp Asn Leu Pro Gln Tyr Leu Glu Ala Tyr His Gln Gln
        100                 105                 110

```
His Ser Val Arg Asn Pro Trp Asn His Ile Lys Thr Asn Gly Tyr His
        115                 120                 125

Leu Phe Pro Leu Leu Glu Lys Glu Tyr Leu Ser Ser Glu Val Arg
    130                 135                 140

Gly Phe Pro Val Arg Thr Glu Thr Trp His Pro Glu Thr Glu Ile Lys
145                 150                 155                 160

Glu Val Gln Leu Asn Asp Glu Glu Lys Asn Tyr Leu Lys Gln Leu Val
                165                 170                 175

Lys Ile Asn Gln Tyr Gln Gln Lys Phe Thr Phe Pro His Tyr Phe Gln
                180                 185                 190

Ala Val His Pro Gln Gln Ile Ala Leu Asn Pro Trp Asn Arg Leu Lys
                195                 200                 205

Glu Asn Thr Tyr Pro Phe Ile Leu Thr Leu Leu Gly Ser Leu Asn Gln
        210                 215                 220

Phe Gly Pro Pro Asp Asp Glu Lys Gly Leu Asp Tyr Phe Ser Lys
225                 230                 235

<210> SEQ ID NO 83
<211> LENGTH: 720
<212> TYPE: DNA
<213> ORGANISM: Felis catus
<220> FEATURE:
<221> NAME/KEY: misc_feature
<222> LOCATION: (0)...(0)
<223> OTHER INFORMATION: Casein alpha-S2 cDNA

<400> SEQUENCE: 83
atgtccggtg cagaggcagt ggactgggaa gttagtgaga agaagctgca catatgtcgt      60 cttttcaagag gctgcggggt cagtccccga gtaaccatga atttcctcct ctttacctgc    120
cttttggctg tggctctggc aaagcatgag ctaaagcagc tctcctccag cgaggaatct    180
gccaccagtt catctagtca ggaaactggt gatgtcccta ctgacacaat tgagctgact    240
gaggaagaaa aggtctacct caatcaactg agcaaaatca accagttta tcaggcatgg    300 aatcttcccc agtatcttga ggcttatcat caacagcaca gtgttaggaa cccatggaat    360
cacattaaga caaatggcta tcatctattt ccccttctgg aaaaagagta cctgtcctcc    420
agtgaggtga gggctttcc tgtgaggaca gaaacatggc atccagaaac agagattaag    480
gaagttcagc tgaatgatga agaaaagaat tacctgaaac agctggtcaa atcaaccag    540 tatcaacaga gttcaccttc ccccactat ttccaggctg ttcatccaca gcagatagct    600 ctgaacccttt ggaatcgcct taaggaaaat acttaccca tcattctcac tttgcttggt    660
tctctgaacc agtttggtcc tcctgatgat gaaaagggat tagactactt ttctaaataa    720

<210> SEQ ID NO 84
<211> LENGTH: 121
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Casein alpha-S2

<400> SEQUENCE: 84

Met Lys Phe Phe Ile Phe Thr Cys Leu Leu Ala Ile Ala Leu Ala Lys
1               5                   10                  15

His Glu Ser Ala Glu Val Ser Thr Glu Glu Val Lys His Thr Val Asp
                20                  25                  30
```

```
Gln Lys His Tyr Val Lys Gln Leu Asn Lys Ile Asn Pro Phe Tyr Gln
             35                  40                  45
Lys Trp Asn Phe Leu Pro Phe Leu Gln Lys Thr Glu Leu Thr Glu Glu
 50                      55                  60
Glu Lys Asn Asp Gln Lys His Leu Asn Lys Ile Asn Gln Tyr Tyr Gln
 65                  70                  75                  80
Phe Thr Leu Pro Gln Tyr Val Lys Ala Val Tyr Gln Tyr His Lys Ile
                 85                  90                  95
Met Lys Pro Trp Lys Asn Met Lys Thr Asn Ala Tyr Gln Val Ile Pro
                100                 105                 110
Thr Leu Gly Ser Leu Arg Phe Leu Asn
             115                 120

<210> SEQ ID NO 85
<211> LENGTH: 84
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Casein alpha-S2

<400> SEQUENCE: 85
atgaagttct tcatctttac ctgccttttg gctgttgctc tggcacatca tgagataaag      60
cactcctcct cttccagtga gtaa                                            84

<210> SEQ ID NO 86
<211> LENGTH: 182
<212> TYPE: PRT
<213> ORGANISM: Oryctolagus cuniculus
<220> FEATURE:
<221> NAME/KEY: VARIANT
<222> LOCATION: (0)...(0)
<223> OTHER INFORMATION: Casein alpha-S2

<400> SEQUENCE: 86

Met Lys Phe Phe Ile Phe Thr Cys Leu Leu Ala Val Ala Leu Ala Lys
 1               5                  10                  15
Pro Lys Ile Glu Gln Ser Ser Glu Glu Thr Ile Ala Val Ser Gln
             20                  25                  30
Glu Val Ser Pro Asn Leu Glu Asn Ile Cys Ser Thr Ala Cys Glu Glu
             35                  40                  45
Pro Ile Lys Asn Ile Asn Glu Val Glu Tyr Val Glu Val Pro Thr Glu
 50                  55                  60
Ile Lys Asp Gln Glu Phe Tyr Gln Lys Val Asn Leu Leu Gln Tyr Leu
 65                  70                  75                  80
Gln Ala Leu Tyr Gln Tyr Pro Thr Val Met Asp Pro Trp Thr Arg Ala
                 85                  90                  95
Glu Thr Lys Ala Ile Pro Phe Ile Arg Thr Met Gln Tyr Lys Gln Glu
                100                 105                 110
Lys Asp Ala Thr Lys His Thr Ser Gln Lys Thr Glu Leu Thr Glu Glu
             115                 120                 125
Glu Lys Ala Phe Leu Lys Tyr Leu Asp Glu Met Lys Gln Tyr Tyr Gln
 130                 135                 140
Lys Phe Val Phe Pro Gln Tyr Leu Lys Asn Ala His His Phe Gln Lys
 145                 150                 155                 160
Thr Met Asn Pro Trp Asn His Val Lys Thr Ile Ile Tyr Gln Ser Val
                 165                 170                 175
```

```
Pro Thr Leu Arg Tyr Leu
            180

<210> SEQ ID NO 87
<211> LENGTH: 549
<212> TYPE: DNA
<213> ORGANISM: Oryctolagus cuniculus
<220> FEATURE:
<221> NAME/KEY: misc_feature
<222> LOCATION: (0)...(0)
<223> OTHER INFORMATION: Casein alpha-S2 cDNA

<400> SEQUENCE: 87
atgaagttct tcattttcac ctgccttctg gctgttgctc tggcaaagcc taagattgag      60
caatcttcaa gtgaggaaac tattgctgtc tcccaagaag tatccccaaa cttagaaaac     120
atttgttcta cagcctgtga ggaacccata aagaatatca atgaagtgga atacgttgaa     180
gttcccacag agataaaaga tcaggaattt tatcagaagg tgaacctcct ccagtatctc     240
caggctcttt accaatatcc cactgtcatg gacccatgga ctcgggctga gacaaaggcc     300 atcccctta ttcgcactat gcaatataag caggaaaagg atgccactaa gcataccagt     360
cagaaaaccg aactgaccga agaagaaaag gctttctaa aatacttgga tgaaatgaaa      420
caatattatc agaagttcgt ttttccccaa tacctaaaaa atgctcatca ttttcagaaa     480
actatgaacc cttggaatca tgttaagaca attatttacc aaagtgtgcc cactctgaga     540
tacttataa                                                              549

<210> SEQ ID NO 88
<211> LENGTH: 223
<212> TYPE: PRT
<213> ORGANISM: Ovis aries
<220> FEATURE:
<221> NAME/KEY: VARIANT
<222> LOCATION: (0)...(0)
<223> OTHER INFORMATION: Casein alpha-S2

<400> SEQUENCE: 88

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Ser
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asp
    50                  55                  60

Glu Glu Glu Tyr Ser Ile Arg Ser Ser Glu Glu Ser Ala Glu Val
65                  70                  75                  80

Ala Pro Glu Glu Val Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Leu Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Lys Asn Arg
                165                 170                 175
```

-continued

```
Leu Asn Phe Leu Lys Lys Ile Ser Gln Tyr Tyr Gln Lys Phe Ala Trp
                180                 185                 190
Pro Gln Tyr Leu Lys Thr Val Asp Gln His Gln Lys Ala Met Lys Pro
            195                 200                 205
Trp Thr Gln Pro Lys Thr Asn Ala Ile Pro Tyr Val Arg Tyr Leu
        210                 215                 220

<210> SEQ ID NO 89
<211> LENGTH: 672
<212> TYPE: DNA
<213> ORGANISM: Ovis aries
<220> FEATURE:
<221> NAME/KEY: misc_feature
<222> LOCATION: (0)...(0)
<223> OTHER INFORMATION: Casein alpha-S2 cDNA

<400> SEQUENCE: 89
atgaagttct tcatttttac ctgccttttg gccgttgccc ttgcaaagca taagatggaa      60
catgtctcct ccagtgagga acctatcaat atctcccagg aaatatataa gcaggaaaag     120
aatatggcca ttcatcccag aaaggagaaa ctttgcacca catcctgtga ggaagttgta     180
aggaacgcag atgaagagga atattctatc agatcatcta gtgaggaatc tgctgaagtt     240
gccccagagg aagttaagat tactgtggac gataagcact accagaaagc actgaatgaa     300
atcaatcagt tttatcagaa gttcccccag tacctccagt atctgtatca aggcccaatt     360
gttttgaacc catgggatca ggttaagaga aatgctggcc cctttactcc caccgtgaac     420
agagagcagc tctccaccag tgaggaaaat tcaaagaaga ccattgatat ggaatcaaca     480
gaagtattca ctaagaaaac taaactgact gaagaagaaa agaatcgcct aaattttctg     540
aaaaaaatca gccagtatta ccagaaattt gcctggcccc agtatctcaa gactgttgat     600
cagcatcaga aagctatgaa gccatggact caacctaaga caaacgctat tccctatgtg     660
aggtaccttt aa                                                         672

<210> SEQ ID NO 90
<211> LENGTH: 243
<212> TYPE: PRT
<213> ORGANISM: Physeter catodon
<220> FEATURE:
<221> NAME/KEY: VARIANT
<222> LOCATION: (0)...(0)
<223> OTHER INFORMATION: Casein alpha-S2

<400> SEQUENCE: 90

Met Lys Phe Phe Leu Phe Thr Cys Leu Leu Ala Val Ala Leu Ala Lys
1               5                   10                  15
His Glu Met Glu His Val Ser Ser Ser Glu Glu Ser Ile Asn Met Phe
            20                  25                  30
Gln Glu Lys Tyr Lys Gln Arg Lys Asn Val Val Leu His Pro Ser Lys
        35                  40                  45
Glu Asn Ile Cys Ser Thr Ser Cys Glu Val Cys Ile Asp Phe Thr Ser
    50                  55                  60
Val Val Gln Cys Glu Val Lys Tyr Ser Ile Arg Ser Ser Pro Lys Glu
65                  70                  75                  80
Thr Ala Glu Val Pro Arg Glu Lys Val Lys Leu Thr Val Glu Asp Lys
                85                  90                  95
Gln Tyr Leu Lys Gln Leu Ser Lys Ile Ser Gln Phe Tyr Gln Lys Phe
            100                 105                 110
```

Pro Gln Tyr Ile Gln Ala Leu Tyr Gln Ala Pro Thr Val Met Asn Pro
                115                 120                 125

Trp Gly Gln Val Lys Arg Ser Ala Glu Pro Phe Ile Leu Thr Val Ser
    130                 135                 140

Arg Gln Gln Leu Ser Thr Gly Glu Glu Asn Ser Lys Lys Thr Val Asp
145                 150                 155                 160

Met Glu Ser Thr Glu Val Leu Thr Lys Lys Thr Leu Thr Glu Glu
                165                 170                 175

Glu Lys Asn Arg Leu Lys Phe Leu Asn Lys Ile Asn Gln Tyr Tyr Gln
                180                 185                 190

Lys Leu Thr Trp Pro Gln Tyr Leu Lys Thr Ile Ser Gln Tyr Gln Lys
            195                 200                 205

Thr Val Lys Pro Trp Asn His Ile Lys Thr Asn Val Ile Pro Tyr Leu
        210                 215                 220

Asp Tyr Ser Gly Asn Pro Gly Ser Pro Tyr Pro Val Asn Pro Thr Leu
225                 230                 235                 240

Asn Ile Pro

<210> SEQ ID NO 91
<211> LENGTH: 732
<212> TYPE: DNA
<213> ORGANISM: Physeter catodon
<220> FEATURE:
<221> NAME/KEY: misc_feature
<222> LOCATION: (0)...(0)
<223> OTHER INFORMATION: Casein alpha-S2 cDNA

<400> SEQUENCE: 91

```
atgaagttct tccttttac ctgccttttg gctgttgctc ttgcaaagca tgagatggaa      60
catgtctcct ccagtgagga atctatcaac atgttccagg aaaaatataa gcagagaaag    120
aatgtggtcc ttcatcccag caaggagaac atttgttcca catcctgtga ggtatgtatt    180
gatttcacat cagtagtaca atgtgaagta aaatatagta ttagatcttc ccctaaggaa    240
actgctgaag ttcccaggga gaaagttaag cttactgtgg aagataagca atacctgaaa    300
caactgagca aaatcagtca gttttatcag aagttccccc aatatatcca ggctctatat    360
caagctccaa ctgttatgaa cccatggggt caagttaaga gaagtgctga gcccttatt     420
ctcactgtga gcagacagca gctctctacc ggtgaggaaa attcaaagaa gactgttgat    480
atggaatcaa cggaagtact cactaagaaa actacattga ctgaagaaga aagaatcgc    540
ctaaatttc tgaacaaaat caaccaatat tatcagaaat taacctggcc ccagtatctc     600
aagactattt ctcagtatca gaaaactgtg aagccgtgga atcacattaa gacaaatgtt    660
atccctatc tggattacag cggcaatcct ggcagtcctt acccagttaa cccaactctg     720
aatattcctt aa                                                        732
```

<210> SEQ ID NO 92
<211> LENGTH: 142
<212> TYPE: PRT
<213> ORGANISM: Bos taurus
<220> FEATURE:
<221> NAME/KEY: VARIANT
<222> LOCATION: (0)...(0)
<223> OTHER INFORMATION: alpha-lactalbumin

<400> SEQUENCE: 92

Met Met Ser Phe Val Ser Leu Leu Leu Val Gly Ile Leu Phe His Ala
1               5                   10                  15

```
Thr Gln Ala Glu Gln Leu Thr Lys Cys Glu Val Phe Arg Glu Leu Lys
             20                  25                  30

Asp Leu Lys Gly Tyr Gly Gly Val Ser Leu Pro Glu Trp Val Cys Thr
         35                  40                  45

Thr Phe His Thr Ser Gly Tyr Asp Thr Gln Ala Ile Val Gln Asn Asn
     50                  55                  60

Asp Ser Thr Glu Tyr Gly Leu Phe Gln Ile Asn Asn Lys Ile Trp Cys
 65                  70                  75                  80

Lys Asp Asp Gln Asn Pro His Ser Ser Asn Ile Cys Asn Ile Ser Cys
                 85                  90                  95

Asp Lys Phe Leu Asp Asp Asp Leu Thr Asp Asp Ile Met Cys Val Lys
            100                 105                 110

Lys Ile Leu Asp Lys Val Gly Ile Asn Tyr Trp Leu Ala His Lys Ala
            115                 120                 125

Leu Cys Ser Glu Lys Leu Asp Gln Trp Leu Cys Glu Lys Leu
            130                 135                 140

<210> SEQ ID NO 93
<211> LENGTH: 429
<212> TYPE: DNA
<213> ORGANISM: Bos taurus
<220> FEATURE:
<221> NAME/KEY: misc_feature
<222> LOCATION: (0)...(0)
<223> OTHER INFORMATION: alpha-lactalbumin cDNA

<400> SEQUENCE: 93
atgatgtcct ttgtctctct gctcctggta ggcatcctat tccatgccac ccaggctgaa      60
cagttaacaa aatgtgaggt gttccgggag ctgaaagact tgaagggcta cggaggtgtc     120
agtttgcctg aatgggtctg taccacgttt cataccagtg gttatgacac acaagccata     180
gtacaaaaca atgacagcac agaatatgga ctcttccaga taaataataa aatttggtgc     240
aaagacgacc agaaccctca ctcaagcaac atctgtaaca tctcctgtga caagttcctg     300
gatgatgatc ttactgatga cattatgtgt gtcaagaaga ttctggataa agtaggaatt     360
aactactggt tggcccataa agcactctgt tctgagaagc tggatcagtg gctctgtgag     420
aagttgtga                                                              429

<210> SEQ ID NO 94
<211> LENGTH: 142
<212> TYPE: PRT
<213> ORGANISM: Capra hircus
<220> FEATURE:
<221> NAME/KEY: VARIANT
<222> LOCATION: (0)...(0)
<223> OTHER INFORMATION: alpha-lactalbumin

<400> SEQUENCE: 94

Met Met Ser Phe Val Ser Leu Leu Val Gly Ile Leu Phe His Ala
 1               5                  10                  15

Thr Gln Ala Glu Gln Leu Thr Lys Cys Glu Val Phe Lys Leu Lys
             20                  25                  30

Asp Leu Lys Asp Tyr Gly Gly Val Ser Leu Pro Glu Trp Val Cys Thr
         35                  40                  45

Ala Phe His Thr Ser Gly Tyr Asp Thr Gln Ala Ile Val Gln Asn Asn
     50                  55                  60

Asp Ser Thr Glu Tyr Gly Leu Phe Gln Ile Asn Asn Lys Ile Trp Cys
 65                  70                  75                  80
```

Lys Asp Asp Gln Asn Pro His Ser Arg Asn Ile Cys Asn Ile Ser Cys
            85                  90                  95

Asp Lys Phe Leu Asp Asp Leu Thr Asp Asp Ile Val Cys Ala Lys
        100                 105                 110

Lys Ile Leu Asp Lys Val Gly Ile Asn Tyr Trp Leu Ala His Lys Ala
        115                 120                 125

Leu Cys Ser Glu Lys Leu Asp Gln Trp Leu Cys Glu Lys Leu
        130                 135                 140

<210> SEQ ID NO 95
<211> LENGTH: 735
<212> TYPE: DNA
<213> ORGANISM: Capra hircus
<220> FEATURE:
<221> NAME/KEY: misc_feature
<222> LOCATION: (0)...(0)
<223> OTHER INFORMATION: alpha-lactalbumin cDNA

<400> SEQUENCE: 95

| | | | | |
|---|---|---|---|---|
| gggggggtaac | caaaatgatg | tcctttgtct | ctctgctcct | ggtaggcatc | ctgttccacg | 60 |
| ccacccaggc | tgaacaatta | acaaaatgtg | aggtgttcca | gaagctgaag | gacttgaagg | 120 |
| actacggagg | tgtcagtttg | cctgaatggg | tctgtactgc | atttcatacc | agtggttatg | 180 |
| acacacaagc | catagtacaa | aacaatgaca | gcacagaata | tggactcttc | cagataaata | 240 |
| ataaaatttg | gtgcaaagac | gaccagaacc | ctcactcaag | gaacatctgt | aacatctcct | 300 |
| gtgacaagtt | cctggatgat | gatcttactg | atgacattgt | gtgtgccaag | aagattctgg | 360 |
| ataaagtagg | aattaactac | tggttggccc | ataaagcact | ctgttctgag | aagctggatc | 420 |
| agtggctctg | tgagaagttg | tgaacacctg | ctgtctttgc | tgcttctgtc | ctctttctgt | 480 |
| tcctggaact | cctctgcccc | ttggctacct | cgttttgctt | ctttgtaccc | ccttgaagct | 540 |
| aactcgtctc | tgagccctgg | gccctgtagt | gacgatggac | atgtaaggac | taatctccag | 600 |
| ggatgcgtga | atggtgctca | ggacatttga | cccttgctcg | gtgcccctga | tagcacttttt | 660 |
| aatgcaacag | tgcatattcc | acttctgtcc | tgaataaaag | gcctgattct | gaaaaaaaaa | 720 |
| aaaaaaaaaa | aaaaa | | | | | 735 |

<210> SEQ ID NO 96
<211> LENGTH: 142
<212> TYPE: PRT
<213> ORGANISM: Homo sapiens
<220> FEATURE:
<221> NAME/KEY: VARIANT
<222> LOCATION: (0)...(0)
<223> OTHER INFORMATION: alpha-lactalbumin

<400> SEQUENCE: 96

Met Arg Phe Phe Val Pro Leu Phe Leu Val Gly Ile Leu Phe Pro Ala
1               5                   10                  15

Ile Leu Ala Lys Gln Phe Thr Lys Cys Glu Leu Ser Gln Leu Leu Lys
            20                  25                  30

Asp Ile Asp Gly Tyr Gly Gly Ile Ala Leu Pro Glu Leu Ile Cys Thr
        35                  40                  45

Met Phe His Thr Ser Gly Tyr Asp Thr Gln Ala Ile Val Glu Asn Asn
    50                  55                  60

Glu Ser Thr Glu Tyr Gly Leu Phe Gln Ile Ser Asn Lys Leu Trp Cys
65                  70                  75                  80

Lys Ser Ser Gln Val Pro Gln Ser Arg Asn Ile Cys Asp Ile Ser Cys
            85                  90                  95

Asp Lys Phe Leu Asp Asp Asp Ile Thr Asp Asp Ile Met Cys Ala Lys
                100                 105                 110

Lys Ile Leu Asp Ile Lys Gly Ile Asp Tyr Trp Leu Ala His Lys Ala
            115                 120                 125

Leu Cys Thr Glu Lys Leu Glu Gln Trp Leu Cys Glu Lys Leu
        130                 135                 140

<210> SEQ ID NO 97
<211> LENGTH: 701
<212> TYPE: DNA
<213> ORGANISM: Homo sapiens
<220> FEATURE:
<221> NAME/KEY: misc_feature
<222> LOCATION: (0)...(0)
<223> OTHER INFORMATION: alpha-lactalbumin

<400> SEQUENCE: 97
atgaggttct tgtccctct gttcctggtg ggcatcctgt tccctgccat cctggccaag    60
caattcacaa aatgtgagct gtcccagctg ctgaaagaca tagatggtta tggaggcatc   120
gctttgcctg aattgatctg taccatgttt cacaccagtg gttatgacac acaagccata   180
gttgaaaaca atgaaagcac ggaatatgga ctcttccaga tcagtaataa gctttggtgc   240
aagagcagcc aggtccctca gtcaaggaac atctgtgaca tctcctgtga caagttcctg   300
gatgatgaca ttactgatga cataatgtgt gccaagaaga tcctggatat aaaggaatt    360 gactactggt tggcccataa agccctctgc actgagaagc tggaacagtg gctttgtgag   420
aagttgtgag tgtctgctgt ccttggcacc cctgccccact ccacactcct ggaataccctc  480 ttccctaatg ccacctcagt ttgtttcttt ctgttccccc aaagcttatc tgtctctgag   540
ccttgggccc tgtagtgaca tcaccgaatt cttgaagact attttccagg gatgcctgag   600
tggtgcactg agctctagac ccttactcag tgccttcgat ggcactttca ctacagcaca   660
gatttcacct ctgtcttgaa taaaggtccc actttgaagt c                      701

<210> SEQ ID NO 98
<211> LENGTH: 142
<212> TYPE: PRT
<213> ORGANISM: Ovis aries
<220> FEATURE:
<221> NAME/KEY: VARIANT
<222> LOCATION: (0)...(0)
<223> OTHER INFORMATION: alpha-lactalbumin

<400> SEQUENCE: 98

Met Met Ser Phe Val Ser Leu Leu Leu Val Gly Ile Leu Phe His Ala
1               5                   10                  15

Thr Gln Ala Glu Gln Leu Thr Lys Cys Glu Ala Phe Gln Lys Leu Lys
            20                  25                  30

Asp Leu Lys Asp Tyr Gly Gly Val Ser Leu Pro Glu Trp Val Cys Thr
        35                  40                  45

Ala Phe His Thr Ser Gly Tyr Asp Thr Gln Ala Ile Val Gln Asn Asn
    50                  55                  60

Asp Ser Thr Glu Tyr Gly Leu Phe Gln Ile Asn Asn Lys Ile Trp Cys
65                  70                  75                  80

Lys Asp Asp Gln Asn Pro His Ser Arg Asn Ile Cys Asn Ile Ser Cys
                85                  90                  95

Asp Lys Phe Leu Asp Asp Asp Leu Thr Asp Asp Ile Val Cys Ala Lys
                100                 105                 110

Lys Ile Leu Asp Lys Val Gly Ile Asn Tyr Trp Leu Ala His Lys Ala
        115                 120                 125

Leu Cys Ser Glu Lys Leu Asp Gln Trp Leu Cys Glu Lys Leu
        130                 135                 140

<210> SEQ ID NO 99
<211> LENGTH: 723
<212> TYPE: DNA
<213> ORGANISM: Ovis aries
<220> FEATURE:
<221> NAME/KEY: misc_feature
<222> LOCATION: (0)...(0)
<223> OTHER INFORMATION: alpha-lactalbumin

<400> SEQUENCE: 99
ttccaggatc ttagggggta accaaaatga tgtcctttgt ctctctgctc ctggtaggca     60
tcctattcca tgccacccag gctgaacaat taacaaaatg tgaggcgttc cagaagctga    120
aggacttgaa ggactacgga ggtgtcagtt tgcctgaatg ggtctgtacc gcatttcata    180
ccagtggtta tgacacacaa gccatagtac aaaacaatga cagcacagaa tatggactct    240
tccagataaa taataaaatt tggtgcaaag acgaccagaa ccctcactca aggaacatct    300
gtaacatctc ctgtgacaag ttcctggatg atgatcttac tgatgacatt gtgtgtgcca    360
agaagattct ggataaagta ggaattaact actggttggc ccataaagca ctctgttctg    420
agaagctgga tcagtggctc tgtgagaagt tgtgaacacc tgctgtcttt gctgcttctg    480
ccctctttct gttcctggaa ctcctctgcc ccttggctac ctcgttttgc ttctttgtac    540
ccccttgaag ctaacttgtc tctgagccct gggccctgta gtggcgatgg acatgtaagg    600
actaatctct agggatgcat gaatggtgct cgggacattt gacccttgct cggtgcccct    660
gatagcactt ttaatgcaac agtgcatatt ccacttctgt cctgaataaa aggcctgatt    720
ctg                                                                  723

<210> SEQ ID NO 100
<211> LENGTH: 178
<212> TYPE: PRT
<213> ORGANISM: Bos taurus
<220> FEATURE:
<221> NAME/KEY: VARIANT
<222> LOCATION: (0)...(0)
<223> OTHER INFORMATION: Beta-lactoglobulin

<400> SEQUENCE: 100

Met Lys Cys Leu Leu Leu Ala Leu Ala Leu Thr Cys Gly Ala Gln Ala
1               5                   10                  15

Leu Ile Val Thr Gln Thr Met Lys Gly Leu Asp Ile Gln Lys Val Ala
            20                  25                  30

Gly Thr Trp Tyr Ser Leu Ala Met Ala Ala Ser Asp Ile Ser Leu Leu
        35                  40                  45

Asp Ala Gln Ser Ala Pro Leu Arg Val Tyr Val Glu Glu Leu Lys Pro
    50                  55                  60

Thr Pro Glu Gly Asp Leu Glu Ile Leu Leu Gln Lys Trp Glu Asn Asp
65                  70                  75                  80

Glu Cys Ala Gln Lys Lys Ile Ile Ala Glu Lys Thr Lys Ile Pro Ala
                85                  90                  95

Val Phe Lys Ile Asp Ala Leu Asn Glu Asn Lys Val Leu Val Leu Asp
            100                 105                 110

Thr Asp Tyr Lys Lys Tyr Leu Leu Val Cys Met Glu Asn Ser Ala Glu
        115                 120                 125

```
Pro Gln Ser Leu Val Cys Gln Cys Leu Val Arg Thr Pro Glu Val
    130                 135                 140

Asp Asp Glu Ala Leu Glu Lys Phe Asp Lys Ala Leu Lys Ala Leu Pro
145                 150                 155                 160

Met His Ile Arg Leu Ser Phe Asn Pro Thr Gln Leu Glu Glu Gln Cys
                165                 170                 175

His Ile

<210> SEQ ID NO 101
<211> LENGTH: 790
<212> TYPE: DNA
<213> ORGANISM: Bos taurus
<220> FEATURE:
<221> NAME/KEY: misc_feature
<222> LOCATION: (0)...(0)
<223> OTHER INFORMATION: Beta-lactoglobulin

<400> SEQUENCE: 101
actccactcc ctgcagagct cagaagcgtg atcccggctg cagccatgaa gtgcctcctg      60
cttgccctgg ccctcacctg tggcgcccag gccctcatcg tcacccagac catgaagggc     120
ctggatatcc agaaggtggc ggggacttgg tactccttgg ccatggcggc cagcgacatc     180
tccctgctgg acgcccagag tgccccccctg agagtgtatg tggaggagct gaagcccacc     240
cctgagggcg acctggagat cctgctgcag aaatgggaga atgatgagtg tgctcagaag     300
aagatcattg cagaaaaaac caagatccct gcggtgttca agatcgatgc cttgaacgag     360
aacaaagtcc ttgtgctgga caccgactac aaaaagtacc tgctcgtctg catggagaac     420
agtgctgagc ccgagcaaag cctggtctgc cagtgcctgg tcaggacccc ggaggtggac     480
gacgaggccc tggagaaatt cgacaaagcc ctcaaggccc tgcccatgca catccggctg     540
tccttcaacc aacccagct ggaggagcag tgccacatct aggtgagccc ctgccggcgc     600
ctctgggagc ccgggagcct tggcccctct ggggacagac gatgtcatcc ccgcctgccc     660
catcagggga ccaggaggaa ccgggaccac attcacccct cctgggaccc aggcccctcc     720
aggcccctcc tggggcctcc tgcttggggc cgctcctcct tcagcaataa aggcataaac     780
ctgtgctctc                                                           790

<210> SEQ ID NO 102
<211> LENGTH: 180
<212> TYPE: PRT
<213> ORGANISM: Capra hircus
<220> FEATURE:
<221> NAME/KEY: VARIANT
<222> LOCATION: (0)...(0)
<223> OTHER INFORMATION: Beta-lactoglobulin

<400> SEQUENCE: 102

Met Lys Cys Leu Leu Leu Ala Leu Gly Leu Ala Leu Ala Cys Gly Ile
1               5                   10                  15

Gln Ala Ile Ile Val Thr Gln Thr Met Lys Gly Leu Asp Ile Gln Lys
                20                  25                  30

Val Ala Gly Thr Trp Tyr Ser Leu Ala Met Ala Ala Ser Asp Ile Ser
            35                  40                  45

Leu Leu Asp Ala Gln Ser Ala Pro Leu Arg Val Tyr Val Glu Glu Leu
        50                  55                  60

Lys Pro Thr Pro Glu Gly Asn Leu Glu Ile Leu Leu Gln Lys Trp Glu
65                  70                  75                  80
```

```
Asn Gly Glu Cys Ala Gln Lys Lys Ile Ile Ala Glu Lys Thr Lys Ile
                85                  90                  95

Pro Ala Val Phe Lys Ile Asp Ala Leu Asn Glu Asn Lys Val Leu Val
            100                 105                 110

Leu Asp Thr Asp Tyr Lys Lys Tyr Leu Leu Phe Cys Met Glu Asn Ser
        115                 120                 125

Ala Glu Pro Glu Gln Ser Leu Ala Cys Gln Cys Leu Val Arg Thr Pro
    130                 135                 140

Glu Val Asp Lys Glu Ala Leu Glu Lys Phe Asp Lys Ala Leu Lys Ala
145                 150                 155                 160

Leu Pro Met His Ile Arg Leu Ala Phe Asn Pro Thr Gln Leu Glu Gly
                165                 170                 175

Gln Cys His Val
            180

<210> SEQ ID NO 103
<211> LENGTH: 786
<212> TYPE: DNA
<213> ORGANISM: Capra hircus
<220> FEATURE:
<221> NAME/KEY: misc_feature
<222> LOCATION: (0)...(0)
<223> OTHER INFORMATION: Beta-lactoglobulin

<400> SEQUENCE: 103
actccctgca gagctcagaa gcacgacccc agctgcagcc atgaagtgcc tcctgcttgc      60
cctgggcctg gccctcgcct gtggcatcca ggccatcatc gtcacccaga ccatgaaagg     120
cctggacatc cagaaggtgg cggggacttg gtactccttg gctatggcgg ccagcgacat     180
ctccctgctg gacgcccaga gtgccccccct gagagtgtac gtggaggagc tgaagcccac     240
ccccgagggc aacctggaga tcctgctgca gaaatgggag aacggtgagt gtgctcagaa     300
gaagattatt gcagaaaaaa ccaagatccc tgcggtgttc aagatcgatg ccttgaacga     360
gaacaaagtc cttgtgctgg acaccgacta caaaaagtac ctgctcttct gcatggaaaa     420
cagtgctgag cccgagcaaa gcctggcctg ccagtgcctg gtcaggaccc cagaggtgga     480
caaggaggcc ctggagaaat cgacaaagc cctcaaggcc ctgcccatgc acatccggct     540
cgccttcaac ccgacccagc tgaggggca gtgccacgtc taggtgagcc ctgccggcg     600 cctctgtggg cccgggagcc ttggcccctc tggggacaga cgacgtcacc cccgcctccc     660
ccatcagggg gaccaggagg gaccgggacc acggtcacct ctcctgggac ccaggcccct     720
ccaggcccct cctgtggcct cctgctcggg gccgctcctc cttcagcaat aaaggcataa     780
acctgt                                                                786

<210> SEQ ID NO 104
<211> LENGTH: 181
<212> TYPE: PRT
<213> ORGANISM: Homo sapiens
<220> FEATURE:
<221> NAME/KEY: misc_feature
<222> LOCATION: (0)...(0)
<223> OTHER INFORMATION: Beta-lactoglobulin

<400> SEQUENCE: 104

Met Ala Leu Glu Lys Gly Pro Leu Leu Leu Ala Leu Gly Leu
1               5                   10                  15

Leu Ala Gly Ala Gln Lys Ala Leu Glu Glu Val Pro Val Gln Pro Gly
            20                  25                  30
```

```
Phe Asn Ala Gln Lys Val Glu Gly Arg Trp Leu Thr Leu Gln Leu Ala
            35                  40                  45

Ala Asn His Ala Asp Leu Val Ser Pro Ala Asp Pro Leu Arg Leu Ala
 50                  55                  60

Leu His Ser Ile Arg Thr Arg Asp Gly Gly Asp Val Asp Phe Val Leu
 65                  70                  75                  80

Phe Trp Lys Gly Glu Gly Val Cys Lys Glu Thr Asn Ile Thr Val His
                 85                  90                  95

Pro Thr Gln Leu Gln Gly Gln Tyr Gln Gly Ser Phe Glu Gly Gly Ser
            100                 105                 110

Met His Val Cys Phe Val Ser Thr Asp Tyr Ser Asn Leu Ile Leu Tyr
            115                 120                 125

Val Arg Phe Glu Asp Asp Glu Ile Thr Asn Leu Trp Val Leu Leu Ala
130                 135                 140

Arg Arg Met Leu Glu Asp Pro Lys Trp Leu Gly Arg Tyr Leu Glu Tyr
145                 150                 155                 160

Val Glu Lys Phe His Leu Gln Lys Ala Pro Val Phe Asn Ile Asp Gly
                165                 170                 175

Pro Cys Pro Pro Pro
            180

<210> SEQ ID NO 105
<211> LENGTH: 1505
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Beta-lactoglobulin

<400> SEQUENCE: 105 tccccttcc ccggagccat ggccctggag aaaggcccgc tcctgctgct ggcccttggc      60
ctgggcctgg cgggtgccca gaaggctctg gaagaggtac cggtacagcc gggcttcaat    120
gcgcagaagg tggagggcg ctggctcacc ctgcagctgg cagccaacca cgcagacctg     180
gtctccccgg ccgaccccct gaggctcgct ctccactcca tccggaccag ggacggcggg    240
gacgtggact tcgtgctgtt ctggaaggga gaaggggtgt gtaaagaaac aaacatcacc    300
gtccatccaa cccagttgca aggccagtac caaggctcat tcgagggcgg cagcatgcac    360
gtatgcttcg tcagcaccga ctacagcaac ctcattcttt acgtgcgctt tgaggatgat    420
gagatcacca acctgtgggt gctgctggcg agaagaatgc tggaggaccc caaatggctg    480
ggaagatact tggagtacgt ggagaaattc cacctgcaga aagccccggt cttcaacata    540
gatggcccat gtccccccacc ctgagcctag gtctggcggt tctggagtct tcctgcctgg    600 gccctcacc cctctgctgc cctcagcctc ccttccacct ccttcacctt ggcttgtggc     660
ctggactgtc cccaggtccc cctggaagcc cttttgcatc tcaggactc aaggaagctc     720 cccagctgag cccaaccctg cctctctcct ggtcccctcc cctgctggga aggcctcttc    780
cctctgtgcg tctccaggtc ctgccaacca cctgccaacc aacagccaag gccagcagt    840 gtgcccagc ctggcctgtg ggcctggagc acacccaggg tggtgaggag ggggcacatg    900 gcccctgag ctcctgcccg cagcgccaga ggcctccaaa acttatacaa tgagtggagc    960
actgtagtcc caggtgcctc cgatgcaccc cctcccccag ggtgctggg gtggccctca    1020 agtgtccttc aggaacatga ccccacggag gctgttctca gactccagct cccctccact   1080
gtgacccacc tcacctgggt ctgctgggga ccctccagag aggtggcctc catgctccgt   1140
```

-continued

| | |
|---|---|
| gagcaaacgc atatgtcccc actgaggtcc aagagcccta agtgagccca gctccagacc | 1200 |
| ctgctctctg cagaagccca gcggggctgc caggtaaaca cagacagctg tacctgtgtg | 1260 |
| gcaggtgaga ccagccaacg cccactcctc ggagcccagg attctgaagg gcggcgccca | 1320 |
| cttctgcacc cggtgagcca gggctgccca tcggcagggc aggctctgag gaaattgggt | 1380 |
| cagggactca atacttgtcg tctggaactc ccaagacagg tatgtccaga ggctgccccg | 1440 |
| aaaacgcctc cagtgaggcc ttctcccccct tctccccctt ctccccttc tccccaatct | 1500 |
| ccccc | 1505 |

<210> SEQ ID NO 106
<211> LENGTH: 180
<212> TYPE: PRT
<213> ORGANISM: Ovis aries
<220> FEATURE:
<221> NAME/KEY: VARIANT
<222> LOCATION: (0)...(0)
<223> OTHER INFORMATION: Beta-lactoglobulin

<400> SEQUENCE: 106

Met Lys Cys Leu Leu Leu Ala Leu Gly Leu Ala Leu Ala Cys Gly Val
1               5                   10                  15

Gln Ala Ile Ile Val Thr Gln Thr Met Lys Gly Leu Asp Ile Gln Lys
            20                  25                  30

Val Ala Gly Thr Trp His Ser Leu Ala Met Ala Ala Ser Asp Ile Ser
        35                  40                  45

Leu Leu Asp Ala Gln Ser Ala Pro Leu Arg Val Tyr Val Glu Glu Leu
    50                  55                  60

Lys Pro Thr Pro Glu Gly Asn Leu Glu Ile Leu Leu Gln Lys Trp Glu
65                  70                  75                  80

Asn Gly Glu Cys Ala Gln Lys Lys Ile Ile Ala Glu Lys Thr Lys Ile
                85                  90                  95

Pro Ala Val Phe Lys Ile Asp Ala Leu Asn Glu Asn Lys Val Leu Val
            100                 105                 110

Leu Asp Thr Asp Tyr Lys Lys Tyr Leu Leu Phe Cys Met Glu Asn Ser
        115                 120                 125

Ala Glu Pro Glu Gln Ser Leu Ala Cys Gln Cys Leu Val Arg Thr Pro
    130                 135                 140

Glu Val Asp Asn Glu Ala Leu Glu Lys Phe Asp Lys Ala Leu Lys Ala
145                 150                 155                 160

Leu Pro Met His Ile Arg Leu Ala Phe Asn Pro Thr Gln Leu Glu Gly
                165                 170                 175

Gln Cys His Val
            180

<210> SEQ ID NO 107
<211> LENGTH: 785
<212> TYPE: DNA
<213> ORGANISM: Ovis aries
<220> FEATURE:
<221> NAME/KEY: misc_feature
<222> LOCATION: (0)...(0)
<223> OTHER INFORMATION: Beta-lactoglobulin

<400> SEQUENCE: 107

| | |
|---|---|
| ctccctgcag agttcagaag cacgacccca gctgcagcca tgaagtgcct cctgcttgcc | 60 |
| ctgggcctgg ccctcgcctg tggcgtccag gccatcatcg tcacccagac catgaaaggc | 120 |

-continued

```
ctggacatcc agaaggtggc ggggacttgg cactccttgg ctatggcggc cagcgacatc      180
tccctgctgg atgcccagag tgcccccctg agagtgtacg tggaggagct gaagcccacc      240
cccgagggca acctggagat cctgctgcag aaatgggaga cggcgagtg tgctcagaag       300 aagattattg cagaaaaaac caagatccct gcggtgttca agatcgatgc cttgaatgag      360
aacaaagtcc ttgtgctgga caccgactac aaaaagtacc tgctcttctg catggaaaac     420
agtgctgagc ccgagcaaag cctggcctgc cagtgcctgg tcaggacccc ggaggtggac     480
aacgaggccc tggagaaatt cgacaaagcc ctcaaggccc tgcccatgca catccggctt    540
gccttcaacc cgacccagct ggaggggcag tgccacgtct aggtgagccc ctgccggtgc    600
ctctgggggc ccgggagcct tggctcctct ggggacagac gacgtcacca ccgccccccc    660
ccatcagggg gactagaagg gaccaggact gcagtcaccc ttcctgggac ccaggccccct   720 ccaggcccct cctgggctct gctctgggg cagcttctcc ttcaccaata aaggcataaa     780
cctgt                                                                 785
```

<210> SEQ ID NO 108
<211> LENGTH: 708
<212> TYPE: PRT
<213> ORGANISM: Bos taurus
<220> FEATURE:
<221> NAME/KEY: VARIANT
<222> LOCATION: (0)...(0)
<223> OTHER INFORMATION: Lactoferri

<400> SEQUENCE: 108

```
Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Val Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
```

-continued

```
                225                 230                 235                 240
        Ala Asp Arg Asp Gln Tyr Glu Leu Leu Cys Leu Asn Asn Ser Arg Ala
                        245                 250                 255

Pro Val Asp Ala Phe Lys Glu Cys His Leu Ala Gln Val Pro Ser His
                        260                 265                 270

Ala Val Ala Arg Ser Val Asp Gly Lys Glu Asp Leu Ile Trp Lys
                        275                 280                 285

Leu Leu Ser Lys Ala Gln Glu Lys Phe Gly Lys Asn Lys Ser Arg Ser
                        290                 295                 300

Phe Gln Leu Phe Gly Ser Pro Pro Gly Gln Arg Asp Leu Leu Phe Lys
        305                 310                 315                 320

Asp Ser Ala Leu Gly Phe Leu Arg Ile Pro Ser Lys Val Asp Ser Ala
                        325                 330                 335

Leu Tyr Leu Gly Ser Arg Tyr Leu Thr Thr Leu Lys Asn Leu Arg Glu
                        340                 345                 350

Thr Ala Glu Glu Val Lys Ala Arg Tyr Thr Arg Val Val Trp Cys Ala
                        355                 360                 365

Val Gly Pro Glu Glu Gln Lys Lys Cys Gln Gln Trp Ser Gln Gln Ser
        370                 375                 380

Gly Gln Asn Val Thr Cys Ala Thr Ala Ser Thr Thr Asp Cys Ile
        385                 390                 395                 400

Val Leu Val Leu Lys Gly Glu Ala Asp Ala Leu Asn Leu Asp Gly Gly
                        405                 410                 415

Tyr Ile Tyr Thr Ala Gly Lys Cys Gly Leu Val Pro Val Leu Ala Glu
                        420                 425                 430

Asn Arg Lys Thr Ser Lys Tyr Ser Ser Leu Asp Cys Val Leu Arg Pro
                        435                 440                 445

Thr Glu Gly Tyr Leu Ala Val Ala Val Val Lys Lys Ala Asn Glu Gly
                        450                 455                 460

Leu Thr Trp Asn Ser Leu Lys Asp Lys Lys Ser Cys His Thr Ala Val
        465                 470                 475                 480

Asp Arg Thr Ala Gly Trp Asn Ile Pro Met Gly Leu Ile Val Asn Gln
                        485                 490                 495

Thr Gly Ser Cys Ala Phe Asp Glu Phe Phe Ser Gln Ser Cys Ala Pro
                        500                 505                 510

Gly Arg Asp Pro Lys Ser Arg Leu Cys Ala Leu Cys Ala Gly Asp Asp
                        515                 520                 525

Gln Gly Leu Asp Lys Cys Val Pro Asn Ser Lys Glu Lys Tyr Tyr Gly
                        530                 535                 540

Tyr Thr Gly Ala Phe Arg Cys Leu Ala Glu Asp Val Gly Asp Val Ala
        545                 550                 555                 560

Phe Val Lys Asn Asp Thr Val Trp Glu Asn Thr Asn Gly Glu Ser Thr
                        565                 570                 575

Ala Asp Trp Ala Lys Asn Leu Asn Arg Glu Asp Phe Arg Leu Leu Cys
                        580                 585                 590

Leu Asp Gly Thr Arg Lys Pro Val Thr Glu Ala Gln Ser Cys His Leu
                        595                 600                 605

Ala Val Ala Pro Asn His Ala Val Val Ser Arg Ser Asp Arg Ala Ala
                        610                 615                 620

His Val Lys Gln Val Leu Leu His Gln Gln Ala Leu Phe Gly Lys Asn
        625                 630                 635                 640

Gly Lys Asn Cys Pro Asp Lys Phe Cys Leu Phe Lys Ser Glu Thr Lys
                        645                 650                 655
```

```
Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 109
<211> LENGTH: 2357
<212> TYPE: DNA
<213> ORGANISM: Bos taurus
<220> FEATURE:
<221> NAME/KEY: misc_feature
<222> LOCATION: (0)...(0)
<223> OTHER INFORMATION: Lactoferrin cDNA

<400> SEQUENCE: 109
```

| | | | | |
|---|---|---|---|---|
| gcagagcctt | cgttccggag | tcgccccagg | accccagcca | tgaagctctt cgtccccgcc | 60 |
| ctgctgtccc | ttggagccct | tggactgtgt | ctggctgccc | cgaggaaaaa cgttcgatgg | 120 |
| tgtaccatct | cccaacccga | gtggttcaaa | tgccgccgat | ggcagtggag gatgaagaag | 180 |
| ctgggtgctc | cctctatcac | ctgtgtgagg | agggcctttg | ccttggaatg tatccgggcc | 240 |
| atcgcggaga | aaaaggcgga | tgctgtgacc | ctggatggtg | gcatggtgtt tgaggcgggc | 300 |
| cgggaccccc | tacaaactgcg | gccagtagca | gcagagatct | atgggacgaa agagtctccc | 360 |
| caaacccact | attatgctgt | ggccgtcgtg | aagaagggca | gcaactttca gctggaccag | 420 |
| ctgcaaggcc | ggaagtcctg | ccatacgggc | cttggcaggt | ccgctgggtg ggtcatccct | 480 |
| atgggaatcc | ttcgcccgta | cttgagctgg | acagagtcac | tcgagcccct ccagggagct | 540 |
| gtggctaaat | tcttctctgc | cagctgtgtt | ccctgcattg | atagacaagc ataccccaac | 600 |
| ctgtgtcaac | tgtgcaaggg | ggaggggggag | aaccagtgtg | cctgctcctc ccgggaacca | 660 |
| tacttcggtt | attctggtgc | cttcaagtgt | ctgcaggacg | gggctggaga cgtggctttt | 720 |
| gttaaagaga | cgacagtgtt | tgagaacttg | ccagagaagg | ctgacaggga ccagtatgag | 780 |
| cttctctgcc | tgaacaacag | tcgggcgcca | gtggatgcgt | tcaaggagtg ccacctggcc | 840 |
| caggtccctt | ctcatgctgt | cgtggcccga | agtgtggatg | caaggaaga cttgatctgg | 900 |
| aagcttctca | gcaaggcgca | ggagaaattt | ggaaaaaaca | agtctcggag cttccagctc | 960 |
| tttggctctc | caccccggcca | gagggacctg | ctgttcaaag | actctgctct tgggttttg | 1020 |
| aggatcccct | cgaaggtaga | ttcggcgctg | taccttggct | cccgctactt gaccaccttg | 1080 |
| aagaacctca | gggaaactgc | ggaggaggtg | aaggcgcggt | acaccagggt cgtgtggtgt | 1140 |
| gccgtgggac | ccgaggagca | gaagaagtgc | cagcagtgga | gccagcagag cggccagaac | 1200 |
| gtgacctgtg | ccacggcgtc | caccaccgac | gactgcatcg | tcctggtgct gaaaggggaa | 1260 |
| gcagatgccc | tgaacttgga | tggaggatat | atctacactg | cgggcaagtg tggcctggtg | 1320 |
| cctgtcctgg | cagagaaccg | gaaaacctcc | aaatacagta | gcctagattg tgtgctgaga | 1380 |
| ccaacagaag | ggtaccttgc | cgtggcagtt | gtcaagaaag | caaatgaggg gctcacatgg | 1440 |
| aattctctga | agacaagaa | gtcgtgccac | accgccgtgg | acaggactgc aggctggaac | 1500 |
| atccccatgg | gcctgatcgt | caaccagaca | ggctcctgcg | catttgatga attctttagt | 1560 |
| cagagctgtg | cccctgggcg | tgacccgaaa | tccagactct | gtgccttgtg tgctggcgat | 1620 |

```
gaccagggcc tggacaagtg tgtgcccaac tctaaggaga agtactatgg ctataccggg    1680
gctttcaggt gcctggctga ggacgttggg gacgttgcct ttgtgaaaaa cgacacagtc    1740
tgggagaaca cgaatggaga gagcactgca gactgggcta agaacttgaa tcgtgaggac    1800
ttcaggttgc tctgcctcga tggcaccagg aagcctgtga cggaggctca gagctgccac    1860
ctggcggtgg ccccgaatca cgctgtggtg tctcggagcg atagggcagc acacgtgaaa    1920
caggtgctgc tccaccagca ggctctgttt gggaaaaatg gaaaaactg cccggacaag     1980 ttttgtttgt tcaaatctga aaccaaaaac cttctgttca atgacaacac tgagtgtctg    2040
gccaaacttg gaggcagacc aacgtatgaa gaatatttgg ggacagagta tgtcacggcc    2100
attgccaacc tgaaaaaatg ctcaacctcc ccgcttctgg aagcctgcgc cttcctgacg    2160
aggtaaagcc tgcaaagaag ctagcctgcc tccctgggcc tcagctcctc cctgctctca    2220
gccccaatct ccaggcgcga gggaccttcc tctcccttcc tgaagtcgga ttttttgccaa   2280 gctcatcagt atttacaatt ccctgctgtc attttagcaa gaaataaaat tagaaatgct    2340
gttgattttc attccct                                                  2357

<210> SEQ ID NO 110
<211> LENGTH: 708
<212> TYPE: PRT
<213> ORGANISM: Capra hircus
<220> FEATURE:
<221> NAME/KEY: VARIANT
<222> LOCATION: (0)...(0)
<223> OTHER INFORMATION: Lactoferrin

<400> SEQUENCE: 110

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Ala Ile Ser Leu
            20                  25                  30

Pro Glu Trp Ser Lys Cys Tyr Gln Trp Gln Arg Arg Met Arg Lys Leu
        35                  40                  45

Gly Ala Pro Ser Ile Thr Cys Val Arg Arg Thr Ser Ala Leu Glu Cys
    50                  55                  60

Ile Arg Ala Ile Ala Gly Lys Asn Ala Asp Ala Val Thr Leu Asp Ser
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Glu Lys Ser Pro Gln Thr His Tyr Tyr
            100                 105                 110

Ala Val Ala Val Val Lys Lys Gly Ser Asn Phe Lys Leu Asp Gln Leu
        115                 120                 125

Gln Gly Gln Lys Ser Cys His Met Gly Leu Gly Arg Ser Ala Gly Trp
    130                 135                 140

Asn Ile Pro Val Gly Ile Leu Arg Pro Pro Leu Ser Trp Thr Glu Ser
145                 150                 155                 160

Ala Glu Pro Leu Gln Gly Ala Val Ala Arg Phe Phe Ser Ala Ser Cys
                165                 170                 175

Val Pro Cys Val Asp Gly Lys Ala Tyr Pro Asn Leu Cys Gln Leu Cys
            180                 185                 190

Lys Gly Val Gly Glu Asn Lys Cys Ala Cys Ser Ser Gln Glu Pro Tyr
        195                 200                 205

Phe Gly Tyr Ser Gly Ala Phe Lys Cys Leu Gln Asp Gly Ala Gly Asp
    210                 215                 220
```

```
Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Thr Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asn Leu Ile Trp Glu
        275                 280                 285

Leu Leu Arg Lys Ala Gln Glu Lys Phe Gly Lys Asn Lys Ser Gln Arg
    290                 295                 300

Phe Gln Leu Phe Gly Ser Pro Glu Gly Arg Arg Asp Leu Leu Phe Lys
305                 310                 315                 320

Asp Ser Ala Leu Gly Phe Val Arg Ile Pro Ser Lys Val Asp Ser Ala
                325                 330                 335

Leu Tyr Leu Gly Ser Arg Tyr Leu Thr Ala Leu Lys Asn Leu Arg Glu
            340                 345                 350

Thr Ala Glu Glu Leu Lys Ala Arg Cys Thr Arg Val Val Trp Cys Ala
        355                 360                 365

Val Gly Pro Glu Glu Gln Ser Lys Cys Gln Gln Trp Ser Glu Gln Ser
    370                 375                 380

Gly Gln Asn Val Thr Cys Ala Thr Ala Ser Thr Thr Asp Asp Cys Ile
385                 390                 395                 400

Ala Leu Val Leu Lys Gly Glu Ala Asp Ala Leu Ser Leu Gly Gly Gly
                405                 410                 415

Tyr Ile Tyr Thr Ala Gly Lys Cys Gly Leu Val Pro Val Met Ala Glu
            420                 425                 430

Asn Arg Lys Ser Ser Lys Tyr Ser Ser Leu Asp Cys Val Leu Arg Pro
        435                 440                 445

Thr Glu Gly Tyr Leu Ala Val Ala Val Val Lys Lys Ala Asn Glu Gly
    450                 455                 460

Leu Thr Trp Asn Ser Leu Lys Gly Lys Lys Ser Cys His Thr Ala Val
465                 470                 475                 480

Asp Arg Thr Ala Gly Trp Asn Ile Pro Met Gly Leu Ile Ala Asn Gln
                485                 490                 495

Thr Gly Ser Cys Ala Phe Asp Glu Phe Phe Ser Gln Ser Cys Ala Pro
            500                 505                 510

Gly Ala Asp Pro Lys Ser Ser Leu Cys Ala Leu Cys Ala Gly Asp Asp
        515                 520                 525

Gln Gly Leu Asp Lys Cys Val Pro Asn Ser Lys Glu Lys Tyr Tyr Gly
    530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Ser
                565                 570                 575

Ala Asp Trp Ala Lys Asn Leu Asn Arg Glu Asp Phe Arg Leu Leu Cys
            580                 585                 590

Leu Asp Gly Thr Thr Lys Pro Val Thr Glu Ala Gln Ser Cys Tyr Leu
        595                 600                 605

Ala Val Ala Pro Asn His Ala Val Val Ser Arg Ser Asp Arg Ala Ala
    610                 615                 620

His Val Glu Gln Val Leu Leu His Gln Gln Ala Leu Phe Gly Lys Asn
625                 630                 635                 640
```

```
Gly Lys Asn Cys Pro Asp Gln Phe Cys Leu Phe Lys Ser Glu Thr Lys
            645                 650                 655

Asn Leu Leu Phe Asn Asp Asn Thr Glu Cys Leu Ala Lys Leu Gly Gly
        660                 665                 670

Arg Pro Thr Tyr Glu Lys Tyr Leu Gly Thr Glu Tyr Val Thr Ala Ile
    675                 680                 685

Ala Asn Leu Lys Lys Cys Ser Thr Ser Pro Leu Leu Glu Ala Cys Ala
690                 695                 700

Phe Leu Thr Arg
705

<210> SEQ ID NO 111
<211> LENGTH: 2411
<212> TYPE: DNA
<213> ORGANISM: Capra hircus
<220> FEATURE:
<221> NAME/KEY: misc_feature
<222> LOCATION: (0)...(0)
<223> OTHER INFORMATION: Lactoferrin

<400> SEQUENCE: 111
agcactggat aaagggacgc agaacgaggg caggtggcag agcttcgttc cggagtcgcc      60
ccaggacccc agacatgaag ctcttcgtcc ccgccctgct gtcccttgga gcccttggac     120
tgtgtctggc tgccccgagg aaaaacgttc gatggtgtgc catctcactg ccggagtggt     180
ccaaatgcta ccaatggcag aggaggatga ggaagctggg tgctcccctct atcacctgtg     240 tgaggaggac ctctgccttg aatgtatcc gggccatcgc gggaaaaaat gcggatgctg     300
tgaccctgga tagtggcatg gtgtttgagg cgggccggga cccctacaaa ctgcggccag     360
tagcggcaga gatctatggg acagaaaaat ctccccaaac ccactattat gctgtggccg     420
tcgtgaagaa gggcagcaac tttaagctgg accagctgca aggtcagaag tcctgccaca     480
tgggccttgg caggtccgct gggtggaaca tccctgtggg aatccttcgc cgcccttga     540 gctggacaga gtcggccgag cccctccagg gagctgtggc tagattcttc tctgccagct     600
gtgttccctg cgttgatgga aaagcgtacc ccaacctgtg tcaactgtgc aaggggggtgg     660 gagagaacaa gtgtgcctgc tcctcccagg aaccatactt tggttattct ggtgccttca     720
agtgcctgca ggacgggct ggagacgtgg cttttgtcaa ggagacgaca gtgtttgaga     780
acttgccaga gaaggctgac agggaccagt atgagcttct ctgcctaaac aacactcggg     840
cgccagtgga tgcattcaag gagtgccacc tggcccaggt ccctgctcat gctgttgtgg     900
cccgcagtgt ggatgcaag gagaacttga tctgggagct tctcaggaag cacaggagaa     960
agtttggaaa aaacaagtct cagcgcttcc agctctttgg ctctccagaa ggccggaggg    1020
acctgctatt caaagactct gccctttggg ttgtgaggat cccctcaaaa gtagattcgg    1080
cgctgtacct gggctcccgt tacttgaccg ccttgaagaa cctcagggaa accgcggagg    1140
agttgaaggc gcggtgcacg cgggtcgtgt ggtgcgcggt gggaccccgag gagcagagta    1200 agtgccagca gtggagcgag cagagcggcc agaacgtgac ctgtgccacg gcctccacca    1260
ccgacgactg catcgccctg gtgctgaaag gggaagcgga cgccctgagc ttgggtggag    1320
gatatatcta cactgccggc aagtgcggcc tggtgcctgt catggcagag aaccggaaat    1380
cctccaaata cagtagccta gattgtgtgc tgagaccaac ggaagggtac cttgccgtgg    1440
cagttgtcaa gaaagcaaat gagggggctca cttggaattc tctgaaaggc aagaagtcgt    1500
gccacaccgc cgtggacagg actgcaggct ggaacatccc catgggcctg atcgccaacc    1560
```

-continued

```
agacaggctc ctgcgcattt gatgaattct ttagtcagag ctgtgcccct ggggccgacc    1620
cgaaatccag cctctgtgca ttgtgtgccg gcgatgacca gggcctggac aagtgtgtgc    1680
ccaactctaa ggagaagtac tatggctaca ccggggcttt caggtgcctg gctgaggacg    1740
ttggggacgt tgcatttgtg aaaaacgaca cagtctggga gaacacaaat ggagagagct    1800
ctgcagactg gctaagaac ttgaatcgcg aggacttcag gctgctctgc ctcgatggca    1860
ccacgaagcc tgtgacggag ctcagagct gctacctggc ggtggccccg aatcacgctg     1920
tggtgtctcg gagcgatagg gcagcgcacg tggaacaggt gctgctccac cagcaggctc    1980
tgtttgggaa aaatggaaaa aactgcccgg accagttttg tttgttcaaa tctgaaacca    2040
aaaaccttct gttcaatgac aacactgagt gtctggccaa acttggaggc agaccaacgt    2100
atgaaaaata tttggggaca gagtatgtca cggccattgc caacctgaaa aaatgctcaa    2160
cctccccgct tctggaagcc tgcgccttcc tgacgaggta aagcctgcaa agaagctagc    2220
ctgcctcccc gggcctcagc tcctccctgc tctcagcccc agtcttcagg cgcgagggac    2280
cttcctctcc cttcctgaag tcggattttt gccaagctca tcagtattca caattccctg    2340
ctgtcatctt agcaagaaat taaattagaa atgctgttga ttttcattcc ctaaaaaaaa    2400
aaaaaaaaaa a                                                         2411
```

<210> SEQ ID NO 112
<211> LENGTH: 711
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Lactoferrin

<400> SEQUENCE: 112

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Thr Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
```

-continued

```
            195                 200                 205
Tyr Phe Ser Tyr Ser Gly Ala Phe Lys Cys Leu Arg Asp Gly Ala Gly
    210                 215                 220
Asp Val Ala Phe Ile Arg Glu Ser Thr Val Phe Glu Asp Leu Ser Asp
225                 230                 235                 240
Glu Ala Glu Arg Asp Glu Tyr Glu Leu Leu Cys Pro Asp Asn Thr Arg
                245                 250                 255
Lys Pro Val Asp Lys Phe Lys Asp Cys His Leu Ala Arg Val Pro Ser
                260                 265                 270
His Ala Val Val Ala Arg Ser Val Asn Gly Lys Glu Asp Ala Ile Trp
            275                 280                 285
Asn Leu Leu Arg Gln Ala Gln Glu Lys Phe Gly Lys Asp Lys Ser Pro
290                 295                 300
Lys Phe Gln Leu Phe Gly Ser Pro Ser Gly Gln Lys Asp Leu Leu Phe
305                 310                 315                 320
Lys Asp Ser Ala Ile Gly Phe Ser Arg Val Pro Pro Arg Ile Asp Ser
                325                 330                 335
Gly Leu Tyr Leu Gly Ser Gly Tyr Phe Thr Ala Ile Gln Asn Leu Arg
                340                 345                 350
Lys Ser Glu Glu Glu Val Ala Ala Arg Arg Ala Arg Val Val Trp Cys
            355                 360                 365
Ala Val Gly Glu Gln Glu Leu Arg Lys Cys Asn Gln Trp Ser Gly Leu
370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
                420                 425                 430
Glu Asn Tyr Lys Ser Gln Gln Ser Ser Asp Pro Asp Pro Asn Cys Val
            435                 440                 445
Asp Arg Pro Val Glu Gly Tyr Leu Ala Val Ala Val Val Arg Arg Ser
450                 455                 460
Asp Thr Ser Leu Thr Trp Asn Ser Val Lys Gly Lys Lys Ser Cys His
465                 470                 475                 480
Thr Ala Val Asp Arg Thr Ala Gly Trp Asn Ile Pro Met Gly Leu Leu
                485                 490                 495
Phe Asn Gln Thr Gly Ser Cys Lys Phe Asp Glu Tyr Phe Ser Gln Ser
                500                 505                 510
Cys Ala Pro Gly Ser Asp Pro Arg Ser Asn Leu Cys Ala Leu Cys Ile
            515                 520                 525
Gly Asp Glu Gln Gly Glu Asn Lys Cys Val Pro Asn Ser Asn Glu Arg
530                 535                 540
Tyr Tyr Gly Tyr Thr Gly Ala Phe Arg Cys Leu Ala Glu Asn Ala Gly
545                 550                 555                 560
Asp Val Ala Phe Val Lys Asp Val Thr Val Leu Gln Asn Thr Asp Gly
                565                 570                 575
Asn Asn Asn Asp Ala Trp Ala Lys Asp Leu Lys Leu Ala Asp Phe Ala
                580                 585                 590
Leu Leu Cys Leu Asp Gly Lys Arg Lys Pro Val Thr Glu Ala Arg Ser
            595                 600                 605
Cys His Leu Ala Met Ala Pro Asn His Ala Val Val Ser Arg Met Asp
610                 615                 620
```

```
Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
            645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
690                 695                 700

Ala Cys Glu Phe Leu Arg Lys
705                 710

<210> SEQ ID NO 113
<211> LENGTH: 2259
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Lactoferrin cDNA

<400> SEQUENCE: 113
cagaccgcag acatgaaact tgtcttcctc gtcctgctgt tcctcggggc cctcggactg      60
tgtctggctg gccgtaggag aaggagtgtt cagtggtgca ccgtatccca acccgaggcc    120
acaaaatgct tccaatggca aggaatatg agaagagtgc gtggccctcc tgtcagctgc     180
ataaagagag actcccccat ccagtgtatc caggccattg cggaaaacag ggccgatgct    240
gtgacccttg atggtggttt catatacgag gcaggcctgg cccctacaa actgcgacct     300 gtagcggcgg aagtctacgg gaccgaaaga cagccacgaa ctcactatta tgccgtggct    360
gtggtgaaga agggcggcag ctttcagctg aacgaactgc aaggtctgaa gtcctgccac    420
acaggccttc gcaggaccgc tggatggaat gtccctatag ggacacttcg tccattcttg    480
aattggacgg tcccacctga gcccattgag gcagctgtgg ccaggttctt ctcagccagc    540
tgtgttcccg gtgcagataa aggacagttc cccaacctgt gtcgcctgtg tgcggggaca    600
ggggaaaaca atgtgccttt ctcctcccag gaaccgtact tcagctactc tggtgccttc    660
aagtgtctga gagacgggc tggagacgtg gcttttatca gagagagcac agtgtttgag    720
gacctgtcag acgaggctga aagggacgag tatgagttac tctgcccaga caacactcgg    780
aagccagtga caagttcaa agactgccat ctggcccggg tcccttctca tgccgttgtg    840
gcacgaagtg tgaatggcaa ggaggatgcc atctggaatc ttctccgcca ggcacaggaa    900
aagtttggaa aggacaagtc accgaaattc cagctctttg gctcccctag tgggcagaaa    960
gatctgctgt tcaaggactc tgccattggg ttttcgaggg tgccccgag atagattct    1020 gggctgtacc ttggctccgg ctacttcact gccatccaga acttgaggaa aagtgaggag   1080
gaagtggctg cccggcgtgc gcgggtcgtg tggtgtgcgg tgggcgagca ggagctgcgc   1140
aagtgtaacc agtggagtgg cttgagcgaa ggcagcgtga cctgctcctc ggcctccacc   1200
acagaggact gcatcgccct ggtgctgaaa ggagaagctg atgccatgag tttgatgga    1260 ggatatgtgt acactgcagg caaatgtggt ttggtgcctg tcctggcaga gaactacaaa   1320
tcccaacaaa gcagtgaccc tgatcctaac tgtgtggata gacctgtgga aggatatctt   1380
gctgtggcgg tggttaggag atcagacact agccttacct ggaactctgt gaaaggcaag   1440
```

```
aagtcctgcc acaccgccgt ggacaggact gcaggctgga atatccccat gggcctgctc   1500
ttcaaccaga cgggctcctg caaatttgat gaatatttca gtcaaagctg tgcccctggg   1560
tctgacccga gatctaatct ctgtgctctg tgtattggcg acgagcaggg tgagaataag   1620
tgcgtgccca acagcaatga gagatactac ggctacactg gggctttccg gtgcctggct   1680
gagaatgctg gagacgttgc atttgtgaaa gatgtcactg tcttgcagaa cactgatgga   1740
aataacaatg acgcatgggc taaggatttg aagctggcag actttgcgct gctgtgcctc   1800
gatggcaaac ggaagcctgt gactgaggct agaagctgcc atcttgccat ggccccgaat   1860
catgccgtgg tgtctcggat ggataaggtg gaacgcctga acaggtgtt gctccaccaa   1920 caggctaaat ttgggagaaa tggatctgac tgcccggaca gttttgctt attccagtct   1980 gaaaccaaaa accttctgtt caatgacaac actgagtgtc tggccagact ccatggcaaa   2040
acaacatatg aaaaatattt gggaccacag tatgtcgcag gcattactaa tctgaaaaag   2100
tgctcaacct ccccctcct ggaagcctgt gaattcctca ggaagtaaaa ccgaagaaga   2160
tggcccagct ccccaagaaa gcctcagcca ttcactgccc ccagctcttc tccccaggtg   2220
tgttggggcc ttggctcccc tgctgaaggt ggggattgc                          2259
```

<210> SEQ ID NO 114
<211> LENGTH: 708
<212> TYPE: PRT
<213> ORGANISM: Ovis aries
<220> FEATURE:
<221> NAME/KEY: VARIANT
<222> LOCATION: (0)...(0)
<223> OTHER INFORMATION: Lactoferrin

<400> SEQUENCE: 114

```
Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Ala Ile Ser Pro
            20                  25                  30

Pro Glu Gly Ser Lys Cys Tyr Gln Trp Gln Arg Arg Met Arg Lys Leu
        35                  40                  45

Gly Ala Pro Ser Ile Thr Cys Val Arg Thr Ser Ala Leu Glu Cys
    50                  55                  60

Ile Arg Ala Ile Ala Gly Lys Lys Ala Asp Ala Val Thr Leu Asp Ser
65                  70                  75                  80

Gly Met Val Phe Glu Ala Gly Leu Asp Pro Tyr Lys Leu Arg Pro Val
                85                  90                  95

Ala Ala Glu Ile Tyr Gly Thr Glu Lys Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Gln Lys Ser Cys His Met Gly Leu Gly Arg Ser Ala Gly Trp
130                 135                 140

Asn Ile Pro Met Gly Ile Leu Arg Pro Phe Leu Ser Trp Thr Glu Ser
145                 150                 155                 160

Ala Glu Pro Leu Gln Gly Ala Val Ala Arg Phe Phe Ser Ala Ser Cys
                165                 170                 175

Val Pro Cys Val Asp Gly Lys Ala Tyr Pro Asn Leu Cys Gln Leu Cys
            180                 185                 190

Lys Gly Val Gly Glu Asn Lys Cys Ala Cys Ser Ser Gln Glu Pro Tyr
        195                 200                 205
```

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Thr Arg Ala
                245                 250                 255

Pro Val Asp Ala Phe Lys Glu Cys His Leu Ala Gln Val Pro Ser His
        260                 265                 270

Ala Val Val Ala Arg Ser Val Asp Gly Lys Glu Asn Leu Ile Trp Glu
            275                 280                 285

Leu Leu Arg Lys Ala Gln Glu Lys Phe Gly Lys Asn Lys Ser Gln Arg
290                 295                 300

Phe Gln Leu Phe Gly Ser Pro Gln Gly Gln Lys Asp Leu Leu Phe Lys
305                 310                 315                 320

Asp Ser Ala Leu Gly Phe Val Arg Ile Pro Ser Lys Val Asp Ser Ala
                325                 330                 335

Leu Tyr Leu Gly Ser Arg Tyr Leu Thr Ala Leu Lys Asn Leu Arg Glu
            340                 345                 350

Thr Ala Glu Glu Val Lys Ala Arg Cys Thr Arg Val Val Trp Cys Ala
        355                 360                 365

Val Gly Pro Glu Glu His Ser Lys Cys Gln Gln Trp Ser Glu Gln Ser
370                 375                 380

Gly Gln Asn Val Thr Cys Ala Met Ala Ser Thr Thr Asp Asp Cys Ile
385                 390                 395                 400

Ala Leu Val Leu Lys Gly Glu Ala Asp Ala Leu Ser Leu Asp Gly Gly
                405                 410                 415

Tyr Ile Tyr Thr Ala Gly Lys Cys Gly Leu Val Pro Val Met Ala Glu
            420                 425                 430

Asn Arg Glu Ser Ser Lys Tyr Ser Ser Leu Asp Cys Val Leu Arg Pro
        435                 440                 445

Thr Glu Gly Tyr Leu Ala Val Ala Val Val Lys Lys Ala Asn Glu Gly
450                 455                 460

Leu Thr Trp Asn Ser Leu Lys Gly Lys Lys Ser Cys His Thr Ala Val
465                 470                 475                 480

Asp Arg Thr Ala Gly Trp Asn Ile Pro Met Gly Leu Ile Ala Asn Gln
                485                 490                 495

Thr Gly Ser Cys Ala Phe Asp Glu Phe Phe Ser Gln Ser Cys Ala Pro
            500                 505                 510

Gly Ala Asp Pro Lys Ser Ser Leu Cys Ala Leu Cys Ala Gly Asp Asp
        515                 520                 525

Gln Gly Leu Asn Lys Cys Val Pro Asn Ser Lys Glu Lys Tyr Tyr Gly
530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Ser
                565                 570                 575

Ala Asp Trp Ala Lys Asn Leu Asn Arg Glu Asp Phe Arg Leu Leu Cys
            580                 585                 590

Leu Asp Gly Thr Thr Lys Pro Val Thr Glu Ala Gln Ser Cys Tyr Leu
        595                 600                 605

Ala Val Ala Pro Asn His Ala Val Val Ser Arg Ser Asp Arg Ala Ala
610                 615                 620

His Val Glu Gln Val Leu Leu His Gln Gln Ala Leu Phe Gly Lys Asn

```
                625                 630                 635                 640
Gly Lys Asn Cys Pro Asp Gln Phe Cys Leu Phe Lys Ser Glu Thr Lys
                    645                 650                 655

Asn Leu Leu Phe Asn Asp Asn Thr Glu Cys Leu Ala Lys Leu Gly Gly
                660                 665                 670

Arg Pro Thr Tyr Glu Lys Tyr Leu Gly Thr Glu Tyr Val Thr Ala Ile
                675                 680                 685

Ala Asn Leu Lys Lys Cys Ser Thr Ser Pro Leu Leu Glu Ala Cys Ala
    690                 695                 700

Phe Leu Thr Arg
705

<210> SEQ ID NO 115
<211> LENGTH: 2127
<212> TYPE: DNA
<213> ORGANISM: Ovis aries
<220> FEATURE:
<221> NAME/KEY: misc_feature
<222> LOCATION: (0)...(0)
<223> OTHER INFORMATION: Lactoferrin cDN

<400> SEQUENCE: 115
atgaagctct tcgtccccgc cctgctgtcc cttggagccc ttggactgtg tctggctgcc      60
ccgaggaaaa acgttcgatg tgtgccatc tcaccgccgg aggggtccaa atgctaccaa     120
tggcagagga ggatgaggaa gctgggtgct ccctctatca cctgtgtgag gaggacctct     180
gccctggaat gtatccgggc catcgcggga aaaaaggcgg atgctgtgac cctggatagt     240
ggcatggtgt ttgaggcggg cctggacccc tacaaactgc ggccagtagc ggcagagatc     300
tatgggacag aaaagtctcc ccaaacccac tattatgctg tggccgtcgt gaagaagggc     360
agcaactttc agctggacca gctgcaaggc cagaagtcct gccacatggg ccttggtagg     420
tccgctgggt ggaacatccc tatgggaatc cttcgcccgt tcttgagctg acagagtcg     480
gccgagcccc tccagggagc tgtggctaga ttcttctctg ccagctgtgt tccctgcgtt     540
gatgaaaaag cgtatcccaa cctgtgtcaa ctgtgcaagg gggtgggaga gaacaagtgt     600
gcctgctcct cccaggaacc atactttggt tattctggtg ccttcaagtg cctgcaggac     660
ggggctggag acgtggcttt tgtcaaggag acgacagtgt ttgagaactt gccagagaag     720
gctgacaggg accagtatga gcttctctgc ctaaacaaca ctcgggcgcc agtggatgca     780
ttcaaggagt gccacctggc ccaggtccct tctcatgctg ttgtggcccg cagtgtggat     840
ggcaaggaga acttgatctg ggagcttctc aggaaggcac aggagaagtt tggaaaaaac     900
aagtctcagc gcttccagct ctttggctct ccacaaggcc agaaggacct gctattcaaa     960
gactctgccc ttgggtttgt gaggatcccc tcaaaagtag attcggcgct gtacttaggc    1020
tcccgctact tgaccgcctt gaagaacctc aggggaaaccg cggaagaagt gaaggcgcgg    1080
tgcactccgg tcgtgtggtg cgcggtggga ccccaggagc atagtaagtg ccagcagtgg    1140
agcgagcaga gcggccagaa cgtgacttgt gccatggcct ccaccaccga cgaatgcatc    1200
gccctggtgt tgaaagggga agcggacgcc ctgagcttgg atggaggata tatctacact    1260
gccggcaagt gtggcctggt gcctgtcatg gcagagaacc gggaatcctc caaatacagt    1320
agcctagatt gtgtgctgag accaacggaa gggtaccttg ccgtggcagt tgtcaagaaa    1380
gcaaatgagg ggctcacttg gaattctctg aaaggcaaga gtcgtgcca caccgccgtg    1440
gacaggactg caggctggaa catccccatg ggcctgatcg ccaaccagac aggctcctgc    1500
```

-continued

```
gcatttgatg aattctttag tcagagctgt gccctgggg ccgacccgaa atccagcctc    1560
tgtgcattgt gtgccggcga tgaccagggc ctgaacaagt gtgtgcccaa ctctaaggag    1620
aagtactatg gctacaccgg ggctttcagg tgcctggctg aggacgttgg ggacgttgca    1680
tttgtgaaaa acgacacagt ctgggagaac acgaatggag agagctctgc agactgggct    1740
aagaacttga atcgcgagga cttcaggttg ctctgcctcg atggcaccac gaagcctgtg    1800
acggaggctc agagctgcta cctggcggtg gccccgaatc acgctgtggt gtctcggagc    1860
gatagggcag cacacgtgga acaggtgctg ctccaccagc aggctctgtt cgggaaaaat    1920
ggaaaaaact gcccggacca gttttgtttg ttcaaatctg aaaccaaaaa ccttctgttc    1980
aatgacaaca ctgagtgtct ggccaaactt ggaggcagac caacgtatga aaaatatttg    2040
gggacagagt atgtcacggc cattgccaac ctgaaaaaat gctcaacctc cccgcttctg    2100
gaagcctgcg ccttcctgac gaggtaa                                        2127
```

<210> SEQ ID NO 116
<211> LENGTH: 704
<212> TYPE: PRT
<213> ORGANISM: Bos taurus
<220> FEATURE:
<221> NAME/KEY: VARIANT
<222> LOCATION: (0)...(0)
<223> OTHER INFORMATION: Transferrin

<400> SEQUENCE: 116

```
Met Arg Pro Ala Val Arg Ala Leu Leu Ala Cys Ala Val Leu Gly Leu
1               5                   10                  15

Cys Leu Ala Asp Pro Glu Arg Thr Val Arg Trp Cys Thr Ile Ser Thr
            20                  25                  30

His Glu Ala Asn Lys Cys Ala Ser Phe Arg Glu Asn Val Leu Arg Ile
        35                  40                  45

Leu Glu Ser Gly Pro Phe Val Ser Cys Val Lys Lys Thr Ser His Met
    50                  55                  60

Asp Cys Ile Lys Ala Ile Ser Asn Asn Glu Ala Asp Ala Val Thr Leu
65                  70                  75                  80

Asp Gly Gly Leu Val Tyr Glu Ala Gly Leu Lys Pro Asn Asn Leu Lys
                85                  90                  95

Pro Val Val Ala Glu Phe His Gly Thr Lys Asp Asn Pro Gln Thr His
            100                 105                 110

Tyr Tyr Ala Val Ala Val Val Lys Lys Asp Thr Asp Phe Lys Leu Asn
        115                 120                 125

Glu Leu Arg Gly Lys Lys Ser Cys His Thr Gly Leu Gly Arg Ser Ala
    130                 135                 140

Gly Trp Asn Ile Pro Met Ala Lys Leu Tyr Lys Glu Leu Pro Asp Pro
145                 150                 155                 160

Gln Glu Ser Ile Gln Arg Ala Ala Ala Asn Phe Phe Ser Ala Ser Cys
                165                 170                 175

Val Pro Cys Ala Asp Gln Ser Ser Phe Pro Lys Leu Cys Gln Leu Cys
            180                 185                 190

Ala Gly Lys Gly Thr Asp Lys Cys Ala Cys Ser Asn His Glu Pro Tyr
        195                 200                 205

Phe Gly Tyr Ser Gly Ala Phe Lys Cys Leu Met Glu Gly Ala Gly Asp
    210                 215                 220

Val Ala Phe Val Lys His Ser Thr Val Phe Asp Asn Leu Pro Asn Pro
225                 230                 235                 240
```

-continued

```
Glu Asp Arg Lys Asn Tyr Glu Leu Leu Cys Gly Asp Asn Thr Arg Lys
                245                 250                 255
Ser Val Asp Asp Tyr Gln Glu Cys Tyr Leu Ala Met Val Pro Ser His
        260                 265                 270
Ala Val Ala Arg Thr Val Gly Lys Glu Asp Val Ile Trp Glu
        275                 280                 285
Leu Leu Asn His Ala Gln Glu His Phe Gly Lys Asp Lys Pro Asp Asn
        290                 295                 300
Phe Gln Leu Phe Gln Ser Pro His Gly Lys Asp Leu Leu Phe Lys Asp
305                 310                 315                 320
Ser Ala Asp Gly Phe Leu Lys Ile Pro Ser Lys Met Asp Phe Glu Leu
                325                 330                 335
Tyr Leu Gly Tyr Glu Tyr Val Thr Ala Leu Gln Asn Leu Arg Glu Ser
                340                 345                 350
Lys Pro Pro Asp Ser Ser Lys Asp Glu Cys Met Val Lys Trp Cys Ala
            355                 360                 365
Ile Gly His Gln Glu Arg Thr Lys Cys Asp Arg Trp Ser Gly Phe Ser
        370                 375                 380
Gly Gly Ala Ile Glu Cys Glu Thr Ala Glu Asn Thr Glu Glu Cys Ile
385                 390                 395                 400
Ala Lys Ile Met Lys Gly Glu Ala Asp Ala Met Ser Leu Asp Gly Gly
                405                 410                 415
Tyr Leu Tyr Ile Ala Gly Lys Cys Gly Leu Val Pro Val Leu Ala Glu
                420                 425                 430
Asn Tyr Lys Thr Glu Gly Glu Ser Cys Lys Asn Thr Pro Glu Lys Gly
            435                 440                 445
Tyr Leu Ala Val Ala Val Lys Thr Ser Asp Ala Asn Ile Asn Trp
450                 455                 460
Asn Asn Leu Lys Asp Lys Lys Ser Cys His Thr Ala Val Asp Arg Thr
465                 470                 475                 480
Ala Gly Trp Asn Ile Pro Met Gly Leu Leu Tyr Ser Lys Ile Asn Asn
                485                 490                 495
Cys Lys Phe Asp Glu Phe Phe Ser Ala Gly Cys Ala Pro Gly Ser Pro
            500                 505                 510
Arg Asn Ser Ser Leu Cys Ala Leu Cys Ile Gly Ser Glu Lys Gly Thr
        515                 520                 525
Gly Lys Glu Cys Val Pro Asn Ser Asn Glu Arg Tyr Tyr Gly Tyr Thr
        530                 535                 540
Gly Ala Phe Arg Cys Leu Val Glu Lys Gly Asp Val Ala Phe Val Lys
545                 550                 555                 560
Asp Gln Thr Val Ile Gln Asn Thr Asp Gly Asn Asn Asn Glu Ala Trp
                565                 570                 575
Ala Lys Asn Leu Lys Lys Glu Asn Phe Glu Val Leu Cys Lys Asp Gly
            580                 585                 590
Thr Arg Lys Pro Val Thr Asp Ala Glu Asn Cys His Leu Ala Arg Gly
            595                 600                 605
Pro Asn His Ala Val Val Ser Arg Lys Asp Lys Ala Thr Cys Val Glu
        610                 615                 620
Lys Ile Leu Asn Lys Gln Gln Asp Asp Phe Gly Lys Ser Val Thr Asp
625                 630                 635                 640
Cys Thr Ser Asn Phe Cys Leu Phe Gln Ser Asn Ser Lys Asp Leu Leu
                645                 650                 655
Phe Arg Asp Asp Thr Lys Cys Leu Ala Ser Ile Ala Lys Lys Thr Tyr
```

```
              660             665             670
Asp Ser Tyr Leu Gly Asp Asp Tyr Val Arg Ala Met Thr Asn Leu Arg
            675             680             685

Gln Cys Ser Thr Ser Lys Leu Leu Glu Ala Cys Thr Phe His Lys Pro
        690             695             700
```

<210> SEQ ID NO 117
<211> LENGTH: 2584
<212> TYPE: DNA
<213> ORGANISM: Bos taurus
<220> FEATURE:
<221> NAME/KEY: misc_feature
<222> LOCATION: (0)...(0)
<223> OTHER INFORMATION: Transferrin cDNA

<400> SEQUENCE: 117

```
gctcggccag ccccgcggga gatatagggg cgcggggagc agggaggcta cgcagaagcc      60
ggtcggtctg tgctctgcac tccacattac agaccgggga ggatgaggcc cgctgtccgc     120
gctctgttag cctgcgcggt tctggggctg tgtctggcgg accctgagag aactgtgaga     180
tggtgcacca tttcaactca tgaggccaat aagtgtgcca gttttcgtga aaatgtgctt     240
cgtatcttgg agagtggtcc ttttgtctcc tgtgtgaaga aaacctcaca catggattgc     300
atcaaggcta tctcgaataa cgaagcagat gctgtgacgt ggatggaggt tttggtgtat     360
gaggcaggcc tgaagcccaa caacctgaag cctgtggtgg cagagttcca tgggacaaaa     420
gacaacccac aaactcacta ttatgctgtg gcggtggtga agaaggacac tgacttcaag     480
ctgaatgagc tcagaggcaa gaagtcctgc cacacaggcc tcggcaggtc cgctgggtgg     540
aacatcccca tgggcaaaact ttataaggaa ttgcctgatc acaggaatc aattcagaga     600
gctgcggcca acttcttctc tgccagctgt gtcccctgtg cggatcaatc atcatttccc     660
aaactctgtc aactgtgtgc ggggaaaggg acagacaagt gtgcctgctc caaccacgaa     720
ccatacttcg ctactcagg ggcctttaaa tgtctgatgg agggcgctgg ggatgtggcc     780
tttgtcaagc actcaacggt attcgacaac ctgcctaacc cagaagacag gaaaaactat     840
gagctgctct gcggggacaa caccggaag tctgtagatg attaccaaga atgctacttg     900
gcaatggttc cttcccatgc ggttgtggct cgaactgtgg gcggcaagga ggatgtgatc     960
tgggaacttc tcaatcacgc ccaggaacat tttggcaaag ataaaccaga caatttccag    1020
cttttccaat cccctcatgg gaaggacctg ctgtttaagg actctgctga tgggttttta    1080
aagattcctt ctaagatgga ttttgagctg tacttgggat atgaatatgt cactgctctt    1140
cagaatctaa gagaaagtaa accccggac tcctcaaagg atgagtgcat ggtgaagtgg    1200
tgtgcaattg gtcaccagga gaggacaaag tgtgatcgtt ggagtgggtt cagcggcggg    1260
gcaatagagt gtgaaacagc agagaacact gaagagtgca tcgccaagat catgaaagga    1320
gaagctgatg ccatgagctt ggacggaggc tacctctaca gcaggcaa atgtggcctg    1380
gtgcctgtcc tggcagagaa ctacaaaact gagggtgaaa gttgcaagaa cacaccagaa    1440
aaagggtatc ttgctgtagc tgtggttaaa acatcagatg ctaatatcaa ctggaacaat    1500
ctgaaagaca agaagtcctg ccacactgca gtagacagaa ccgctggctg gaacatcccc    1560
atgggtttgc tctacagcaa gattaataac tgtaaatttg atgaattttt cagcgcaggt    1620
tgtgcacctg gatctccgcg aaattccagt ctctgtgctc tgtgcattgg ctcagagaag    1680
ggtacaggaa aggagtgtgt tcccaacagc aatgaaagat actatggcta tacaggggct    1740
ttcaggtgtc tggtggagaa gggagacgtg gcctttgtga aggaccagac tgtcatacag    1800
```

-continued

```
aacactgacg gaaataataa tgaagcatgg gcaaaaaatc tgaagaagga aaattttgaa    1860
gtactatgca aagatggcac caggaaacct gtgacagatg ctgagaactg ccacctggcc    1920
cgaggcccga atcatgctgt ggtctcacgg aaagataagg caacttgtgt ggagaaaata    1980
ttaaacaaac agcaggatga ttttggaaaa tctgtaaccg actgcacgag caattttgt     2040 ttattccaat caaattccaa ggaccttctg ttcagggatg acactaaatg tttggcttca    2100
attgcgaaaa aacatatga ctcctactta ggggatgact acgtcagagc tatgaccaac     2160
ctgagacaat gctcaacctc aaaactcctg gaagcatgca ctttccacaa accttaaaat    2220
ccaagagtgg agccaacacc tgatggagat gggagctcat gggacccata agcttcatct    2280
ggtttcgctg gtctgagtga tttggttgcc ctcacaattt ggtggtggcg cctctgcagg    2340
acaaaataaa aataaacatt attattggtt ttatctgtta aaaaaacttc attttcccct    2400
cttaatgctt ggtctgcaac tagcccttcc ttcagagctc aagattcatt tgctctttcc    2460
cacagccaca gttcctgggt acagtccaag taggaattct ttctaaaagg ggtctgcatg    2520
gtcattttaa taaaatcaag tgtacaagga aaaaaaaaaa aaaaaaaaaa aaaaaaaaaa    2580
aaaa                                                                 2584
```

<210> SEQ ID NO 118
<211> LENGTH: 698
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Transferrin

<400> SEQUENCE: 118

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205
```

```
Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620
```

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
    690                 695

```
<210> SEQ ID NO 119
<211> LENGTH: 2808
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Transferrin cDNA

<400> SEQUENCE: 119
tggcaccgag cgagccgcga tgacaatggc tgcattgtgc ttcatgtccc ttcccatcaa      60
catttctgtg ctggactcct tccactcgcg ggtcgtctcc agagctcaga aaatgaggtg     120
atcagtggga cgagtaagga aggggggttg ggagaggggc gattgggcaa cccggctgca     180
caaacacggg aggtcaaaga ttgcgcccag cccgcccagg ccgggaatgg aataaaggga     240
cgcggggcgc cggaggctgc acagaagcga gtccgactgt gctcgctgct cagcgccgca     300
cccggaagat gaggctcgcc gtgggagccc tgctggtctg cgccgtcctg ggctgtgtc      360 tggctgtccc tgataaaact gtgagatggt gtgcagtgtc ggagcatgag gccactaagt     420
gccagagttt ccgcgaccat atgaaaagcg tcattccatc cgatggtccc agtgttgctt     480
gtgtgaagaa agcctcctac cttgattgca tcagggccat gcggcaaac gaagcggatg     540 ctgtgacact ggatgcaggt ttggtgtatg atgcttacct ggctcccaat aacctgaagc     600
ctgtggtggc agagttctat gggtcaaaag aggatccaca gacttttat tatgctgttg     660 ctgtggtgaa gaaggatagt ggcttccaga tgaaccagct tcgaggcaag aagtcctgcc     720
acacgggtct aggcaggtcc gctgggtgga acatccccat aggcttactt tactgtgact     780
tacctgagcc acgtaaacct cttgagaaag cagtggccaa tttcttctcg ggcagctgtg     840 cccttgtgc ggatgggacg gacttccccc agctgtgtca actgtgtcca gggtgtggct     900
gctccaccct taaccaatac ttcggctact cgggagcctt caagtgtctg aaggatggtg     960
ctggggatgt ggcctttgtc aagcactcga ctatatttga aacttggca acaaggctg    1020 acagggacca gtatgagctg ctttgcctgg acaacacccg gaagccggta gatgaataca    1080
aggactgcca cttggcccag gtcccttctc ataccgtcgt ggcccgaagt atgggcggca    1140
aggaggactt gatctgggag cttctcaacc aggcccagga acattttggc aaagacaaat    1200
caaaagaatt ccaactattc agctctcctc atgggaagga cctgctgttt aaggactctg    1260
cccacgggtt tttaaaagtc ccccccagga tggatgccaa gatgtacctg gctatgagt    1320 atgtcactgc catccggaat ctacgggaag cacatgccc agaagcccca acagatgaat    1380
gcaagcctgt gaagtggtgt gcgctgagcc accacgagag gctcaagtgt gatgagtgga    1440
gtgttaacag tgtagggaaa atagagtgtg tatcagcaga gaccaccgaa gactgcatcg    1500
ccaagatcat gaatggagaa gctgatgcca tgagcttgga tggagggttt gtctacatag    1560
```

```
cgggcaagtg tggtctggtg cctgtcttgg cagaaaacta caataagagc gataattgtg   1620
aggatacacc agaggcaggg tatttgctg tagcagtggt gaagaaatca gcttctgacc   1680
tcacctggga caatctgaaa ggcaagaagt cctgccatac ggcagttggc agaaccgctg   1740
gctggaacat ccccatgggc ctgctctaca ataagatcaa ccactgcaga tttgatgaat   1800
ttttcagtga aggttgtgcc cctgggtcta agaaagactc cagtctctgt aagctgtgta   1860
tgggctcagg cctaaacctg tgtgaaccca acaacaaaga gggatactac ggctacacag   1920
gcgctttcag gtgtctggtt gagaagggag atgtggcctt tgtgaaacac cagactgtcc   1980
cacagaacac tggggaaaaa aaccctgatc catgggctaa gaatctgaat gaaaaagact   2040
atgagttgct gtgccttgat ggtaccagga aacctgtgga ggagtatgcg aactgccacc   2100
tggccagagc cccgaatcac gctgtggtca cacggaaaga taaggaagct tgcgtccaca   2160
agatattacg tcaacagcag cacctatttg gaagcaacgt aactgactgc tcgggcaact   2220 tttgttttgtt ccggtcggaa accaaggacc ttctgttcag agatgacaca gtatgtttgg   2280
ccaaacttca tgacagaaac acatatgaaa atacttagg agaagaatat gtcaaggctg   2340
ttggtaacct gagaaaatgc tccacctcat cactcctgga agcctgcact ttccgtagac   2400
cttaaaatct cagaggtagg gctgccacca aggtgaagat gggaacgcag atgatccatg   2460
agtttgccct ggtttcactg gcccaagtgg tttgtgctaa ccacgtctgt cttcacagct   2520
ctgtgttgcc atgtgtgctg aacaaaaaat aaaaattatt attgattta tatttcaaaa   2580 actccattct ttcctaaata ttttcaacaa aggatttctt tatgcattct gcctaaatac   2640
ctatgcaact gagcccttcc ttctcagctc aagattcgtc tggtcttcc ctacagcttt   2700 gtgtgtgcca tggccacatc tcctgggtac agttcaagga gacatcttt ctaaaagggt   2760 ctgcgtgatc attaaaatat aatcaaatgt aaaaaaaaa aaaaaaaa              2808
```

<210> SEQ ID NO 120
<211> LENGTH: 607
<212> TYPE: PRT
<213> ORGANISM: Bos taurus
<220> FEATURE:
<221> NAME/KEY: VARIANT
<222> LOCATION: (0)...(0)
<223> OTHER INFORMATION: Serum albumin

<400> SEQUENCE: 120

```
Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
```

```
                130                 135                 140
Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Glu Thr Met
                195                 200                 205

Arg Glu Lys Val Leu Thr Ser Ser Ala Arg Gln Arg Leu Arg Cys Ala
210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
                275                 280                 285

Asp Asn Gln Asp Thr Ile Ser Ser Lys Leu Lys Glu Cys Cys Asp Lys
                290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
                340                 345                 350

Phe Leu Tyr Glu Tyr Ser Arg Arg His Pro Glu Tyr Ala Val Ser Val
                355                 360                 365

Leu Leu Arg Leu Ala Lys Glu Tyr Glu Ala Thr Leu Glu Glu Cys Cys
                370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
                420                 425                 430

Arg Tyr Thr Arg Lys Val Pro Gln Val Ser Thr Pro Thr Leu Val Glu
                435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Val Pro Lys Ala Phe Asp Glu Lys
                515                 520                 525

Leu Phe Thr Phe His Ala Asp Ile Cys Thr Leu Pro Asp Thr Glu Lys
                530                 535                 540

Gln Ile Lys Lys Gln Thr Ala Leu Val Glu Leu Leu Lys His Lys Pro
545                 550                 555                 560
```

```
Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
            595                 600                 605

<210> SEQ ID NO 121
<211> LENGTH: 1883
<212> TYPE: DNA
<213> ORGANISM: Bos taurus
<220> FEATURE:
<221> NAME/KEY: misc_feature
<222> LOCATION: (0)...(0)
<223> OTHER INFORMATION: Serum albumin cDNA

<400> SEQUENCE: 121
gtcgactttg gcacaatgaa gtgggtgact tttatttctc ttctccttct cttcagctct    60
gcttattcca ggggtgtgtt tcgtcgagat acacacaaga gtgagattgc tcatcggttt   120
aaagatttgg gagaagaaca ttttaaaggc ctggtactga ttgccttttc tcagtatctc   180
cagcagtgtc catttgatga gcatgtaaaa ttagtgaacg aactaactga gtttgcaaaa   240
acatgtgttg ctgatgagtc ccatgccggc tgtgaaaagt cacttcacac tctctttgga   300
gatgaattgt gtaaagttgc atcccttcgt gaaacctatg gtgacatggc tgactgctgt   360
gagaaacaag agcctgaaag aaatgaatgc ttcctgagcc acaaagatga tagcccagac   420
ctccctaaat gaaaccaga ccccaatact tgtgtgatg agtttaaggc agatgaaaag    480 aagtttggg gaaaatacct atacgaaatt gctagaagac atccctactt ttatgcacca   540
gaactccttt actatgctaa taatataat ggagttttc aagaatgctg ccaagctgaa    600
gataaaggtg cctgcctgct accaaagatt gaaactatga gagaaaaagt actgacttca   660
tctgccagac agagactcag gtgtgccagt attcaaaaat ttggagaaag gctttaaaa    720 gcatggtcag tagctcgcct gagccagaaa tttcccaagg ctgagtttgt agaagttacc   780
aagctagtga cagatctcac aaaagtccac aaggaatgct gccatggtga cctacttgaa   840
tgcgcagatg acagggcaga tcttgccaag tacatatgtg ataatcaaga tacaatctcc   900
agtaaactga aggaatgctg tgataagcct tgttggaaa atccactg cattgctgag     960 gtagaaaaag atgccatacc tgaaaacctg cccccattaa ctgctgactt tgctgaagat  1020
aaggatgttt gcaaaaacta tcaggaagca aaagatgcct tcctgggctc gtttttgtat  1080
gaatattcaa gaaggcatcc tgaatatgct gtctcagtgc tattgagact tgccaaggaa  1140
tatgaagcca cactggagga atgctgtgcc aaagatgatc cacatgcatg ctattccaca  1200
gtgtttgaca aacttaagca tcttgtggat gagcctcaga atttaatcaa acaaaactgt  1260
gaccaattcg aaaaacttgg agagtatgga ttccaaaatg cgctcatagt tcgttacacc  1320
aggaaagtac cccaagtgtc aactccaact ctcgtggagg tttcaagaag cctaggaaaa  1380
gtgggtacta ggtgttgtac aaagccggaa tcagaaagaa tgccctgtac tgaagactat  1440
ctgagcttga tcctgaaccg gttgtgcgtt ctgcatgaga agacaccagt gagtgaaaaa  1500
gtcaccaagt gctgcacaga gtcattggtg aacagacggc catgtttctc tgctctgaca  1560
cctgatgaaa catatgtacc caagcctttt gatgagaaat tgttcacctt ccatgcagat  1620
atatgcacac ttcccgatac tgagaaacaa atcaagaaac aaactgcact tgttgagctg  1680
ttgaaacaca agcccaaggc aacagaggaa caactgaaaa ccgtcatgga aattttgtg   1740
```

-continued

```
gcttttgtag acaagtgctg tgcagctgat gacaaagagg cctgctttgc tgtggagggt    1800
ccaaaacttg ttgtttcaac tcaaacagcc ttagcctaaa cacgacacaa ccacaggcat    1860
ctcagcctac cctgagagtc gac                                            1883
```

<210> SEQ ID NO 122
<211> LENGTH: 607
<212> TYPE: PRT
<213> ORGANISM: Capra hircus
<220> FEATURE:
<221> NAME/KEY: VARIANT
<222> LOCATION: (0)...(0)
<223> OTHER INFORMATION: Serum albumin

<400> SEQUENCE: 122

```
Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Asn Asp Leu Gly Glu Glu Asn Phe Gln Gly Leu Val Leu
            35                  40                  45

Ile Ala Phe Ser Gln Tyr Leu Gln Gln Cys Pro Phe Asp Glu His Val
        50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
            100                 105                 110

Asp Cys Cys Glu Lys Gln Glu Pro Glu Arg Asn Glu Cys Phe Leu Lys
        115                 120                 125

His Lys Asp Asp Ser Pro Asp Leu Pro Lys Leu Lys Pro Glu Pro Asp
    130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp His Gln Asp Thr Leu Ser Ser Lys Leu Lys Glu Cys Cys Asp Lys
    290                 295                 300

Pro Val Leu Glu Lys Ser His Cys Ile Ala Glu Ile Asp Lys Asp Ala
305                 310                 315                 320
```

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Asp Cys Cys
    370                 375                 380

Ala Lys Glu Asp Pro His Ala Cys Tyr Ala Thr Val Phe Asp Lys Leu
385                 390                 395                 400

Lys His Leu Val Asp Glu Pro Gln Asn Leu Ile Lys Lys Asn Cys Glu
            405                 410                 415

Leu Phe Glu Lys His Gly Glu Tyr Gly Phe Gln Asn Ala Leu Ile Val
        420                 425                 430

Arg Tyr Thr Arg Lys Ala Pro Gln Val Ser Thr Pro Thr Leu Val Glu
    435                 440                 445

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
        500                 505                 510

Asp Leu Thr Leu Asp Glu Thr Tyr Val Pro Lys Pro Phe Asp Gly Glu
    515                 520                 525

Ser Phe Thr Phe His Ala Asp Ile Cys Thr Leu Pro Asp Thr Glu Lys
530                 535                 540

Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
            565                 570                 575

Phe Val Asp Lys Cys Cys Ala Ala Asp Asp Lys Glu Gly Cys Phe Leu
        580                 585                 590

Leu Glu Gly Pro Lys Leu Val Ala Ser Thr Gln Ala Ala Leu Ala
    595                 600                 605

<210> SEQ ID NO 123
<211> LENGTH: 2072
<212> TYPE: DNA
<213> ORGANISM: Capra hircus
<220> FEATURE:
<221> NAME/KEY: misc_feature
<222> LOCATION: (0)...(0)
<223> OTHER INFORMATION: Serum albumin cDNA

<400> SEQUENCE: 123
tttccctcta ttcatactat cttttctatc aaccccacaa acctttggca caatgaagtg      60
ggtgactttt atttcccttc tccttctctt cagctctgct tattccaggg gtgtgtttcg     120
tcgagataca cacaaaagtg agattgctca tcggtttaat gatttgggag aagaaaattt     180
tcaaggcctg gtgctgattg ccttttctca gtatctccag cagtgtccat ttgatgaaca     240
tgtaaaatta gtgaaggaac taactgagtt tgcaaaaaca tgtgttgctg atgagtcaca     300
tgccggttgt gataagtcac ttcacactct ctttggagat gaattgtgta agttgcaac     360 ccttcgcgaa acctatggtg acatggccga ctgctgtgag aaacaagagc ctgaaagaaa     420

```
tgaatgcttc ctgaaacaca aagatgatag cccagacctc cctaaactga aaccagagcc    480
cgatactttg tgtgccgagt ttaaggcaga tgaaagaag ttttgggaa aatacctata      540 cgaagttgcc agaagacatc cctacttta tgcaccagaa ctcctttact atgccaataa    600
atataatgga gttttcaag aatgctgcca agctgaagat aaaggtgcct gcctactacc   660
aaagattgaa actatgagag aaaaagtact ggcttcatct gccagacaga gactcaggtg   720
tgccagtatt caaaaattcg gagaaagagc tttaaaagca tggtcagtag ctcgcctgag   780
ccagaaattt cccaaggctg actttacaga tgttaccaag atagtgacag atctcactaa   840
ggtccacaag gagtgctgcc atggcgacct acttgaatgc gcagacgaca gggcagatct   900
tgccaagtac atatgtgatc atcaagacac actctccagt aaactgaagg aatgctgtga   960
taagcctgtg ttggaaaaat cccactgcat tgctgagata gataaagatg ccgtgcctga  1020
aaacctgccc ccattaactg ctgactttgc tgaagataag gaggtttgca aaactatca   1080 ggaagcaaaa gacgtcttcc tgggctcgtt tttgtatgaa tattcaagaa ggcatcctga  1140
gtatgctgtc tcagtgctgt tgagacttgc caaggaatat gaagccacac tggaggactg  1200
ctgtgctaaa aagatccac atgcatgcta tgccacagtg tttgacaaac ttaagcatct   1260
tgtggatgag cctcagaatt taatcaaaaa aaactgtgag ctatttgaaa acatggaga   1320 gtatggattc caaaatgcgc tcatagttcg ttacaccagg aaagcacccc aagtgtcaac   1380
tccaactctg gtggagattt caagaagcct aggaaaagtg ggcactaagt gttgtgcaaa   1440
gcctgaatca gaaagaatgc cctgtaccga agactatctg agcttgatcc tgaaccggtt   1500
gtgcgtgttg cacgagaaga caccagtgag tgaaaaagtc accaagtgct gcacagagtc   1560
attggtgaac agacggccat gtttctctga tctgacactt gacgaaacat atgtacccaa   1620
acccttcgat ggtgaatctt tcaccttcca tgcagatata tgcacacttc ctgatactga   1680
gaaacaaatc aagaaacaaa ctgcacttgt tgagctgttg aaacacaagc ccaaggcaac   1740
agatgaacaa ctgaaaaccg ttatggagaa ttttgtggct tttgtagaca agtgctgcgc   1800
agctgatgac aaagaaggct gctttcttct ggagggtcca aaacttgttg cttcaactca   1860
agcagcctta gcctaaacac gacacaacca caagcatctc agcctaccct gagagtaaga   1920
cggaagaaga gaaatgaaaa ctcagagctt attcatctgt tcttcttttc tgttggtgtt   1980
aaacctacac cctctctaaa gaacataaat ttctttaaat atttgcttc ttttgtttgt    2040 gctacaatta ataaaaatg aaaagactct aa                                  2072
```

<210> SEQ ID NO 124
<211> LENGTH: 609
<212> TYPE: PRT
<213> ORGANISM: Homo sapiens
<220> FEATURE:
<221> NAME/KEY: VARIANT
<222> LOCATION: (0)...(0)
<223> OTHER INFORMATION: Serum Albumin

<400> SEQUENCE: 124

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val

-continued

```
                50                  55                  60
Lys Leu Val Asn Glu Val Thr Glu Phe Ala Lys Thr Cys Val Ala Asp
 65                  70                  75                  80
Glu Ser Ala Glu Asn Cys Asp Lys Ser Leu His Thr Leu Phe Gly Asp
                 85                  90                  95
Lys Leu Cys Thr Val Ala Thr Leu Arg Glu Thr Tyr Gly Glu Met Ala
                100                 105                 110
Asp Cys Cys Ala Lys Gln Glu Pro Glu Arg Asn Glu Cys Phe Leu Gln
                115                 120                 125
His Lys Asp Asp Asn Pro Asn Leu Pro Arg Leu Val Arg Pro Glu Val
                130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
                195                 200                 205
Leu Arg Asp Glu Gly Lys Ala Ser Ser Ala Lys Gln Arg Leu Lys Cys
210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Ile
                275                 280                 285
Cys Glu Asn Gln Asp Ser Ile Ser Ser Lys Leu Lys Glu Cys Cys Glu
                290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
                355                 360                 365
Leu Leu Leu Arg Leu Ala Lys Thr Tyr Lys Thr Thr Leu Glu Lys Cys
                370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
                435                 440                 445
Glu Val Ser Arg Asn Leu Gly Lys Val Gly Ser Lys Cys Cys Lys His
                450                 455                 460
Pro Glu Ala Lys Arg Met Pro Cys Ala Glu Asp Tyr Leu Ser Val Val
465                 470                 475                 480
```

```
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Arg Ala Ala Leu Gly
        595                 600                 605
Leu

<210> SEQ ID NO 125
<211> LENGTH: 2176
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Serum Albumin cDNA

<400> SEQUENCE: 125
tctcttctgt caaccccacg cgcctttggc acaatgaagt gggtaacctt tatttccctt      60
cttttctct ttagctcggc ttattccagg ggtgtgtttc gtcgagatgc acacaagagt     120
gaggttgctc atcggtttaa agatttggga agaaaaatt tcaaagccct agtgttgatt     180
gcctttgctc agtatcttca gcagtgtcca tttgaagatc atgtaaaatt agtgaatgaa     240
gtaactgaat ttgcaaaaac atgtgttgct gatgagtcag ctgaaaattg tgacaaatca     300
cttcataccc ttttttggaga caaattatgc acagttgcaa ctcttcgtga aacctatggt     360
gaaatggctg actgctgtgc aaaacaagaa cctgagagaa atgaatgctt cttgcaacac     420
aaagatgaca acccaaacct cccccgattg gtgagaccag aggttgatgt gatgtgcact     480
gcttttcatg acaatgaaga gacattttg aaaaaatact tatatgaaat tgccagaaga     540
catccttact tctatgcccc ggaactcctt ttctttgcta aaaggtataa agctgctttt     600
acagaatgtt gccaagctgc tgataaggct gcctgcctgt tgccaaagct cgatgaactt     660
cgggatgaag gaaggcttc gtctgccaaa cagaggctca gtgtgccag tctccaaaaa     720
tttggagaaa gagctttcaa agcatgggca gtagctcgcc tgagccagag atttcccaaa     780
gctgagtttg cagaagtttc caagttagtg acagatctta ccaaagtcca cacggaatgc     840
tgccatggag atctgcttga atgtgctgat gacagggcgg accttgccaa gtatatctgt     900
gaaaatcaag attcgatctc cagtaaactg aaggaatgct gtgaaaaacc tctgttggaa     960
aaatcccact gcattgccga gtggaaaat gatgagatgc ctgctgactt gccttcatta    1020
gctgctgatt tgttgaaag taaggatgtt tgcaaaaact atgctgaggc aaaggatgtc    1080
ttcctgggca tgttttgta tgaatatgca agaaggcatc ctgattactc tgtcgtgctg    1140
ctgctgagac ttgccaagac atataaaacc actctagaga agtgctgtgc cgctgcagat    1200
```

-continued

```
cctcatgaat gctatgccaa agtgttcgat gaatttaaac ctcttgtgga agagcctcag    1260
aatttaatca aacaaaattg tgagcttttt gagcagcttg gagagtacaa attccagaat    1320
gcgctattag ttcgttacac caagaaagta ccccaagtgt caactccaac tcttgtagag    1380
gtctcaagaa acctaggaaa agtgggcagc aaatgttgta acatcctga agcaaaaaga    1440 atgccctgtg cagaagacta tctatccgtg gtcctgaacc agttatgtgt gttgcatgag    1500
aaaacgccag taagtgacag agtcaccaaa tgctgcacag aatccttggt gaacaggcga    1560
ccatgctttt cagctctgga agtcgatgaa acatacgttc caaagagtt taatgctgaa     1620 acattcacct tccatgcaga tatatgcaca ctttctgaga aggagagaca aatcaagaaa    1680
caaactgcac ttgttgagct tgtgaaacac aagcccaagg caacaaaaga gcaactgaaa    1740
gctgttatgg atgatttcgc agcttttgta gagaagtgct gcaaggctga cgataaggag    1800
acctgctttg ccgaggaggg taaaaaactt gttgctgcaa gtcgagctgc cttaggctta    1860
taacatcaca tttaaaagca tctcagccta ccatgagaat aagagaaaga aaatgaagat    1920
caaaagctta ttcatctgtt tttctttttc gttggtgtaa agccaacacc ctgtctaaaa    1980
aacataaatt tctttaatca ttttgcctct tttctctgtg cttcaattaa taaaaaatgg    2040
aaagaatcta atagagtggt acagcactgt tattttcaa agatgtgttg ctatcctgaa     2100
aattctgtag gttctgtgga agttccagtg ttctctctta ttccacttcg gtagaggatt    2160
tctagtttct gtgggc                                                    2176
```

<210> SEQ ID NO 126
<211> LENGTH: 607
<212> TYPE: PRT
<213> ORGANISM: Ovis aries
<220> FEATURE:
<221> NAME/KEY: VARIANT
<222> LOCATION: (0)...(0)
<223> OTHER INFORMATION: Serum Albumin

<400> SEQUENCE: 126

```
Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Asn Asp Leu Gly Glu Glu Asn Phe Gln Gly Leu Val Leu
        35                  40                  45

Ile Ala Phe Ser Gln Tyr Leu Gln Gln Cys Pro Phe Asp Glu His Val
    50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
            100                 105                 110

Asp Cys Cys Glu Lys Gln Glu Pro Glu Arg Asn Glu Cys Phe Leu Asn
        115                 120                 125

His Lys Asp Asp Ser Pro Asp Leu Pro Lys Leu Lys Pro Glu Pro Asp
    130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175
```

```
Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Asp Ala Met
        195                 200                 205

Arg Glu Lys Val Leu Ala Ser Ser Ala Arg Gln Arg Leu Arg Cys Ala
        210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp His Gln Asp Ala Leu Ser Ser Lys Leu Lys Glu Cys Cys Asp Lys
        290                 295                 300

Pro Val Leu Glu Lys Ser His Cys Ile Ala Glu Val Asp Lys Asp Ala
305                 310                 315                 320

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Asp Cys Cys
        370                 375                 380

Ala Lys Glu Asp Pro His Ala Cys Tyr Ala Thr Val Phe Asp Lys Leu
385                 390                 395                 400

Lys His Leu Val Asp Glu Pro Gln Asn Leu Ile Lys Lys Asn Cys Glu
                405                 410                 415

Leu Phe Glu Lys His Gly Glu Tyr Gly Phe Gln Asn Ala Leu Ile Val
            420                 425                 430

Arg Tyr Thr Arg Lys Ala Pro Gln Val Ser Thr Pro Thr Leu Val Glu
        435                 440                 445

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Asp Leu Thr Leu Asp Glu Thr Tyr Val Pro Lys Pro Phe Asp Glu Lys
        515                 520                 525

Phe Phe Thr Phe His Ala Asp Ile Cys Thr Leu Pro Asp Thr Glu Lys
        530                 535                 540

Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
                565                 570                 575

Phe Val Asp Lys Cys Cys Ala Ala Asp Asp Lys Glu Gly Cys Phe Val
            580                 585                 590

Leu Glu Gly Pro Lys Leu Val Ala Ser Thr Gln Ala Ala Leu Ala
```

<210> SEQ ID NO 127
<211> LENGTH: 2089
<212> TYPE: DNA
<213> ORGANISM: Ovis aries
<220> FEATURE:
<221> NAME/KEY: misc_feature
<222> LOCATION: (0)...(0)
<223> OTHER INFORMATION: Serum albumin cDNA

<400> SEQUENCE: 127

| | | | | | |
|---|---|---|---|---|---|
| gaattccttt | tttttctttt | ctatcaaccc | cacaaacctt | tggcacaatg aagtgggtga | 60 |
| cttttatttc | ccttctcctt | ctcttcagct | ctgcttattc | caggggtgtg tttcgtcgag | 120 |
| atacacacaa | gagtgagatt | gctcatcggt | ttaatgattt | gggagaagaa aattttcaag | 180 |
| gcctggtgct | gattgccttt | tctcagtatc | tccagcagtg | tccatttgac gaacatgtaa | 240 |
| aattagtgaa | ggagctaact | gagttttgcaa | aaacatgtgt | tgctgatgag tcacatgccg | 300 |
| gttgtgataa | gtcacttcac | actctctttg | gagatgaatt | gtgtaaagtt gcaacccttc | 360 |
| gcgaaaccta | tggtgacatg | gccgactgct | gtgagaaaca | agagcctgaa agaaatgaat | 420 |
| gcttcctgaa | tcacaaagat | gatagcccag | acctccctaa | actgaaacca gagcccgata | 480 |
| ctttgtgtgc | cgagtttaag | gcagatgaaa | agaagttttg | gggaaaatac ctatacgaag | 540 |
| ttgccagaag | acatccctac | ttttatgcac | cagaactcct | ttactatgct aataaatata | 600 |
| atggagtttt | tcaagaatgc | tgccaagctg | aagataaagg | tgcctgccta ctaccaaaga | 660 |
| ttgacgctat | gagagaaaaa | gtactggctt | catctgccag | acagagactc aggtgtgcca | 720 |
| gtattcaaaa | attcggagaa | agagctttaa | agcatggtc | agtagctcgc ctgagccaga | 780 |
| aatttcccaa | ggctgacttt | acagatgtta | ccaagatagt | gacagatctc actaaggtcc | 840 |
| acaaggagtg | ttgccatggt | gacctgcttg | aatgcgcaga | cgacagggca gatcttgcca | 900 |
| agtacatatg | tgatcatcaa | gacgcactct | ccagtaaact | gaaggaatgc tgtgataagc | 960 |
| ctgtgttgga | aaaatcccac | tgcattgctg | aggtagataa | agatgccgtg cctgaaaacc | 1020 |
| tgccccatt | aactgctgac | tttgctgaag | ataaggaggt | ttgcaaaaac tatcaggaag | 1080 |
| caaaagacgt | cttcctgggc | tcgttttttgt | atgaatattc | aagaaggcat cctgagtatg | 1140 |
| ctgtctcagt | gctattgaga | cttgccaagg | aatatgaagc | cacactggag gactgctgtg | 1200 |
| ccaaagaaga | tccacatgcc | tgctatgcca | cagtgtttga | caaacttaag catcttgtgg | 1260 |
| atgagcctca | gaatttaatc | aaaaaaaact | gtgagctatt | cgaaaaacat ggagagtatg | 1320 |
| gattccaaaa | tgcgctcata | gttcgttaca | ccaggaaagc | accccaagtg tcaactccaa | 1380 |
| ctctggtgga | gatttcaaga | agcctaggaa | aagtgggcac | taagtgttgt gcaaagcctg | 1440 |
| aatcagaaag | aatgcctgt | accgaagact | atctgagctt | gatcctgaac cggttgtgcg | 1500 |
| tgttgcatga | aagacacca | gtgagtgaaa | agtcaccaa | gtgctgcacg gagtcattgg | 1560 |
| tgaacagacg | gccatgtttc | tctgatctga | cacttgacga | acatatgta cccaaaccct | 1620 |
| tcgatgagaa | attttcacc | ttccatgcag | atatatgcac | acttcctgat actgagaaac | 1680 |
| aaatcaagaa | acaaactgca | cttgttgagc | tgttgaaaca | caagcccaag gcaacagatg | 1740 |
| aacaactgaa | aaccgttatg | gagaattttg | tggcttttgt | agacaagtgc tgtgcagctg | 1800 |
| atgacaaaga | aggctgcttt | gttctggagg | gtcaaaaact | tgttgcttca actcaagcag | 1860 |
| ccttagccta | aacgacacac | aaccacaagc | atctcagcct | accctgagag tgagacgaaa | 1920 |
| aaagagaaat | gaaaactcag | agcttattca | tctgttcttc | ttttcgggtg ttggtgttaa | 1980 |

```
acctacacccc tctctaaaga acataaattt ctttaaatat tttgcttctt ttgtttgtgc    2040
tacaattaat aaaaaatgaa aagactctaa aaaaaaaaaa aaggaattc                 2089
```

<210> SEQ ID NO 128
<211> LENGTH: 42
<212> TYPE: PRT
<213> ORGANISM: Artificial Sequence
<220> FEATURE:
<223> OTHER INFORMATION: Linker

<400> SEQUENCE: 128

```
Gly Gly Cys Thr Cys Ala Gly Gly Ala Thr Cys Ala Gly Gly Thr
1               5                   10                  15

Cys Gly Ala Ala Ala Ala Gly Ala Gly Gly Cys Thr Cys Ala Gly Gly
            20                  25                  30

Ala Thr Cys Ala Gly Gly Gly Thr Cys Gly
            35                  40
```

<210> SEQ ID NO 129
<211> LENGTH: 943
<212> TYPE: DNA
<213> ORGANISM: Artificial Sequence
<220> FEATURE:
<223> OTHER INFORMATION: AOX1 promoter

<400> SEQUENCE: 129

```
aacatccaaa gacgaaaggt tgaatgaaac cttttgcca tccgacatcc acaggtccat      60
tctcacacat aagtgccaaa cgcaacagga ggggatacac tagcagcaga ccgttgcaaa    120
cgcaggacct ccactcctct tcctcaac acccactttt gccatcgaaa aaccagccca     180
gttattgggc ttgattggag ctcgctcatt ccaattcctt ctattaggct actaacacca    240
tgactttatt agcctgtcta tcctggcccc cctggcgagg ttcatgtttg tttatttccg    300
aatgcaacaa gctccgcatt acacccgaac atcactccag atgagggctt tctgagtgtg    360
gggtcaaata gtttcatgtt ccccaaatgg cccaaaactg acagtttaaa cgctgtcttg    420
gaacctaata tgacaaaagc gtgatctcat ccaagatgaa ctaagtttgg ttcgttgaaa    480
tgctaacggc cagttggtca aaaagaaact tccaaaagtc ggcataccgt ttgtcttgtt    540
tggtattgat tgacgaatgc tcaaaaataa tctcattaat gcttagcgca gtctctctat    600
cgcttctgaa ccccggtgca cctgtgccga aacgcaaatg gggaaacacc cgcttttgg     660 atgattatgc attgtctcca cattgtatgc ttccaagatt ctggtgggaa tactgctgat    720
agcctaacgt tcatgatcaa aatttaactg ttctaacccc tacttgacag caatatataa    780
acagaaggaa gctgccctgt cttaaacctt ttttttatc atcattatta gcttactttc     840
ataattgcga ctggttccaa ttgacaagct tttgatttta acgactttta acgacaactt    900
gagaagatca aaaacaact aattattgaa agaattcaaa acg                       943
```

<210> SEQ ID NO 130
<211> LENGTH: 486
<212> TYPE: DNA
<213> ORGANISM: Artificial Sequence
<220> FEATURE:
<223> OTHER INFORMATION: GAP1 promoter

<400> SEQUENCE: 130

```
tttttgtaga aatgtcttgg tgtcctcgtc caatcaggta gccatctctg aaatatctgg     60
ctccgttgca actccgaacg acctgctggc aacgtaaaat tctccggggt aaaacttaaa   120
```

```
tgtggagtaa tggaaccaga aacgtctctt cccttctctc tccttccacc gcccgttacc    180
gtccctagga aattttactc tgctggagag cttcttctac ggccccttg cagcaatgct     240 cttcccagca ttacgttgcg ggtaaaacgg aggtcgtgta cccgacctag cagcccaggg    300
atggaaaagt cccggccgtc gctggcaata atagcgggcg gacgcatgtc atgagattat    360
tggaaaccac cagaatcgaa tataaaaggc gaacaccttt cccaattttg gtttctcctg    420
acccaaagac tttaaattta atttatttgt ccctatttca atcaattgaa caactatcaa    480
aacaca                                                              486
```

<210> SEQ ID NO 131
<211> LENGTH: 441
<212> TYPE: DNA
<213> ORGANISM: Artificial Sequence
<220> FEATURE:
<223> OTHER INFORMATION: PGK1 promoter

<400> SEQUENCE: 131

```
agaacggaaa ggaatatatt tactgccgat cgcattttgg cctcaaataa atcttgagct    60
tttggacata gattatatgt tctttcttgg aagctctttc agctaatagt gaagtgtttc    120
ctactaagga tcgcctccaa acgttccaac tacgggcgga ggttgcaaag aaaacgggtc    180
tctcagcgaa ttgttctcat ccatgagtga gtcctctccg tcctttcctc gcgcctggca    240
ataaagcctc cttcggagga gctccgtcta gagaataatt gctgcctttc tgactttcgg    300
actagcgcca accgcgaacc acaccaccac accatcactg tcacccgtca tagttcatcc    360
ctctctcctt ataaagcatc taataggttc cacaattgtt tgccacaaaa atctcttagc    420
atagcccaat tgattacgaa a                                             441
```

<210> SEQ ID NO 132
<211> LENGTH: 57
<212> TYPE: DNA
<213> ORGANISM: Artificial Sequence
<220> FEATURE:
<223> OTHER INFORMATION: Signal Peptide of MF alphaT

<400> SEQUENCE: 132

```
atgaggtttc cttctatctt cacggcagtt cttttcgctg catcttccgc attggct       57
```

<210> SEQ ID NO 133
<211> LENGTH: 45
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: Signal Peptide of alpha-S2
<220> FEATURE:
<223> OTHER INFORMATION: Kanamycin Resistance Gene

<400> SEQUENCE: 133

```
atgaagttct tcatcttcac ttgtttgttg gctgttgctt tggct                   45
```

<210> SEQ ID NO 134
<211> LENGTH: 69
<212> TYPE: DNA
<213> ORGANISM: Artificial Sequence
<220> FEATURE:
<223> OTHER INFORMATION: Signal Peptide of ost beta

<400> SEQUENCE: 134

```
atgagacagg tttggttctc ctggatcgtt ggtttgttct tgtgtttctt caacgtttcc    60
tccgctgct                                                            69
```

<210> SEQ ID NO 135
<211> LENGTH: 45
<212> TYPE: DNA
<213> ORGANISM: Artificial Sequence
<220> FEATURE:
<223> OTHER INFORMATION: Signal Peptide of beta

<400> SEQUENCE: 135

```
atgaaggttt tgatcttggc ttgtttggtt gctttggctt tggct                    45
```

<210> SEQ ID NO 136
<211> LENGTH: 69
<212> TYPE: DNA
<213> ORGANISM: Artificial Sequence
<220> FEATURE:
<223> OTHER INFORMATION: Signal Peptide of ost alpha-S2

<400> SEQUENCE: 136

```
atgagacagg tttggttcag ttggatagtc ggtttattcc tatgcttttt taatgtctca    60
tccgccgct                                                            69
```

<210> SEQ ID NO 137
<211> LENGTH: 45
<212> TYPE: DNA
<213> ORGANISM: Artificial Sequence
<220> FEATURE:
<223> OTHER INFORMATION: Signal Peptide of alpha-S1

<400> SEQUENCE: 137

```
atgaagttgt tgatcttgac ttgtttggtt gctgttgctt tggct                    45
```

<210> SEQ ID NO 138
<211> LENGTH: 63
<212> TYPE: DNA
<213> ORGANISM: Artificial Sequence
<220> FEATURE:
<223> OTHER INFORMATION: Signal Peptide of k

<400> SEQUENCE: 138

```
atgatgaagt ccttcttctt ggttgttact atcttggctt tgactttgcc attcttgggt    60
gct                                                                  63
```

<210> SEQ ID NO 139
<211> LENGTH: 69
<212> TYPE: DNA
<213> ORGANISM: Artificial Sequence
<220> FEATURE:
<223> OTHER INFORMATION: Signal Peptide of Ost alpha-S1

<400> SEQUENCE: 139

```
atgaggcaag tttggtttag ttggattgtt ggactgttcc tgtgcttttt caacgtgtca    60
tccgctgcc                                                            69
```

<210> SEQ ID NO 140
<211> LENGTH: 69
<212> TYPE: DNA
<213> ORGANISM: Artificial Sequence
<220> FEATURE:
<223> OTHER INFORMATION: Signal Peptide of Ost k

<400> SEQUENCE: 140

```
atgcgacagg tatggttttc ttggattgtg gggttgtttc tatgtttctt taacgtttct    60
tctgctgca                                                            69
```

<210> SEQ ID NO 141
<211> LENGTH: 48
<212> TYPE: DNA
<213> ORGANISM: Artificial Sequence
<220> FEATURE:
<223> OTHER INFORMATION: Signal Peptide of INU

<400> SEQUENCE: 141

```
atgaagttgg cttactcctt gttgttgcca ttggctggtg tttctgct                 48
```

<210> SEQ ID NO 142
<211> LENGTH: 57
<212> TYPE: DNA
<213> ORGANISM: Artificial Sequence
<220> FEATURE:
<223> OTHER INFORMATION: Signal Peptide of INV

<400> SEQUENCE: 142

```
atgttgttgc aggctttctt gttcttgttg gctggtttcg ctgctaagat ctctgct       57
```

<210> SEQ ID NO 143
<211> LENGTH: 489
<212> TYPE: DNA
<213> ORGANISM: Bos taurus
<220> FEATURE:
<221> NAME/KEY: misc_feature
<222> LOCATION: (0)...(0)
<223> OTHER INFORMATION: Beta-lactoglobulin

<400> SEQUENCE: 143

```
ttaatcgtca ctcagacaat gaaaggtttg acatccaaa aagttgctgg aacttggtat     60
tcattggcaa tggctgcaag cgatatctcc ctgttagacg cccaatcagc tccactaaga   120
gtgtatgtgg aggagctgaa gcccactcca gaaggtgatc ttgaaattct gttgcaaaaa   180
tgggaaaatg gtgagtgtgc tcagaaaaag attatcgccg agaaaaccaa gattccggct   240
gtattcaaga tagatgctct gaacgagaat aaggtgttgg tcctcgatac agactacaaa   300
aagtaccttc tattctgtat ggaaaattcg gcagaacctg agcaatcctt ggcttgtcaa   360
tgcttggtta gaactccaga agttgacgac gaggcttttgg aaaagtttga taaagccctg   420
aaagccttgc ctatgcatat tcgtttaagt tttaacccaa cacaattgga ggaacagtgt   480
cacatttaa                                                           489
```

<210> SEQ ID NO 144
<211> LENGTH: 630
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein beta

<400> SEQUENCE: 144

```
agagagttgg aagagttgaa cgttccaggt gagatcgttg agtctttgtc ctcttcagaa     60
gagtccatca ctagaatcaa caagaagatc gagaagttcc agtccgagga acaacaacaa   120
actgaggacg agttgcagga caagattcac ccattcgctc aaactcagtc cttggtttac   180
ccattcccag gtccaattcc aaactccttg ccacagaaca tcccaccatt gactcagact   240
```

```
ccagttgttg ttccaccatt cttgcagcca gaggttatgg gtgtttccaa ggttaaggaa    300
gctatggctc caaagcacaa agagatgcca ttcccaaagt acccagttga gccattcact    360
gagtcccagt ccttgacttt gactgacgtt gagaacttgc acttgccatt gcctttgttg    420
caatcctgga tgcaccaacc acatcaacca ttgccaccaa ctgttatgtt cccaccacaa    480
tccgttttgt ccttgtccca atccaaggtt ttgccagttc cacagaaggc tgttccatac    540
cctcaaagag acatgccaat ccaggctttc ttgttgtacc aagagccagt tttgggtcca    600
gttagaggtc cattccctat catcgtttga                                     630
```

```
<210> SEQ ID NO 145
<211> LENGTH: 624
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein alpha-S2

<400> SEQUENCE: 145
aagaacacta tggaacacgt ttcatcctcc gaagagtcca tcatctccca agagacttac     60
aagcaagaga agaacatgga catcaaccca tccaaagaaa acttgtgttc cactttctgt    120
aaagaggttg ttagaaacgc taacgaggaa gagtactcca tcggttcctc atctgaagaa    180
tctgctgagg ttgctactga agaggttaag atcactgttg acgacaagca ctaccagaag    240
gctttgaacg agatcaacca gttctacaga aaattcccac aatacttgca gtacttgtac    300
cagggtccaa tcgttttgaa cccatgggac caggttaaga gaaacgctgt tcctatcact    360
ccaactttga acagagagca gttgtccact tccgaagaga actccaagaa aactgttgac    420
atggaatcca ctgaggtttt cactaagaaa actaagttga ctgaggaaga aaagaacaga    480
ttgaacttct tgaagaagat ctcccagaga taccagaagt tcgctttgcc acagtacttg    540
aaaacagttt accagcacca aaaggctatg aagccatgga tccagccaaa gactaaggtt    600
atcccatacg ttagatactt gtga                                            624
```

```
<210> SEQ ID NO 146
<211> LENGTH: 624
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein alpha-S2 K113E Variant

<400> SEQUENCE: 146
aagaacacta tggaacacgt ttcatcctcc gaagagtcca tcatctccca agagacttac     60
aagcaagaga agaacatgga catcaaccca tccaaagaaa acttgtgttc cactttctgt    120
aaagaggttg ttagaaacgc taacgaggaa gagtactcca tcggttcctc atctgaagaa    180
tctgctgagg ttgctactga agaggttaag atcactgttg acgacaagca ctaccagaag    240
gctttgaacg agatcaacca gttctacaga aaattcccac aatacttgca gtacttgtac    300
cagggtccaa tcgttttgaa cccatgggac caggttaagg aaaacgctgt tcctatcact    360
ccaactttga acagagagca gttgtccact tccgaagaga actccaagaa aactgttgac    420
atggaatcca ctgaggtttt cactaagaaa actaagttga ctgaggaaga aaagaacaga    480
ttgaacttct tgaagaagat ctcccagaga taccagaagt tcgctttgcc acagtacttg    540
aaaacagttt accagcacca aaaggctatg aagccatgga tccagccaaa gactaaggtt    600
```

```
atcccatacg ttagatactt gtga                                          624
```

<210> SEQ ID NO 147
<211> LENGTH: 600
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein alpha-S1

<400> SEQUENCE: 147

```
agacctaagc acccaatcaa gcaccaaggt ttgccacaag aggttttgaa cgagaacttg    60
ttgagattct tcgttgctcc attcccagag gttttcggta agagaaggt taacgagttg    120 tccaaggaca tcggttctga atccactgag gaccaggcta tggaagatat caagcagatg    180
gaagctgagt ccatctcctc atccgaagag atcgttccaa actccgttga gcagaagcac    240
atccagaaag aggacgttcc atccgagaga tacttgggtt acttggagca gttgttgaga    300
ttgaagaagt acaaggttcc acagttggaa atcgttccta attccgctga gaaagattg    360 cactccatga aggaaggtat ccacgctcag cagaaagaac ctatgatcgg tgttaatcaa    420
gagttggctt acttctaccc agagttgttc agacagttct accagttgga cgcttaccca    480
tctggtgctt ggtactacgt tccattgggt actcagtaca ctgacgctcc atctttctcc    540
gacattccaa acccaattgg ttccgagaac tccggtaaga ctactatgcc attgtggtaa    600
```

<210> SEQ ID NO 148
<211> LENGTH: 510
<212> TYPE: DNA
<213> ORGANISM: Bos taurus
<220> FEATURE:
<221> NAME/KEY: misc_feature
<222> LOCATION: (0)...(0)
<223> OTHER INFORMATION: Casein k

<400> SEQUENCE: 148

```
caagagcaaa atcaagagca gccaatcaga tgtgagaagg acgagagatt cttctcagac    60
aagatcgcta agtacatccc aatccagtac gtttttgtcca gatacccatc ctacggtttg    120
aactactacc agcagaagcc agttgctttg atcaacaacc agttcttgcc ataccttac    180 tacgctaagc cagctgctgt tagatctcct gctcaaatct tgcagtggca ggttttgtct    240
aacactgttc cagctaagtc ctgtcaggct cagccaacta ctatggctag acatccacat    300
ccacacttgt ccttcatggc tatcccacca aagaagaacc aggacaagac tgagatccca    360
actatcaaca ctatcgcttc cggtgagcca acttccactc caactattga agctgttgag    420
tccactgttg ctactttgga agcttctcca gaggttattg aatccccacc agagatcaac    480
acagttcagg ttacttccac tgctgtttaa                                    510
```

<210> SEQ ID NO 149
<211> LENGTH: 279
<212> TYPE: DNA
<213> ORGANISM: Artificial Sequence
<220> FEATURE:
<223> OTHER INFORMATION: AOX1 Terminator Sequence

<400> SEQUENCE: 149

```
ggttaaaggg gcggccgctc aagaggatgt cagaatgcca tttgcctgag agatgcaggc    60
ttcatttttg atactttttt atttgtaacc tatatagtat aggattttt ttgtcatttt    120
```

| gtttcttctc gtacgagctt gctcctgatc agcctatctc gcagcagatg aatatcttgt | 180 |
| ggtaggggtt tgggaaaatc attcgagttt gatgtttttc ttggtatttc ccactcctct | 240 |
| tcagagtaca gaagattaag tgaaaccttc gtttgtgcg | 279 |

<210> SEQ ID NO 150
<211> LENGTH: 271
<212> TYPE: DNA
<213> ORGANISM: Artificial Sequence
<220> FEATURE:
<223> OTHER INFORMATION: CYC1 Terminator Sequence

<400> SEQUENCE: 150

| atcatgtaat tagttatgtc acgcttacat tcacgccctc cccccacatc cgctctaacc | 60 |
| gaaaaggaag gagttagaca acctgaagtc taggtcccta tttatttttt tatagttatg | 120 |
| ttagtattaa gaacgttatt tatatttcaa attttctttt tttttctgta cagacgcgtg | 180 |
| tacgcatgta acattatact gaaaaccttg cttgagaagg ttttgggacg ctcgaaggct | 240 |
| ttaatttgcg gccccctcacc tgcacgcaaa a | 271 |

<210> SEQ ID NO 151
<211> LENGTH: 375
<212> TYPE: DNA
<213> ORGANISM: Artificial Sequence
<220> FEATURE:
<223> OTHER INFORMATION: Zeocin Resistance Gene

<400> SEQUENCE: 151

| atggctaaac tcacctctgc tgttccagtc ctgactgctc gtgatgttgc tggtgctgtt | 60 |
| gagttctgga ctgatagact cggtttctcc cgtgacttcg tagaggacga ctttgccggt | 120 |
| gttgtacgtg acgacgttac cctgttcatc tccgcagttc aggaccaggt tgtgccagac | 180 |
| aacactctgg catgggtatg ggttcgtggt ctggacgaac tgtacgctga gtggtctgag | 240 |
| gtcgtgtcta ccaacttccg tgatgcatct ggtccagcta tgaccgagat cggtgaacag | 300 |
| ccctggggtc gtgagtttgc actgcgtgat ccagctggta actgcgtgca tttcgtcgca | 360 |
| gaagaacagg actaa | 375 |

<210> SEQ ID NO 152
<211> LENGTH: 816
<212> TYPE: DNA
<213> ORGANISM: Artificial Sequence
<220> FEATURE:
<223> OTHER INFORMATION: Kanamycin Resistance Gene

<400> SEQUENCE: 152

| atgagccata ttcaacggga aacgtcttgc tcgaggccgc gattaaattc caacatggat | 60 |
| gctgatttat atgggtataa atgggctcgc gataatgtcg gcaatcagg tgcgacaatc | 120 |
| tatcgattgt atgggaagcc cgatgcgcca gagttgtttc tgaaacatgg caaaggtagc | 180 |
| gttgccaatg atgttacaga tgagatggtc agactaaact ggctgacgga atttatgcct | 240 |
| cttccgacca tcaagcattt tatccgtact cctgatgatg catggttact caccactgcg | 300 |
| atccccggga aaacagcatt ccaggtatta gaagaatatc ctgattcagg tgaaaatatt | 360 |
| gttgatgcgc tggcagtgtt cctgcgccgg ttgcattcga ttcctgtttg taattgtcct | 420 |
| tttaacagcg atcgcgtatt tcgtctcgct caggcgcaat cacgaatgaa taacggtttg | 480 |
| gttgatgcga gtgattttga tgacgagcgt aatggctggc ctgttgaaca agtctggaaa | 540 |
| gaaatgcata agcttttgcc attctcaccg gattcagtcg tcactcatgg tgatttctca | 600 |

```
cttgataacc ttatttttga cgaggggaaa ttaataggtt gtattgatgt tggacgagtc    660
ggaatcgcag accgatacca ggatcttgcc atcctatgga actgcctcgg tgagttttct    720
ccttcattac agaaacggct ttttcaaaaa tatggtattg ataatcctga tatgaataaa    780
ttgcagtttc atttgatgct cgatgagttt ttctaa                              816
```

\<210\> SEQ ID NO 153
\<211\> LENGTH: 939
\<212\> TYPE: DNA
\<213\> ORGANISM: Artificial Sequence
\<220\> FEATURE:
\<223\> OTHER INFORMATION: Promoter AOX1

\<400\> SEQUENCE: 153

```
gatctaacat ccaaagacga aaggttgaat gaaacctttt tgccatccga catccacagg     60
tccattctca cacataagtg ccaaacgcaa caggagggga tacactagca gcagaccgtt    120
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gccccctgg cgaggttcat gtttgtttat     300
ttccgaatgc aacaagctcc gcattacacc cgaacatcac tccagatgag ggctttctga    360
gtgtggggtc aaatagtttc atgttcccca aatggcccaa aactgacagt ttaaacgctg    420
tcttggaacc taatatgaca aaagcgtgat ctcatccaag atgaactaag tttggttcgt    480
tgaaatgcta acggccagtt ggtcaaaaag aaacttccaa aagtcggcat accgtttgtc    540
ttgtttggta ttgattgacg aatgctcaaa aataatctca ttaatgctta gcgcagtctc    600
tctatcgctt ctgaaccccg gtgcacctgt gccgaaacgc aaatggggaa cacccgctt     660 tttggatgat tatgcattgt ctccacattg tatgcttcca agattctggt gggaatactg    720
ctgatagcct aacgttcatg atcaaaattt aactgttcta accctactt gacagcaata     780 tataaacaga aggaagctgc cctgtcttaa acctttttt ttatcatcat tattagctta     840
ctttcataat tgcgactggt tccaattgac aagcttttga ttttaacgac ttttaacgac    900
aacttgagaa gatcaaaaaa caactaatta ttcgaaacg                           939
```

\<210\> SEQ ID NO 154
\<211\> LENGTH: 267
\<212\> TYPE: DNA
\<213\> ORGANISM: Artificial Sequence
\<220\> FEATURE:
\<223\> OTHER INFORMATION: Signal Peptide of Alpha Mating Factor

\<400\> SEQUENCE: 154

```
atgagatttc cttcaatttt tactgctgtt ttattcgcag catcctccgc attagctgct     60
ccagtcaaca ctacaacaga agatgaaacg gcacaaattc cggctgaagc tgtcatcggt    120
tactcagatt tagaagggga tttcgatgtt gctgttttgc catttccaa cagcacaaat     180 aacggggttat tgtttataaa tactactatt gccagcattg ctgctaaaga agaaggggta    240
tctctcgaga aaagagaggc tgaagct                                        267
```

\<210\> SEQ ID NO 155
\<211\> LENGTH: 66
\<212\> TYPE: DNA
\<213\> ORGANISM: Artificial Sequence
\<220\> FEATURE:
\<223\> OTHER INFORMATION: Signal Peptide of OST1

```
<400> SEQUENCE: 155
atgagacaag tttggttctc atggattgtt ggtttattct tgtgtttctt caacgtttct    60
tccgct                                                              66

<210> SEQ ID NO 156
<211> LENGTH: 57
<212> TYPE: DNA
<213> ORGANISM: Artificial Sequence
<220> FEATURE:
<223> OTHER INFORMATION: Signal Peptide of alpha-lactalbumin

<400> SEQUENCE: 156
atgatgtcat ttgtttcttt gttgttggtt ggtatcctgt tccacgccac tcaagct      57

<210> SEQ ID NO 157
<211> LENGTH: 372
<212> TYPE: DNA
<213> ORGANISM: Bos taurus
<220> FEATURE:
<221> NAME/KEY: misc_feature
<222> LOCATION: (0)...(0)
<223> OTHER INFORMATION: alpha-lactalbumin

<400> SEQUENCE: 157
gagcaattga ccaagtgtga agttttcaga gagttgaagg atttgaaggg ttacggtggt    60
gtttctcttc cagaatgggt tgtaccgct ttccacactt ccggatacga tacacaagct   120
atcgttcaaa acaacgactc caccgagtac ggtttgttcc aaatcaacaa caagatttgg   180
tgtaaagacg atcaaaaccc tcactcttcc aacatttgca acatctcttg tgataagttc   240
ttggatgatg atctcaccga tgatatcatg tgtgttaaga agattttgga caaagttgga   300
atcaactact ggttggctca caaggctctt tgttcagaga agttggacca atggctatgt   360
gagaagttgt aa                                                      372

<210> SEQ ID NO 158
<211> LENGTH: 350
<212> TYPE: DNA
<213> ORGANISM: Artificial Sequence
<220> FEATURE:
<223> OTHER INFORMATION: AOX1 Terminal Seqeunce

<400> SEQUENCE: 158
tcaagaggat gtcagaatgc catttgcctg agagatgcag gcttcatttt tgatactttt    60
ttatttgtaa cctatatagt ataggatttt ttttgtcatt ttgtttcttc tcgtacgagc   120
ttgctcctga tcagcctatc tcgcagctga tgaatatctt gtggtagggg tttgggaaaa   180
tcattcgagt ttgatgtttt tcttggtatt tcccactcct cttcagagta cagaagatta   240
agtgacacgt tcgtttgtgc aagcttcaac gatgccaaaa gggtataata agcgtcattt   300
gcagcattgt gaagaaaact atgtggcaag ccaagcctgc gaagaatgta             350

<210> SEQ ID NO 159
<211> LENGTH: 810
<212> TYPE: DNA
<213> ORGANISM: Artificial Sequence
<220> FEATURE:
<223> OTHER INFORMATION: synthetic oligonucleotide

<400> SEQUENCE: 159
atgggtaagg aaaagactca cgtttccaga ccaagattga actctaacat ggacgctgac    60
ttgtacggtt acaagtgggc tagagacaac gttggtcaat ctggtgctac tatttacaga   120
```

```
ttgtacggta agccagacgc tccagagttg ttcttgaagc acggtaaggg ttctgttgct    180
aacgacgtta ctgacgagat ggttagattg aactggttga ctgagttcat gccattgcca    240
actattaagc acttcattag aactccagac gacgcttggt tgttgactac tgctattcca    300
ggtaagactg ctttccaagt tttggaggag tacccagact ctggtgagaa cattgttgac    360
gctttggctg ttttcttgag aagattgcac tctattccag tttgtaactg tccattcaac    420
tctgacagag ttttcagatt ggctcaagct caatccagaa tgaacaacgg tttggttgac    480
gcttctgact tcgacgacga gagaaacggt tggccagttg agcaagtttg gaaggagatg    540
cacaagttgt tgccattctc tccagactct gttgttactc acggtgactt ctctttggac    600
aacttgattt tcgacgaggg taagttgatt ggttgtattg acgttggtag agttggtatt    660
gctgacagat accaagactt ggctattttg tggaactgtt tgggtgagtt ctctccatct    720
ttgcaaaaga gattgttcca aaagtacggt attgacaacc cagacatgaa caagttgcaa    780
ttccacttga tgttggacga gttcttctaa                                     810
```